United States Patent
Kim et al.

(10) Patent No.: US 12,415,949 B2
(45) Date of Patent: Sep. 16, 2025

(54) COMPOUND, ORGANIC ELECTROLUMINESCENT DEVICE, AND DISPLAY DEVICE

(71) Applicant: SK Inc., Seoul (KR)

(72) Inventors: Jeongmi Kim, Sejong-si (KR); Myeongho Choo, Wonju-si (KR); Mijeong Kim, Sejong-si (KR)

(73) Assignee: SK INC., Seoul (KR)

( * ) Notice: Subject to any disclaimer, the term of this patent is extended or adjusted under 35 U.S.C. 154(b) by 1023 days.

(21) Appl. No.: 17/053,487

(22) PCT Filed: Jun. 14, 2019

(86) PCT No.: PCT/KR2019/007245
§ 371 (c)(1),
(2) Date: Nov. 6, 2020

(87) PCT Pub. No.: WO2020/004844
PCT Pub. Date: Feb. 1, 2020

(65) Prior Publication Data
US 2021/0143337 A1 May 13, 2021

(30) Foreign Application Priority Data
Jun. 28, 2018 (KR) .................. 10-2018-0075092

(51) Int. Cl.
*C09K 11/06* (2006.01)
*C07D 491/048* (2006.01)
(Continued)

(52) U.S. Cl.
CPC .......... *C09K 11/06* (2013.01); *C07D 491/048* (2013.01); *C07D 491/147* (2013.01);
(Continued)

(58) Field of Classification Search
CPC ...................................................... C09K 11/06
See application file for complete search history.

(56) References Cited

U.S. PATENT DOCUMENTS

2005/0236970 A1* 10/2005 Matsudate ........... H10K 59/122
313/500
2016/0141515 A1* 5/2016 Hayama ............. C07D 491/048
544/215
(Continued)

FOREIGN PATENT DOCUMENTS

| CN | 106397460 A | 2/2017 |
| CN | 106661055 A | 5/2017 |

(Continued)

OTHER PUBLICATIONS

International Search Report for PCT/KR2019/007245 mailed Sep. 11, 2019 from Korean Intellectual Property Office.
(Continued)

*Primary Examiner* — Sean M DeGuire
(74) *Attorney, Agent, or Firm* — Paratus Law Group, PLLC

(57) ABSTRACT

Disclosed is a compound applicable to an electron transport layer, an electron transport assisting layer, a light emitting layer (n-type) of an organic electroluminescent device, an organic electroluminescent device in which said compound is used, and an organic EL display device including the organic electroluminescent device. The organic electroluminescent device includes: a first electrode; a second electrode facing the first electrode; and an organic material layer interposed between the first electrode and the second electrode and includes the compound.

7 Claims, 1 Drawing Sheet

(51) Int. Cl.
  *C07D 491/147* (2006.01)
  *C07D 495/04* (2006.01)
  *C07D 495/14* (2006.01)
  *C07D 519/00* (2006.01)
  *H10K 85/60* (2023.01)
  *H10K 50/16* (2023.01)
  *H10K 50/17* (2023.01)

(52) U.S. Cl.
  CPC ......... *C07D 495/04* (2013.01); *C07D 495/14* (2013.01); *C07D 519/00* (2013.01); *H10K 85/654* (2023.02); *H10K 85/657* (2023.02); *H10K 85/6572* (2023.02); *C09K 2211/1018* (2013.01); *H10K 50/16* (2023.02); *H10K 50/171* (2023.02)

(56) References Cited

U.S. PATENT DOCUMENTS

| | | |
|---|---|---|
| 2016/0163997 A1 | 6/2016 | Noh et al. |
| 2018/0053903 A1 | 2/2018 | Suzuki et al. |
| 2019/0131540 A1* | 5/2019 | Sim ................ H10K 85/657 |

FOREIGN PATENT DOCUMENTS

| | | |
|---|---|---|
| KR | 10-2012-0033017 A | 4/2012 |
| KR | 10-2016-0059413 A | 5/2016 |
| KR | 10-2016-0068641 A | 6/2016 |
| KR | 10-1763222 B1 | 7/2017 |
| KR | 10-2018-0032354 A | 3/2018 |
| KR | 10-2019-0049957 A | 5/2019 |
| WO | WO 2018/033820 A1 | 2/2018 |

OTHER PUBLICATIONS

Chinese Office Action for related CN Application No. 201980039276.1 mailed Jul. 13, 2023 from China National Intellectual Property Administration.

* cited by examiner

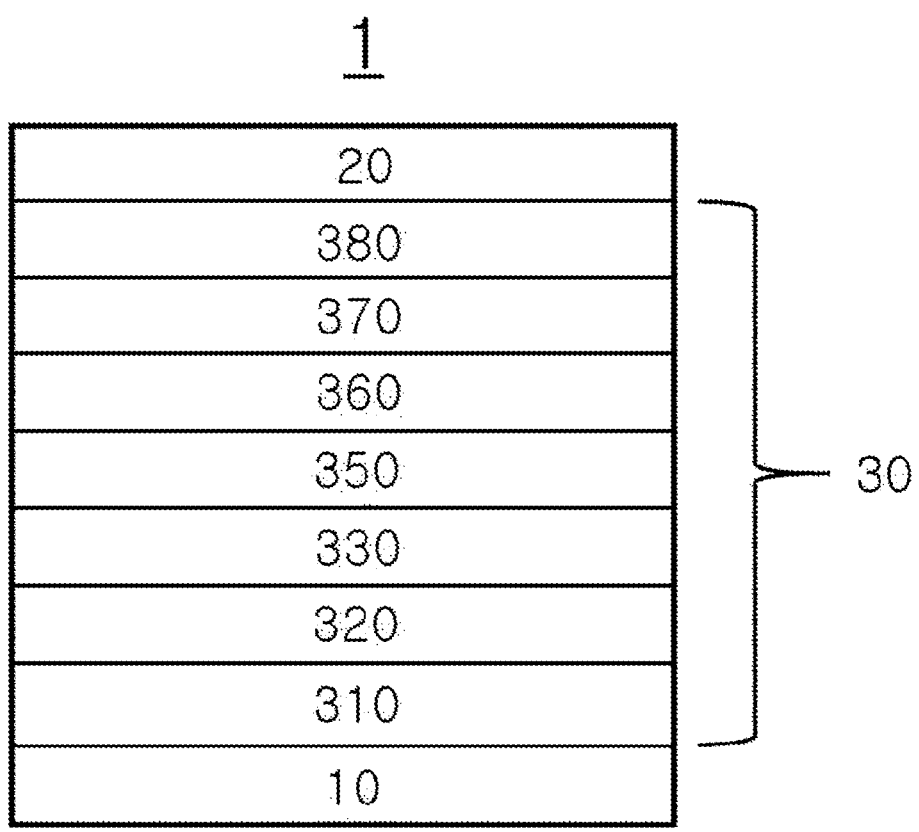

COMPOUND, ORGANIC ELECTROLUMINESCENT DEVICE, AND DISPLAY DEVICE

CROSS-REFERENCE TO PRIOR APPLICATIONS

This application is a National Stage Patent Application of PCT International Patent Application No. PCT/KR2019/007245 (filed on Jun. 14, 2019) under 35 U.S.C. § 371, which claims priority to Korean Patent Application No. 10-2018-0075092 (filed on Jun. 28, 2018), which are all hereby incorporated by reference in their entirety.

BACKGROUND

The present invention relates to a novel organic compound which can be used as a material for an organic electroluminescent device, an organic electroluminescent device comprising the same, and a display device.

Generally, an organic electroluminescent phenomenon refers to a phenomenon in which electrical energy is converted into light energy in an organic material. An organic electroluminescent device employing the organic electroluminescent phenomenon typically has a structure including an anode, a cathode and an organic layer therebetween. In order to increase the efficiency and stability of the organic electroluminescent device, the organic layer may have a multi-layered structure composed of different materials, and, for example, may include a hole injection layer, a hole transport layer, a light emitting layer, an electron transport layer, and an electron injection layer or the like.

When a voltage is applied between two electrodes in the structure of the organic electroluminescent device, holes are injected into the light emitting layer through the hole injection layer and the hole transport layer from the anode, and electrons are injected into the light emitting layer through the electron injection layer and the electron transport layer from the cathode, and excitons are formed by recombination of the injected holes and electrons, and light is emitted when the excitons fall back to the ground state.

Electron transporting materials of organic electroluminescent devices are required to have excellent stability for electrons and high electron transfer rates. Known as typical electron-transporting materials are $Alq_3$, Flavon derivatives, or germanium and silicon cyclopentadiene derivatives, and the like. In addition, PBD (2-biphenyl-4-yl-5-(4-t-butylphenyl)-1,3,4-oxidiazole) derivative bonded to a Spiro compound, and TPBI (2,2',2"-(benzene-1,3,5-triyl)-tris(1-phenyl-1H-benzimidazole) and the like are also known.

However, there is a need for further improvement of efficiency and driving voltage of the conventional electron transporting materials.

In particular, in the conventional organic electroluminescent device, the excitons generated in the light emitting layer are diffused into the electron transport layer to emit light at an interface with the electron transport layer, thereby reducing light-emitting efficiency and decreasing lifetime.

SUMMARY

The objective of the present invention is to provide a compound which has high stability for electrons and high electron mobility and which can suppress the diffusion of excitons to an electron transport layer, and an organic electroluminescent device having high efficiency and low driving voltage by employing the compound, and a display device using the same.

In order to accomplish the objective, according to an aspect of the present invention, provided is a compound represented by chemical formula 1,

  <Chemical Formula 1> wherein $A_1$ is a group represented by the following chemical formula 2:

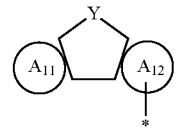  <Chemical Formula 2>

Y is O or S, $A_{11}$ and $A_{12}$ are each independently selected from benzene, naphthalene, pyridine, pyrimidine, pyrazine, pyridazine, 1,2,3-triazine, quinoline, isoquinoline, 2,6-naphthyridine, 1,8-naphthyridine, 1,5-naphthyridine, 1,6-naphthyridine, 1,7-naphthyridine, 2,7-naphthyridine, cinnoline, quinoxaline, phthalazine, quinazoline, and phenazine;

at least one of $A_{11}$ and $A_{12}$ is an aromatic heterocyclic compound containing nitrogen(N)

L is a direct bond; a substituted or unsubstituted arylene group; a substituted or unsubstituted heteroarylene group; or a substituted or unsubstituted $C_9$-$C_{60}$ fused polycyclic group, $A_2$ is hydrogen; deuterium; a halogen group; a nitrile group; a nitro group; a hydroxy group; a carbonyl group; a ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphinic group; a substituted or unsubstituted phosphine oxide group; a substituted or unsubstituted aryl group; or a substituted or unsubstituted heterocyclic group, L or $A_2$ is bonded to a carbon position of $A_1$.

When the novel compound represented by chemical formula 1 of the present invention is used as a material for an electron transport layer or an electron transport assisting layer, an organic electroluminescent device having excellent luminous performance, low driving voltage, high efficiency, and long lifetime compared to a conventional device can be manufactured, and further, a full color display panel with greatly improved performance and lifetime can be manufactured.

BRIEF DESCRIPTION OF THE DRAWINGS

FIG. 1 is a schematic sectional view of an organic electroluminescent device according to an embodiment of the present invention.

DETAILED DESCRIPTION

Hereinafter, embodiments of the present invention will be described in detail with reference to the accompanying drawings. In designation of reference numerals to components in respective drawings, it should be noted that the same components are given the same reference numerals even though they are shown in different FIGURES. Further, in the following description the present invention, a detailed description of known configurations or functions related thereto will be omitted when it is considered that it may make the subject matter of the present invention rather unclear.

It should be noted that if it is described in the specification that one component is "connected", "coupled" or "joined" to another component, a third component may be "connected", "coupled", or "joined" between the first and second components, although the first component may be directly connected, coupled or joined to the second component.

The terms as used in this specification and the accompanying claims, unless otherwise stated, have the following meanings.

The term "halo" or "halogen" as used herein includes fluorine(F), bromine (Br), chlorine (Cl), or iodine(I), unless otherwise indicated.

The term "alkyl" or "alkyl group" as used herein, has a single bond of 1 to 60 carbon atoms unless otherwise indicated, and means aliphatic functional radicals including a linear alkyl group, a branched chain alkyl group, a cycloalkyl group (alicyclic), or an alkyl-substituted cycloalkyl group, a cycloalkyl-substituted alkyl group. Specific examples of alkyl groups include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohextylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like.

The term "haloalkyl group" or "halogen alkyl group" as used herein, means an alkyl group substituted with a halogen unless otherwise indicated.

The term "heteroalkyl group" as used herein, means an alkyl group of which at least one of carbon atoms is substituted with a hetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group. Specific examples include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl) vinyl-1-yl, a stilbenyl group, a styrenyl group, and the like, but are not limited thereto.

The term "cycloalkyl" as used herein, refers to alkyl that forms a ring having 3 to 60 carbon atoms unless otherwise indicated, but is not limited thereto. Specific examples include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

The term "alkoxyl group", "alkoxy group" or "alkyloxy group" as used herein, means an alkyl group to which an oxygen radical is attached, and, unless otherwise indicated, has from 1 to 60 carbon atoms, and is not limited thereto.

The term "alkenoxyl group", "alkenoxy group", "alkenyloxyl group", or "alkenyloxy group" as used herein, means an alkenyl group to which oxygen radical is attached, and, unless otherwise stated, has 2 to 60 carbon atoms, but is not limited thereto.

The term "aryloxyl group" or "aryloxy group" as used herein means an aryl group to which oxygen radical is attached, and, unless otherwise indicated, has 6 to 60 carbon atoms, but is not limited thereto.

The terms "aryl group" and "arylene group" as used herein, unless otherwise indicated, have a carbon number of 6 to 60, respectively, and are not limited thereto.

The aryl group or arylene group herein means a monocyclic or polycyclic aromatic group, and includes an aromatic ring that is formed in conjunction with an adjacent substituent linked thereto or participating in the reaction. Examples of the aryl group may include as a monocyclic aryl group, a phenyl group, a biphenylyl group, and a terphenylyl group, and may include as a polycyclic aryl group, a naphthyl group, an anthracenyl group, a phenanthryl group, a pyrenyl group, a perylenyl group, a chrysenyl group, a fluorenyl group, and a spirofluorenyl group.

The fluorenyl group herein can be substituted and two substituents can be bonded together to form a spiro structure. When the fluorenyl group is substituted, it may be the following structure, but is not limited thereto.

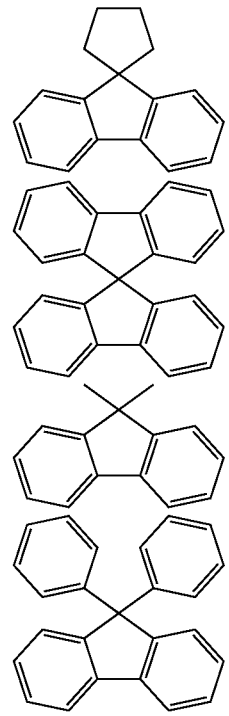

The prefix "aryl" or "Ar" refers to a radical substituted with an aryl group. For example, an arylalkyl group is an alkyl group substituted with an aryl group, and an arylalkenyl group is an alkenyl group substituted with an aryl group, and a radical substituted with an aryl group has the carbon number defined as herein.

Also, when the prefix is subsequently named, it means that substituents are listed in the order described first. For example, an arylalkoxy group refers to an alkoxy group substituted with an aryl group, an alkoxylcarbonyl group means a carbonyl group substituted with an alkoxyl group, and an arylcarbonylalkenyl group means an alkenyl group substituted with an arylcarbonyl group, wherein the arylcarbonyl group is a carbonyl group substituted with an aryl group.

Unless otherwise stated, the term "heteroaryl group" or "heteroarylene group" as used herein means, but not limited to, an aryl or arylene group having 2 to 60 carbon atoms and containing one or more heteroatoms, includes at least one of monocyclic and polycyclic rings, and may also be formed in conjunction with an adjacent functional group.

Unless otherwise stated, the term "heterocyclic group" as used herein contains one or more heteroatoms, has 2 to 60 carbon atoms, includes at least one of monocyclic and polycyclic rings, and includes a heteroaliphatic ring and a heteroaromatic ring. It may be formed in conjunction with adjacent functional groups. "Heteroatom" refers to N, O, S, P, or Si unless otherwise indicated. A "heterocyclic group" may also include a ring containing $SO_2$ instead of carbon forming the ring.

Examples of heterocyclic groups include a thiophene group, a furan group, a pyrrole group, an imidazole group, a thiazole group, an oxazole group, an oxadiazole group, a triazole group, a pyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyrido pyrimidinyl group, a pyrido pyrazinyl group, a pyrazino pyrazinyl group, an isoquinoline group, an indole group, a carbazole group, a benzooxazole group, a benzoimidazole group, a benzothiazole group, a benzocarbazole group, a benzothiophene group, a dibenzothiophene group, a benzofuranyl group, a phenanthroline group, a thiazolyl group, an isooxazolyl group, an oxadiazolyl group, a thiadiazolyl group, a benzothiazolyl group, a phenothiazinyl group, and a dibenzofuranyl group, but are not limited thereto.

Unless otherwise indicated, the term "aliphatic" as used herein refers to aliphatic hydrocarbons having from 1 to 60 carbon atoms, and "aliphatic ring" means an aliphatic hydrocarbon ring having from 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Other heterocompounds or heteroradicals other than the foregoing heterocompounds include, but are not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R or R' independently may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these, respectively.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopene group, a $C_6$-$C_{20}$ arylthiopene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_5$-$C_{20}$ arylalkenyl group, a silane group, a boron group, a germanium group, and a $C_2$-$C_{20}$ heterocyclic group.

Otherwise specified, the formulas used in the present invention are defined as in the index definition of the substituent of the following Formula.

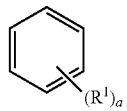

Wherein, when a is an integer of zero, the substituent $R^1$ is absent, when a is an integer of 1, the sole substituent $R^1$ is linked to any one of the carbon atoms constituting the benzene ring, when a is an integer of 2 or 3, the $R^1$s may be the same and different, and are linked to the benzene ring as follows. When a is an integer of 4 to 6, the $R^1$s may be the same and different, and are linked to the benzene ring in a similar manner to that when a is an integer of 2 or 3. Hydrogen atoms linked to carbon constituents of the benzene ring are omitted.

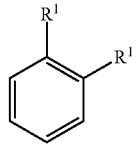
(a=2)

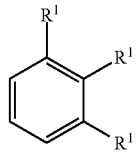
(a=3)

FIG. 1 is a schematic sectional view of an organic electroluminescent device according to an embodiment of the present invention.

As shown in FIG. 1, an organic electroluminescent device 1 according to an embodiment of the present invention includes a first electrode 10 formed on a substrate, a second electrode 20, and an organic material layer 30 formed between the first electrode 10 and the second electrode 20, wherein the organic material layer 30 includes a compound represented by chemical formula 1. The first electrode 10 may be an anode (positive electrode), and the second electrode 20 may be a cathode (negative electrode). In the case of an inverted organic electroluminescent device, the first electrode may be a cathode, and the second electrode may be an anode.

The anode is desirably formed of a material having a high work function so that hole injection into the organic material layer can be facilitated. Specific examples of materials for the anode that may be used in the present invention include metals such as vanadium, chromium, copper, zinc, gold, or alloys thereof, metal oxides such as zinc oxide, indium oxide, indium tin oxide (ITO), indium zinc oxide (IZO); combinations of metals and oxides such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, but are not limited thereto.

It is desired that the cathode is formed of a material having a small work function to facilitate electron injection into the organic material layer. Specific examples of cathode materials include, but are not limited to, metals such as magnesium, calcium, sodium, potassium, titanium, indium, yttrium, lithium, gadolinium, aluminum, silver, tin, and lead, or alloys thereof, multi-layered structure materials such as LiF/Al or $LiO_2$/Al and the like.

The organic material layer 30 may include a hole injection layer 310, a hole transport layer 320, a light emitting layer 350, an electron transport layer 370, and an electron injection layer 380 formed in sequence on the first electrode 10. Here, some of the layers included in the organic material layer, except for the light emitting layer 350, may not be formed. The layers formed between the first electrode 10 and the light-emitting layer 350 comprises a hole transporting region, and the layers formed between the light-emitting layer 350 and the second electrode 20 comprises an electron transporting region.

The hole injection layer 310 is a layer that facilitates injection of holes from the first electrode 10, and is desirably formed of a compound having excellent hole injection effect from the anode and thin film formation capability. For these reasons, it is preferred that the highest occupied molecular orbital (HOMO) of the hole injecting material falls between the work function of the anode material and the HOMO of the surrounding organic material layer. Examples of the hole-injecting material include, but are not limited to, a metal porphyrin, an oligothiophene, an arylamine-based organic material, a hexanitrilehexaazatriphenylene-based organic material, a quinacridone-based organic material, a perylene-based organic material, an anthraquinone, and polyaniline-based and polythiophene-based conductive polymer.

The hole transport layer 320 receives holes from the hole injection layer 310 and transports holes to the light emitting layer 350, and the hole transport material is preferably a material having a high mobility for holes. Specific examples include, but are not limited to, an arylamine-based organic material, a conductive polymer, and a block copolymer having both a conjugated part and a non-conjugated part.

The light emitting layer 350 is a layer emitting light in the visible light region by receiving holes and electrons from the hole transport layer 320 and the electron transport layer 370, respectively, and recombining them. The light-emitting material is preferably a material having good quantum efficiency for fluorescence or phosphorescence. Specific examples include, but are not limited to, 8-hydroxy-quinoline aluminum complex ($Alq_3$); carbazole based compounds; dimerized styryl compounds; BAlq; 10-hydroxybenzo quinoline-metal compounds; benzoxazole, benzthiazole and benzimidazole-based compounds; poly(p-phenylenevinylene) (PPV)-based polymers; spiro compounds; polyfluorenes, rubrene, and the like.

The light emitting layer 350 may include a host material and a dopant material. The host material may be a fused aromatic ring derivative or a heterocyclic-containing compound. Specifically, the fused aromatic ring derivative includes an anthracene derivative, a pyrene derivative, a naphthalene derivative, a pentacene derivative, a phenanthrene compound, a fluoranthene compound, and the like. The heterocyclic-containing compound includes, but is not limited to, a carbazole derivative, a dibenzofuran derivative, a ladder-type furan compound, a pyrimidine derivative, and the like.

The dopant material includes an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and includes a pyrene, an anthracene, a chrysene, and a periflanthene, each of which has an arylamino group. The styrylamine compound is a compound in which at least one arylvinyl group is substituted in a substituted or unsubstituted arylamine, in which at least one or two substituent selected from the group consisting of an aryl group, a silyl group, an alkyl group, a cycloalkyl group, and an arylamino group is substituted or unsubstituted. Specific examples include, but are not limited to, styrylamine, styryldiamine, styryltriamine, styryltetraamine, and the like. In addition, the metal complex includes, but is not limited to, a iridium complex, a platinum complex, and the like.

The electron transport layer 370 receives electrons from the electron injection layer 380 and transports electrons to the light emitting layer 350, and the electron transport material is preferably a material having a high mobility for electrons. Specific examples include, but are not limited to, Al complexes of 8-hydroxyquinoline; complexes including $Alq_3$; organic radical compounds; hydroxyflavone-metal complexes; and the like. The compounds represented by chemical formula 1 according to the present invention may be used as electron transport materials as described below.

The electron injection layer 380 is a layer that facilitates the injection of electrons from the second electrode 20, and it is preferable that the electron injection layer 170 has the ability to transport electrons, and the electron injection effect from the cathode electrode and the ability to form the thin film are excellent. Examples include, but are not limited to, fluorenone, anthraquinodimethane, diphenoquinone, thiopyran dioxide, oxazole, oxadiazole, triazole, imidazole, perylenetetracarboxylic acid, preorenylidene methane, anthrone, and derivatives thereof, metal complex compounds, and nitrogen-containing 5-membered ring derivatives. Metal complex compounds include 8-hydroxyquinolinato lithium, bis(8-hydroxyquinolinato) Zinc, bis(8-hydroxyquinolinato) Copper, bis(8-hydroxyquinolinato) Manganese, tris(8-hydroxyquinolinato) Aluminum, tris(2-methyl-8-hydroxyquinolinato) Aluminum, tris(8-hydroxyquinolinato) Gallium, bis(10-hydroxybenzo [h] quinolinato) beryllium, bis(10-hydroxybenzo[h]quinolinato) zinc, bis(2-methyl-8-quinolinato) chlorogallium, bis (2-methyl-8-quinolinato)(o-cresolato) gallium, bis (2-methyl-8-quinolinato)(1-naphtholato) aluminum, bis (2-methyl-8-quinolinato) (2-naphtholato) gallium, and the like, but are not limited thereto.

The organic material layer 30 may further include a hole transport assisting layer 330 formed between the hole transport layer 320 and the light emitting layer 350 and an electron transport assisting layer 360 formed between the light emitting layer 350 and the electron transport layer 370.

The hole transport assisting layer 330 and the electron transport assisting layer 360 prevent excitons generated in the light emitting layer 350 from being diffused into the electron transporting layer 370 or to the hole transporting layer 320 adjacent to the light emitting layer 350, thereby increasing the number of excitons contributing to electroluminescence in the light emitting layer to improve the luminous efficiency of the device and lower the driving voltage, and improving the durability and stability of the device to increase the lifetime of the device. The compound represented by chemical formula 1 of the present invention may be used preferably as a material for an electron transport assisting layer.

The organic material layer 30 may further include an auxiliary light emitting layer (not shown) formed between the hole transport assisting layer 330 and the light emitting layer 350, and may further include a lifetime-improving layer (not shown) formed between the electron transport assisting layer 360 and the light emitting layer 350.

The auxiliary light emitting layer serves to transport holes to the light emitting layer 350 and adjust the thickness of the organic material layer 30. The auxiliary light emitting layer may contain a hole transporting material, and may be made of the same material as the hole transport layer 320.

The lifetime-improving layer serves to prevent holes transported to the light emitting layer 350 from being diffused, or moving into the electron transport layer 370, thereby limiting the holes within the light emitting layer. The electron transport layer 370 moves electrons by reduction, and when holes are diffused into the electron transport layer, an irreversible decomposition reaction occurs by oxidation, thereby deteriorating the lifetime of the device. Accordingly, the lifetime of the organic light emitting device can be improved by forming the lifetime-improving layer to suppress the diffusion of the hole into the electron transport layer 370.

In addition, although not shown, the organic electroluminescent device according to the present invention may further include a protective layer or a light efficiency improving layer(capping layer) formed between at least one of the first electrode 10 and the second electrode 20 and the organic material layer.

Although the compound according to the present invention is mainly described to be used in an electron transporting region such as the electron transport layer 370 or the electron transport assisting layer 360, the present invention is not limited thereto, and it may be used as a host (especially n-type host) of the light emitting layer 350.

The organic electroluminescent device 1 according to an embodiment of the present invention can be manufactured by vacuum-evaporation. For example, the device can be manufactured by evaporating organic materials inside the vacuum chamber and thereby depositing organic material layers including the hole injection layer 310, the hole transport layer 320, the light emitting layer 350, the electron transport layer 370 and the electron injection layer 380 on a substrate on which the anode 10 is formed and then depositing a material that can be used as the cathode 20 thereon.

In addition, the organic material layer may be formed of a smaller number of layers by using, instead of vacuum evaporation, a soluble process or a solvent process, such as a spin coating process, a nozzle printing process, an inkjet printing process, a slot coating process, a dip coating process, a roll-to-roll process, a doctor blading process, a screen printing process, or a thermal transfer method. Since the organic layer according to the present invention can be formed by various methods, the scope of the present invention is not limited by the formation method thereof.

Depending on a used material, the organic electroluminescent device according to the present invention can be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs have been suggested. Representative among the structures are a parallel side-by-side arrangement of R (Red), G (Green), B (Blue) light-emitting units, a vertical stack arrangement of RGB light-emitting units, and a color conversion material (CCM) structure in which electroluminescence from a blue (B) organic light emitting layer and photoluminescence from an inorganic phosphor using light from the blue (B) organic light emitting layer are combined. The present invention is applicable to these WOLEDs.

Another embodiment of the present invention provides an electronic device including a display device, which includes the above described organic electroluminescent device and a control unit for controlling the display device. Here, the electronic device may be a wired/wireless communication terminal which is currently used or will be used in the future, and includes all kinds of electronic devices including a mobile communication terminal such as a cellular phone, a personal digital assistant (PDA), an electronic dictionary, a point-to-multipoint (PMP), a remote controller, a navigation device, a game player, various kinds of TVs, and various kinds of computers.

Hereinafter, a compound according to an aspect of the present invention will be described.

According to an aspect of the present invention, provided is a compound represented by chemical formula 1, $$A_1\text{-(-L-)-}A_2 \qquad \text{<Chemical Formula 1>}$$

wherein $A_1$ is a group represented by the following chemical formula 2:

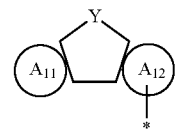

<Chemical Formula 2>

Y is O or S, $A_{11}$ and $A_{12}$ are each independently selected from benzene, naphthalene, pyridine, pyrimidine, pyrazine, pyridazine, 1,2,3-triazine, quinoline, isoquinoline, 2,6-naphthyridine, 1,8-naphthyridine, 1,5-naphthyridine, 1,6-naphthyridine, 1,7-naphthyridine, 2,7-naphthyridine, cinnoline, quinoxaline, phthalazine, quinazoline, and phenazine;

at least one of $A_{11}$ and $A_{12}$ is an aromatic heterocyclic compound containing nitrogen(N)

L is a direct bond; a substituted or unsubstituted arylene group; a substituted or unsubstituted heteroarylene group; or a substituted or unsubstituted $C_9$-$C_{60}$ fused polycyclic group, $A_2$ is hydrogen; deuterium; a halogen group; a nitrile group; a nitro group; a hydroxy group; a carbonyl group; a ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphinic group; a substituted or unsubstituted phosphine oxide group; a substituted or unsubstituted aryl group; or a substituted or unsubstituted heterocyclic group, L or $A_2$ is bonded to a carbon position of $A_1$.

According to a preferred embodiment of the present invention, one of $A_{11}$ and $A_{12}$ is selected from 1,5-naphthyridine, 1,6-naphthyridine, 1,7-naphthyridine, 1,8-naphthyridine, quinoxaline.

According to a preferred embodiment of the present invention, $A_1$ is represented by any one of the following structures.

Core 1-1
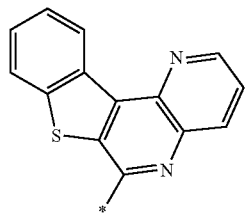

Core 1-2
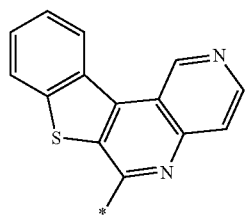

Core 1-3
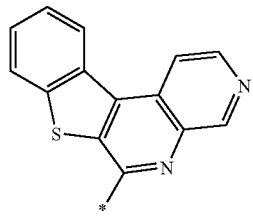

Core 1-4
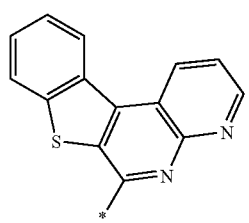

Core 1-5
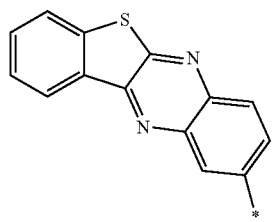

Core 1-6
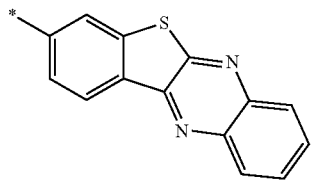

Core 1-7
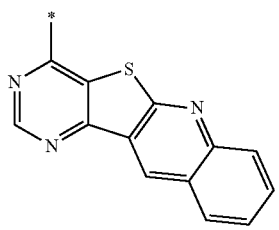

Core 1-8
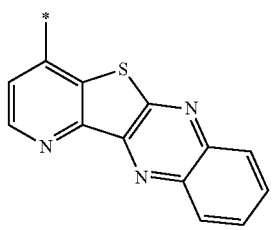

Core 1-9
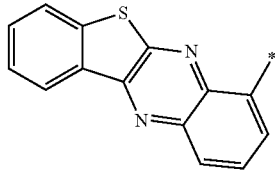

Core 1-10
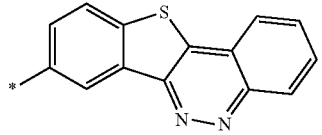

Core 1-11
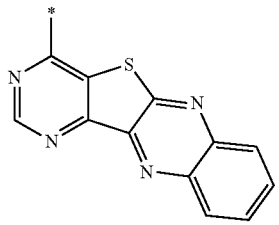

Core 1-12
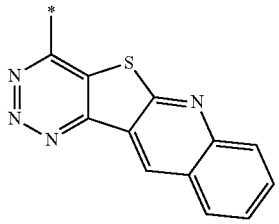

-continued

Core 1-13
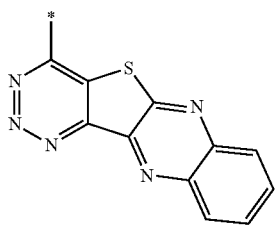

Core 2-1
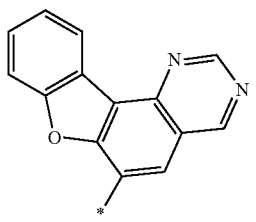

Core 2-2
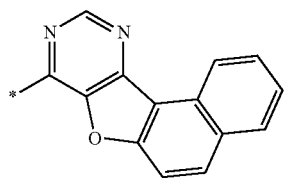

Core 2-3
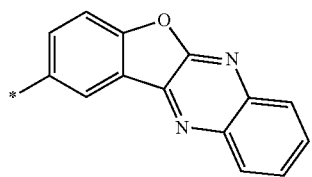

Core 2-4
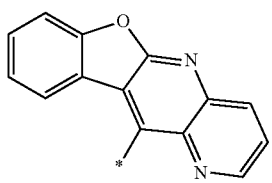

Core 2-5
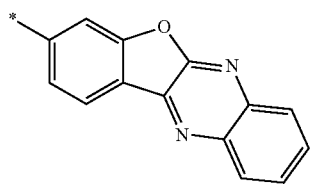

Core 2-6
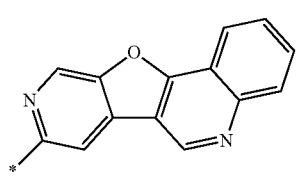

Core 2-7
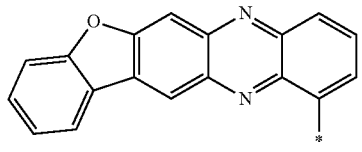

-continued

Core 2-8
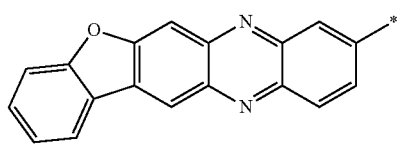

Core 2-9
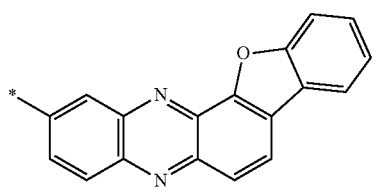

Core 2-10
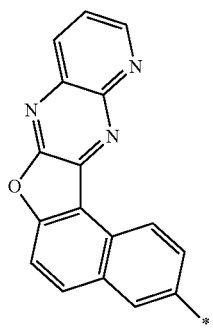

Core 2-11
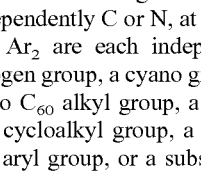

According to a preferred embodiment of the present invention, L of the compound may have the following structure, wherein $L_1$ to $L_3$ may be each independently a direct bond; a substituted or unsubstituted arylene group; a substituted or unsubstituted heteroarylene group; or a substituted or unsubstituted $C_9$-$C_{60}$ fused polycyclic group.

$$-L_1-L_2-L_3-$$

According to a preferred embodiment of the present invention, $A_2$ of the compound may be any one selected from the following structures, wherein $X_1$ to $X_3$ are each independently C or N, at least one of $X_1$ to $X_3$ is N, and $Ar_1$ and $Ar_2$ are each independently hydrogen, deuterium, a halogen group, a cyano group, a substituted or unsubstituted $C_1$ to $C_{60}$ alkyl group, a substituted or unsubstituted $C_3$ to $C_{10}$ cycloalkyl group, a substituted or unsubstituted $C_6$ to $C_{60}$ aryl group, or a substituted or unsubstituted $C_1$ to $C_{60}$ heteroaryl group.

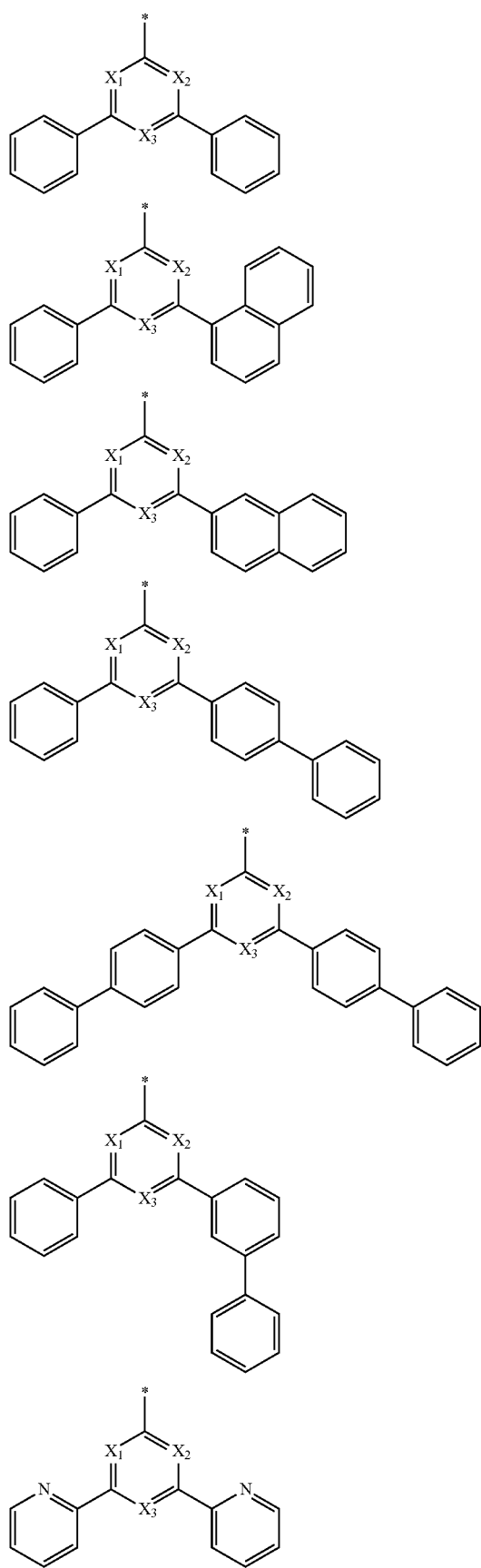
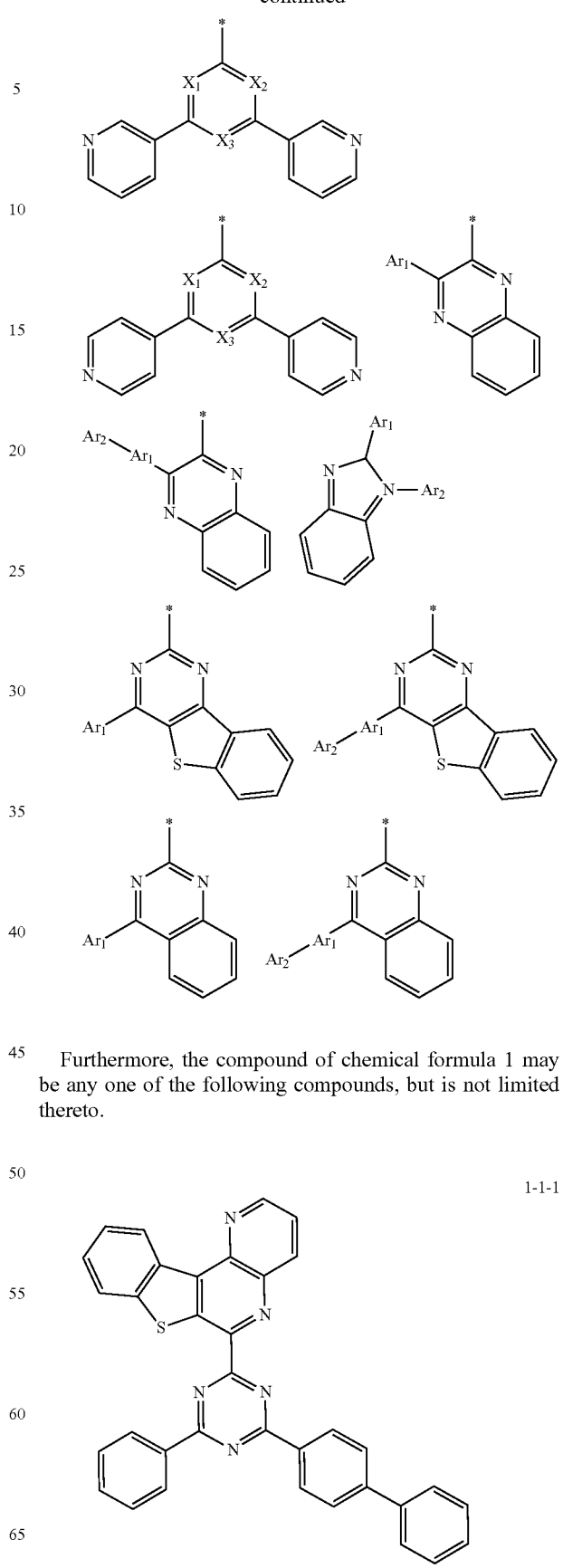
Furthermore, the compound of chemical formula 1 may be any one of the following compounds, but is not limited thereto.

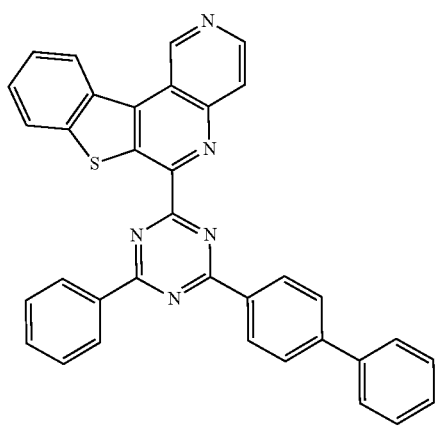
1-1-2
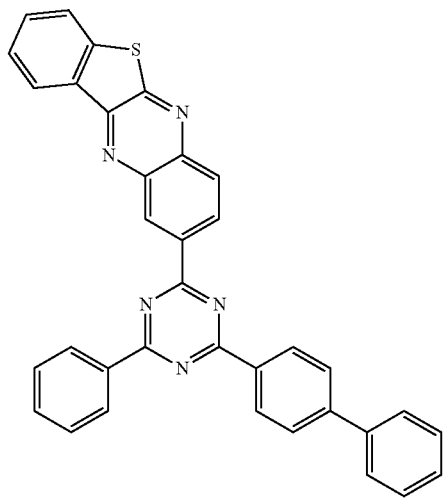
1-1-5
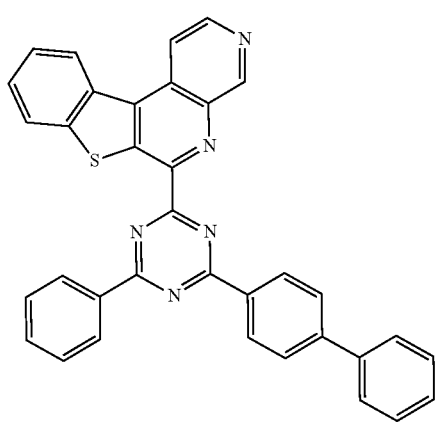
1-1-3
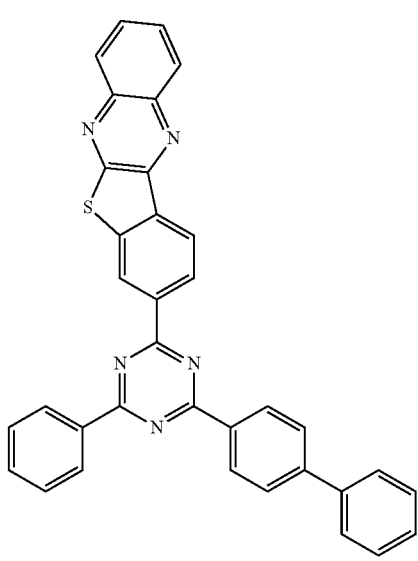
1-1-6
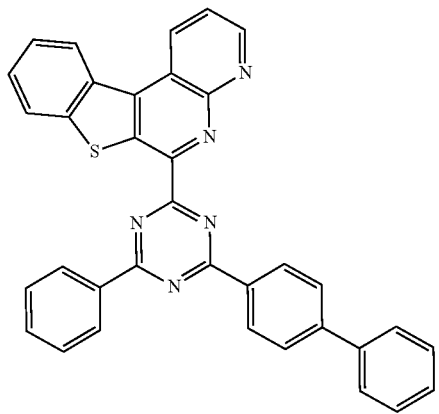
1-1-4
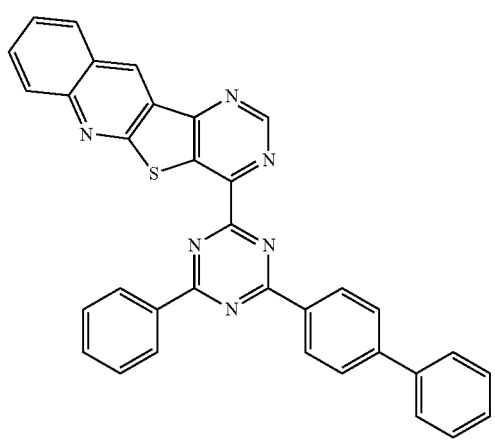
1-1-7

-continued
1-1-8
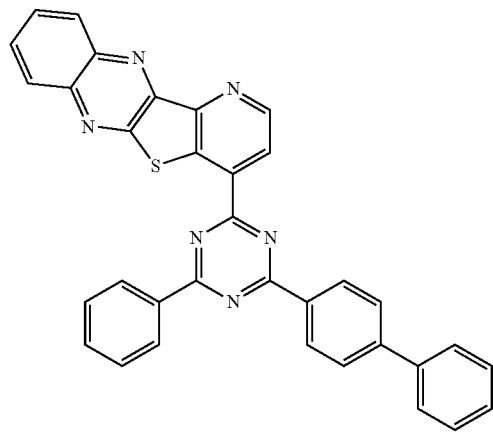
1-1-9
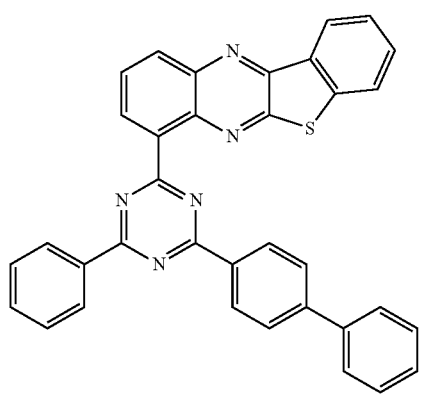
1-1-10
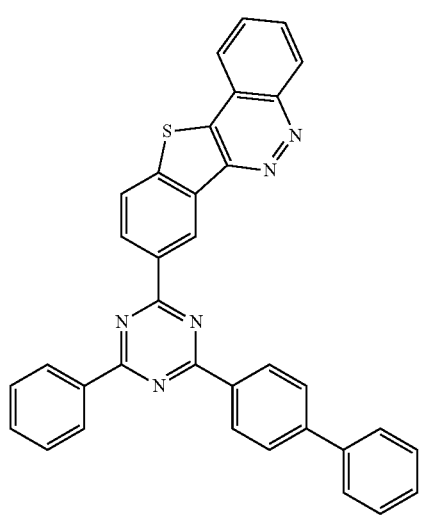
1-1-11
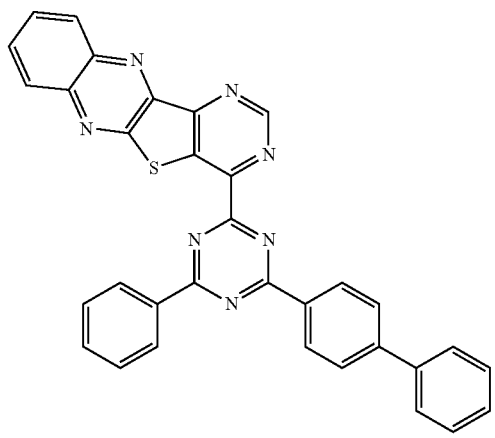
1-1-12
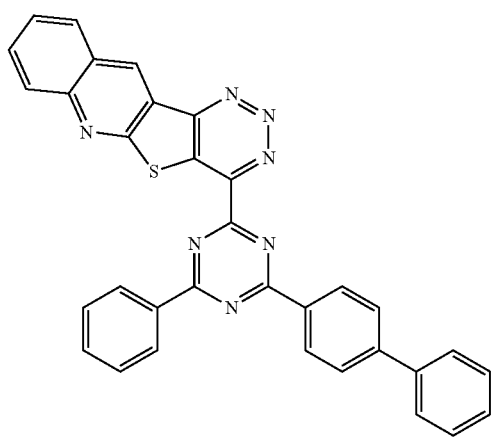
1-1-13
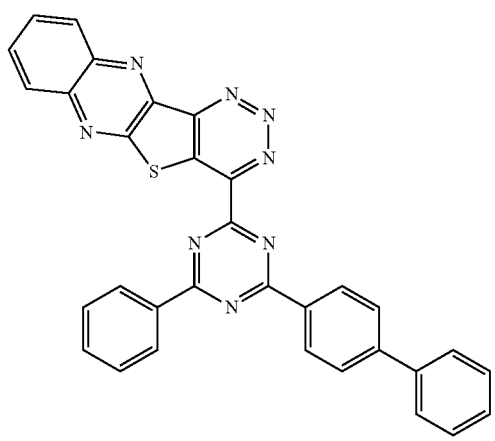

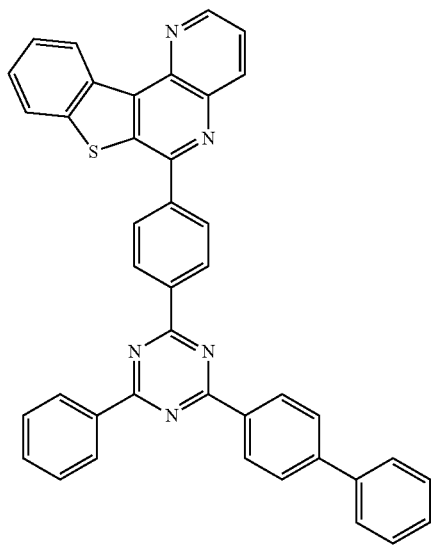
1-2-1
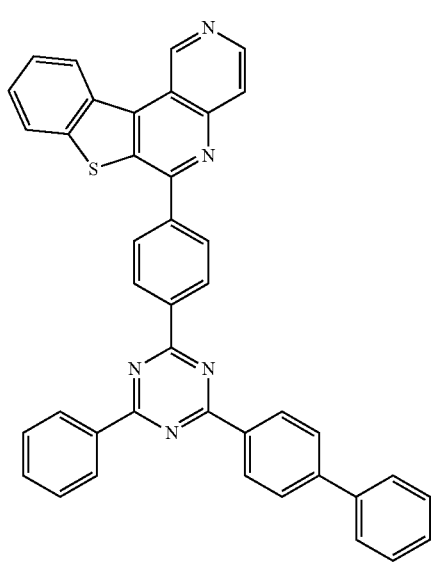
1-2-2
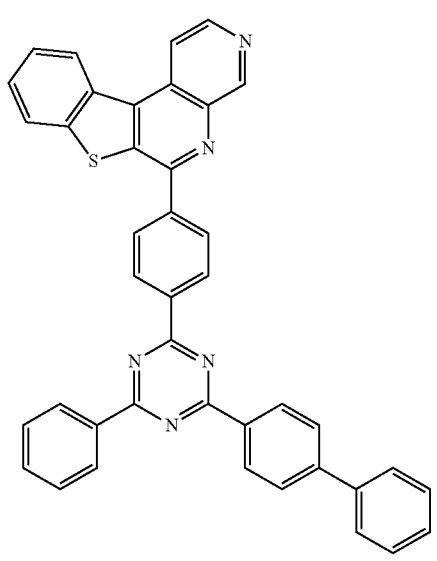
1-2-3
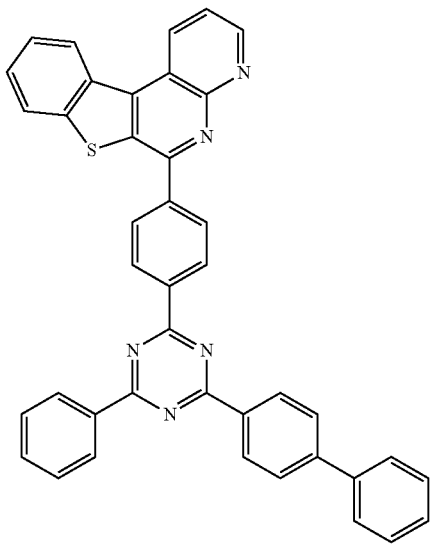
1-2-4
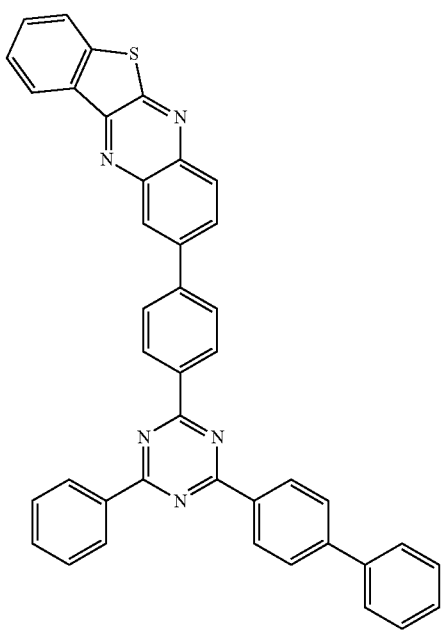
1-2-5

1-2-6
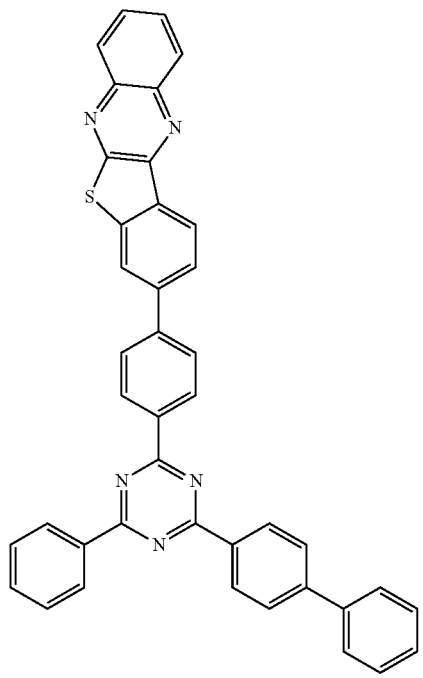
1-2-7
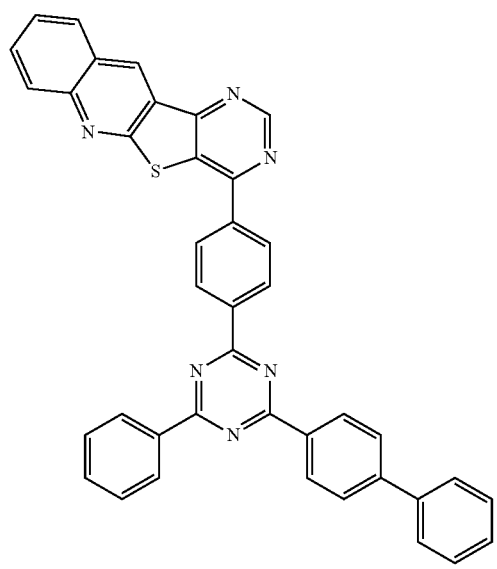
1-2-8
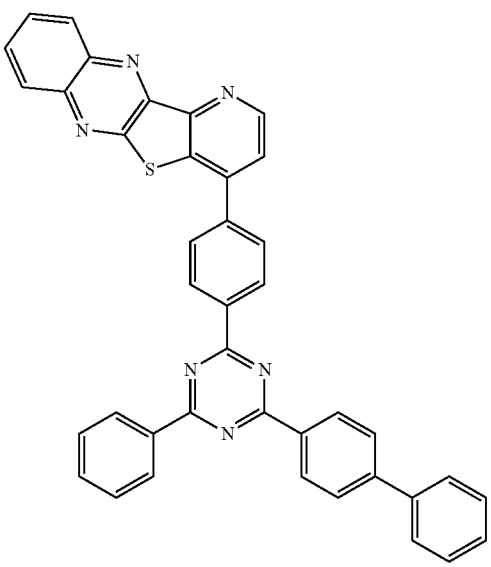
1-2-9
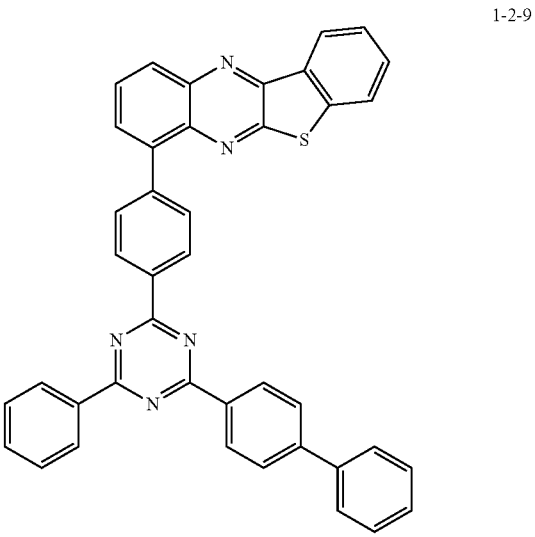

1-2-10
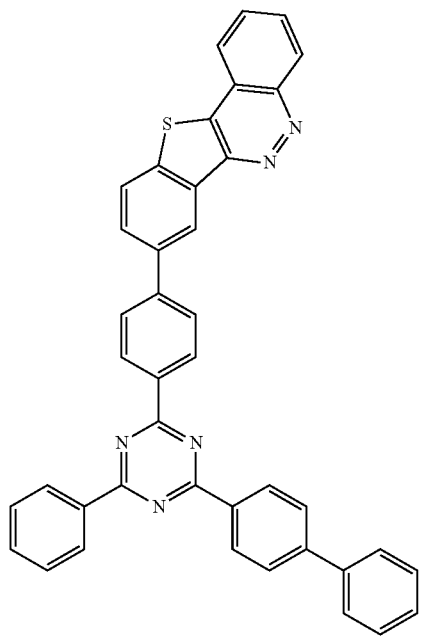
1-2-11
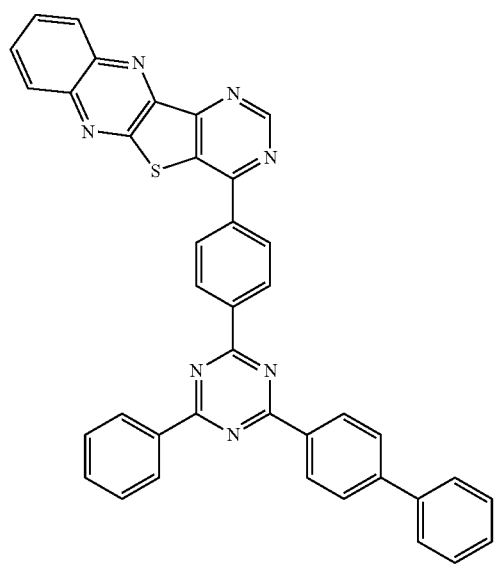
1-2-12
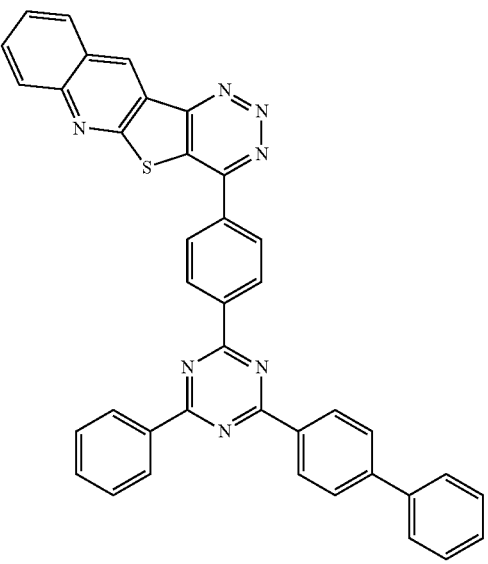
1-2-13
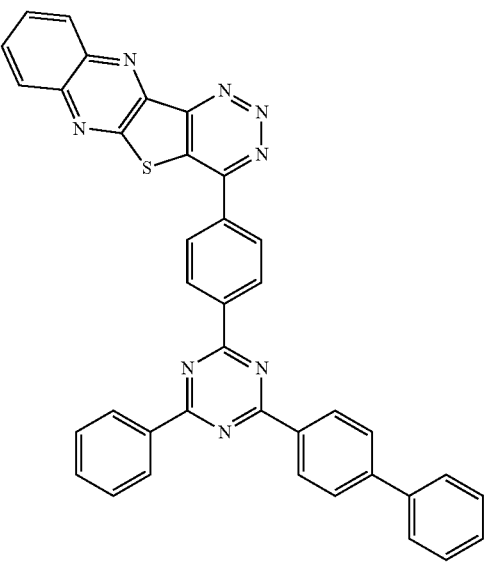

1-2-14
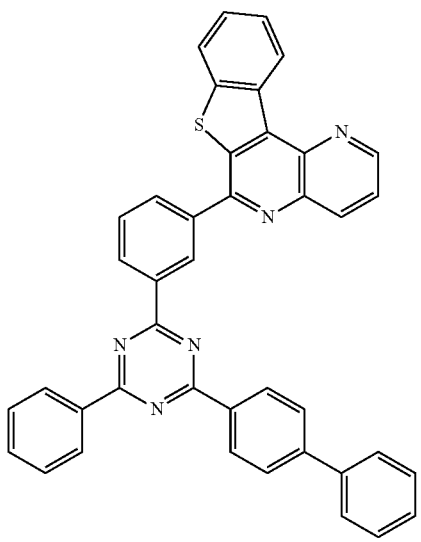
1-2-17
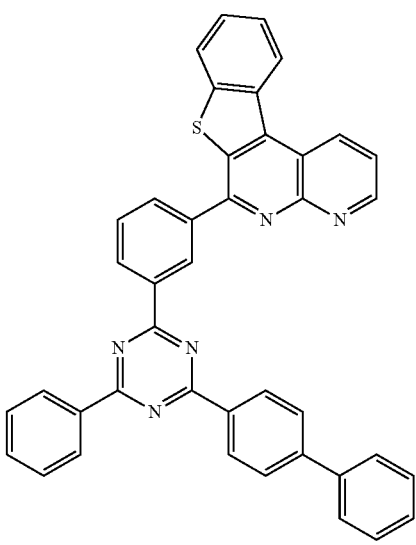
1-2-15
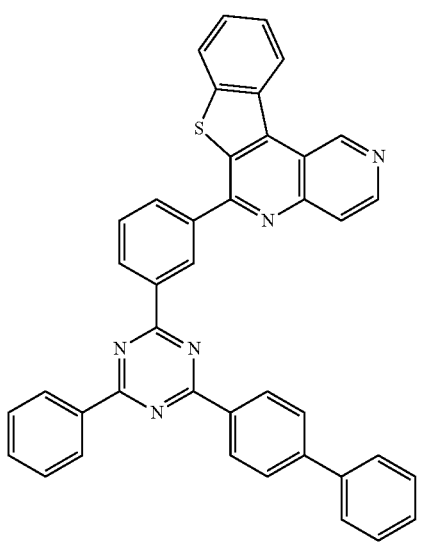
1-2-16
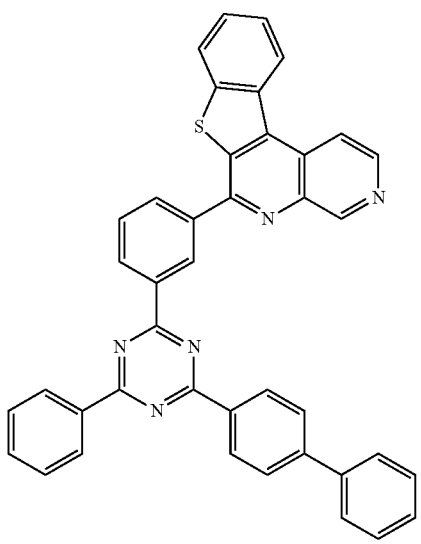
1-2-18
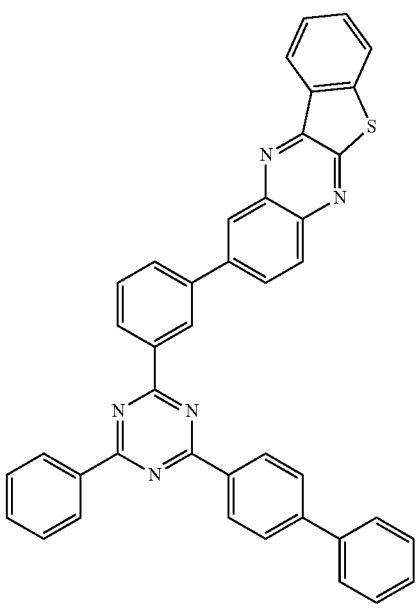

1-2-19
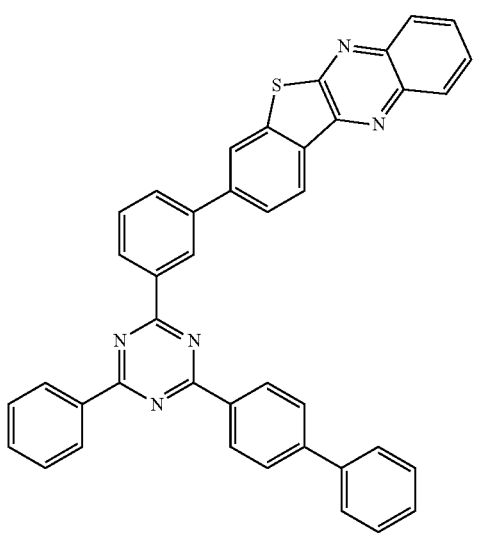
1-2-20
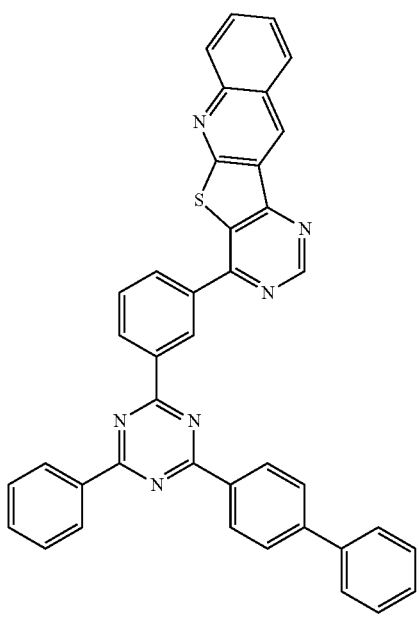
1-2-21
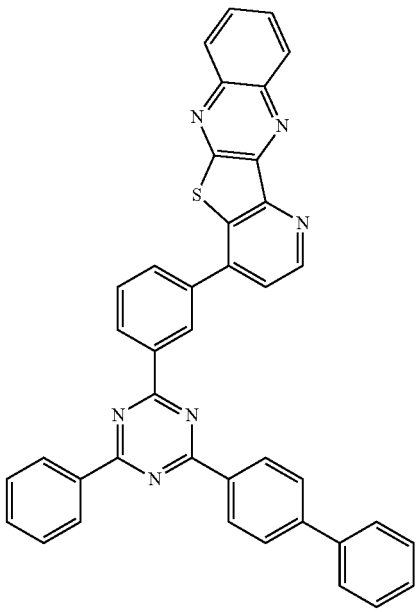
1-2-22
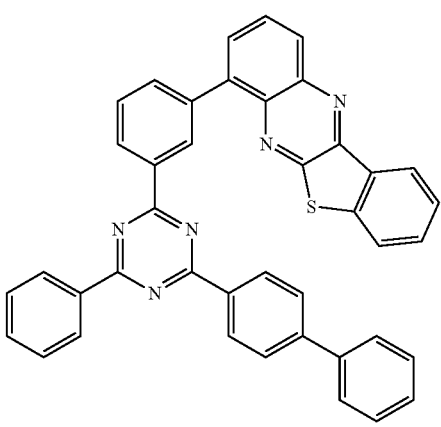
1-2-23
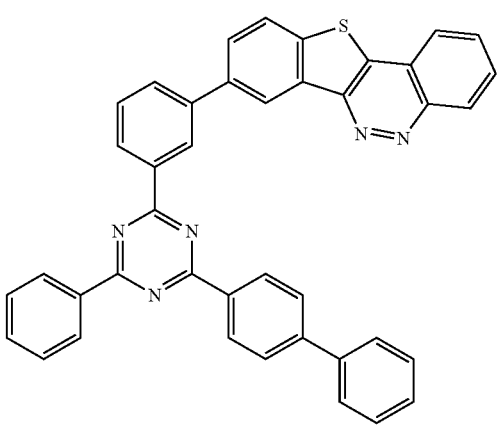

1-2-24
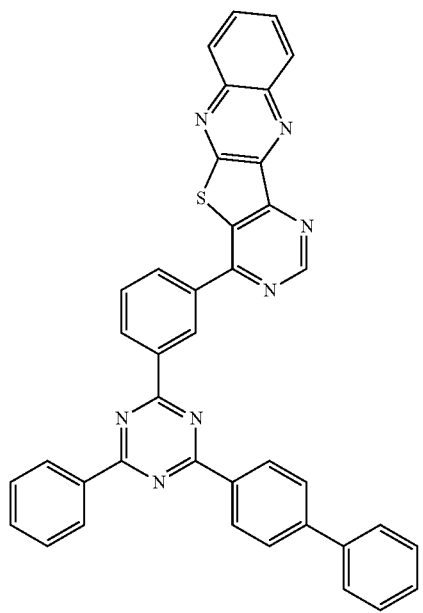
1-2-26
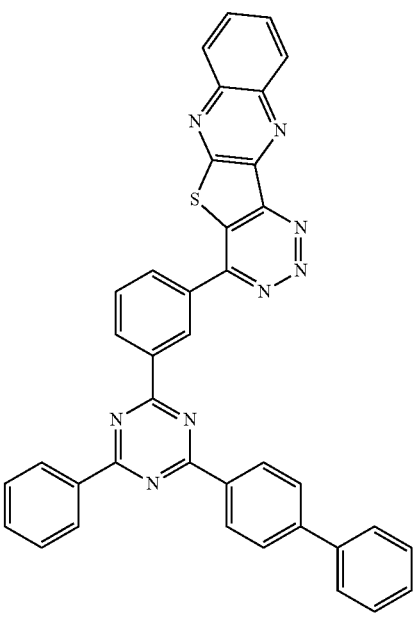
1-2-25
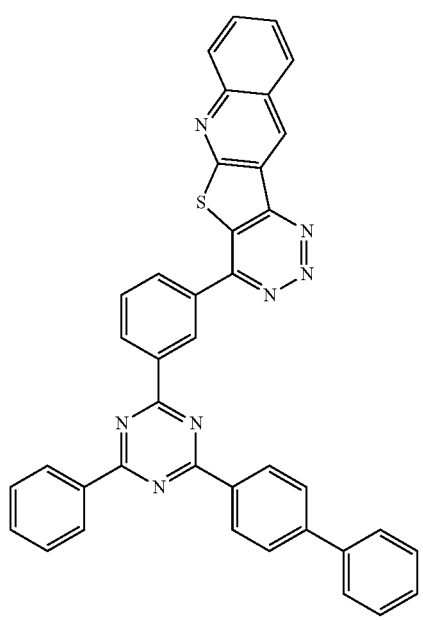
1-3-1
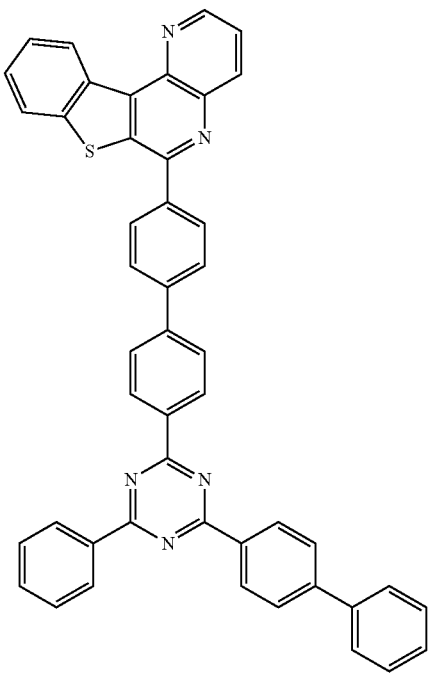

33
-continued
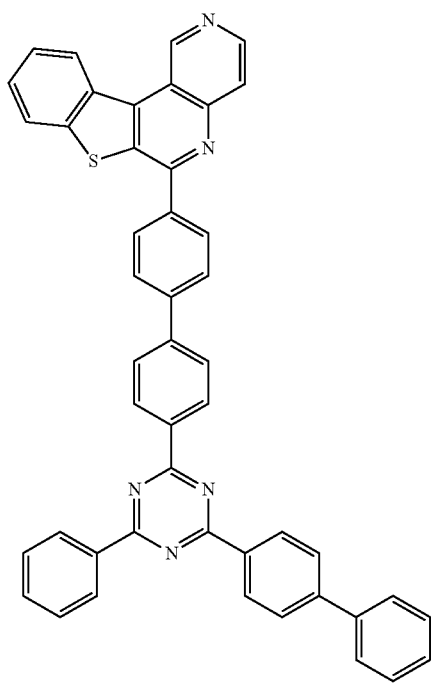
1-3-2
34
-continued
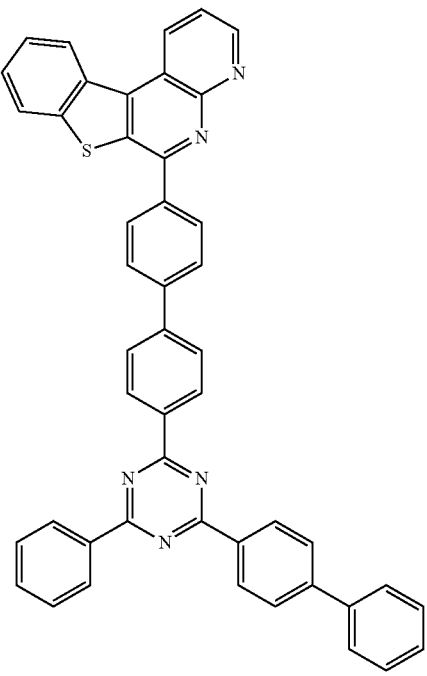
1-3-4
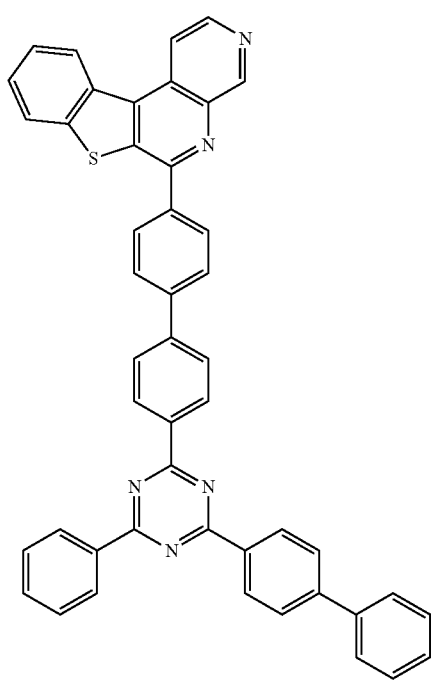
1-3-3
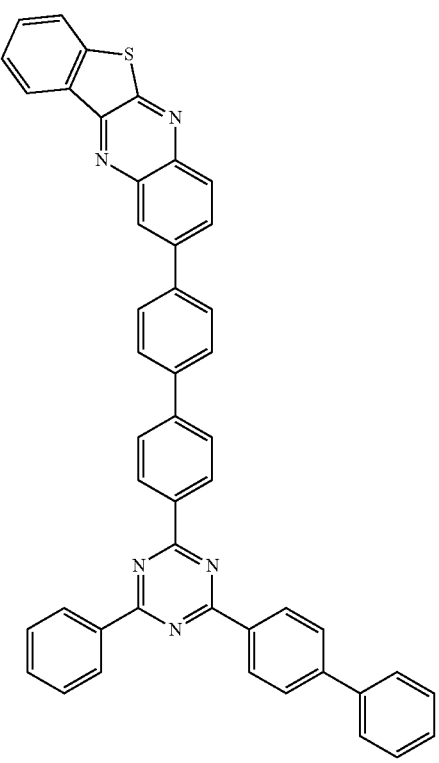
1-3-5

1-3-6
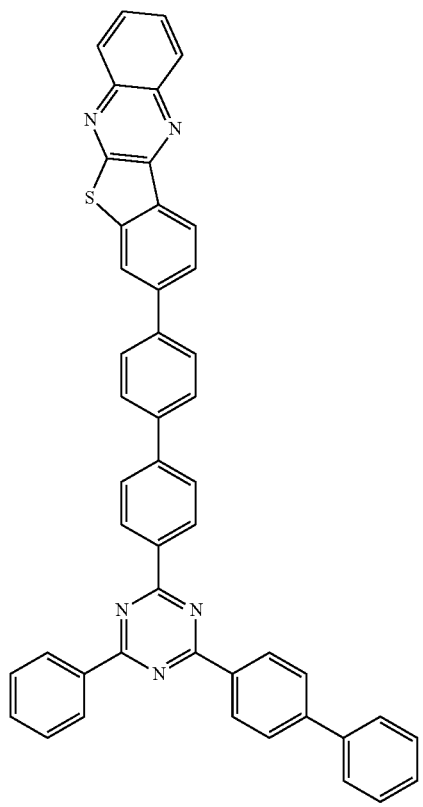
1-3-7
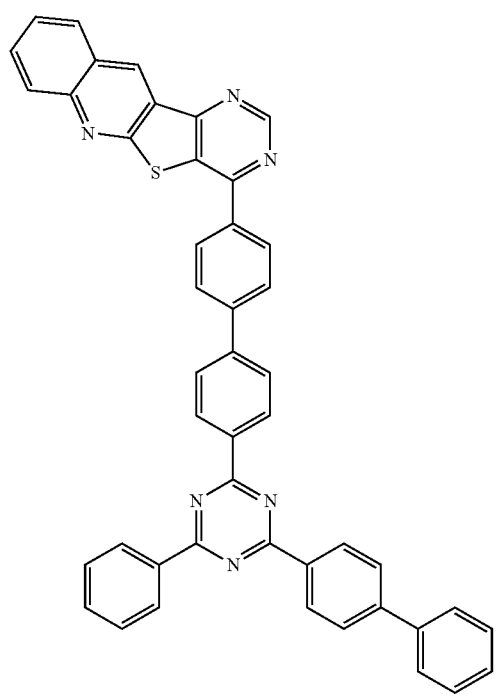
1-3-8
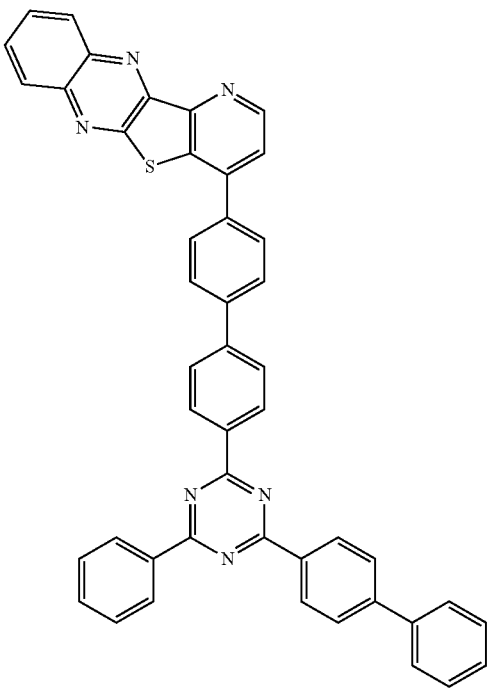
1-3-9
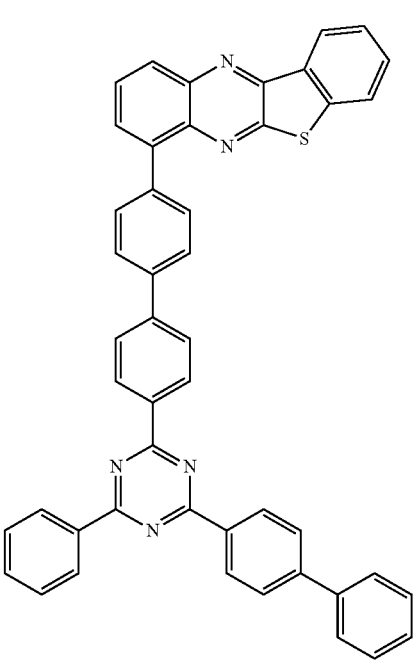

37
-continued
1-3-10
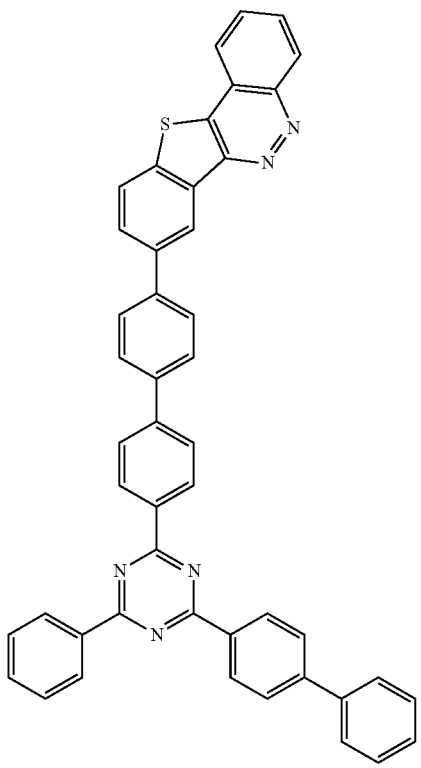
1-3-11
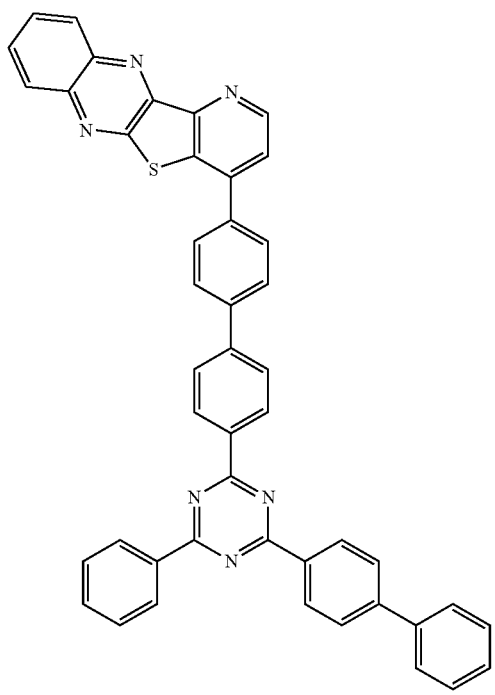
38
-continued
1-3-12
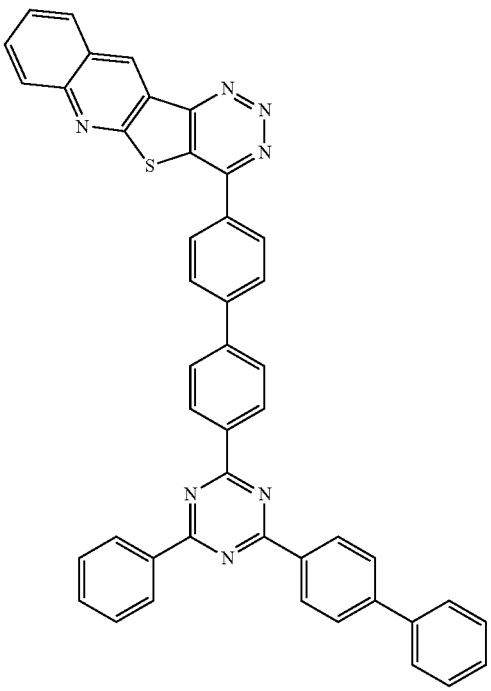
1-3-13
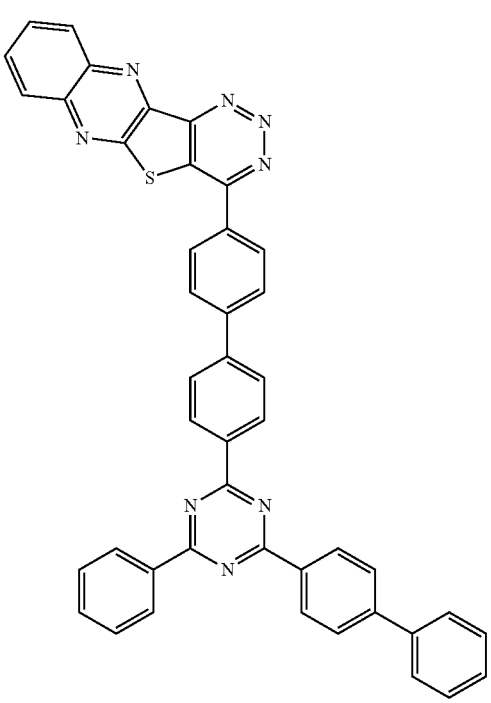

1-3-14
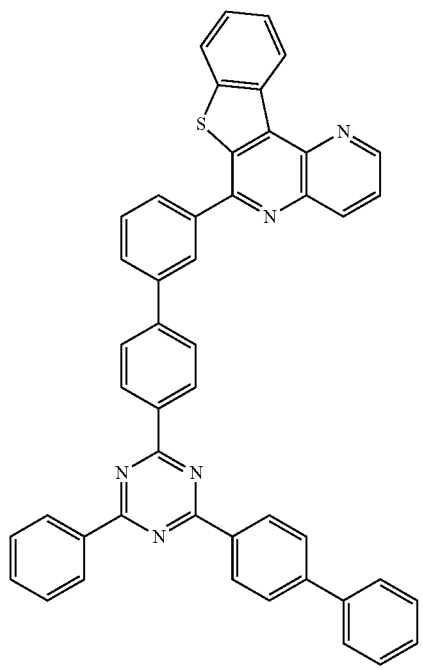
1-3-15
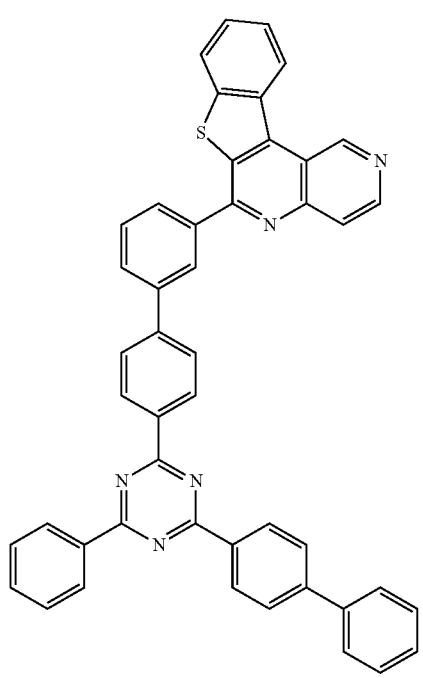
1-3-16
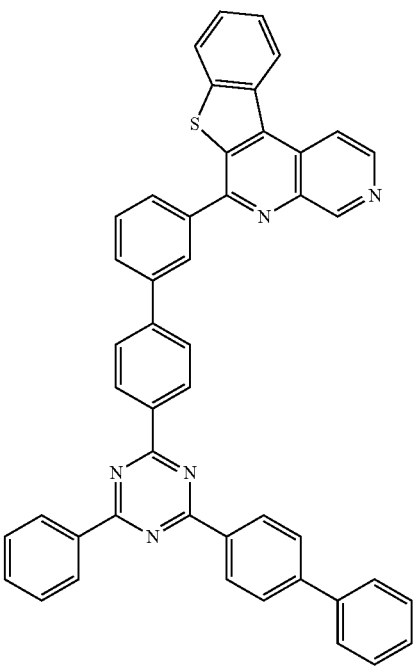
1-3-17
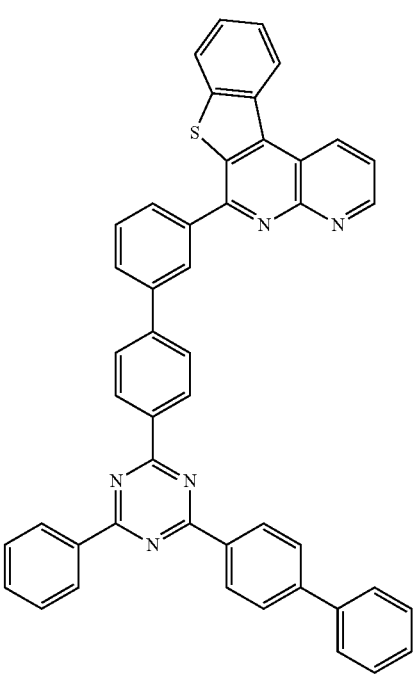

1-3-18
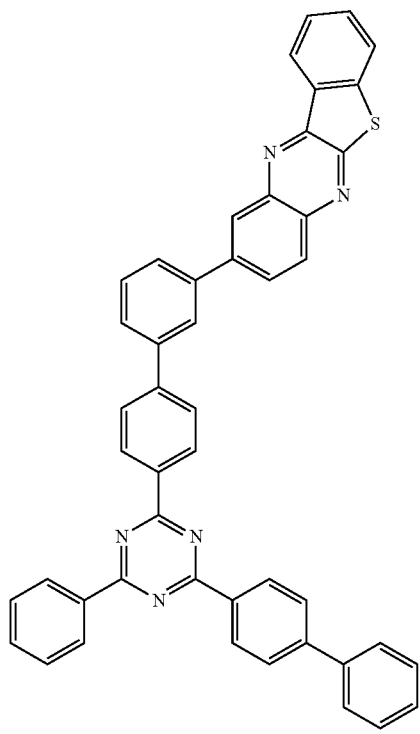
1-3-20
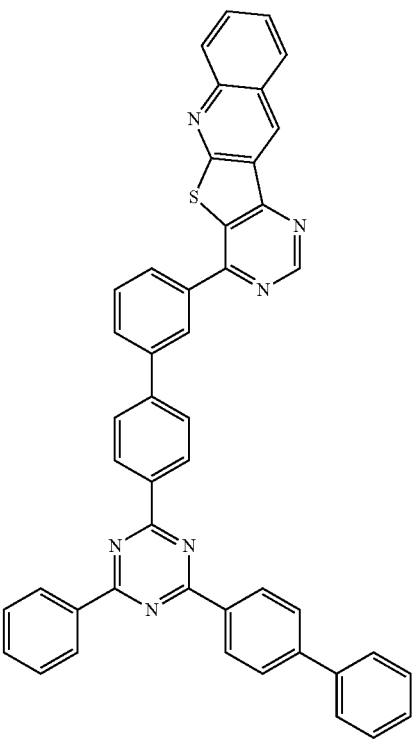
1-3-19
1-3-21
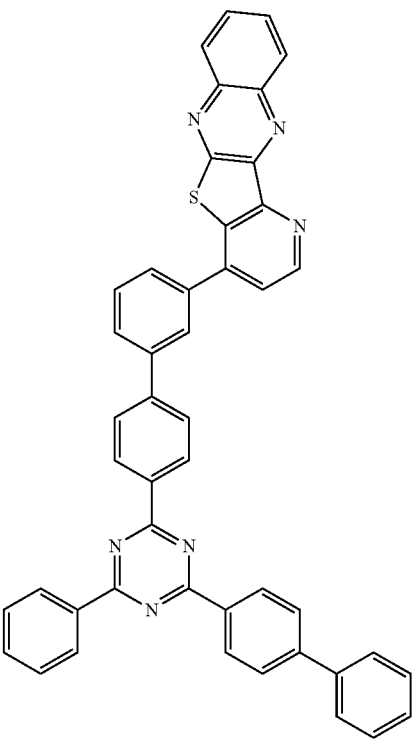

43
-continued
1-3-22
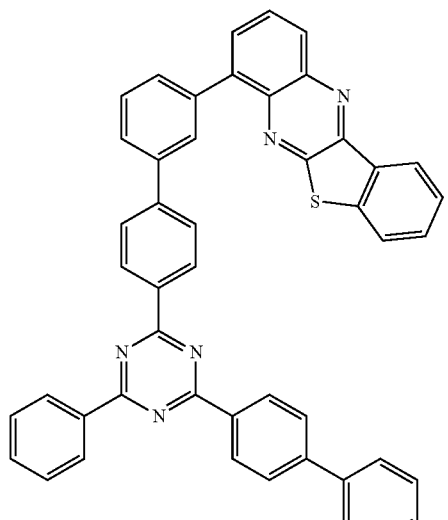
1-3-23
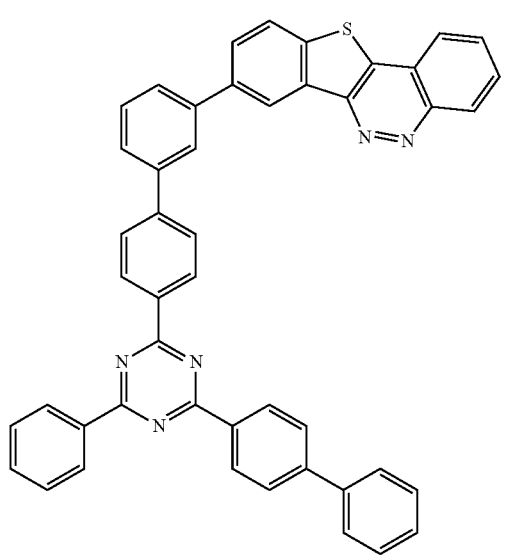
44
-continued
1-3-24
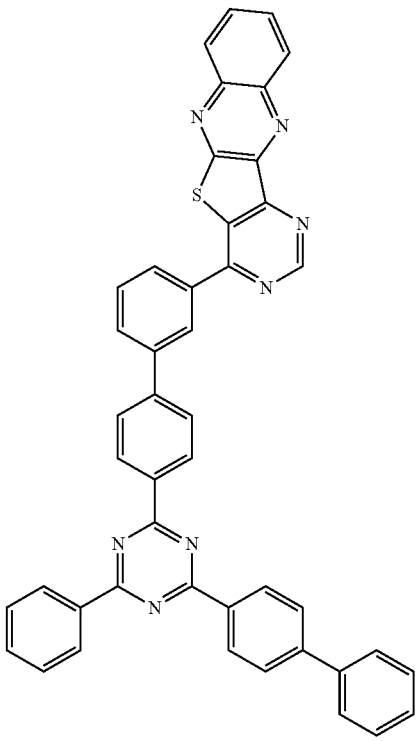
1-3-25

1-3-26
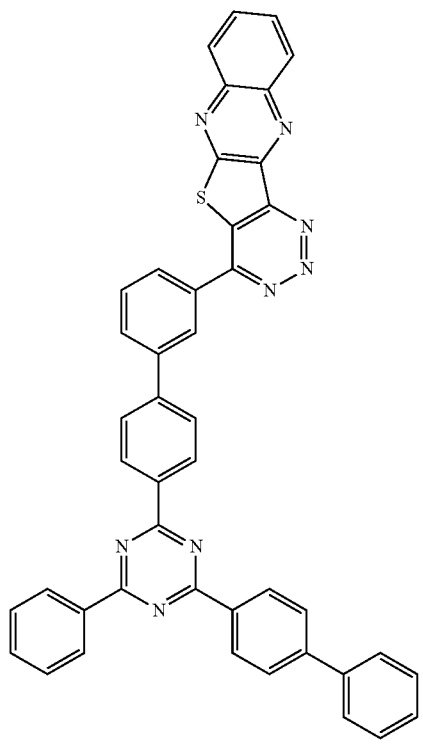
1-3-27
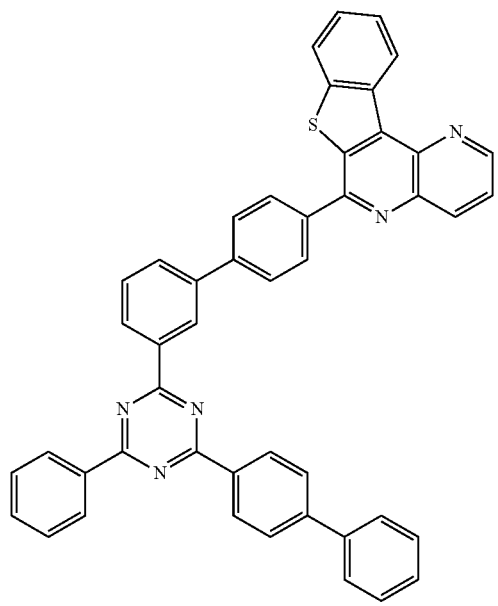
1-3-28
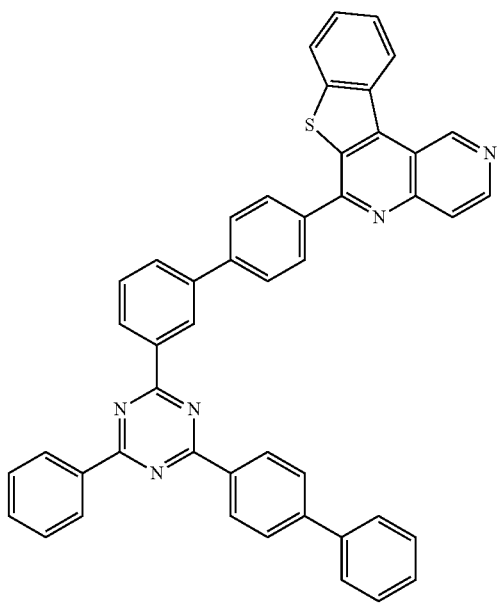
1-3-29
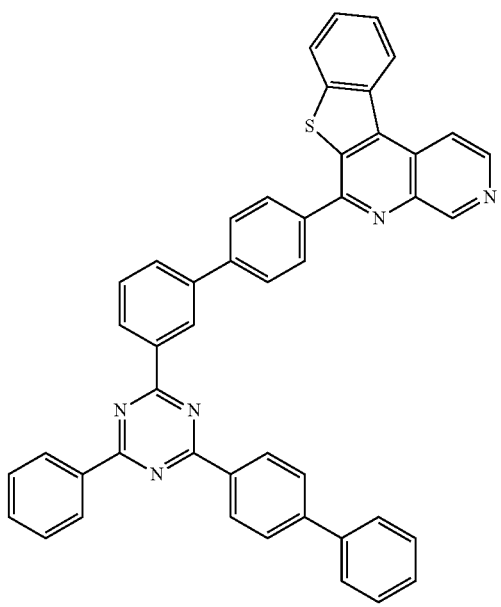

1-3-30
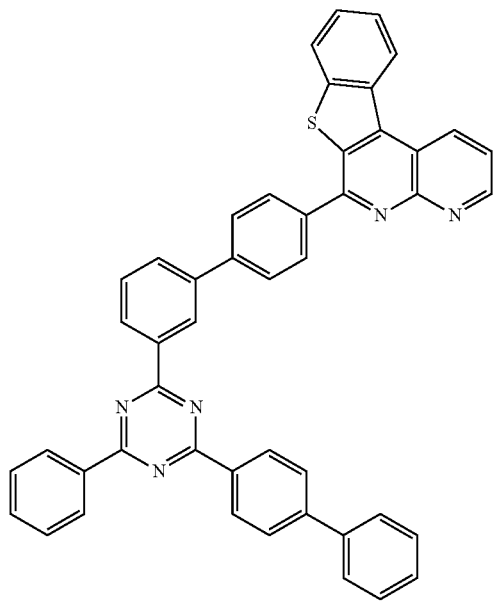
1-3-32
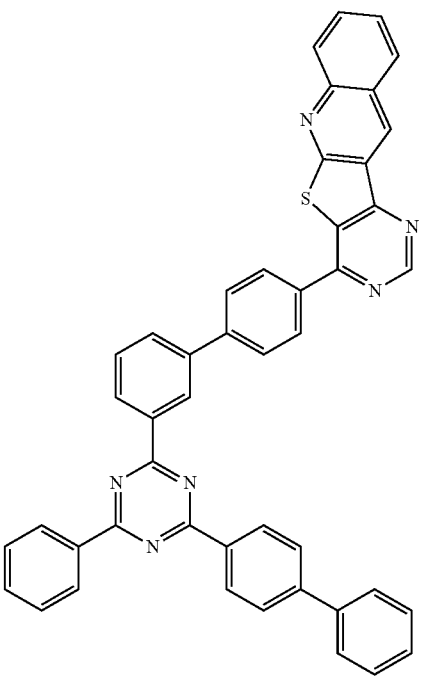
1-3-31
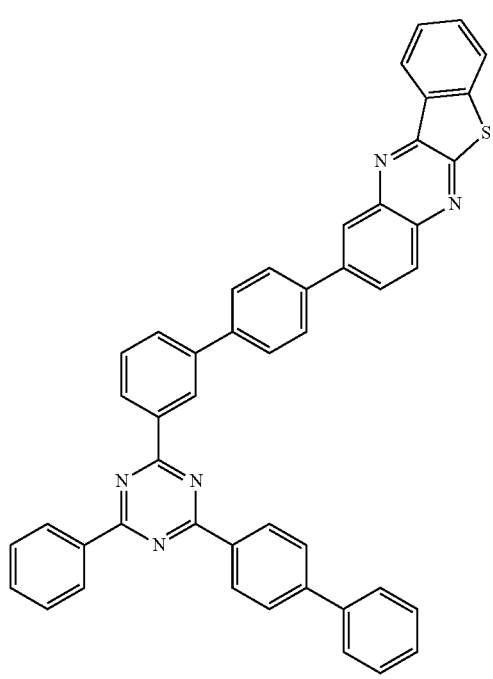
1-3-33
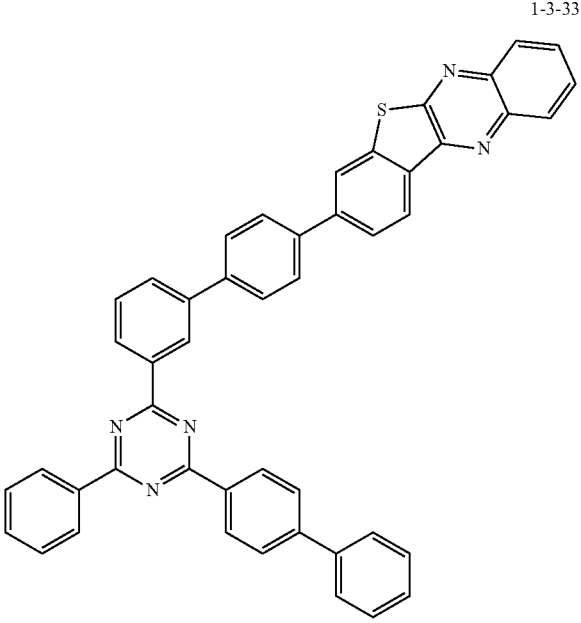

-continued
1-3-34
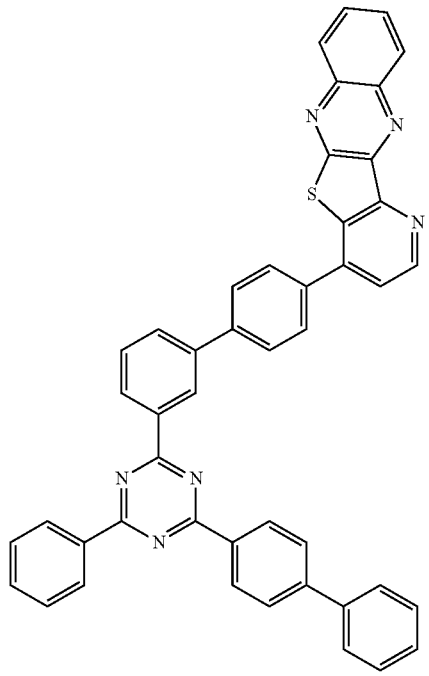
1-3-35
1-3-36
1-3-37
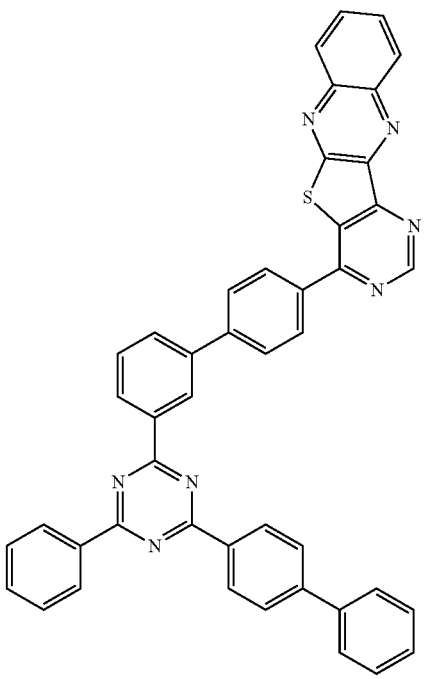
1-3-38
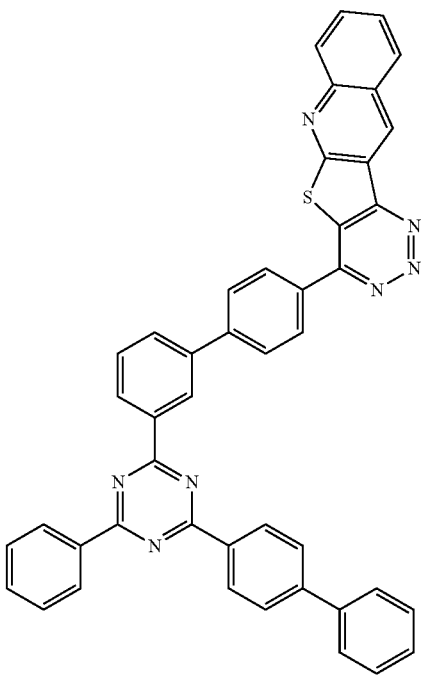

1-3-39
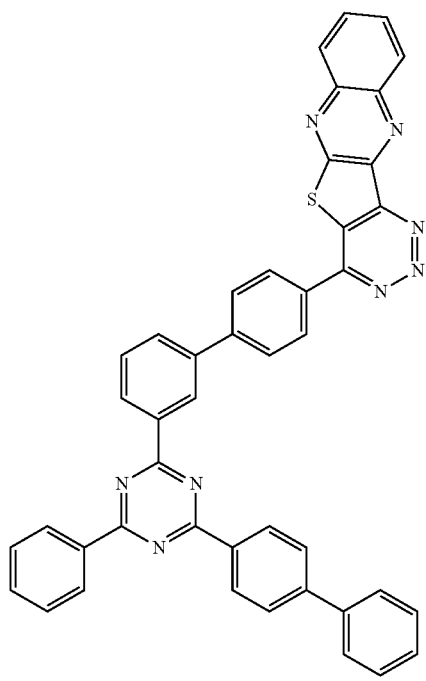
1-3-40
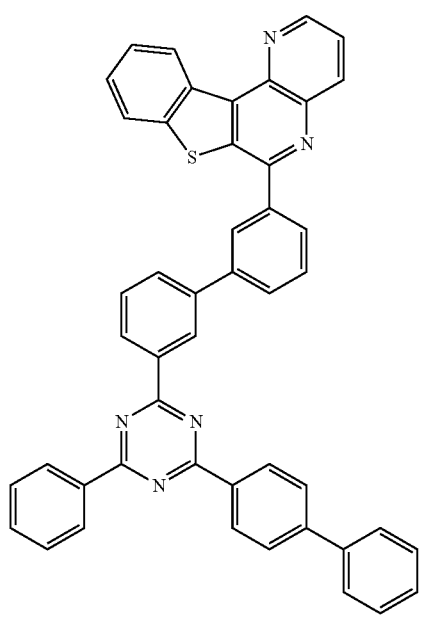
1-3-41
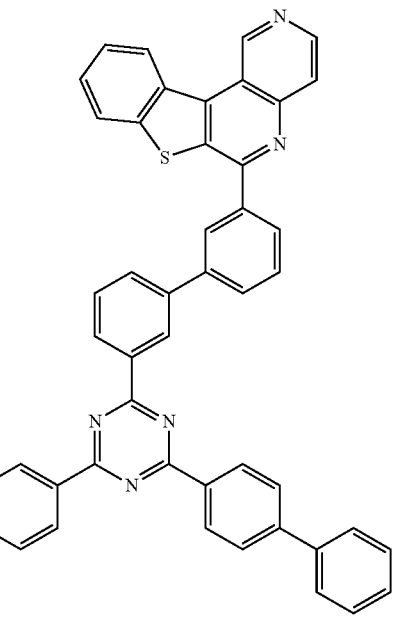
1-3-42
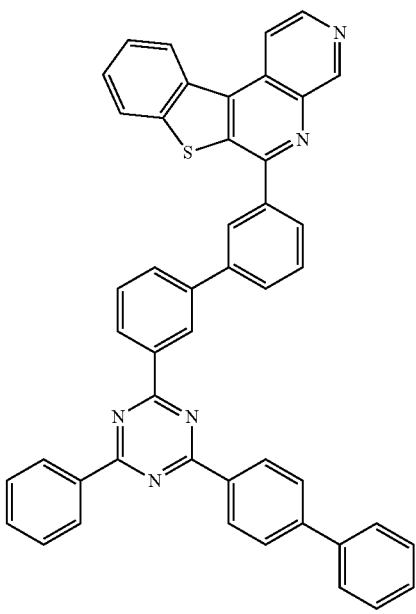

1-3-43
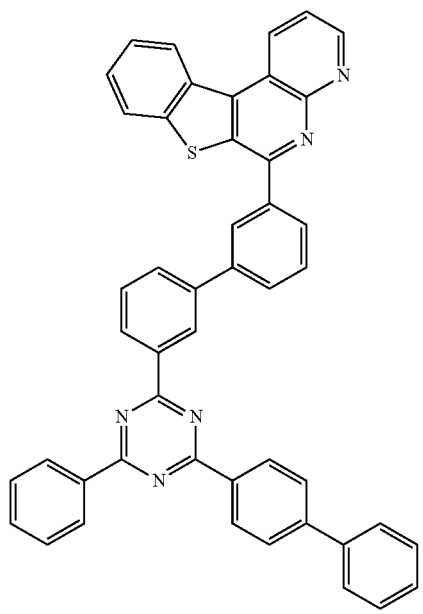
1-3-44
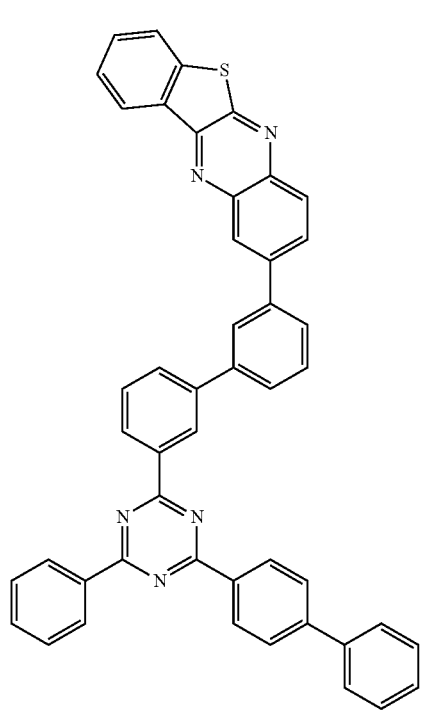
1-3-45
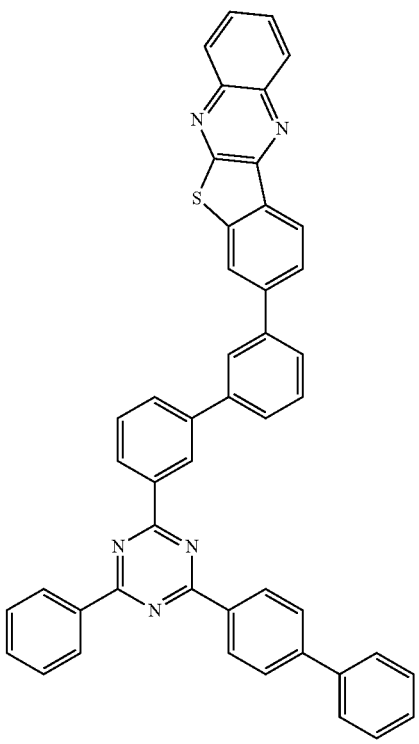
1-3-46
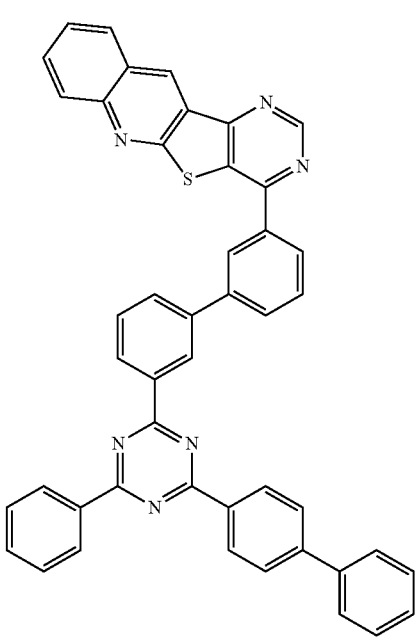

-continued
1-3-47
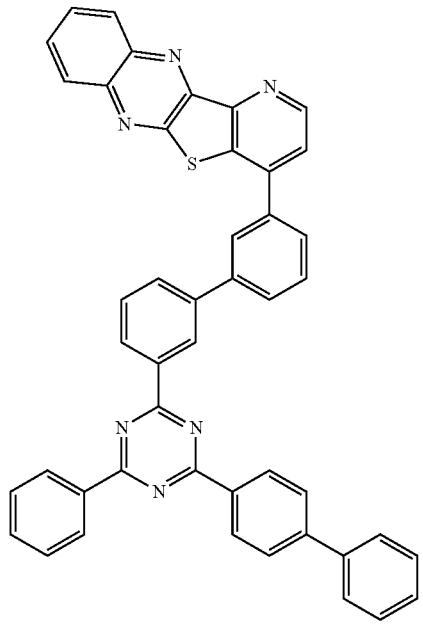
1-3-49
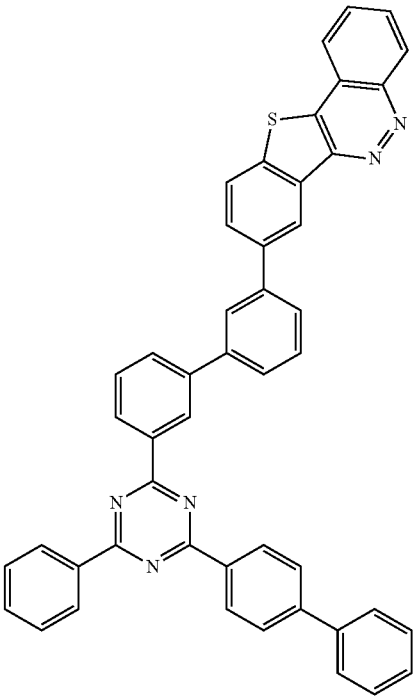
1-3-48
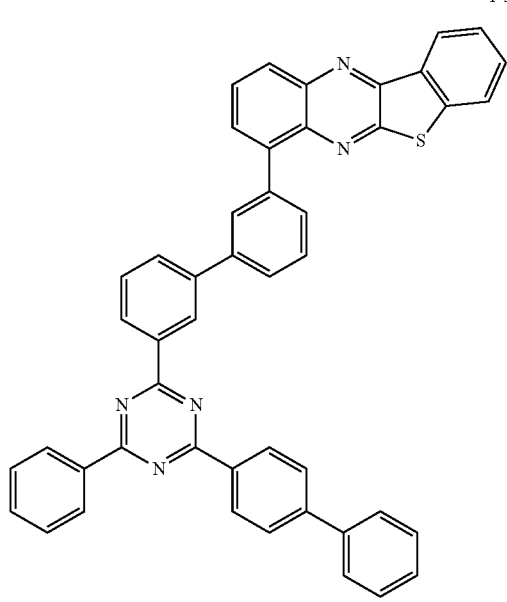
1-3-50
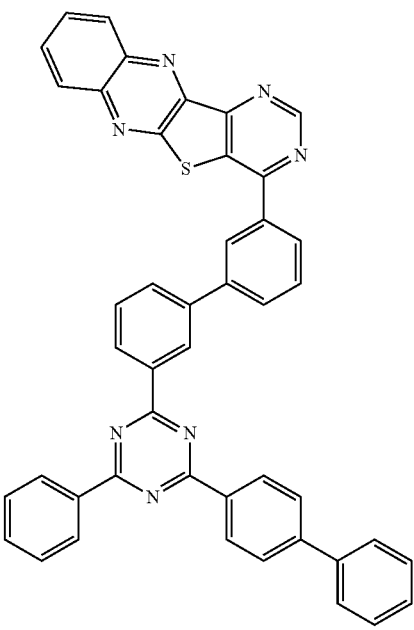

57
-continued
1-3-51
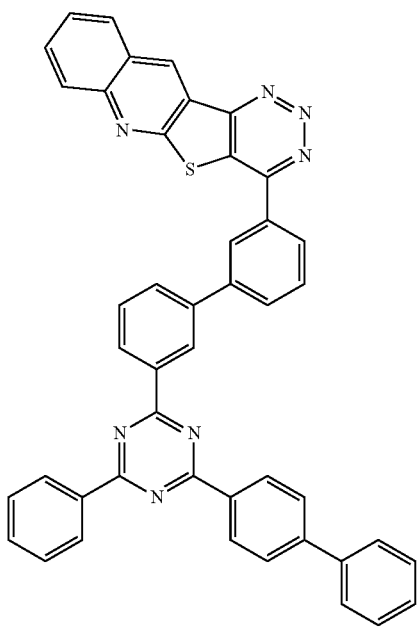
1-3-52
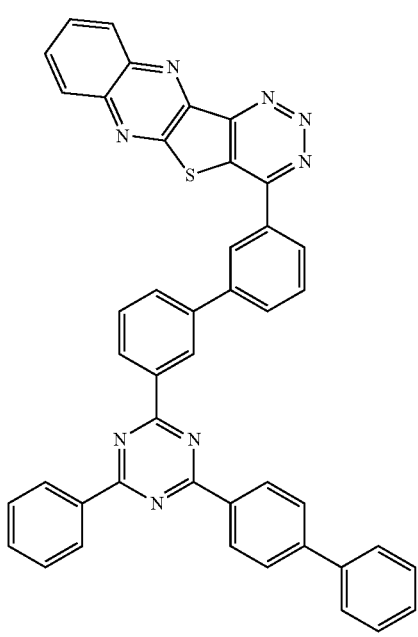
58
-continued
1-4-1
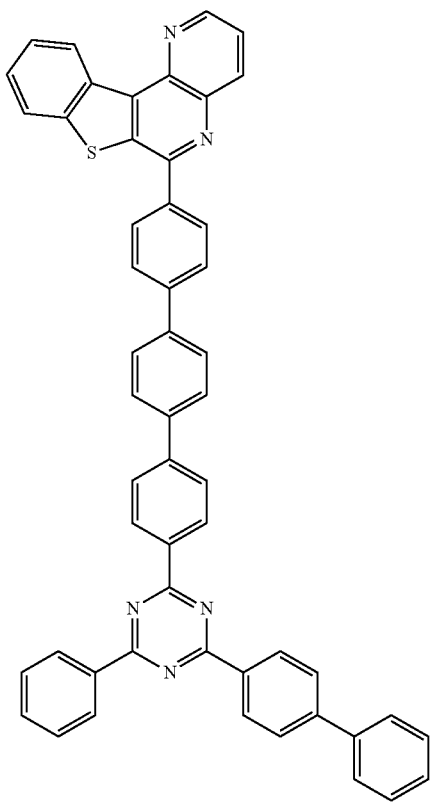
1-4-2
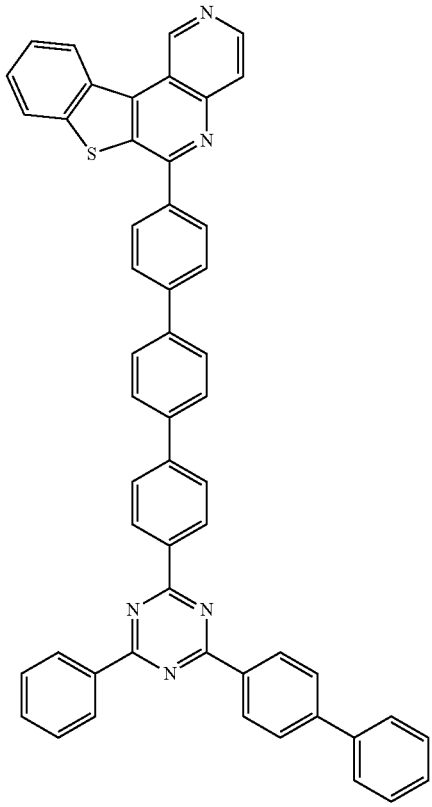

1-4-3
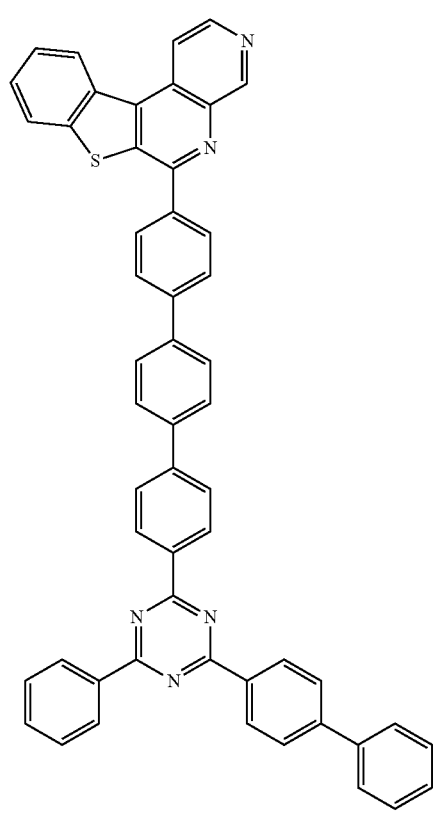
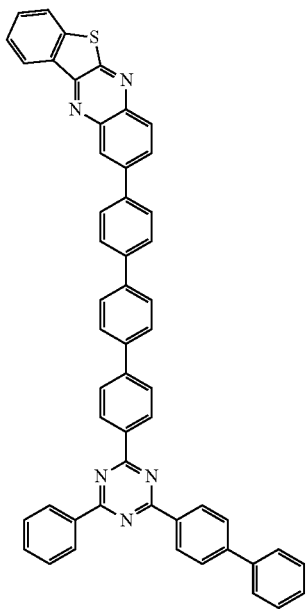
1-4-5
1-4-4
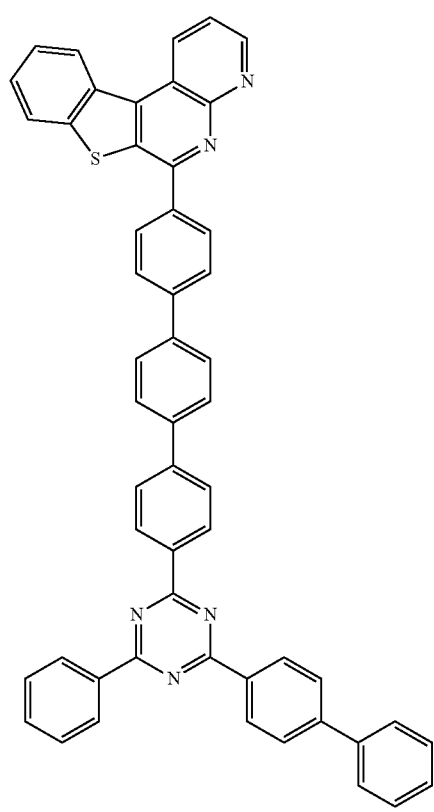
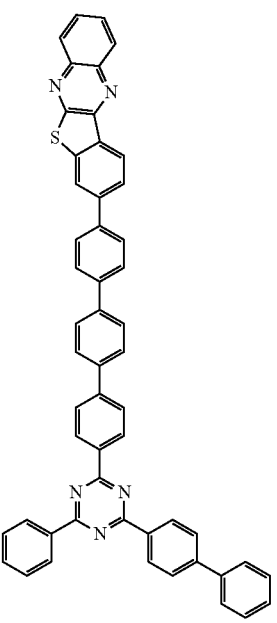
1-4-6

1-4-7
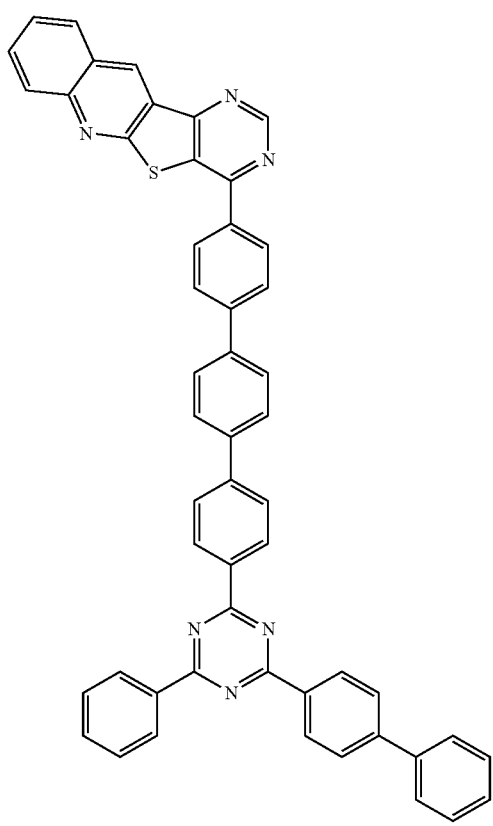
1-4-8
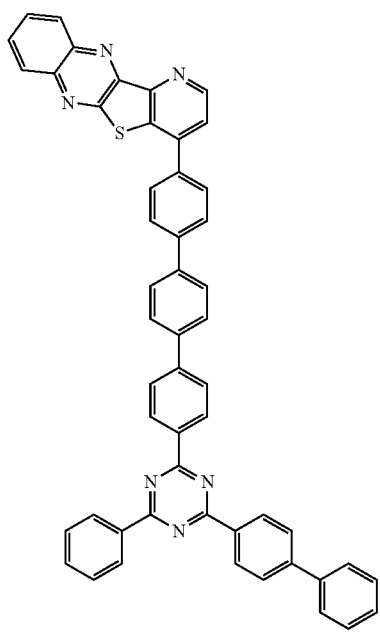
1-4-9
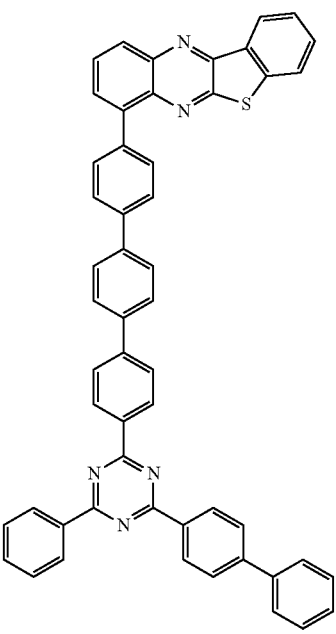
1-4-10
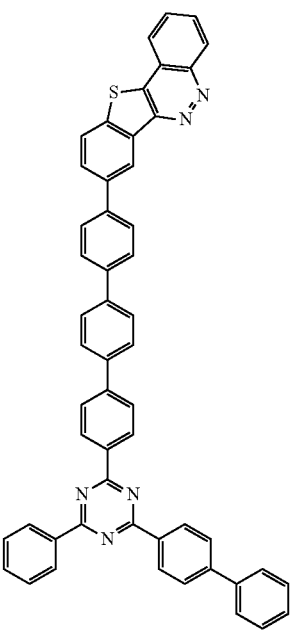

63
-continued
1-4-11
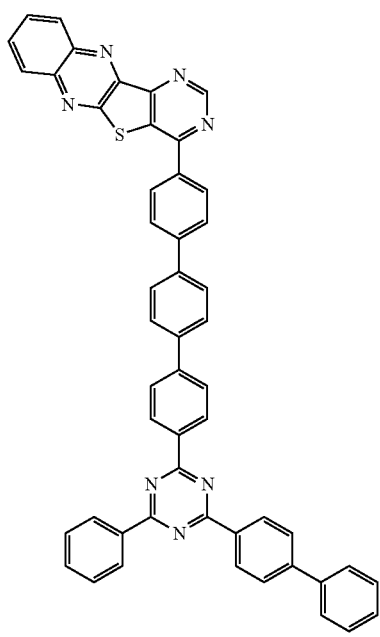
1-4-12
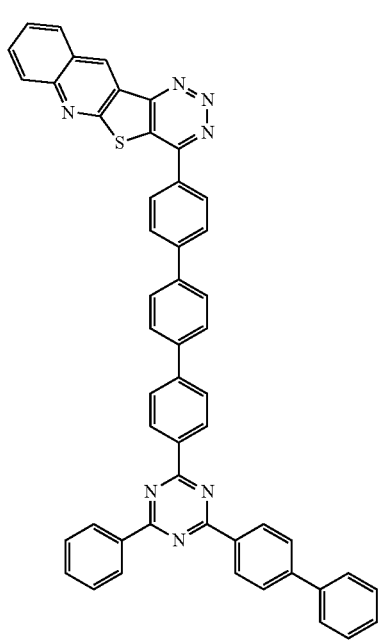
64
-continued
1-4-13
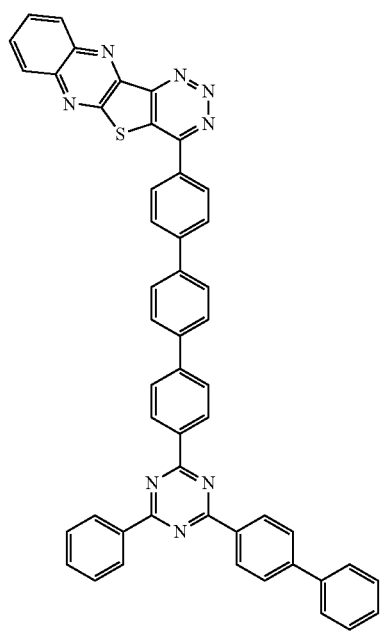
1-4-14
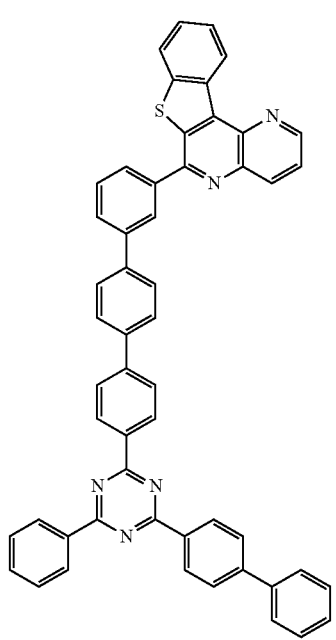

-continued
1-4-15
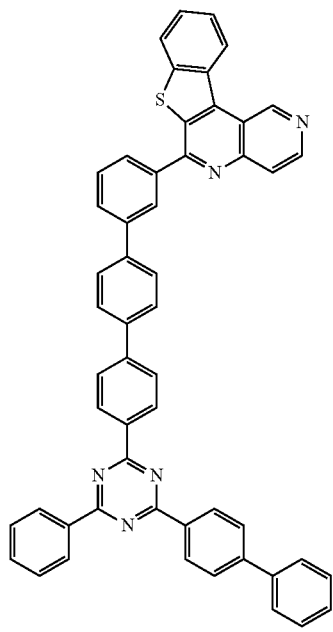
1-4-17
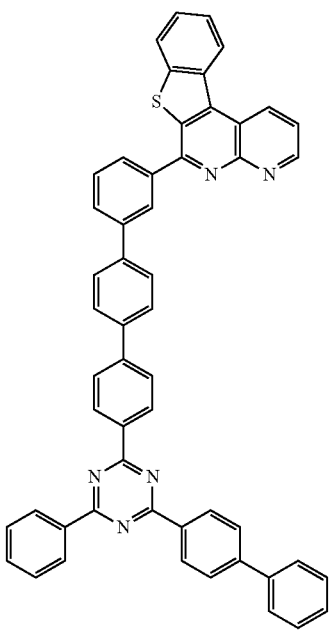
1-4-16
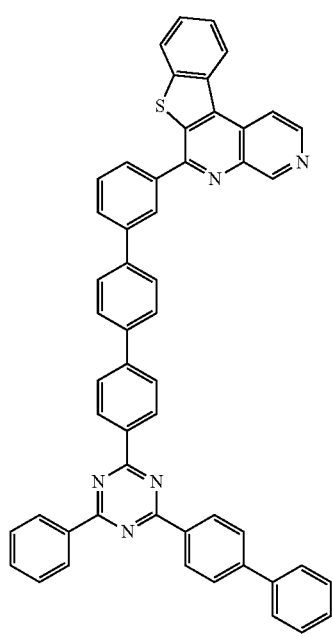
1-4-18
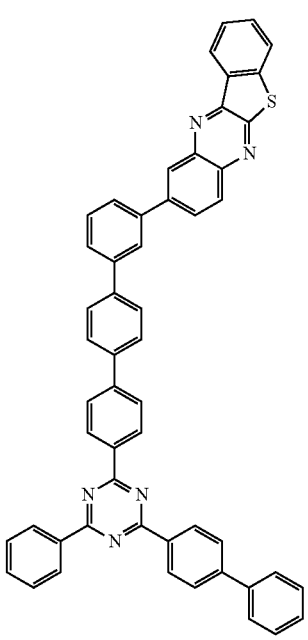

1-4-19
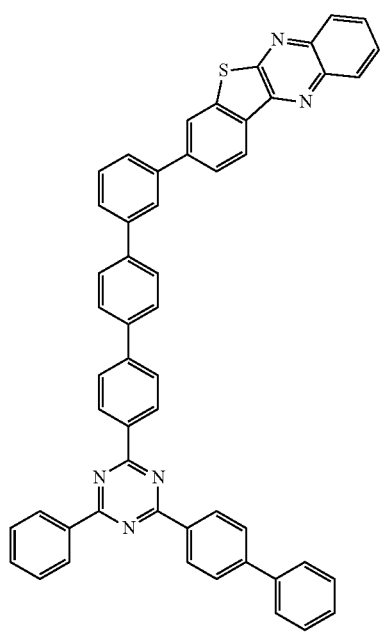
1-4-21
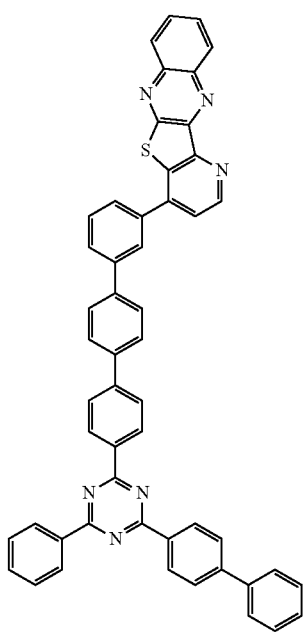
1-4-20
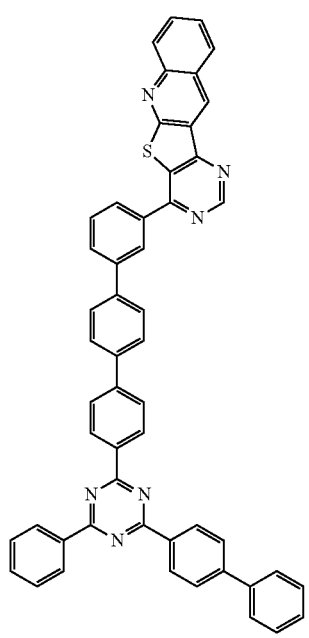
1-4-22
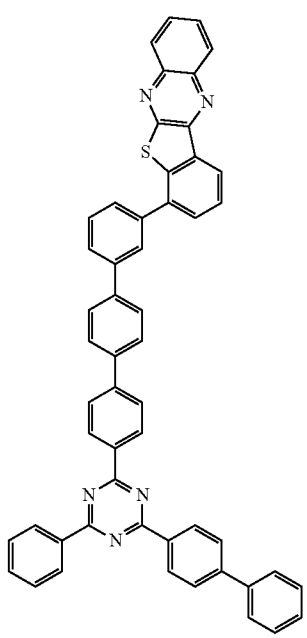

1-4-23
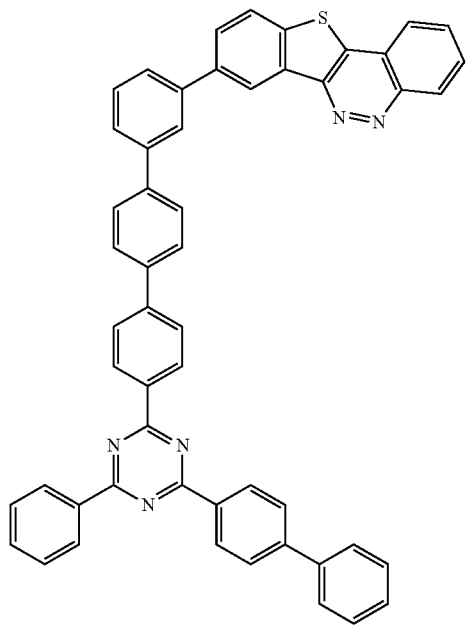
1-4-25
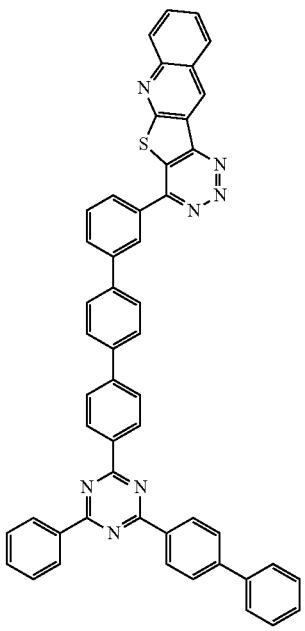
1-4-24
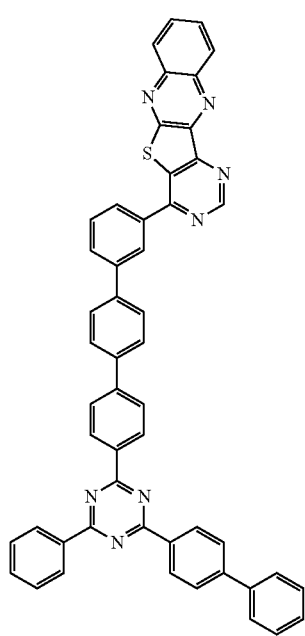
1-4-26
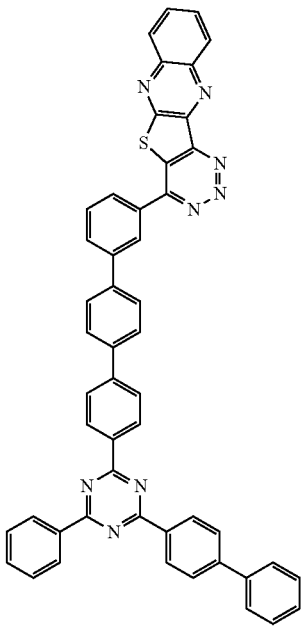

1-4-27
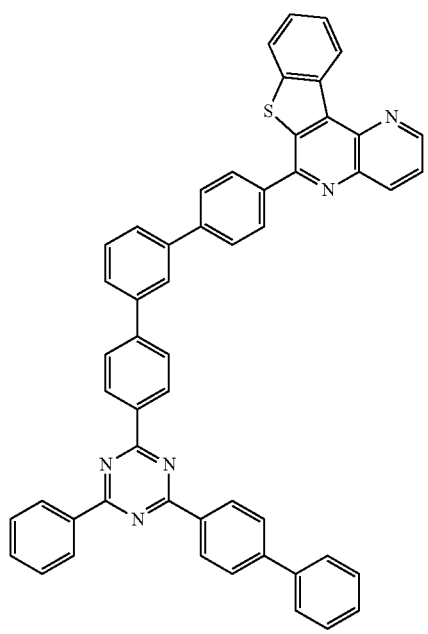
1-4-28
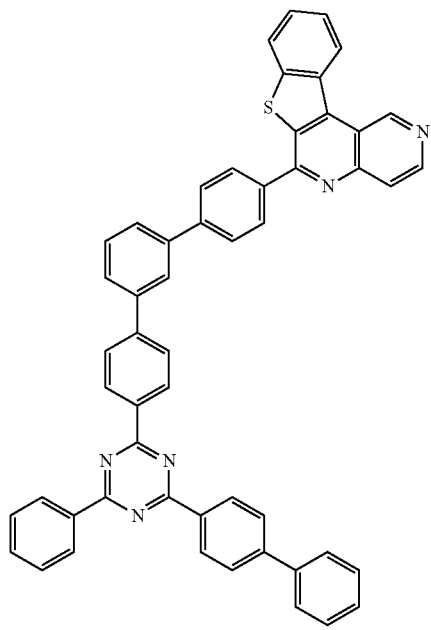
1-4-29
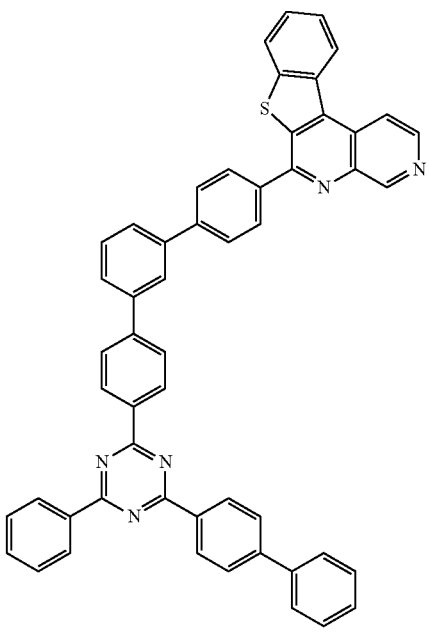
1-4-30
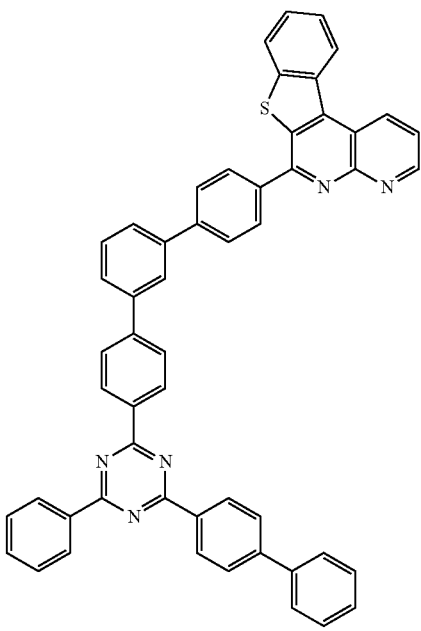

1-4-31
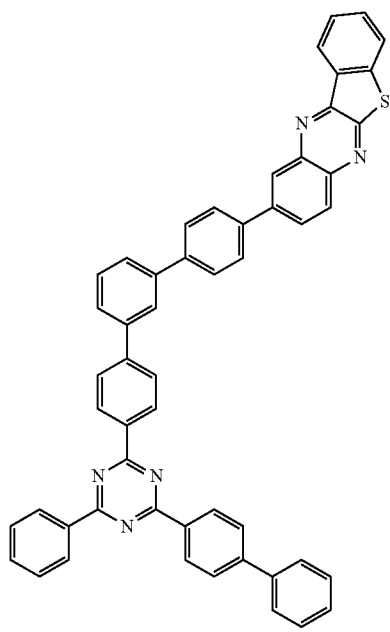
1-4-33
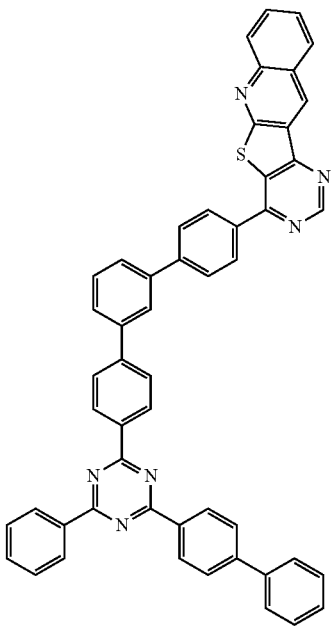
1-4-32
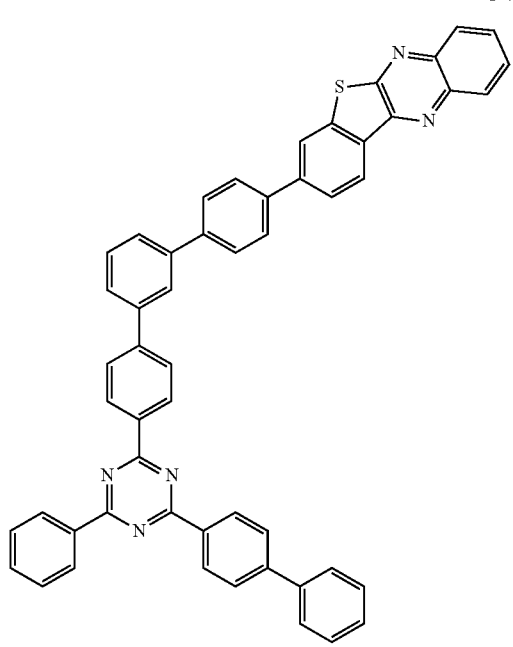
1-4-34
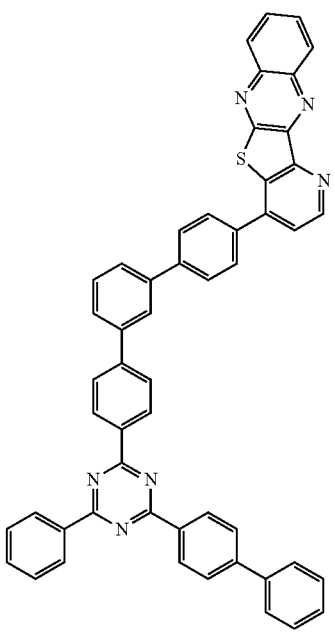

-continued
1-4-35
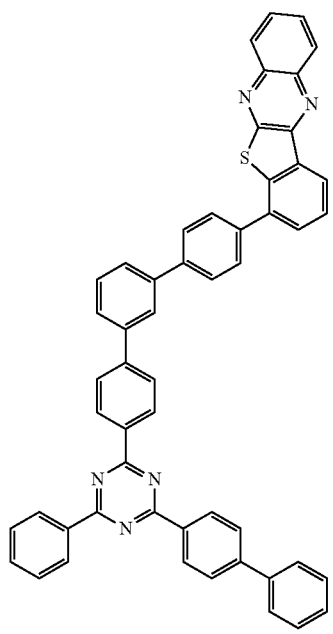
1-4-36
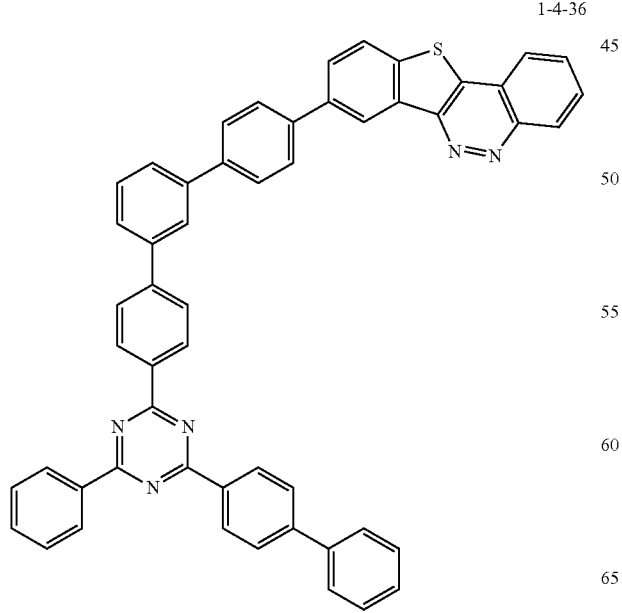
-continued
1-4-37
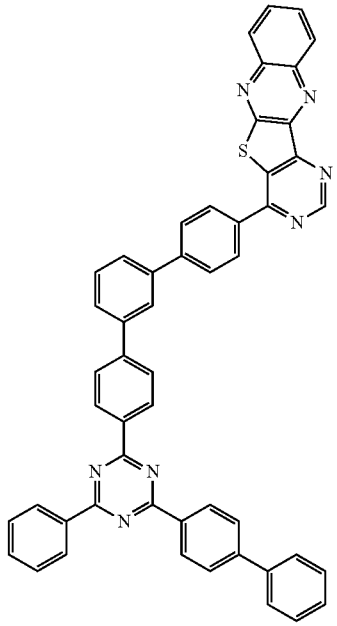
1-4-38
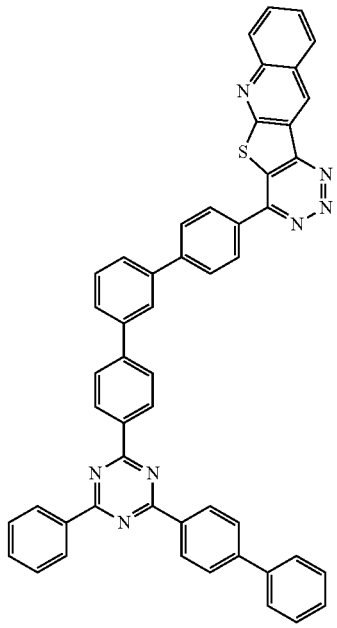

1-4-39
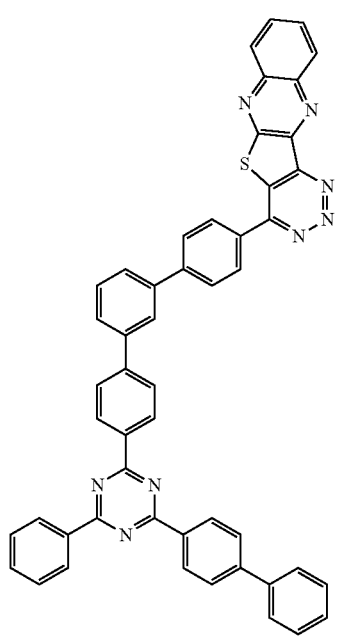
1-4-40
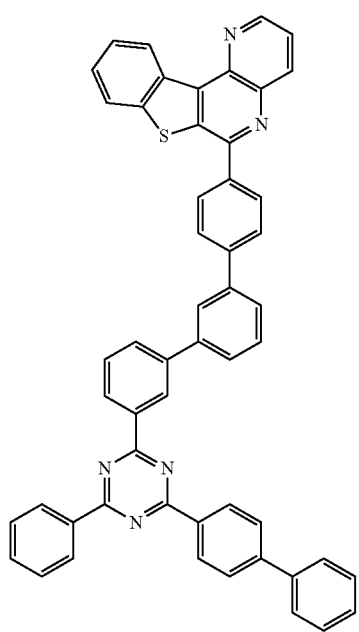
1-4-41
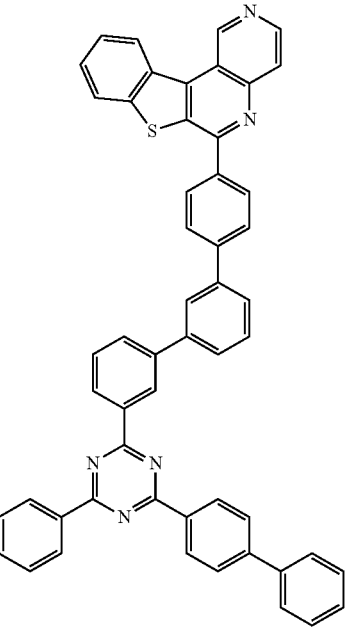
1-4-42
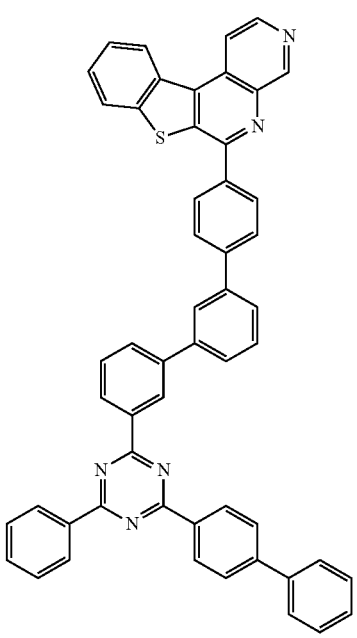

1-4-43
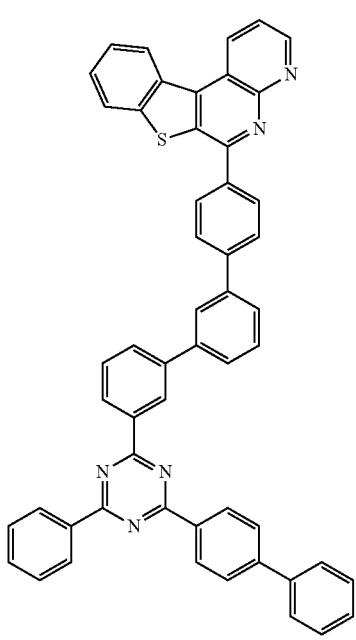
1-4-45
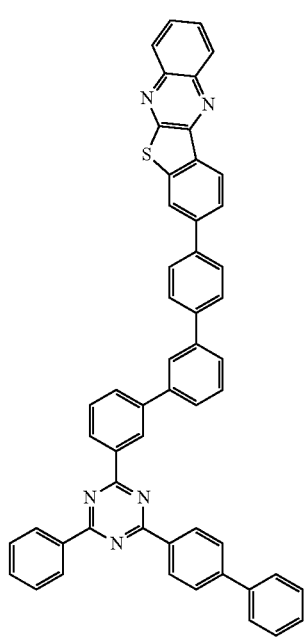
1-4-44
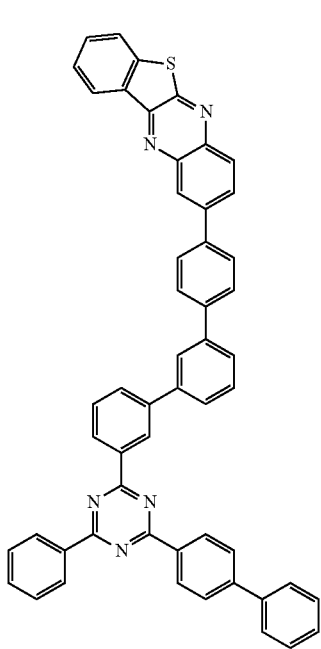
1-4-46
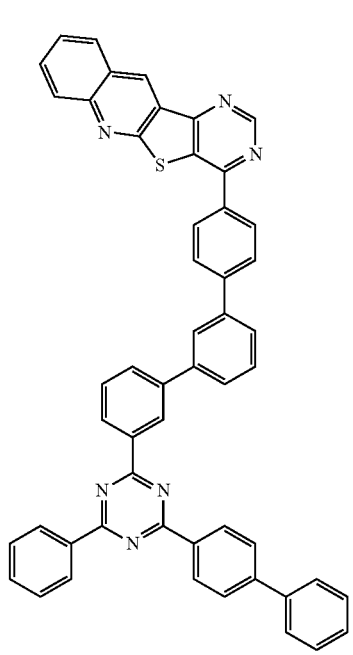

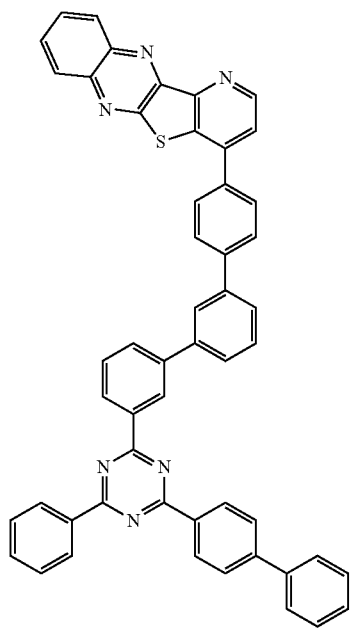
1-4-47
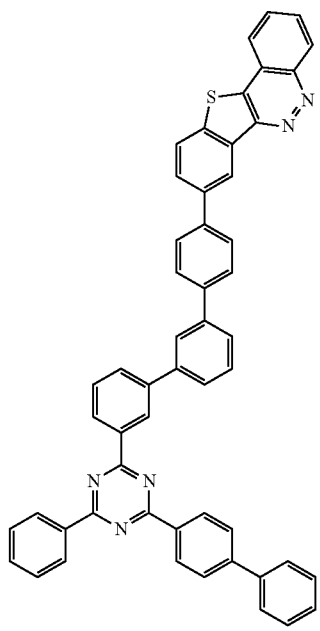
1-4-49
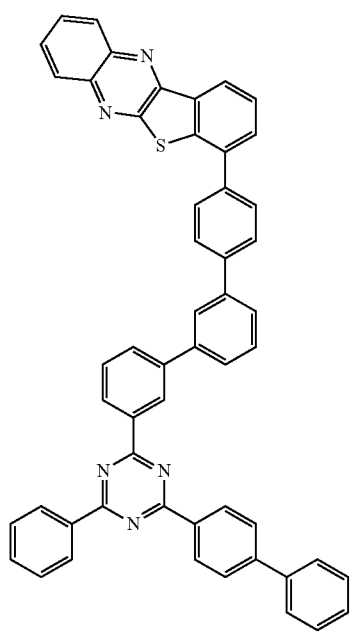
1-4-48
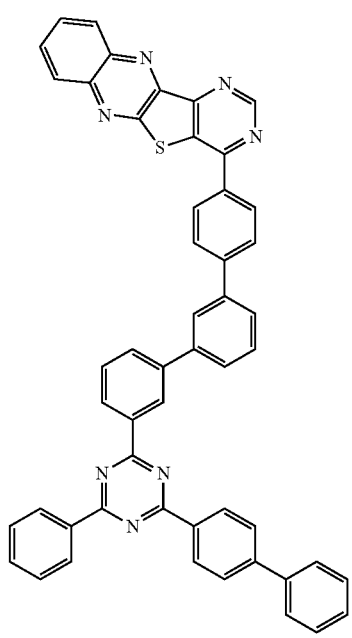
1-4-50

1-4-51
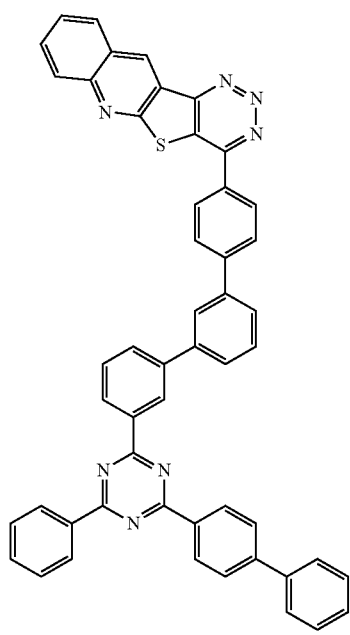
1-4-53
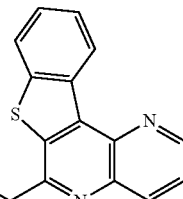
1-4-52
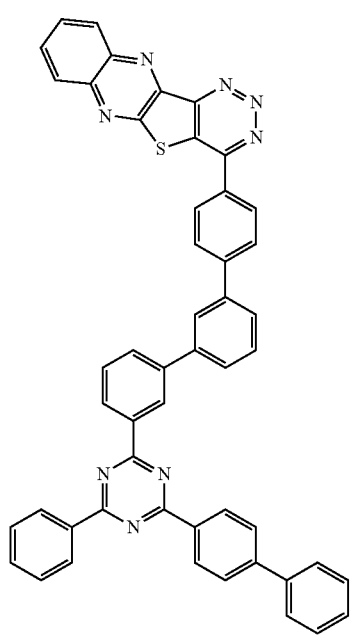
1-4-54
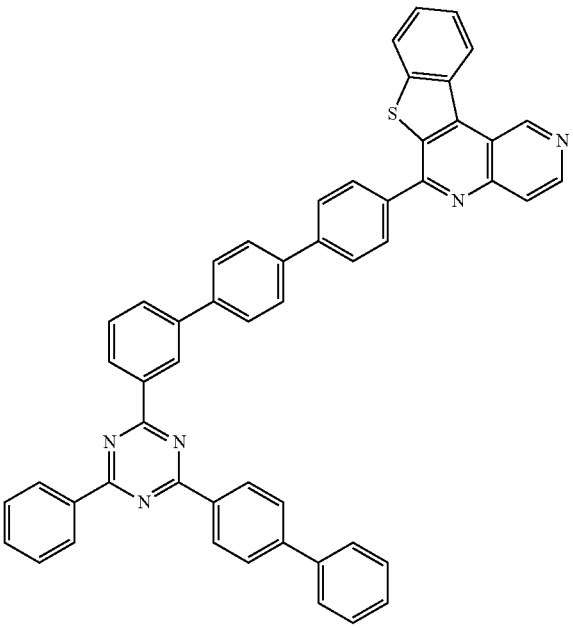

1-4-55
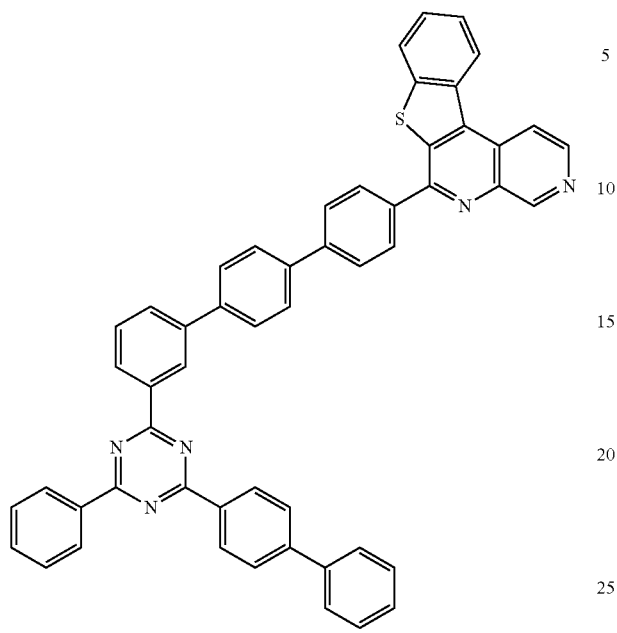
1-4-57
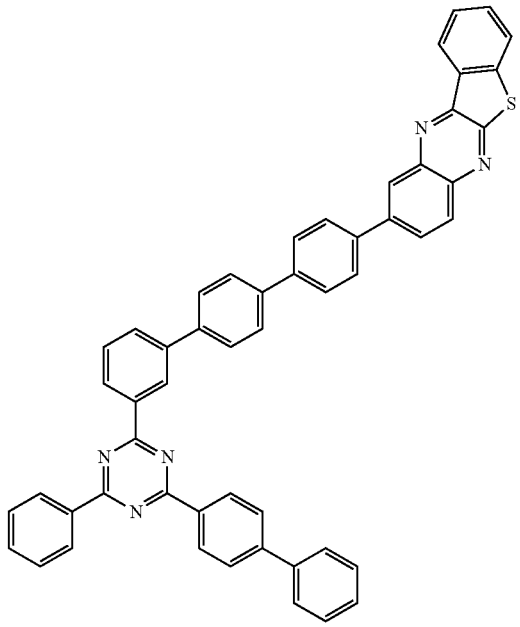
1-4-56
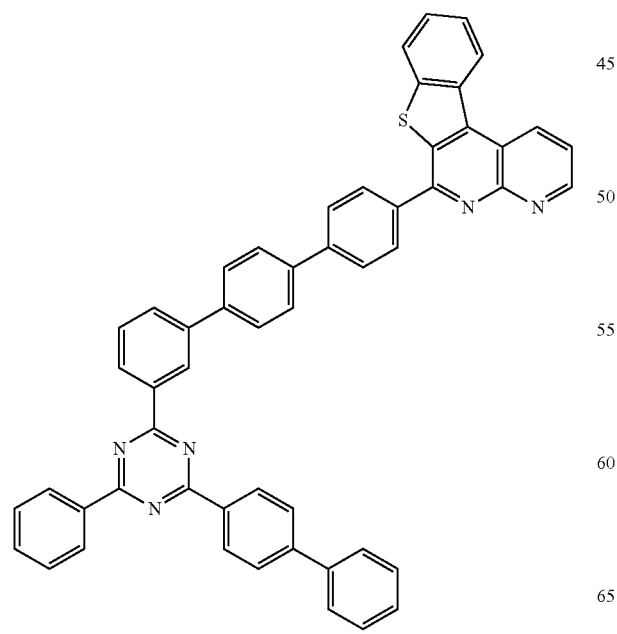
1-4-58
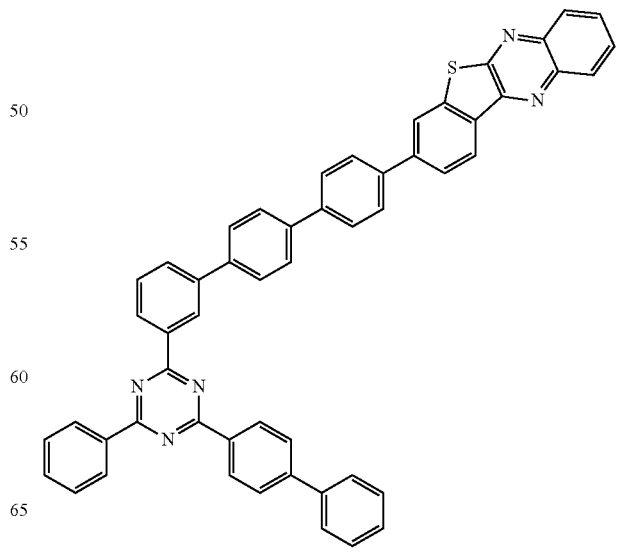

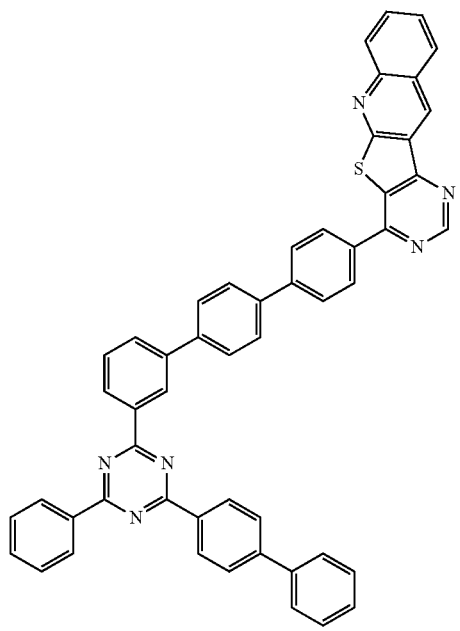
1-4-59
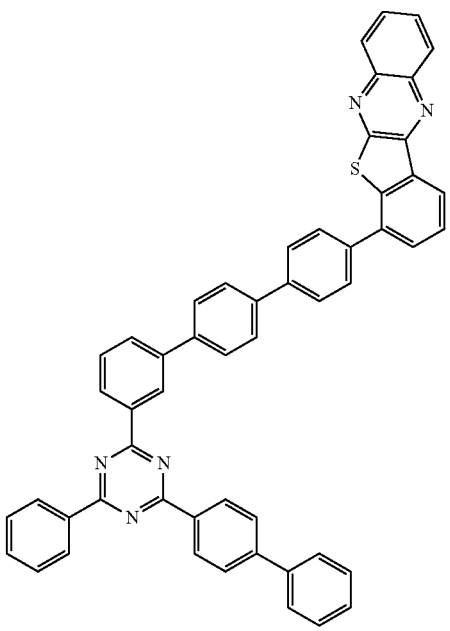
1-4-61
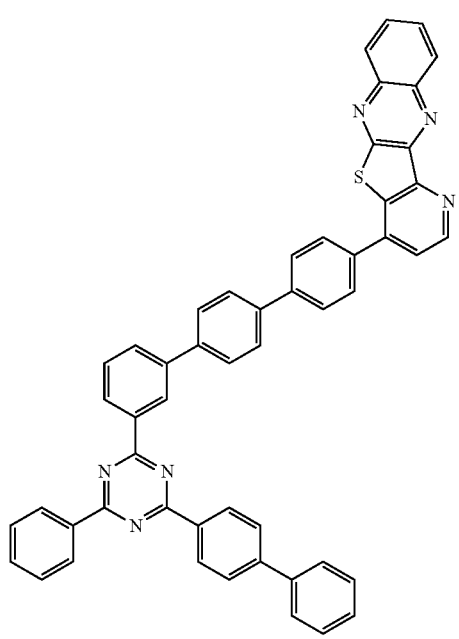
1-4-60
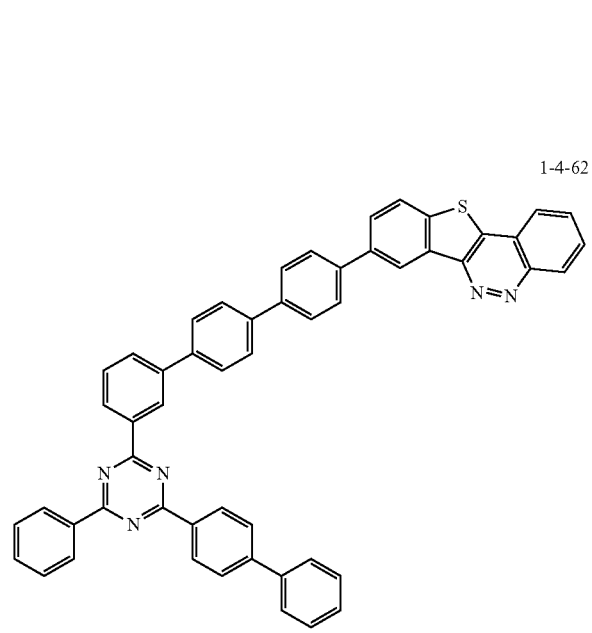
1-4-62

1-4-63
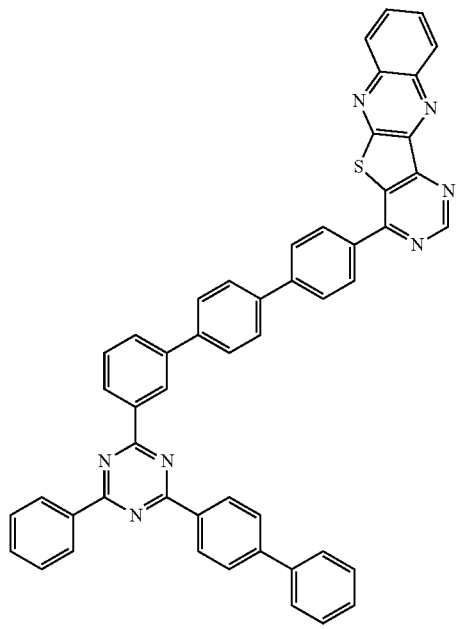
1-4-65
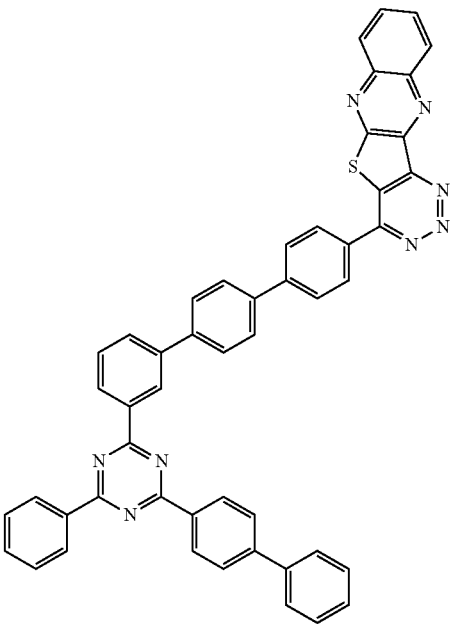
1-4-64
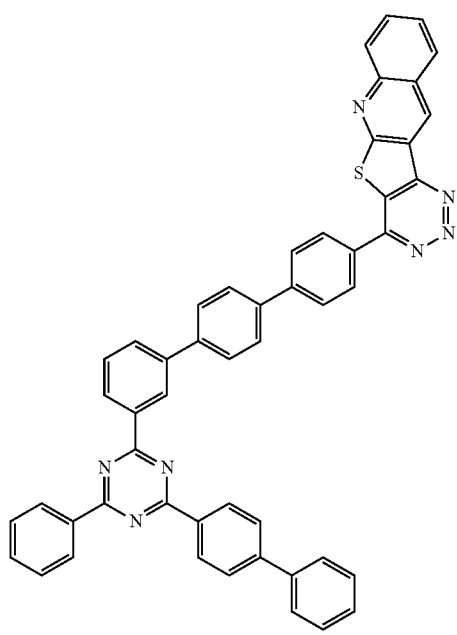
1-4-66
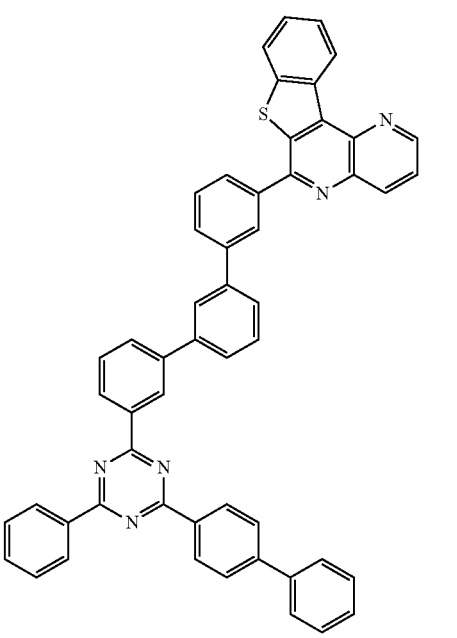

1-4-67
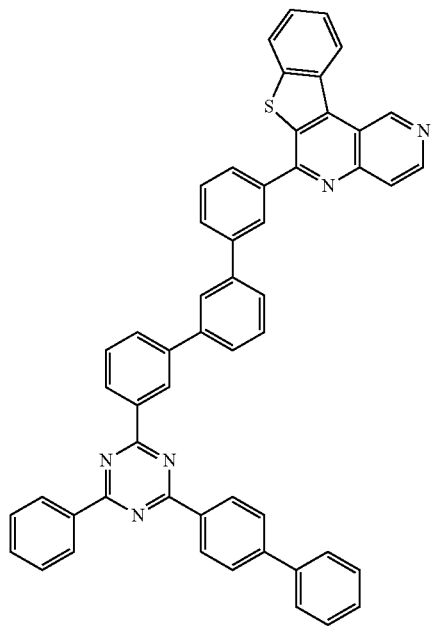
1-4-68
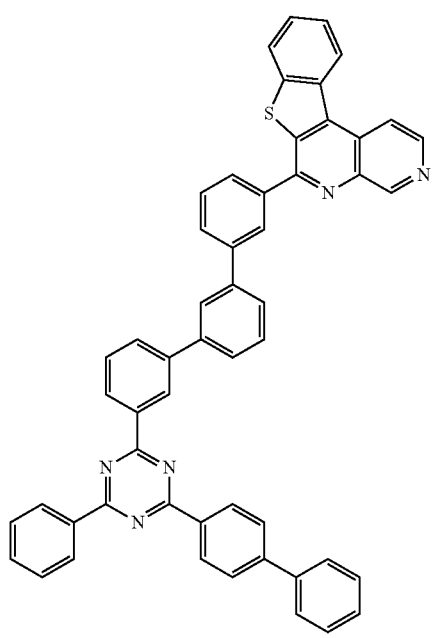
1-4-69
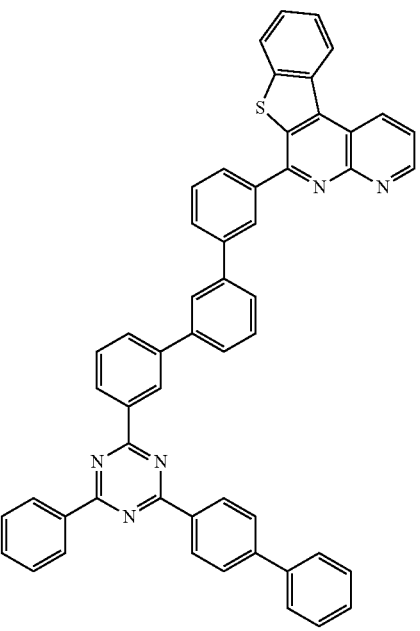
1-4-70
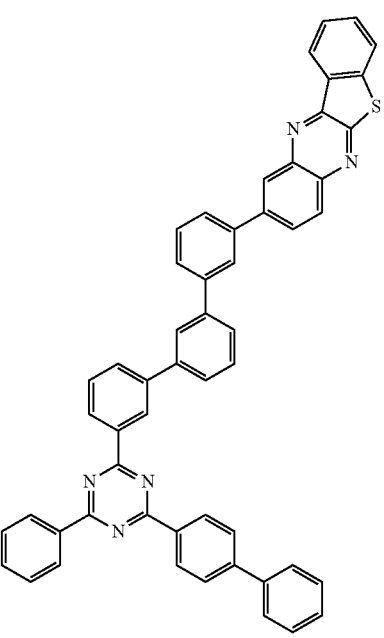

1-4-71
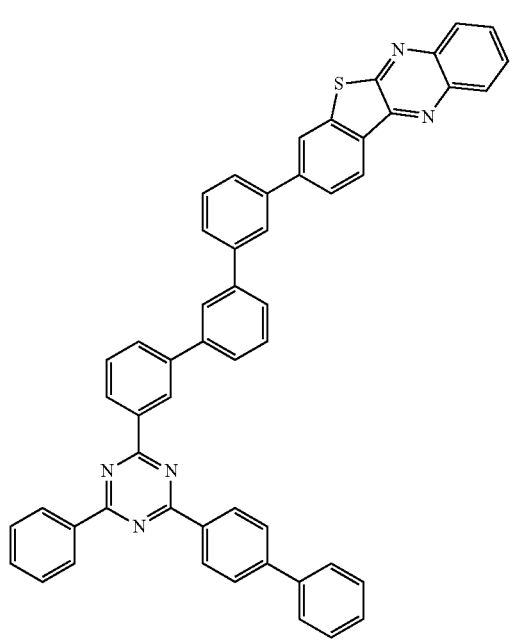
1-4-73
1-4-72
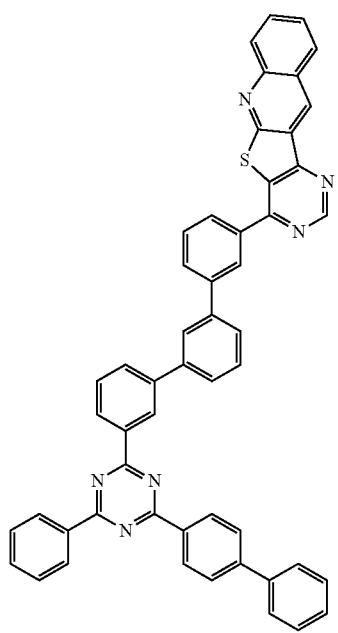
1-4-74
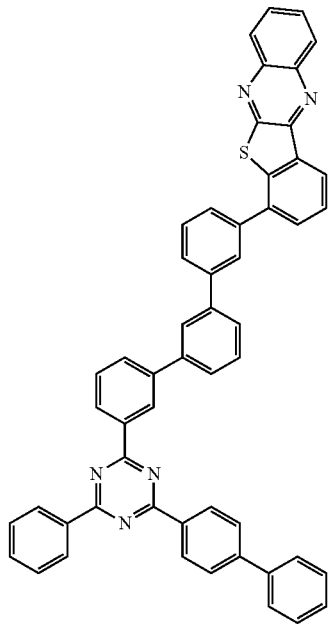

1-4-75
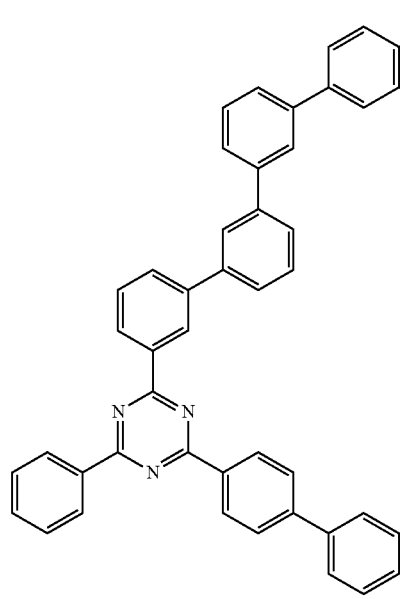
1-4-76
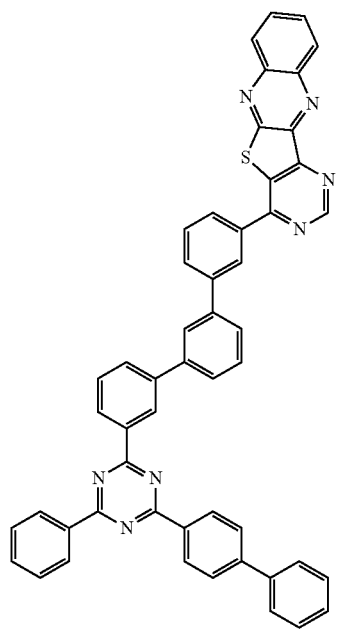
1-4-77
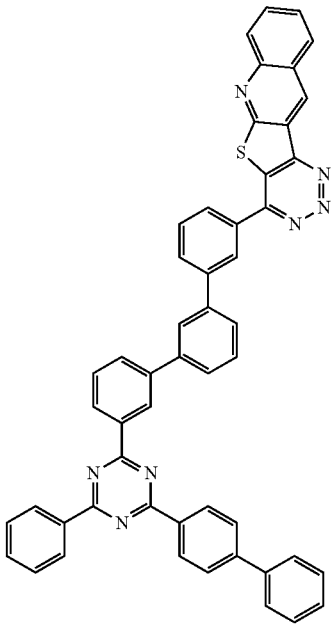
1-4-78
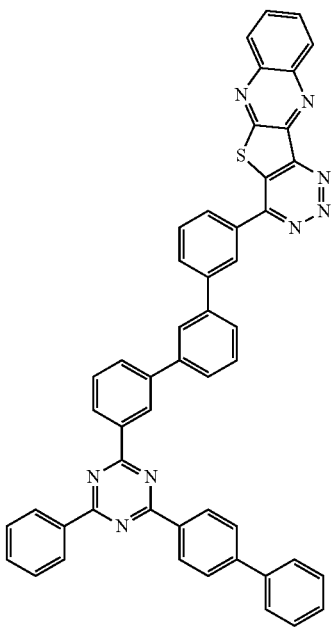

-continued
1-4-79
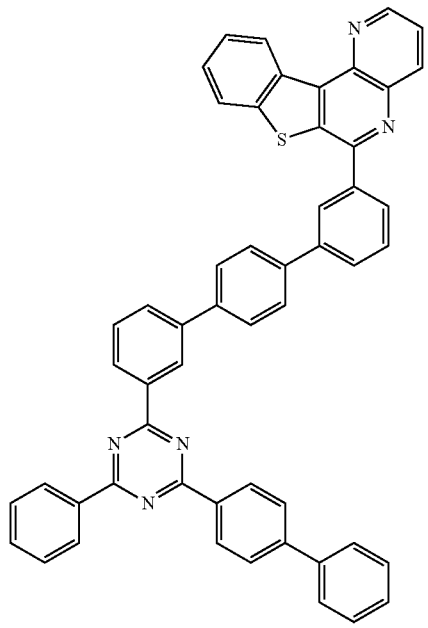
1-4-81
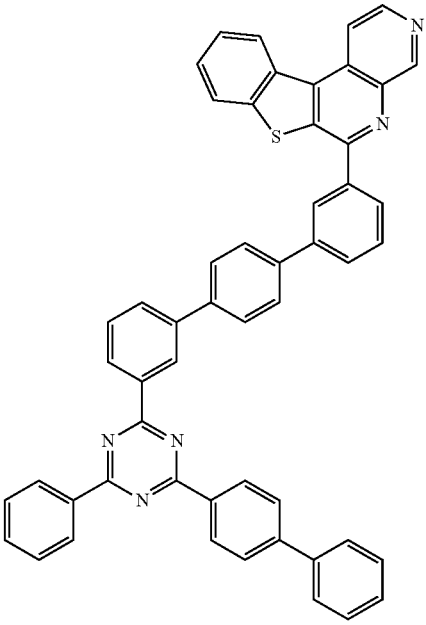
1-4-80
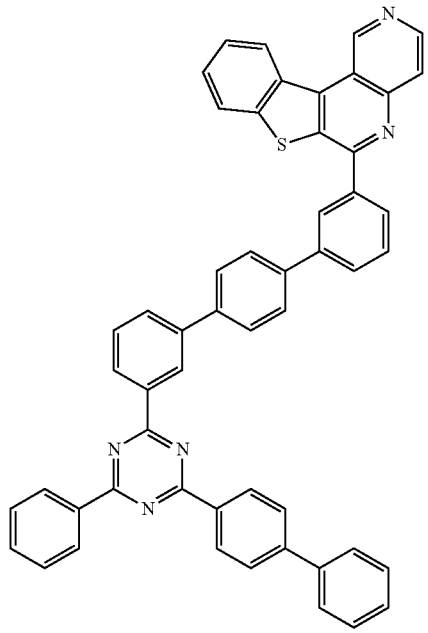
1-4-82
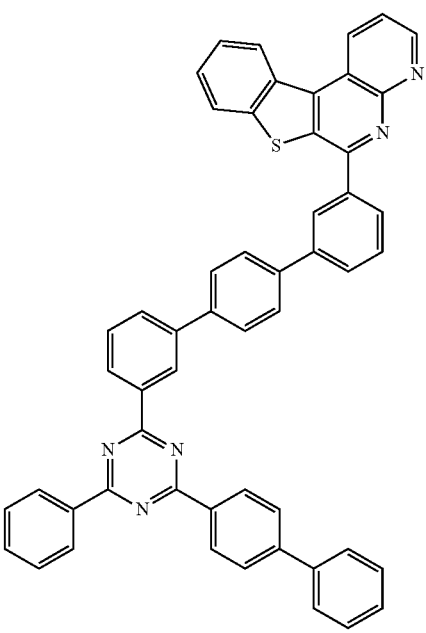

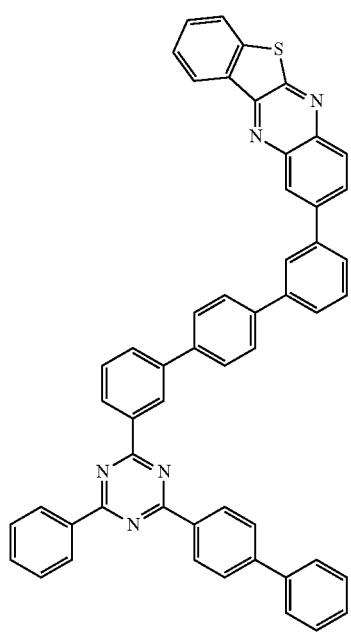
1-4-83
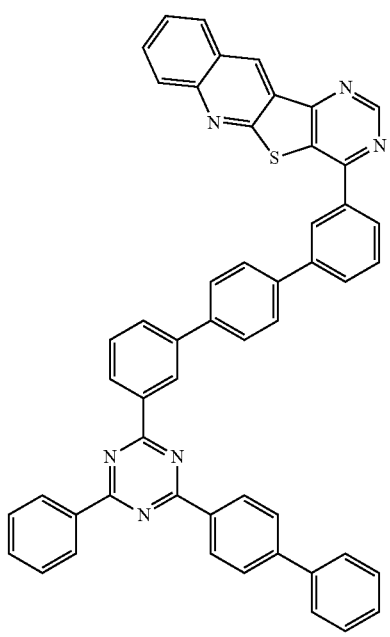
1-4-85
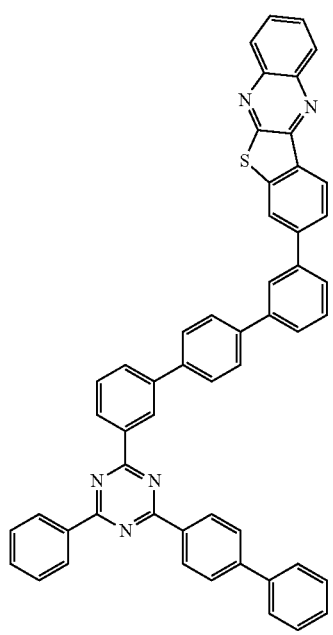
1-4-84
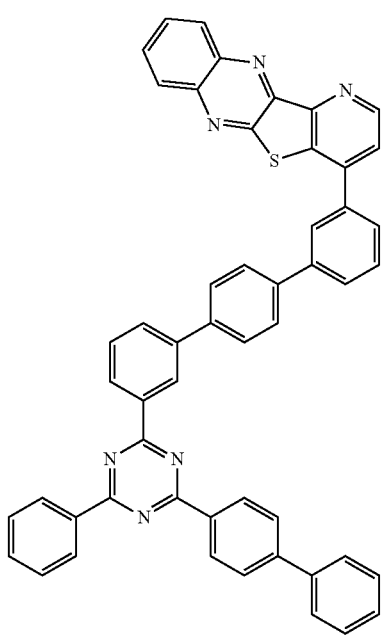
1-4-86

101
-continued
1-4-87
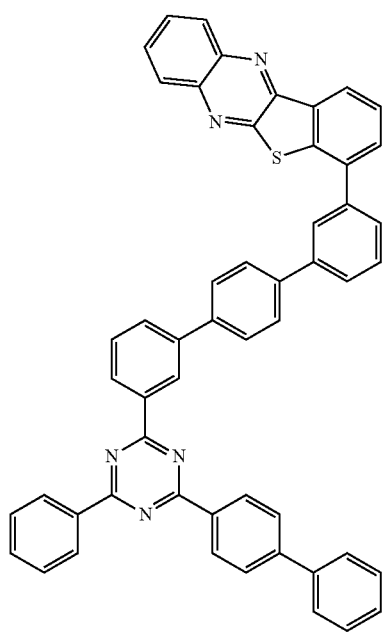
1-4-88
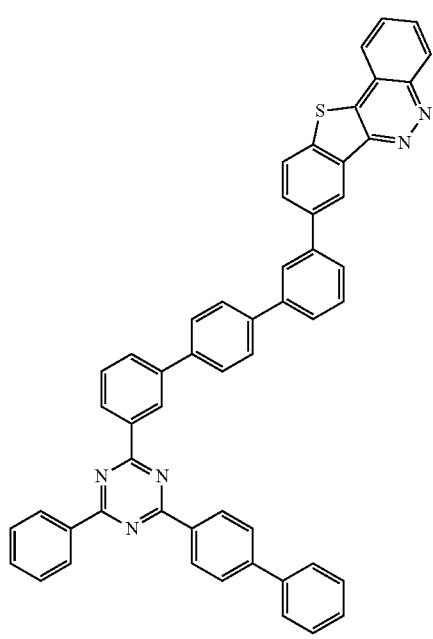
102
-continued
1-4-89
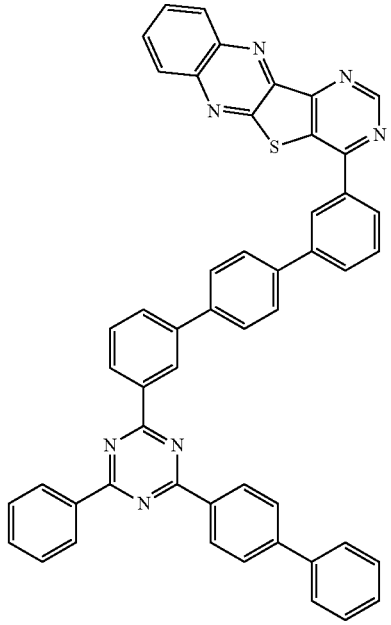
1-4-90
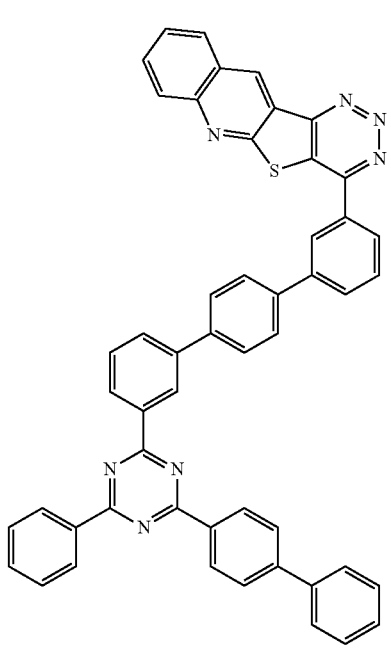

1-4-91
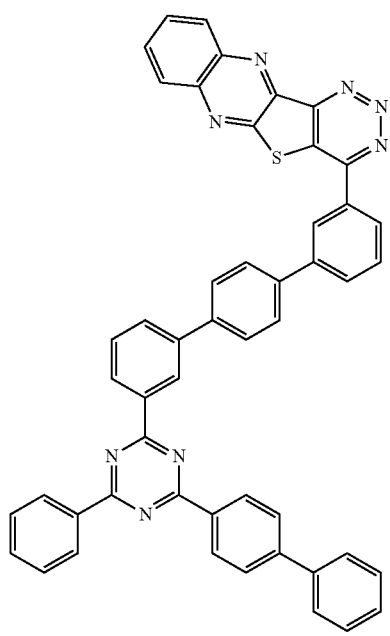
1-4-93
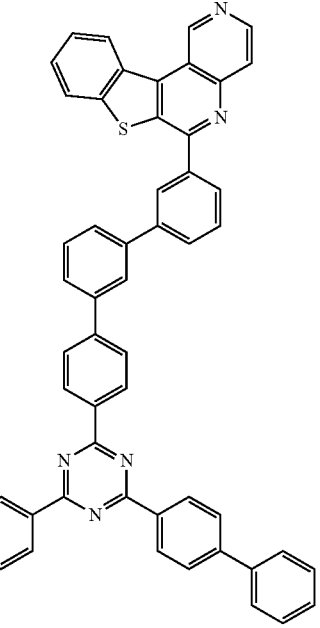
1-4-92
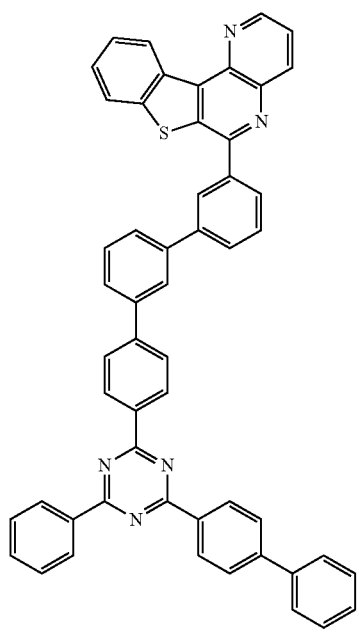
1-4-94
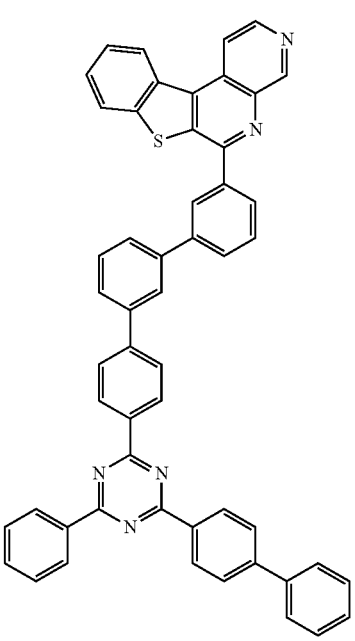

1-4-95
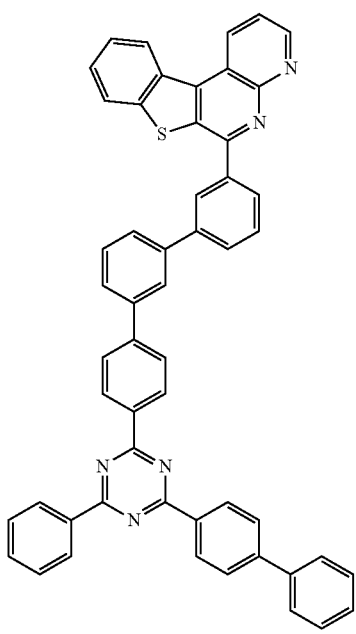
1-4-97
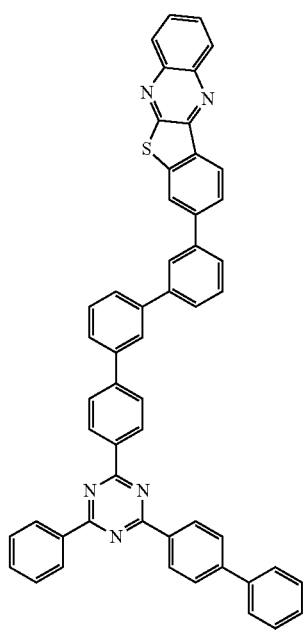
1-4-96
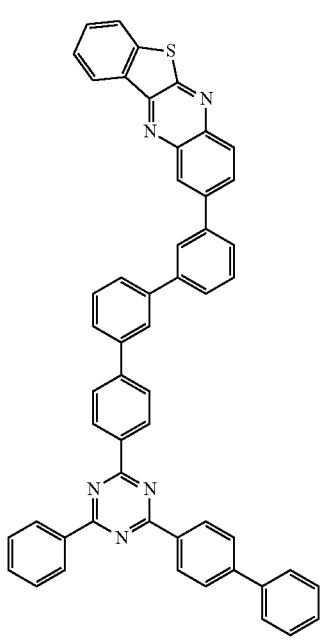
1-4-98
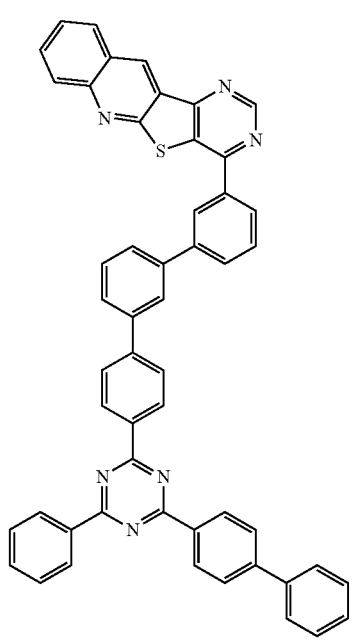

1-4-99
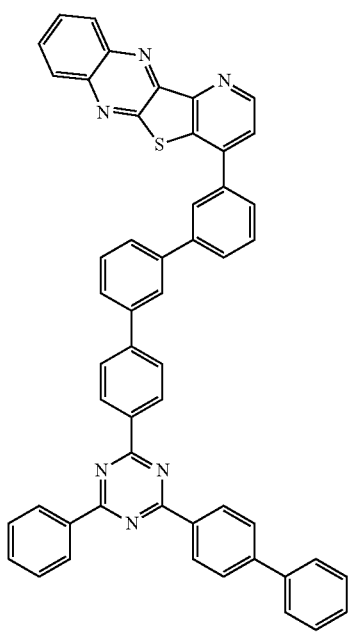
1-4-101
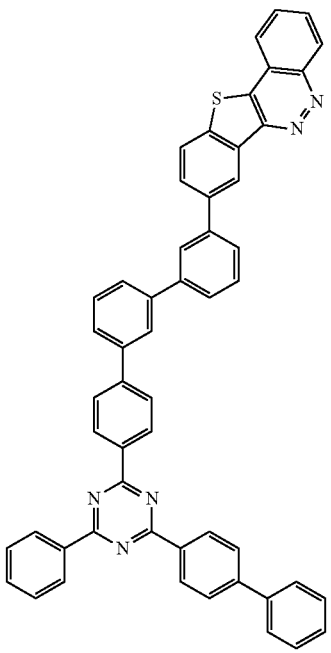
1-4-100
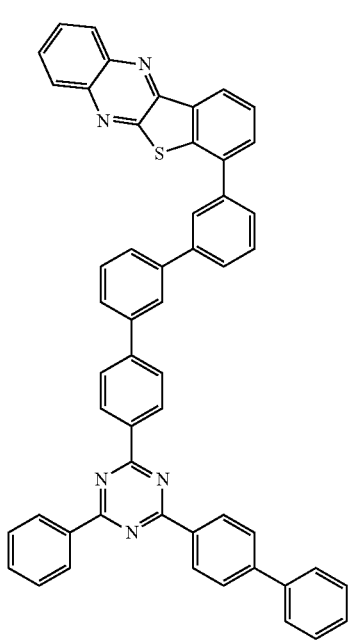
1-4-102
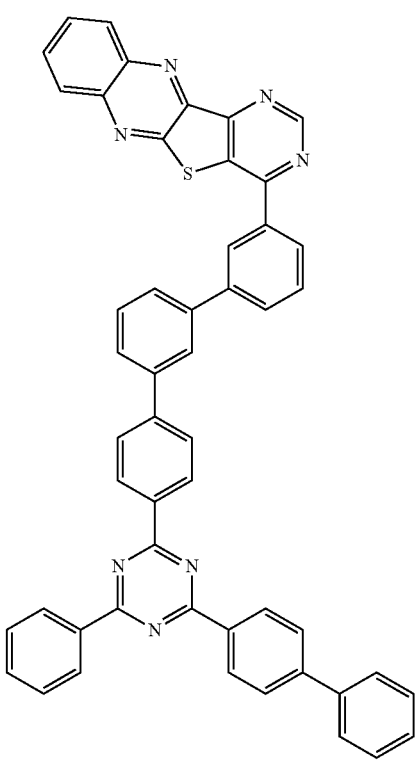

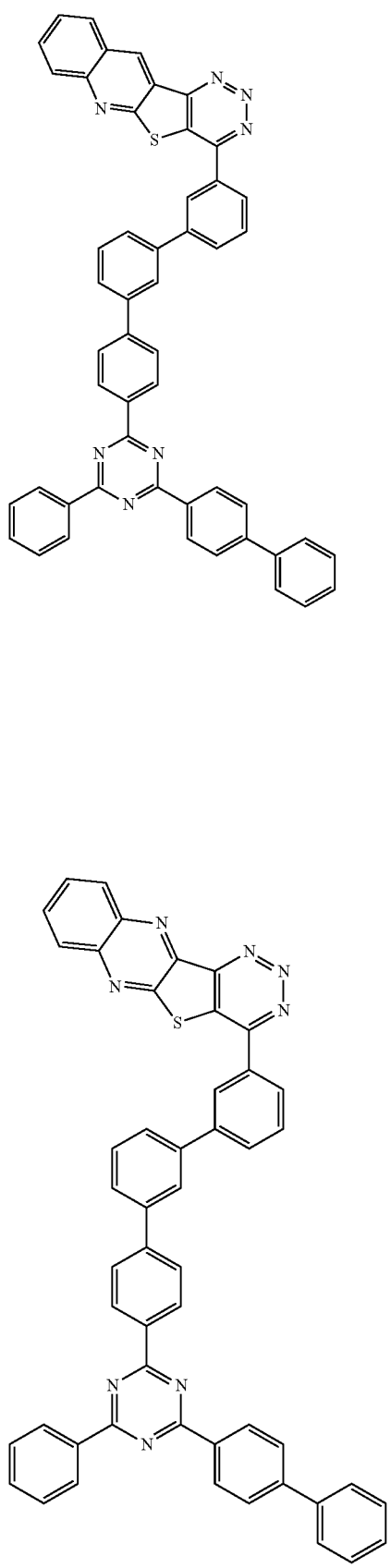
1-4-103
1-4-104
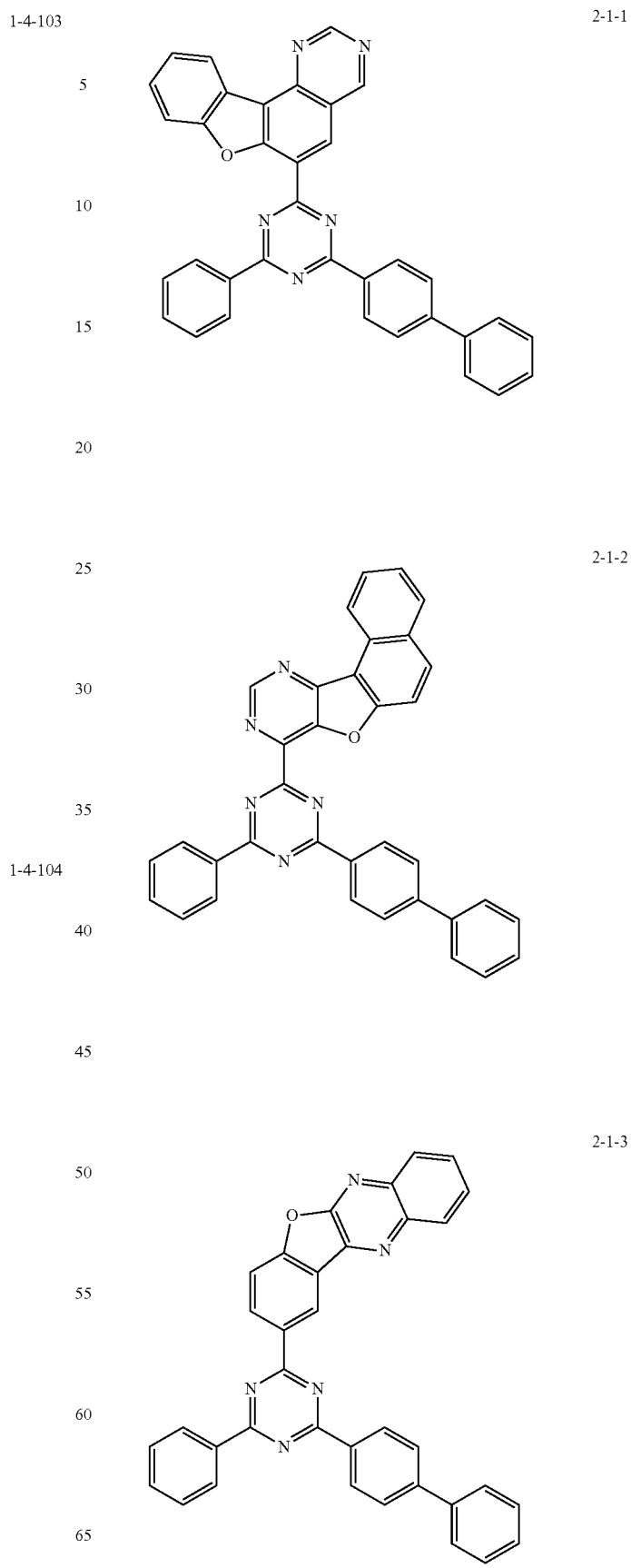
2-1-1
2-1-2
2-1-3

2-1-4
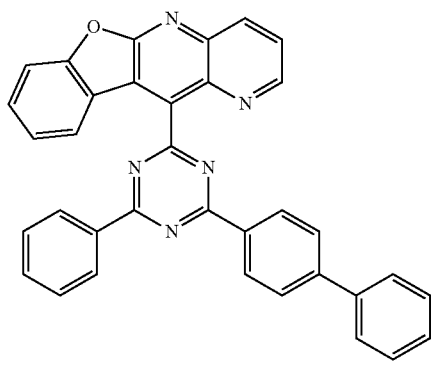
2-1-7
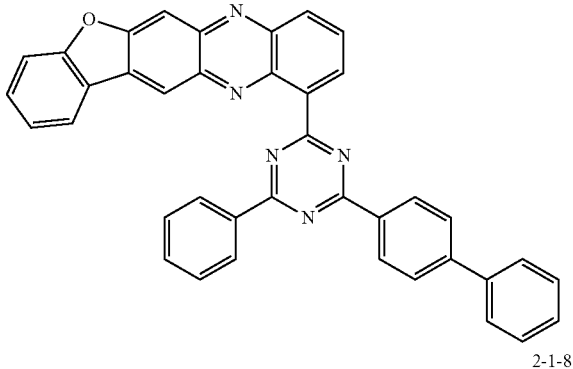
2-1-5
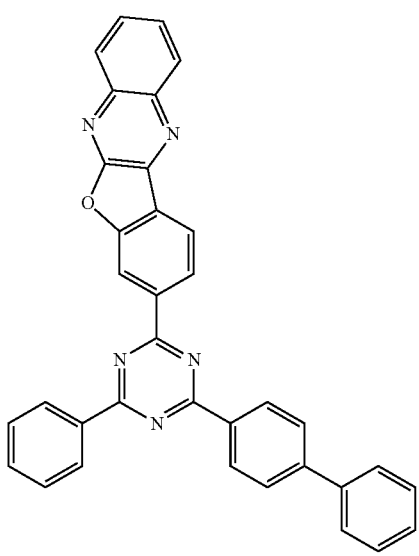
2-1-8
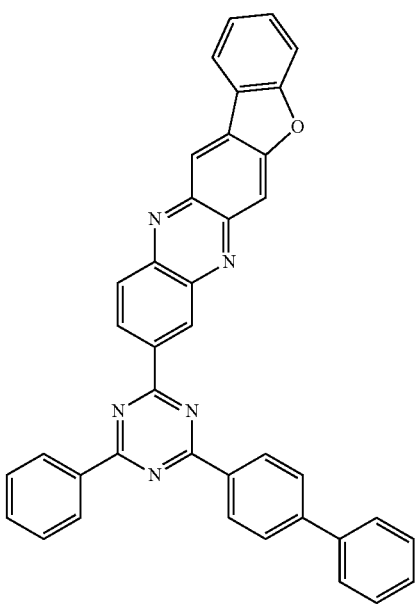
2-1-6
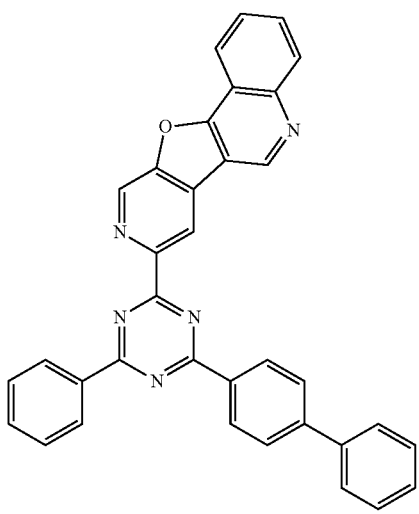
2-1-9
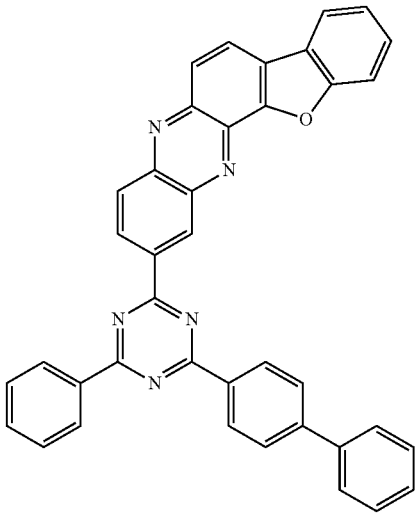

2-1-10
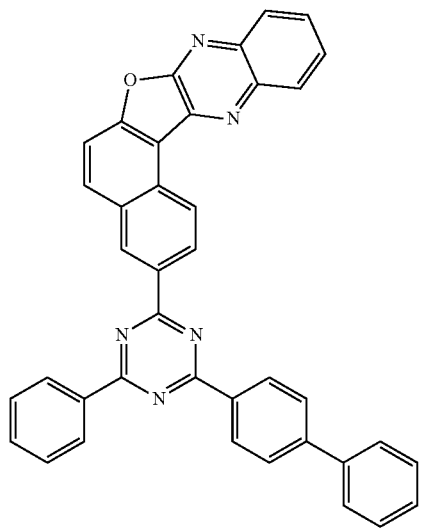
2-1-11
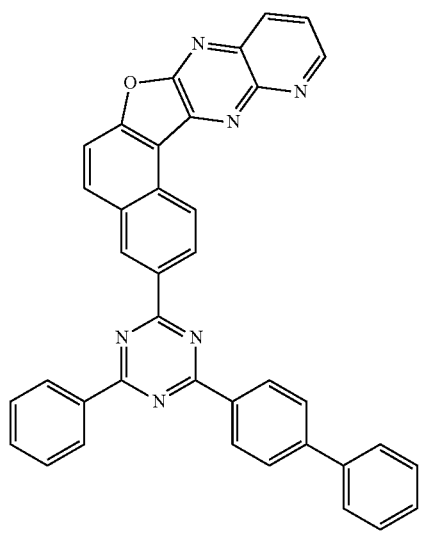
2-2-1
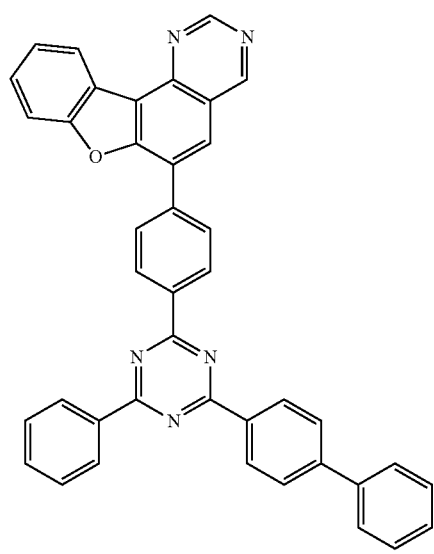
2-2-2
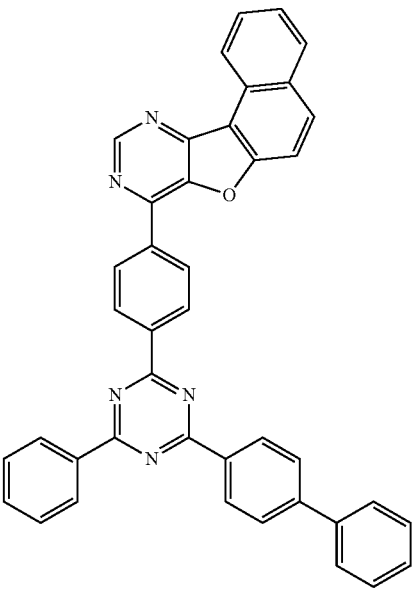
2-2-3
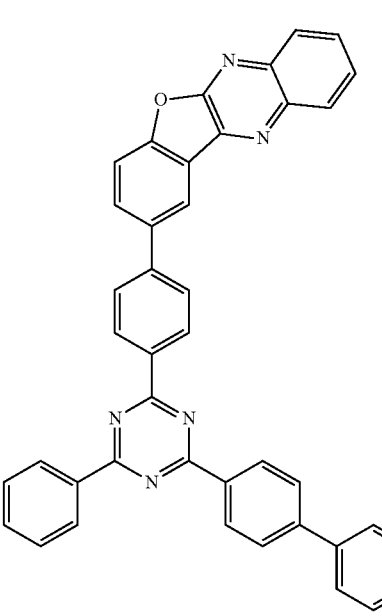
2-2-4
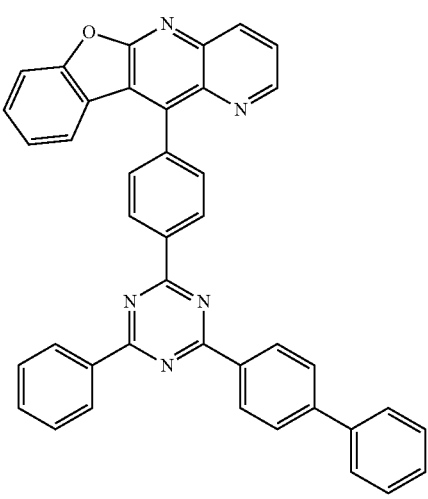

2-2-5
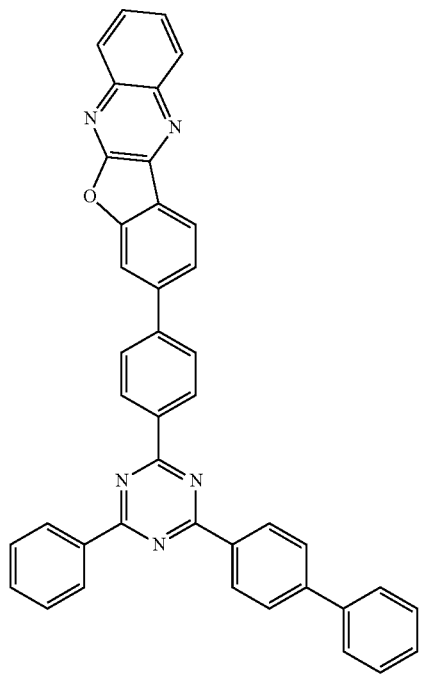
2-2-6
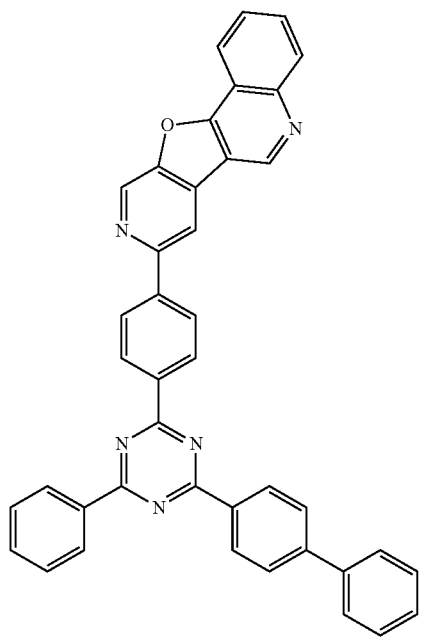
2-2-7
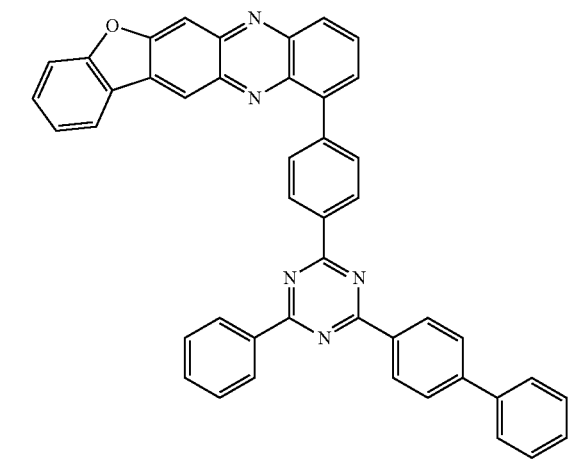
2-2-8
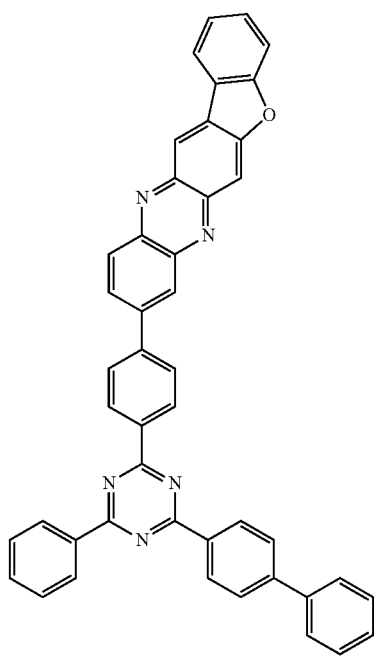

2-2-9
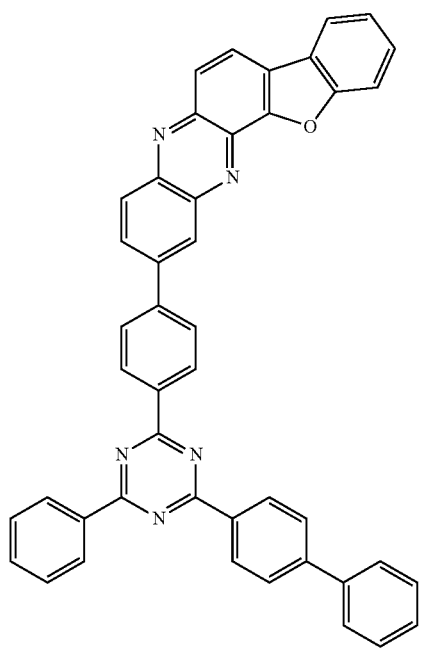
2-2-11
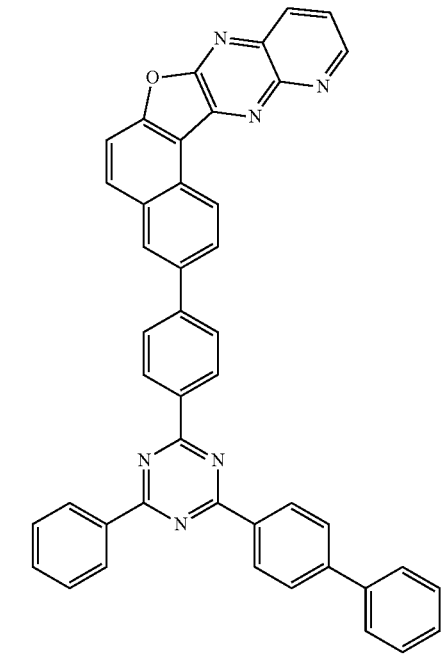
2-2-10
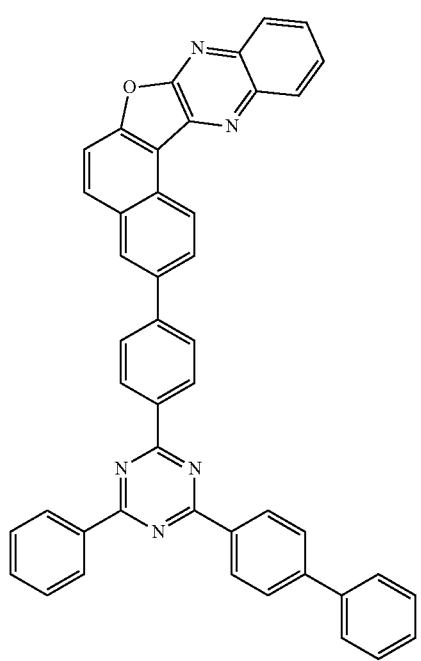
2-2-12
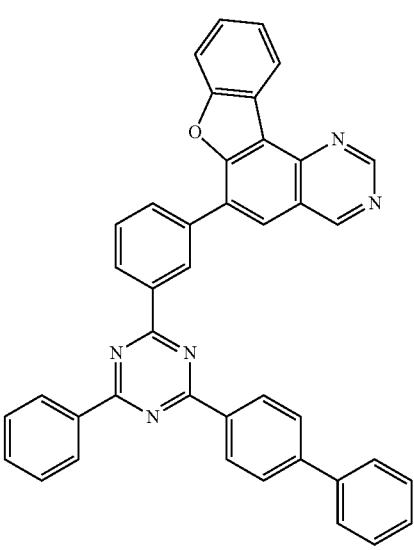
2-2-13
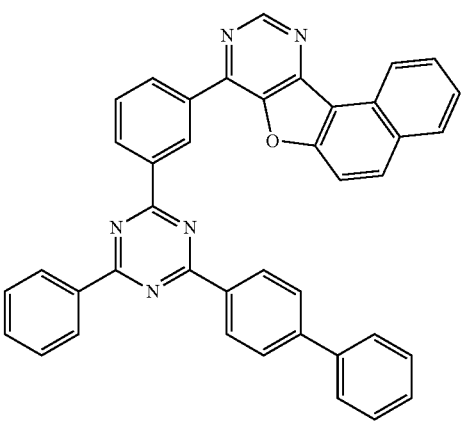

2-2-14
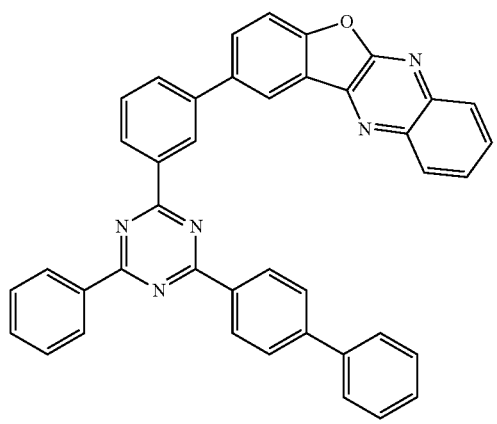
2-2-15
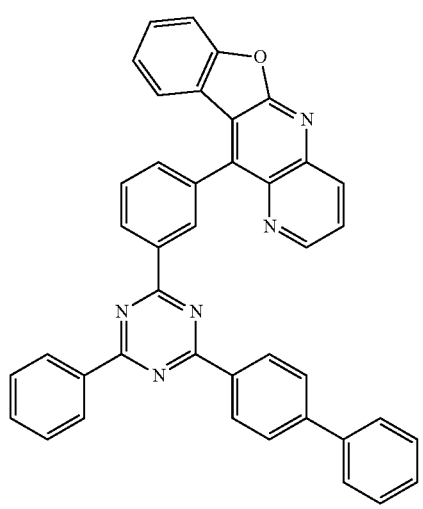
2-2-16
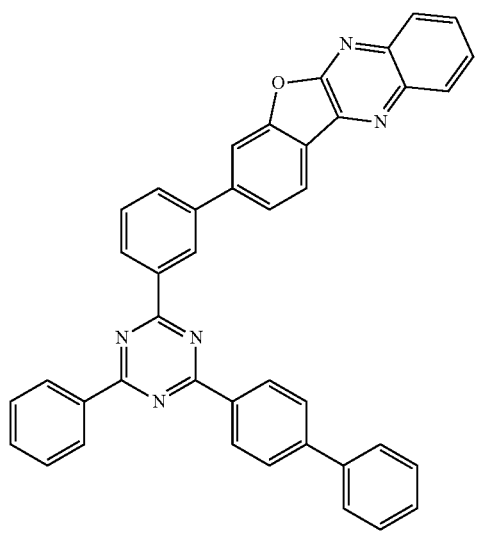
2-2-17
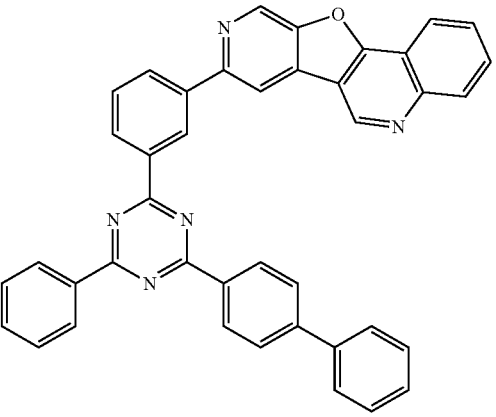
2-2-18
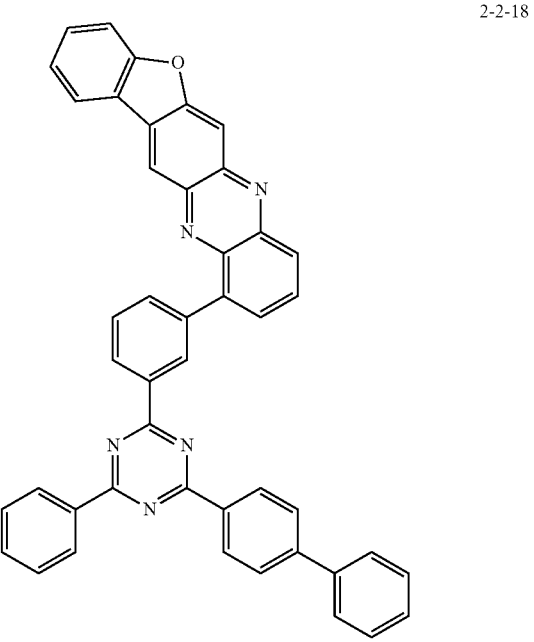
2-2-19
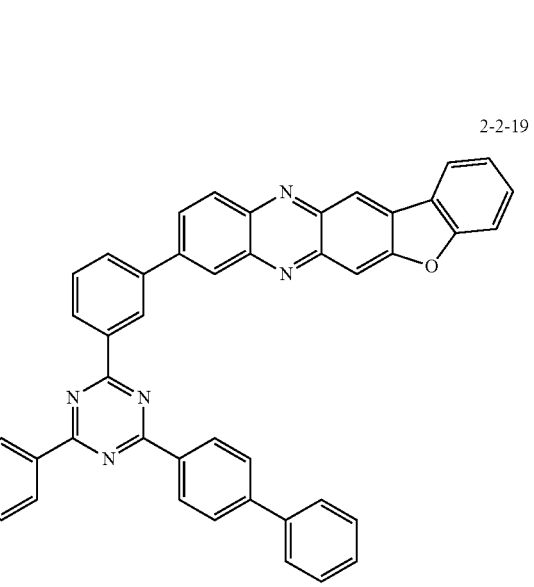

-continued
2-2-20
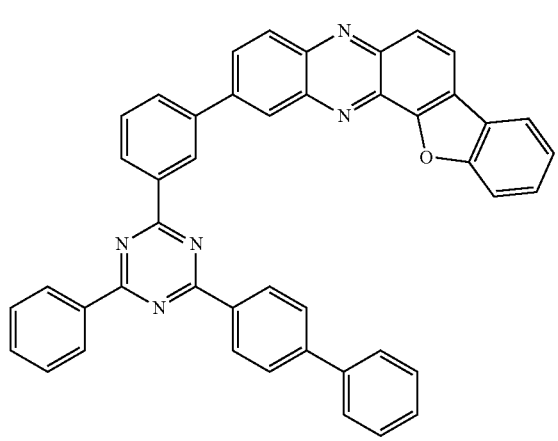
2-2-21
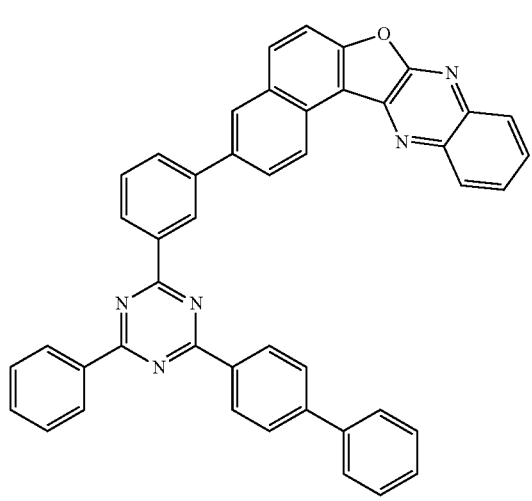
2-2-22
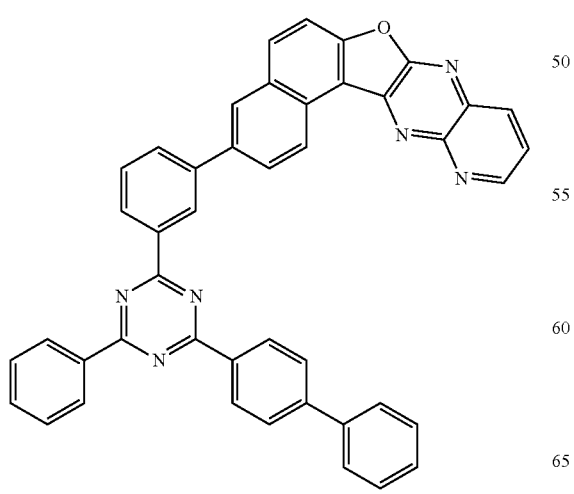
-continued
2-3-1
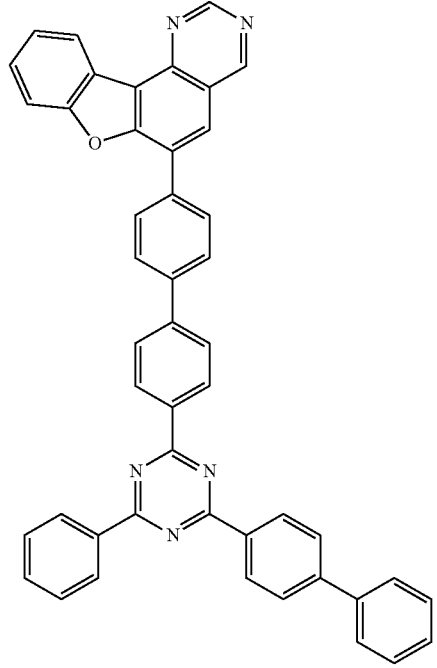
2-3-2
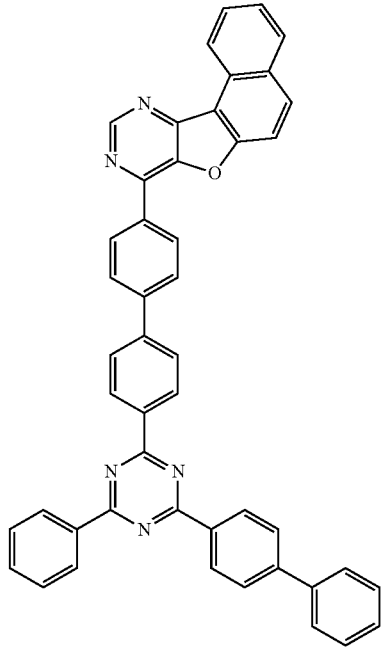

2-3-3
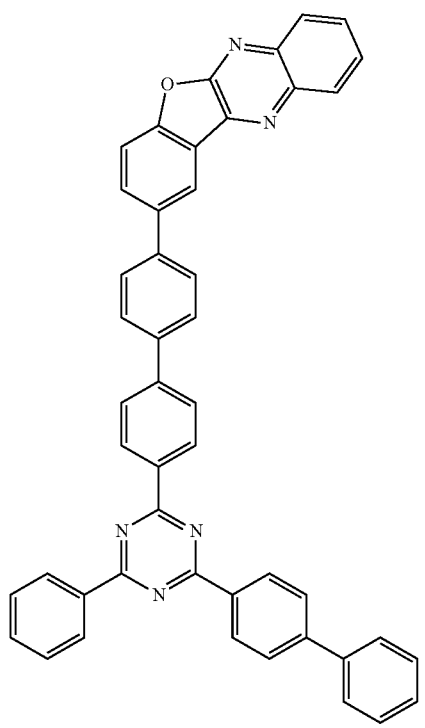
2-3-5
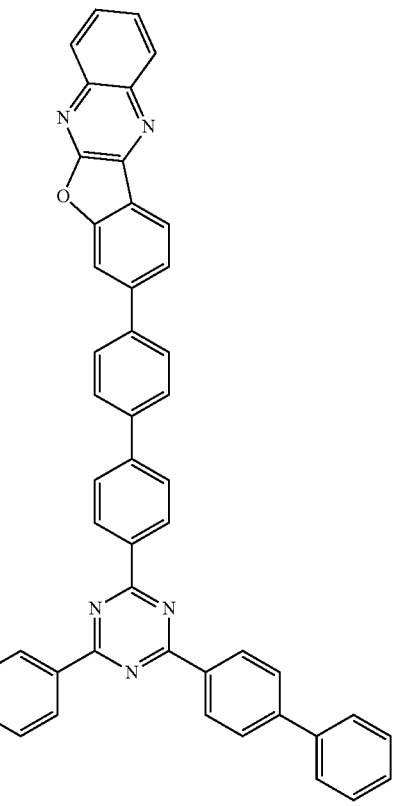
2-3-4
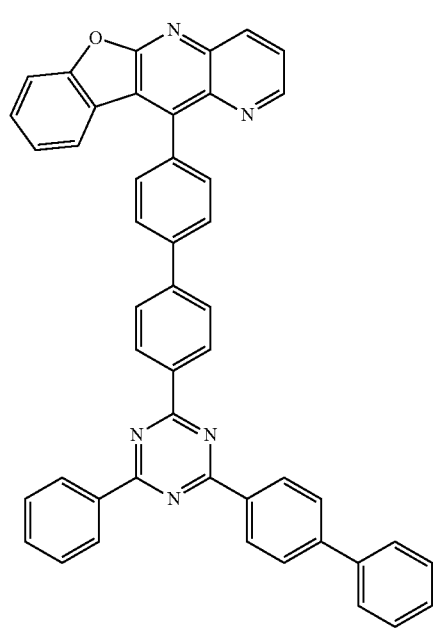
2-3-6
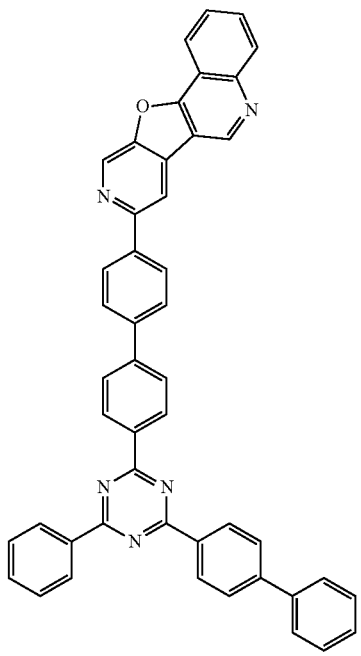

125 -continued
2-3-7
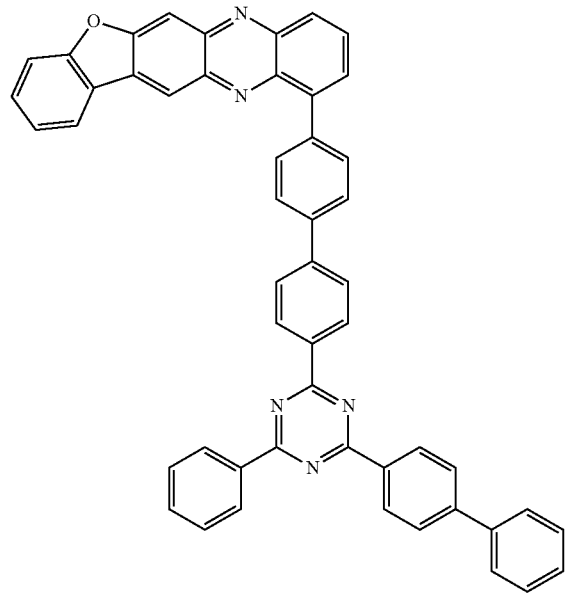
2-3-8
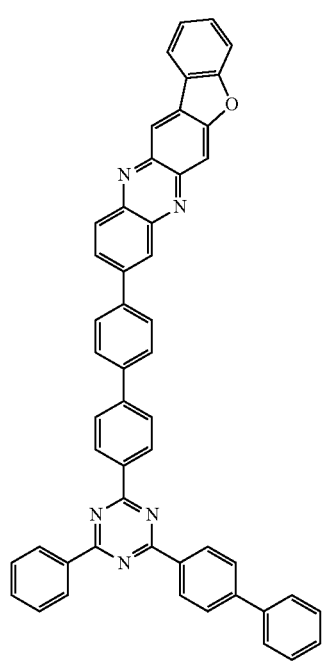
126 -continued
2-3-9
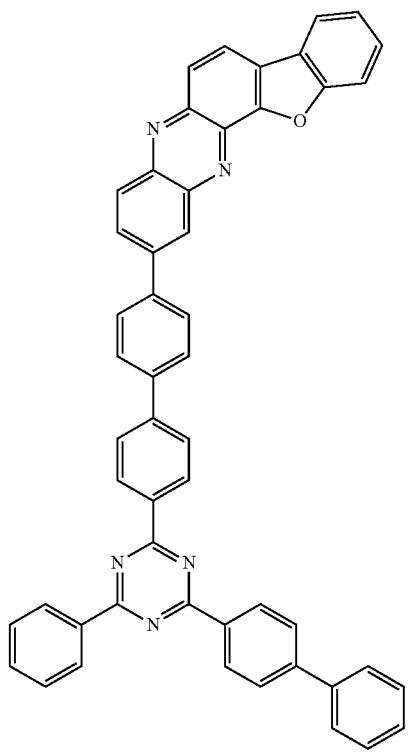
2-3-10
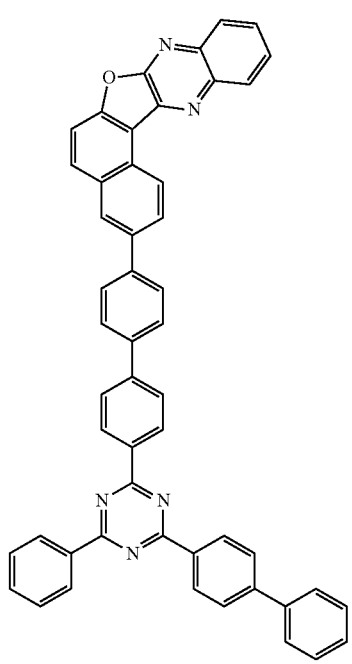

2-3-11
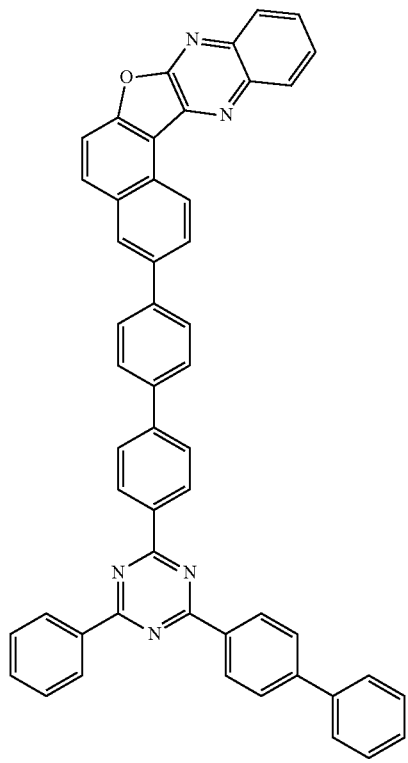
2-3-12
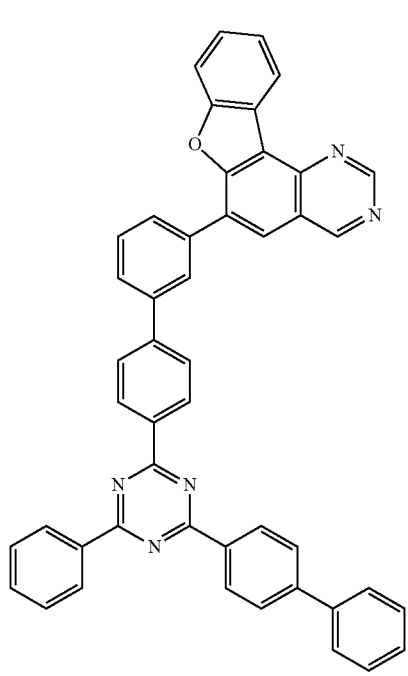
2-3-13
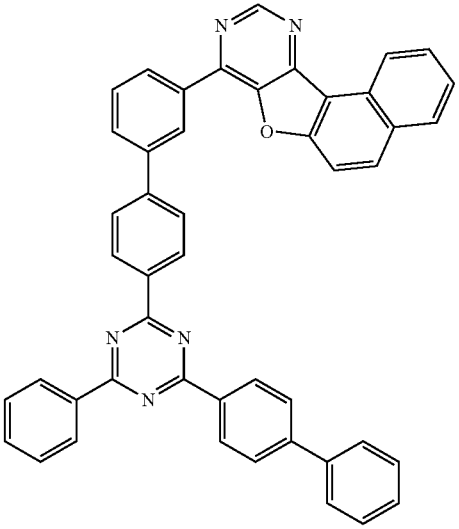
2-3-14
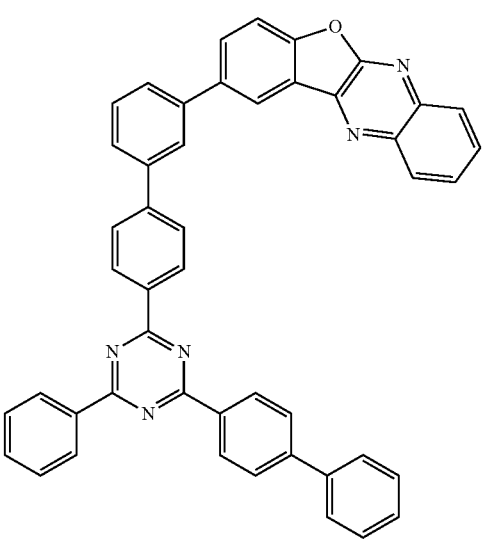

129
-continued
2-3-15
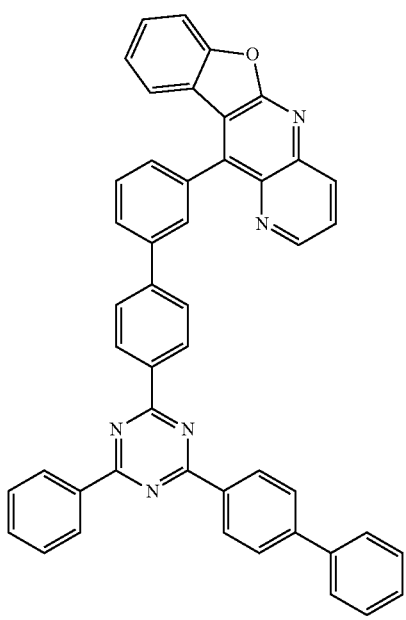
2-3-16
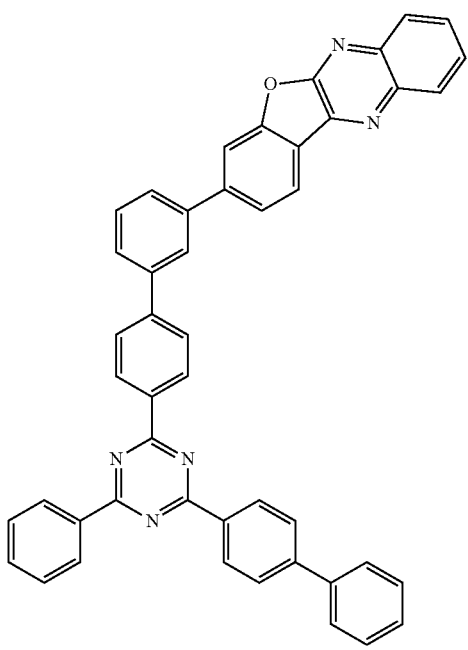
130
-continued
2-3-17
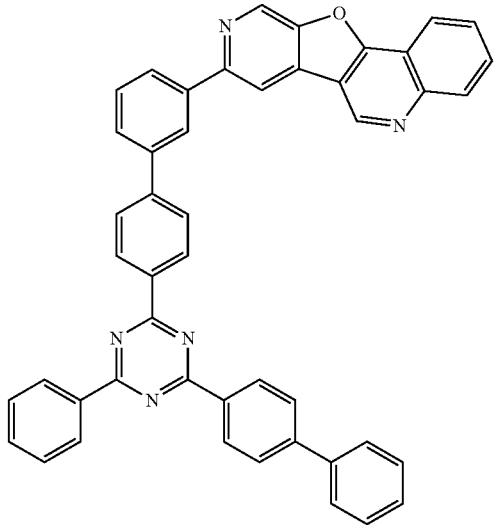
2-3-18
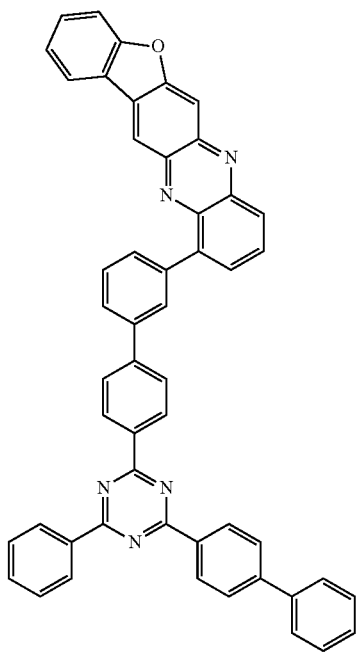

131
-continued
2-3-19
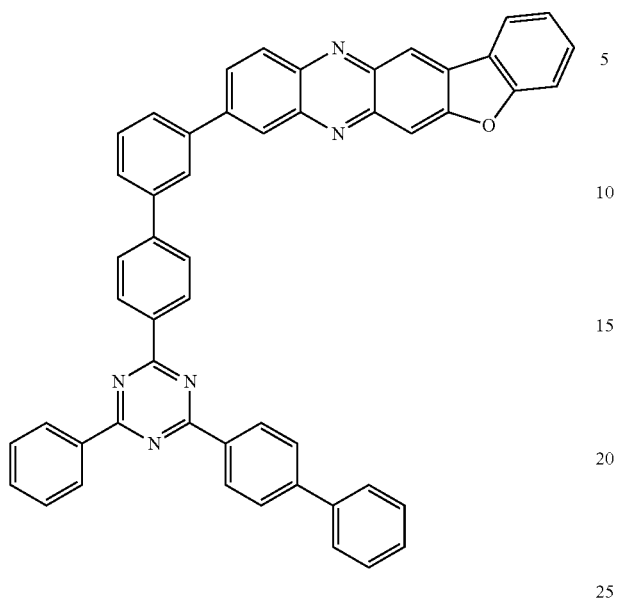
132
-continued
2-3-21
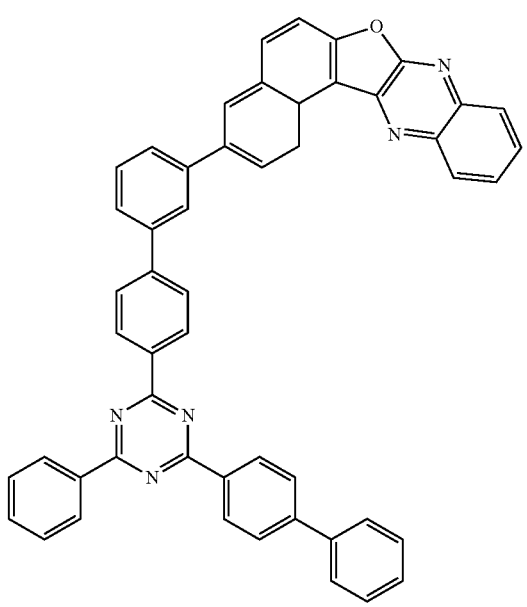
2-3-20
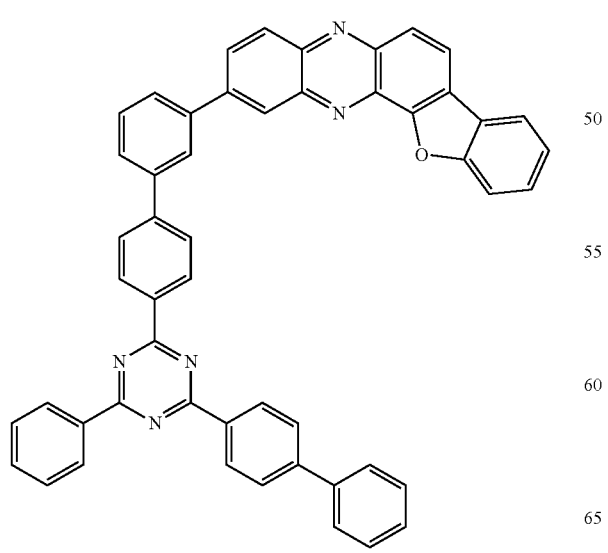
2-3-22
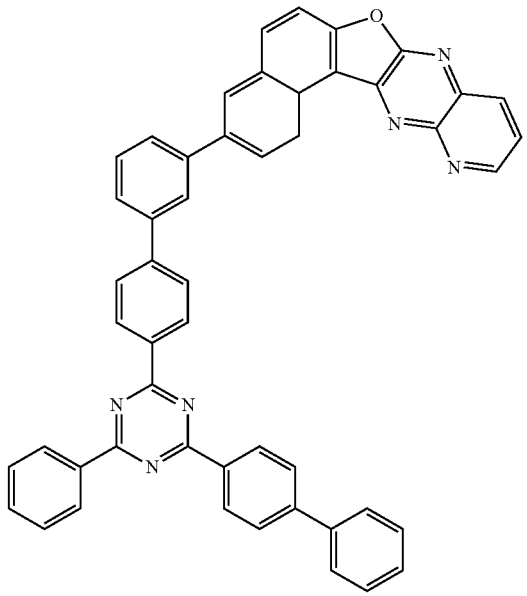

-continued
2-3-23
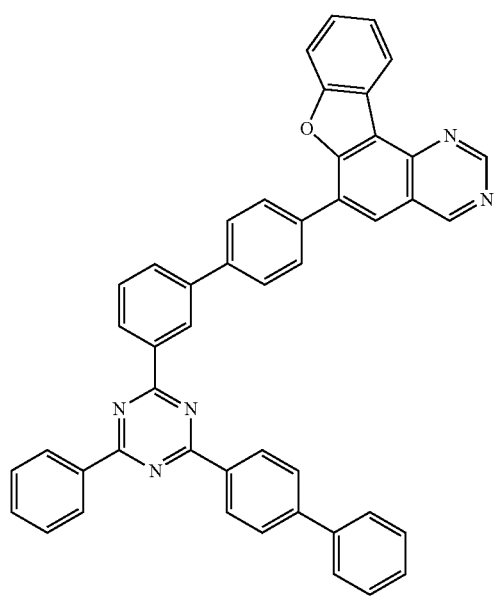
2-3-24
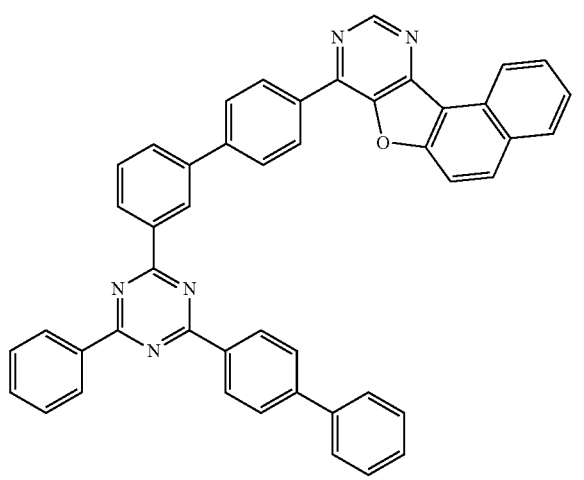
2-3-25
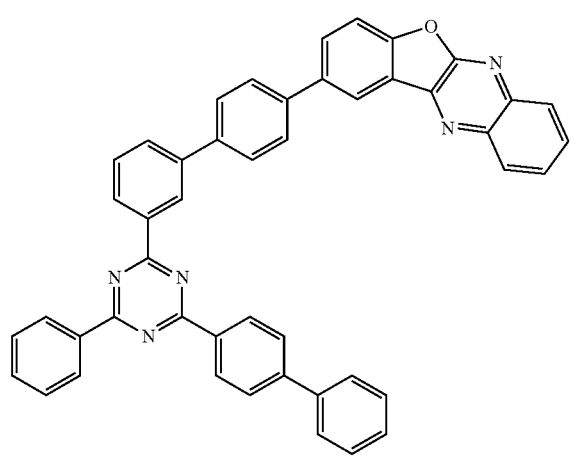
2-3-26
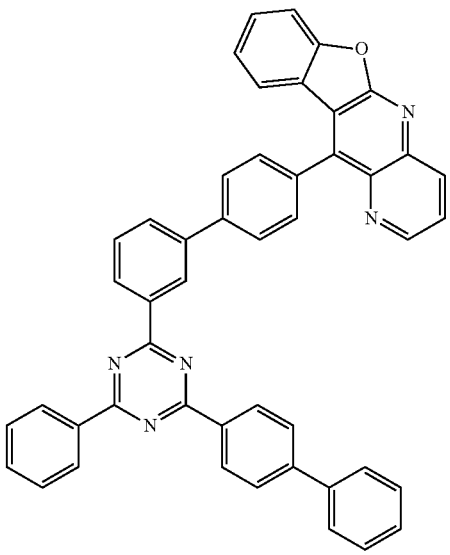
2-3-27
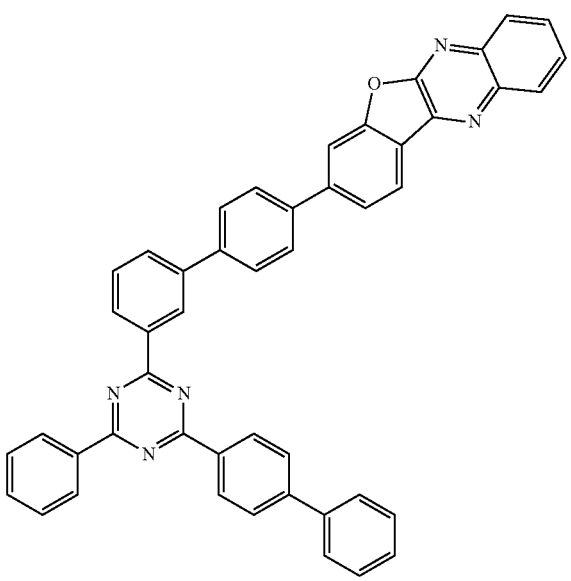
2-3-28
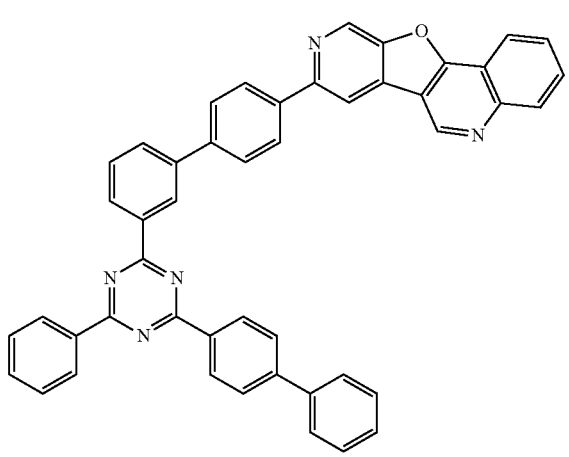

2-3-29
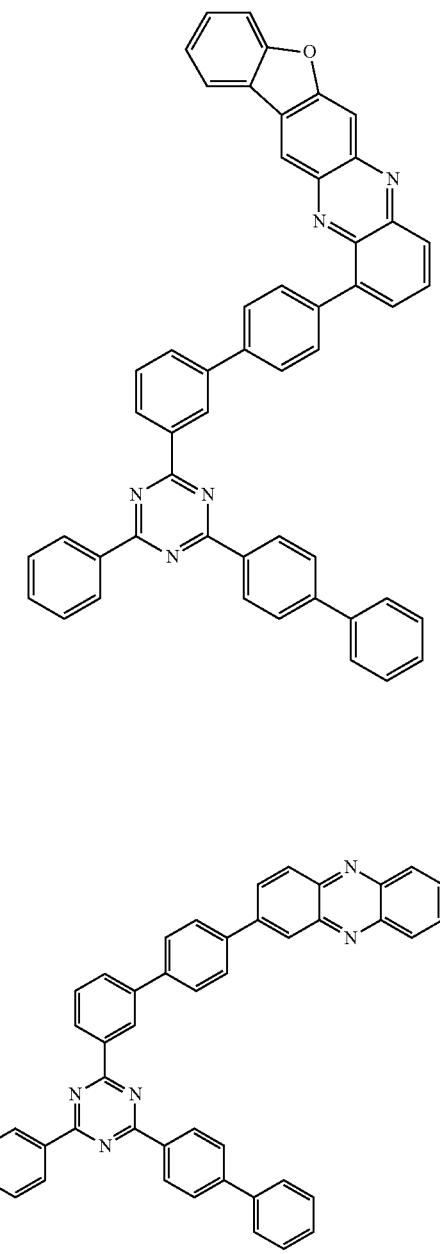
2-3-30
2-3-31
2-3-32
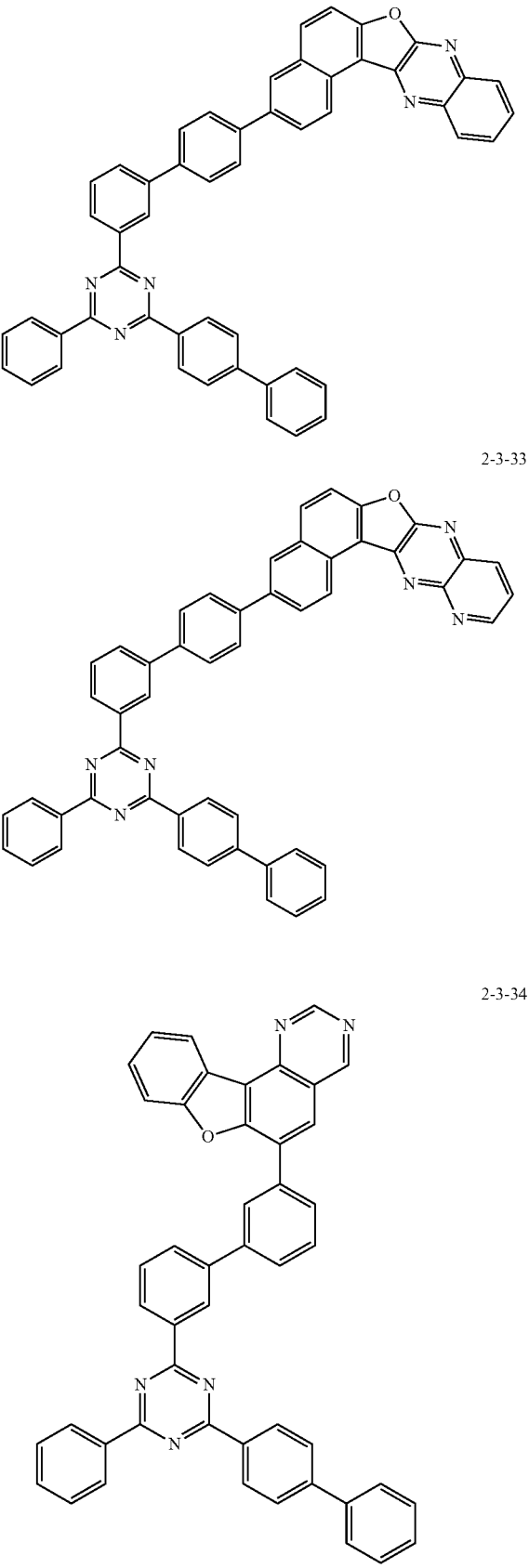
2-3-33
2-3-34

2-3-35
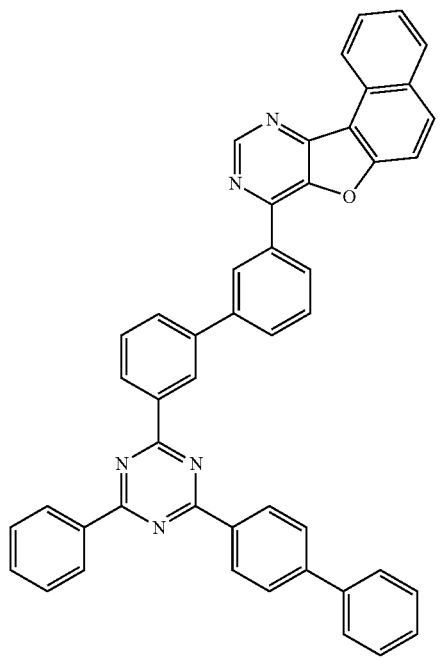
2-3-36
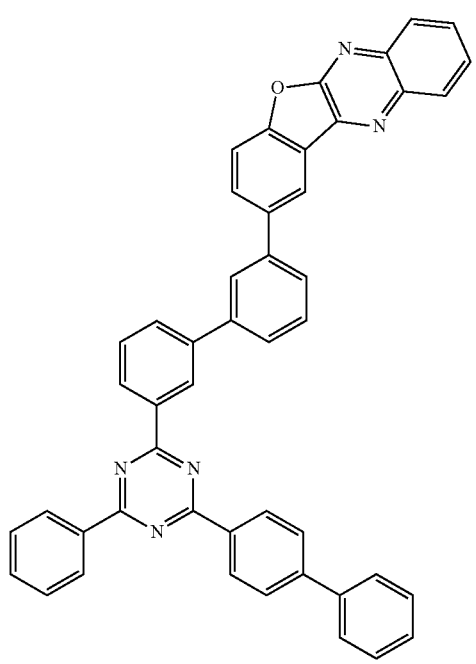
2-3-37
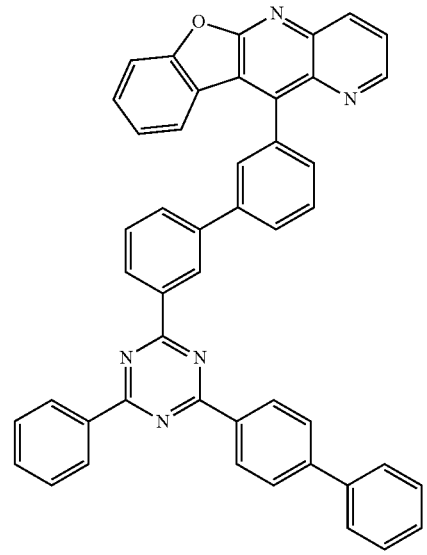
2-3-38
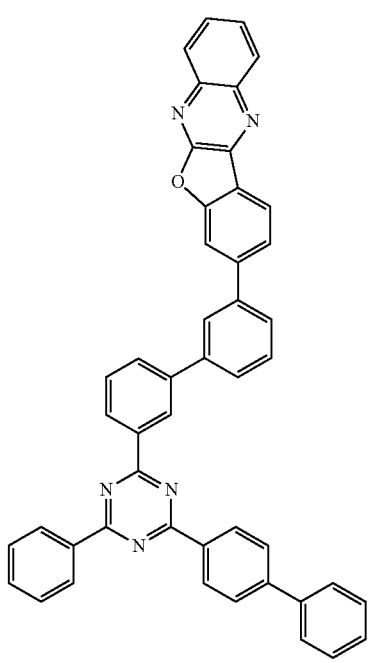

2-3-39
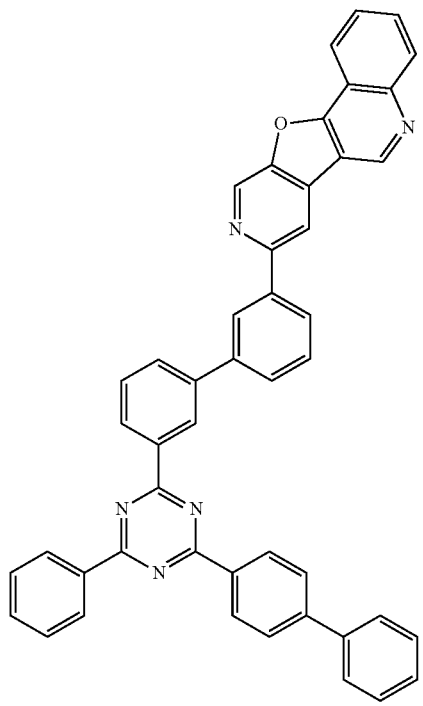
2-3-41
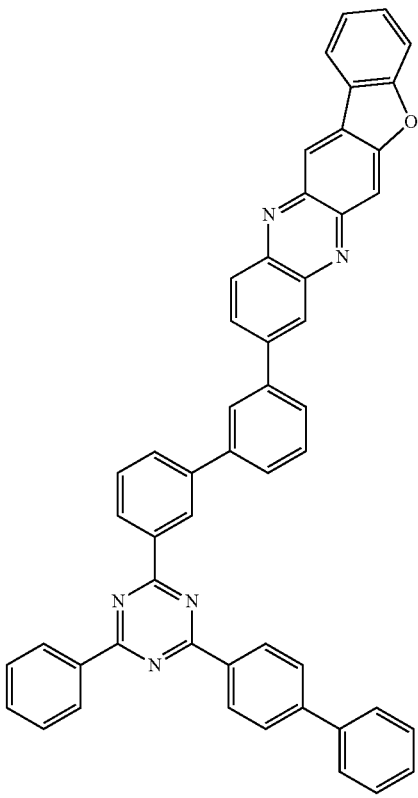
2-3-40
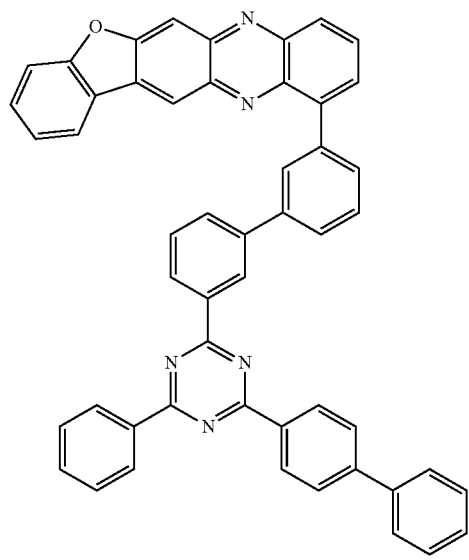
2-3-42
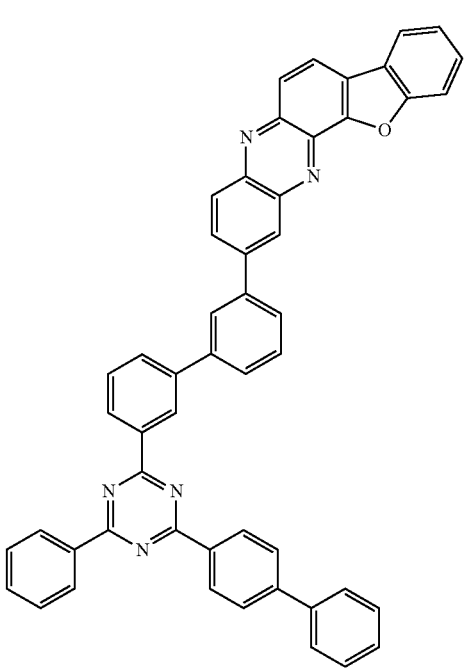

-continued
2-3-43
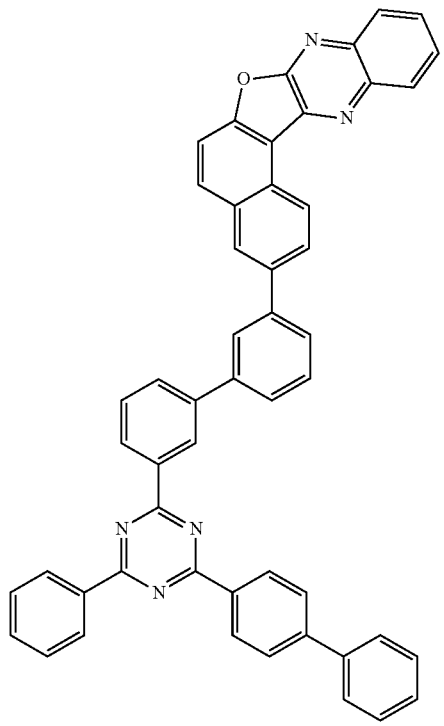
2-3-44
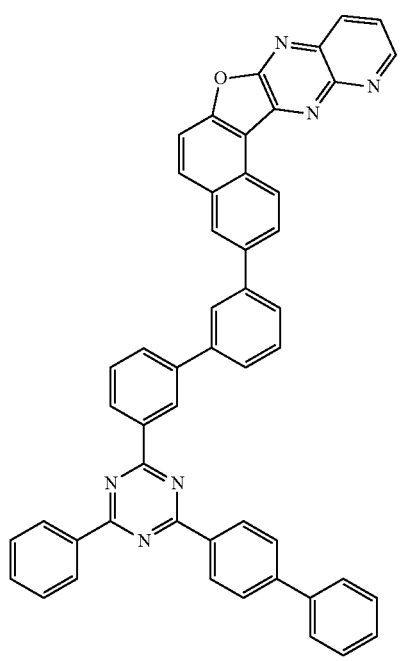
-continued
2-4-1
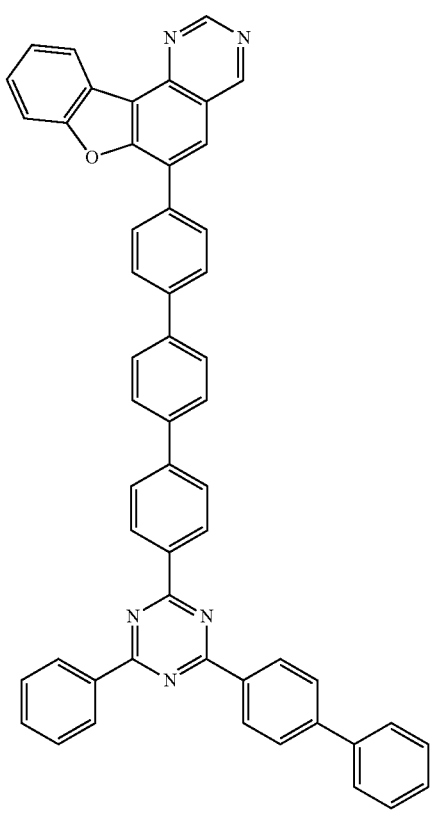
2-4-2
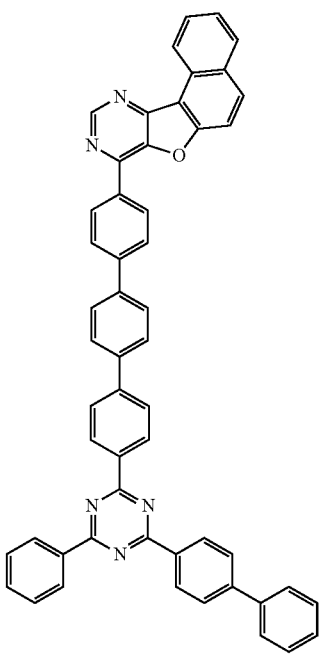

2-4-3
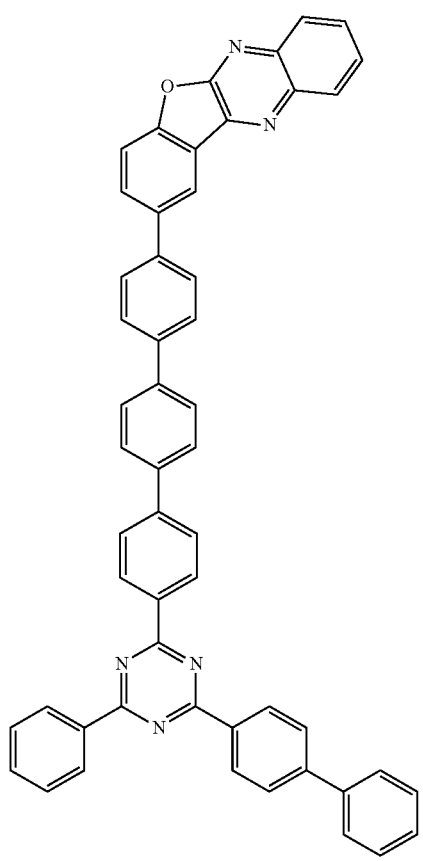
2-4-4
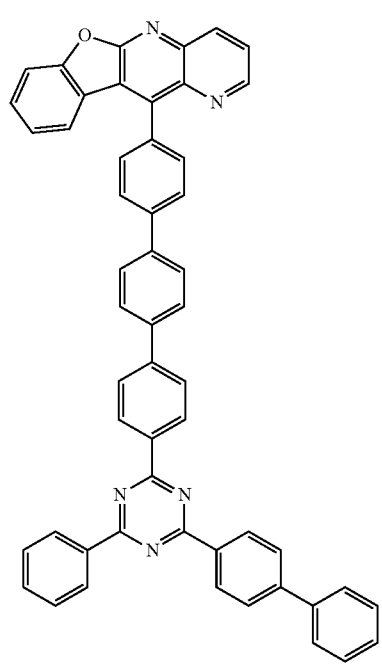
2-4-5
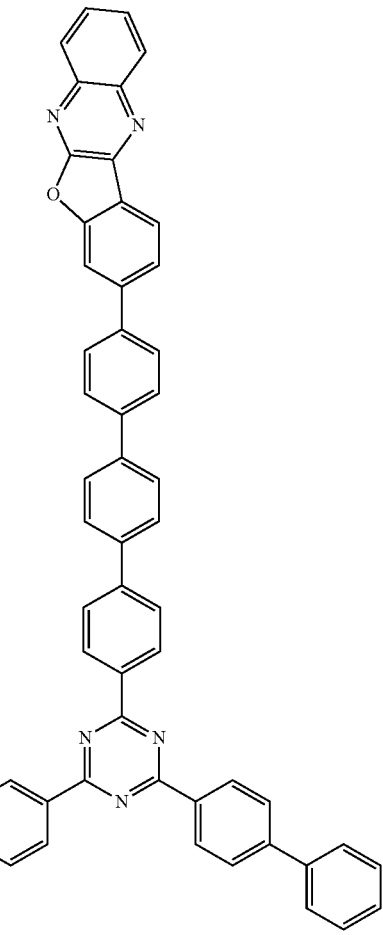
2-4-6
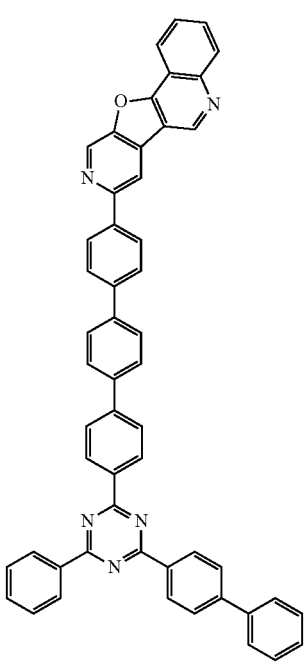

2-4-7
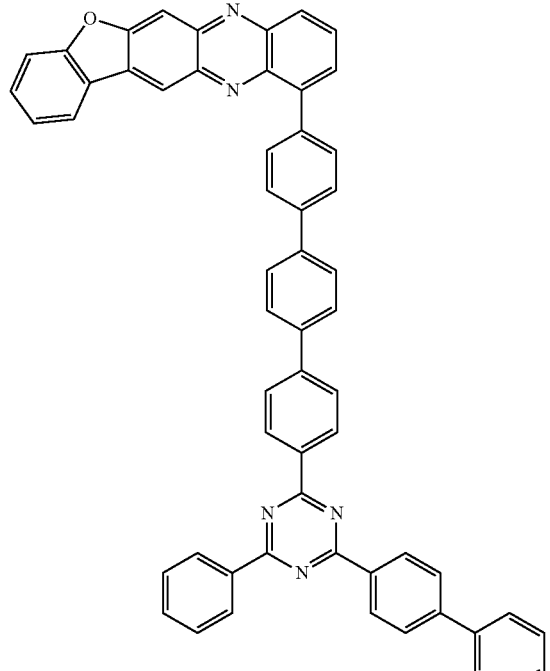
2-4-9
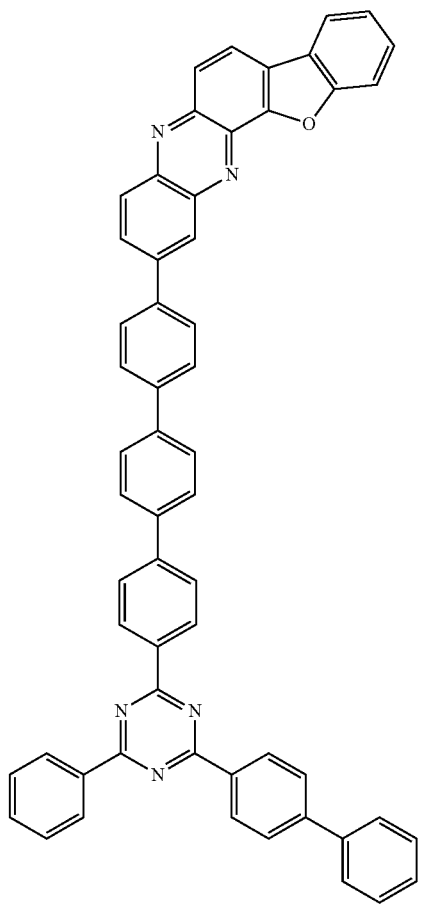
2-4-8
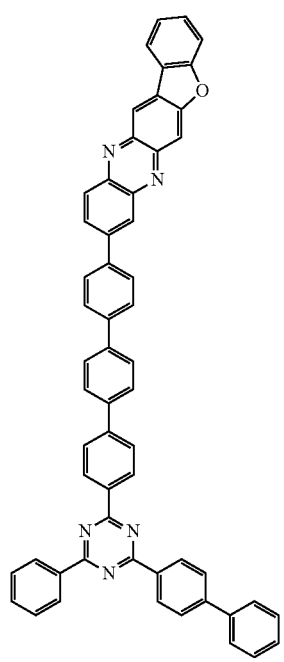
2-4-10
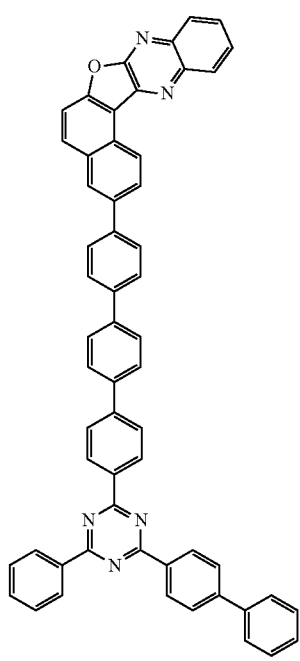

2-4-11
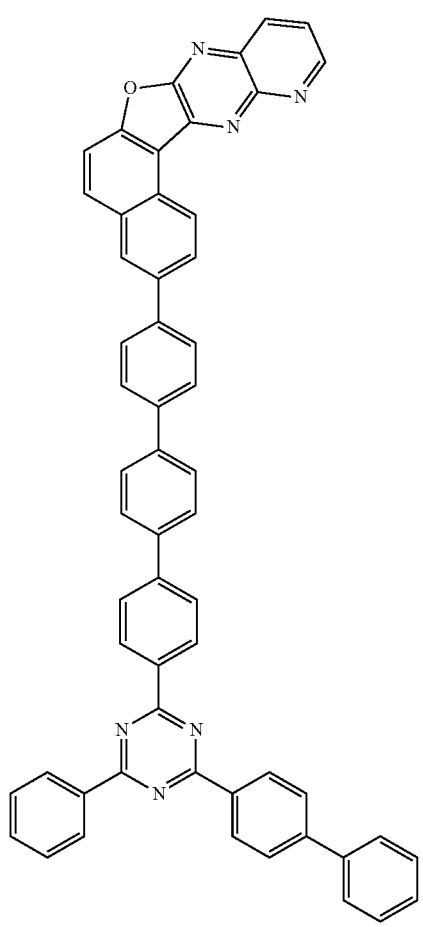
2-4-12
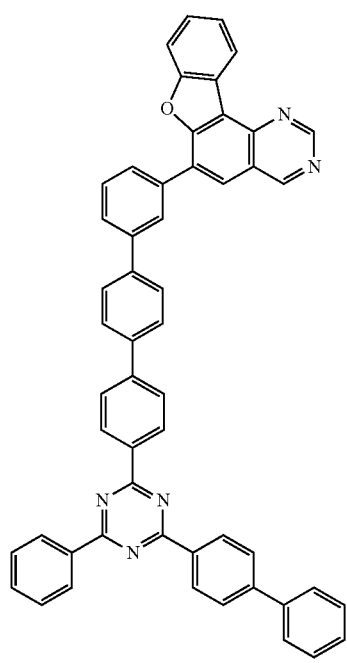
2-4-13
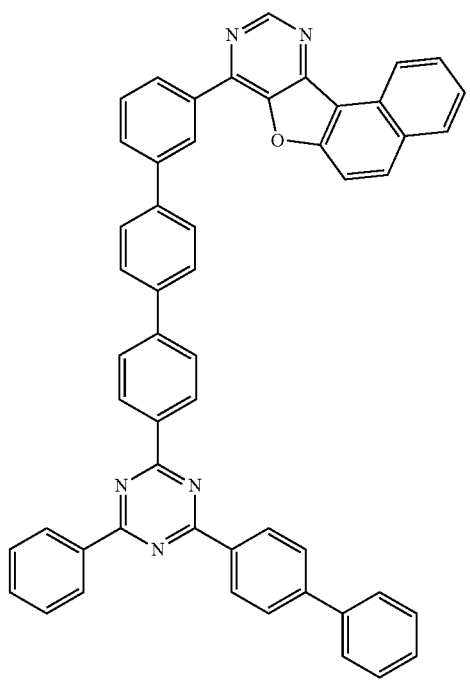
2-4-14
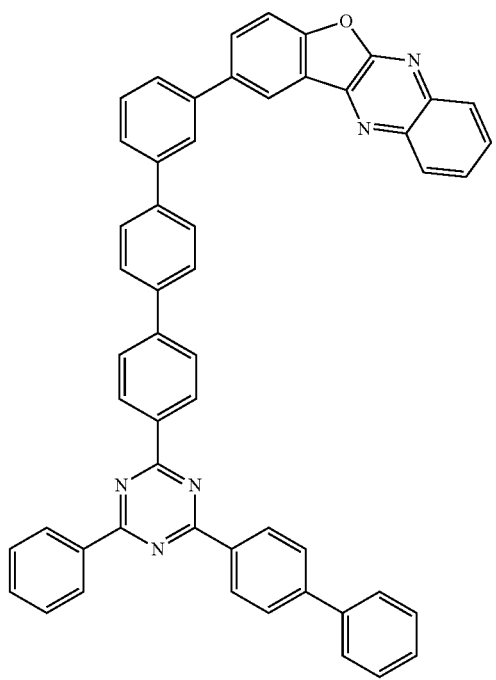

2-4-15
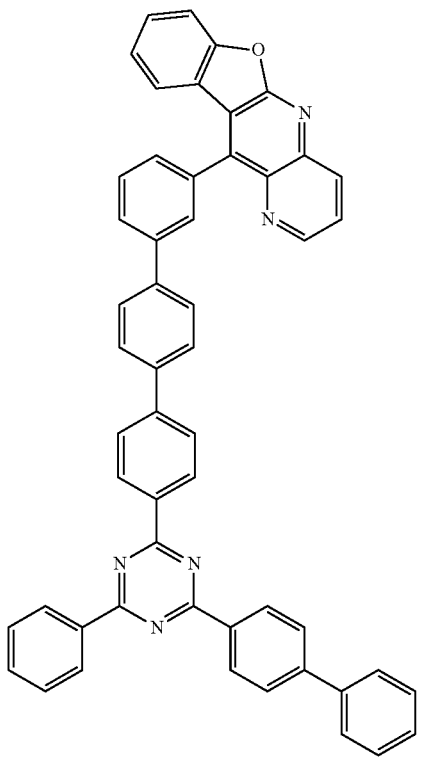
2-4-16
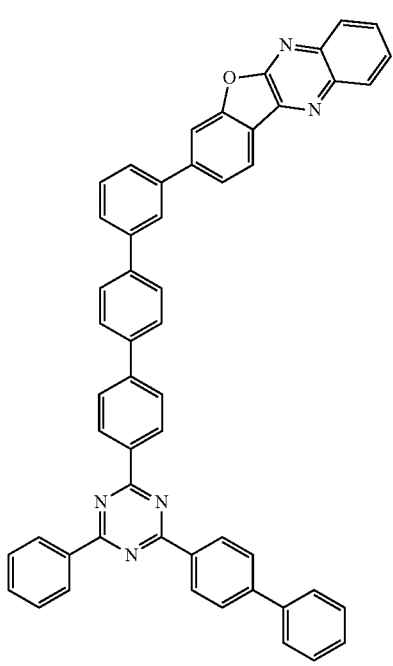
2-4-17
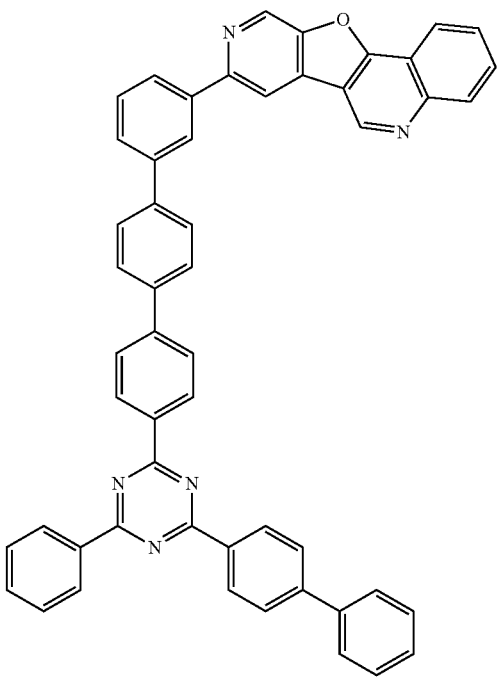
2-4-18
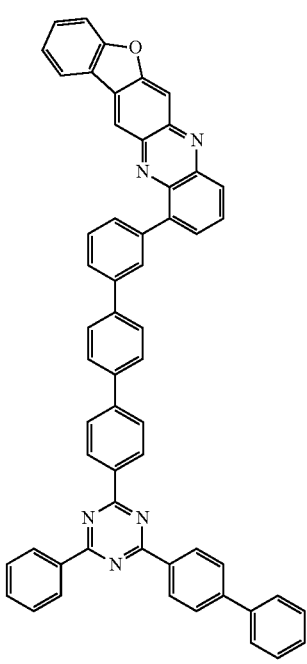

151
-continued
2-4-19
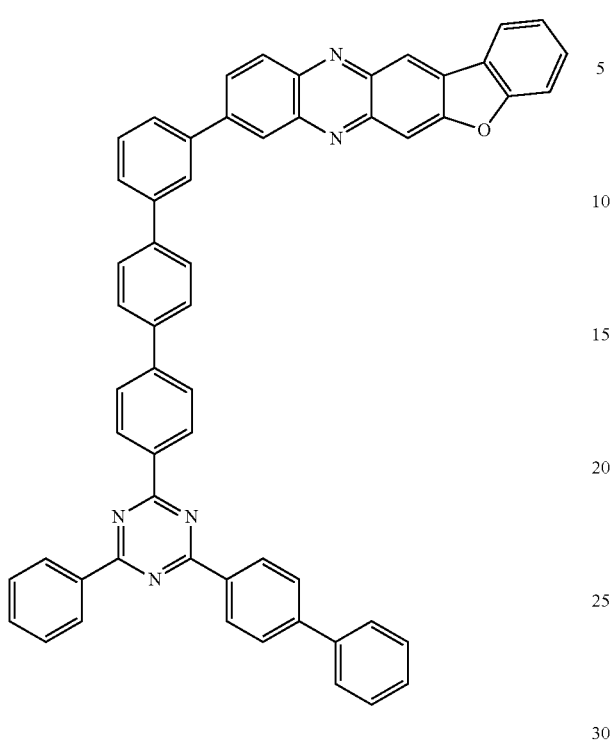
2-4-20
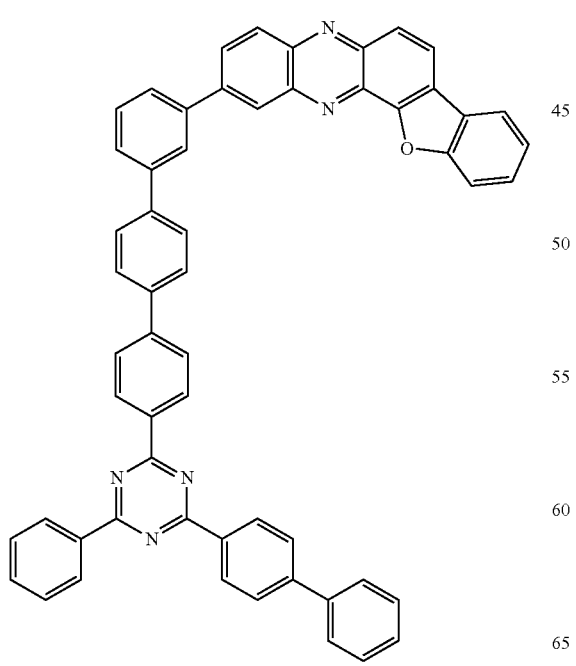
152
2-4-21
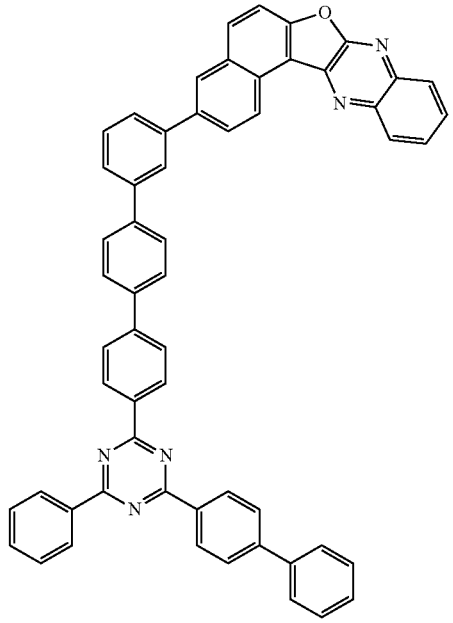
2-4-22
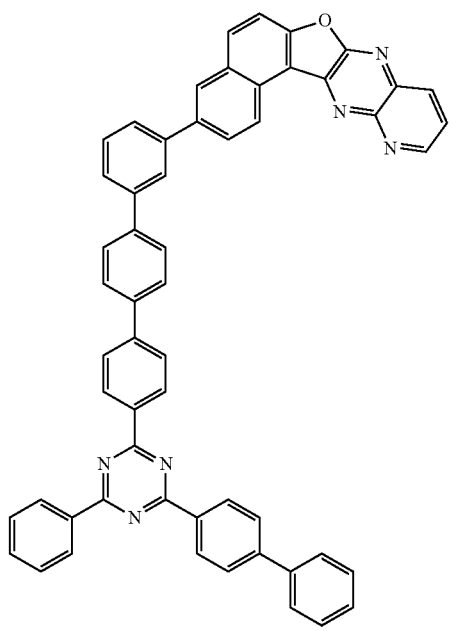

153
-continued
2-4-23
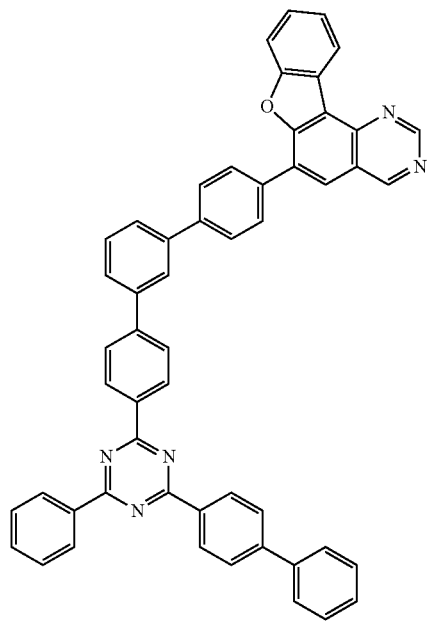
2-4-24
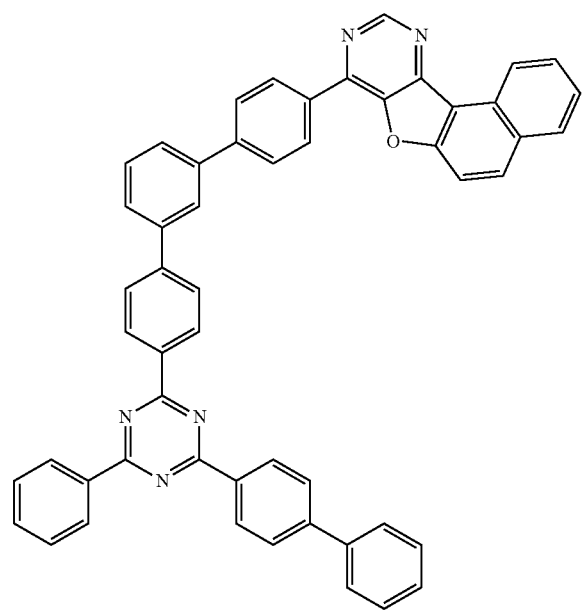
154
-continued
2-4-25
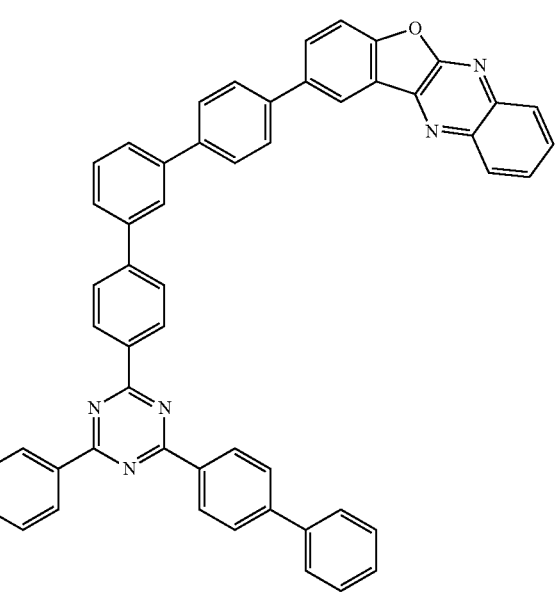
2-4-26
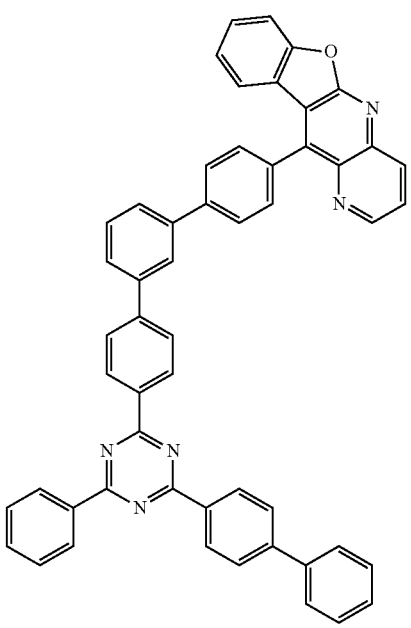

2-4-27
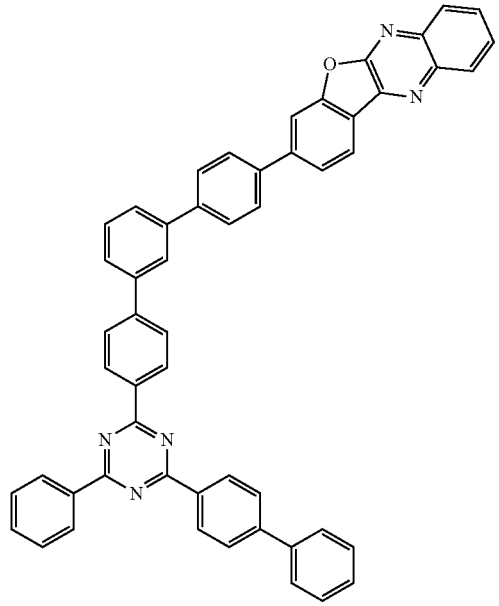
2-4-29
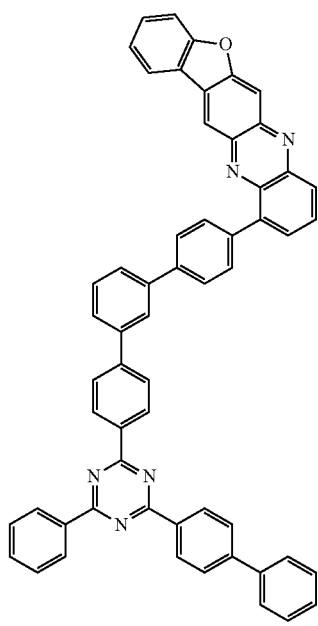
2-4-28
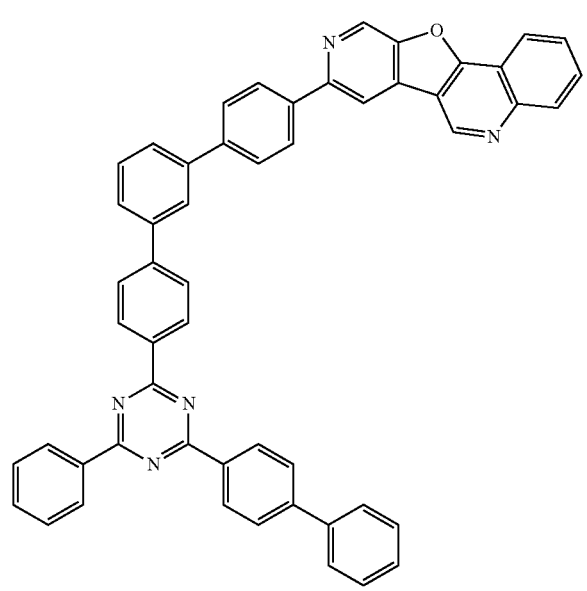
2-4-30
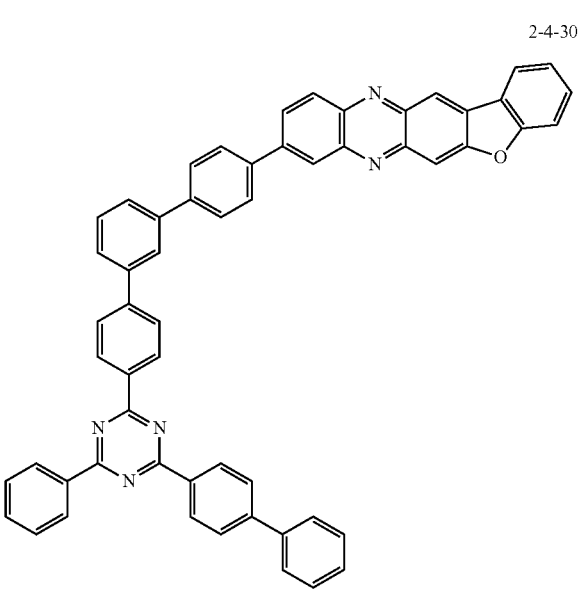

-continued
2-4-31
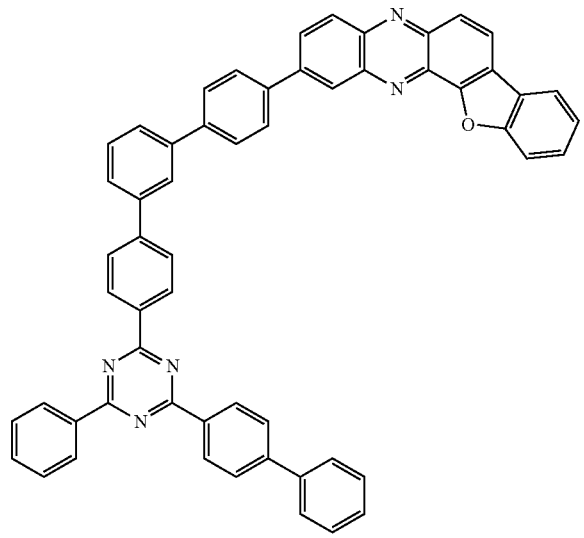
2-4-33
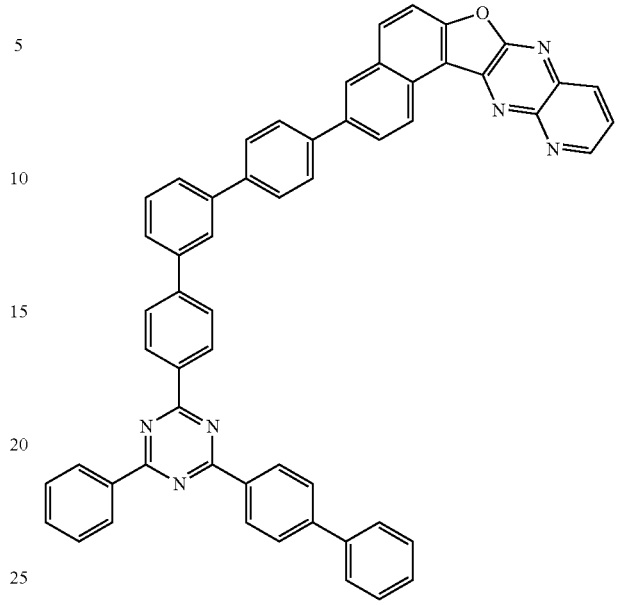
2-4-32
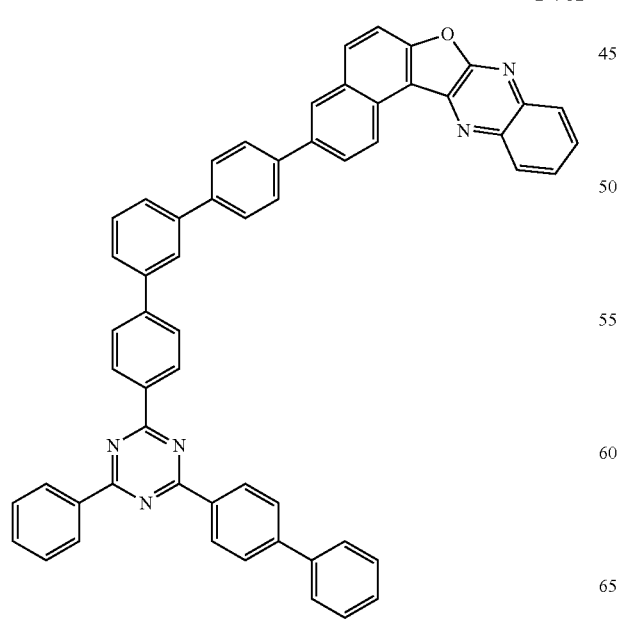
2-4-34
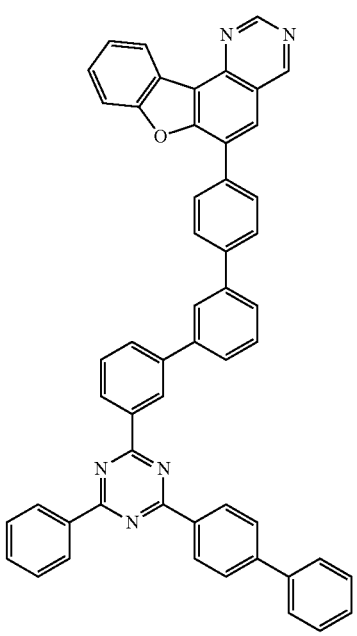

159
-continued
2-4-35
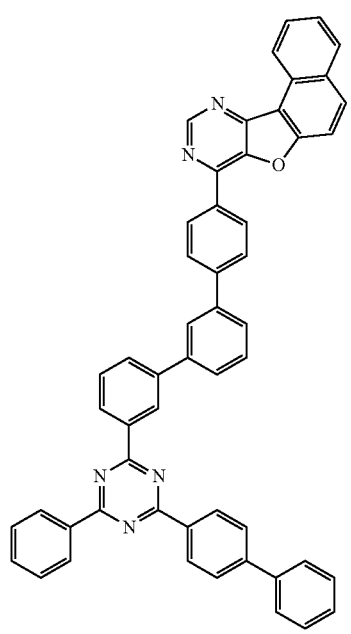
2-4-36
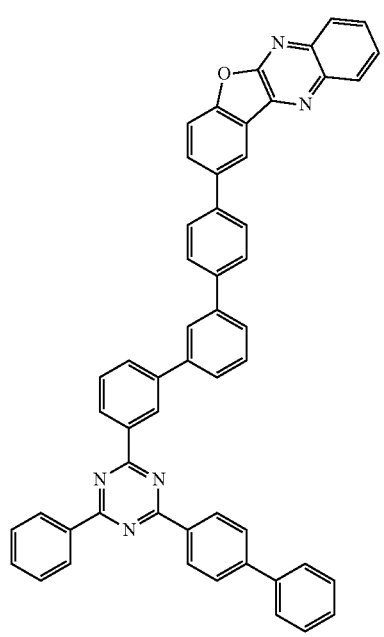
160
-continued
2-4-37
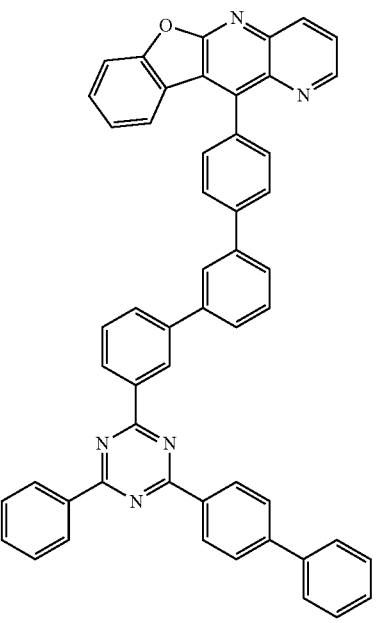
2-4-38
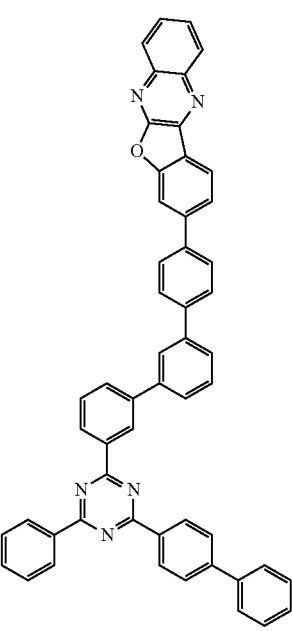

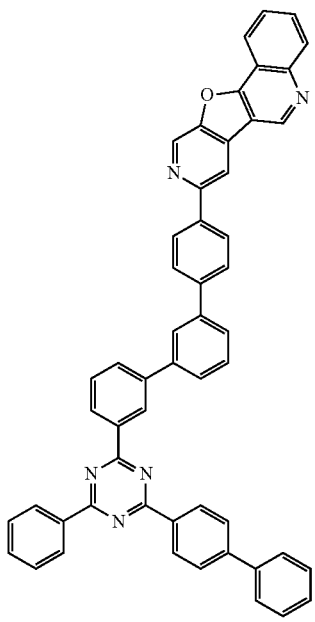
2-4-39
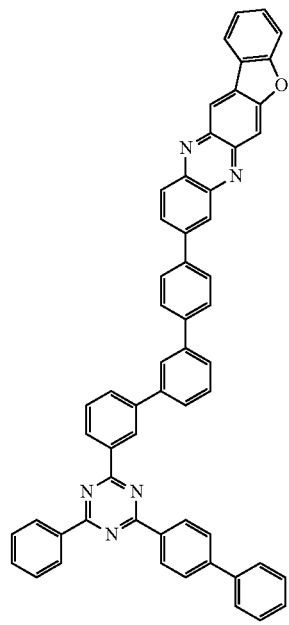
2-4-41
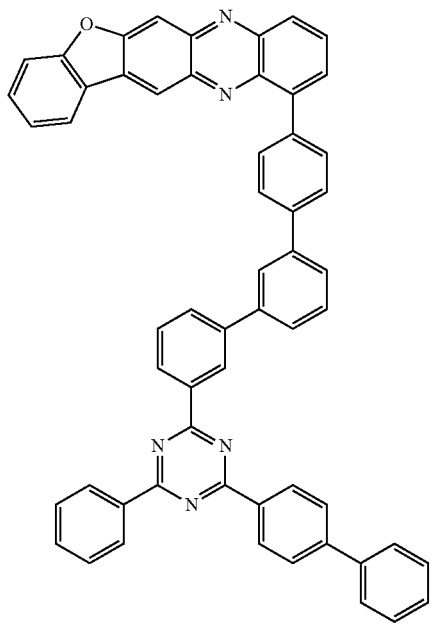
2-4-40
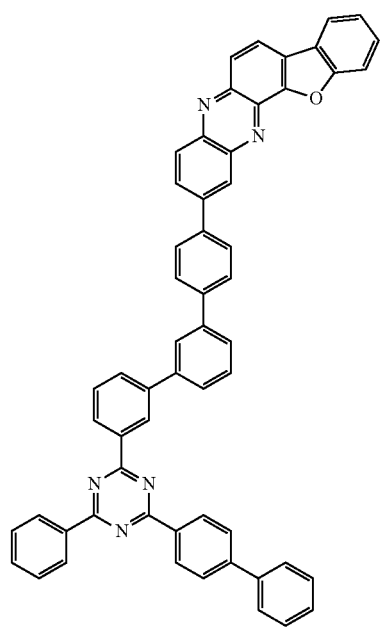
2-4-42

2-4-43
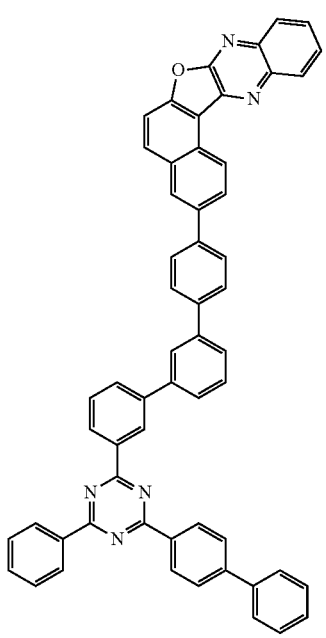
2-4-44
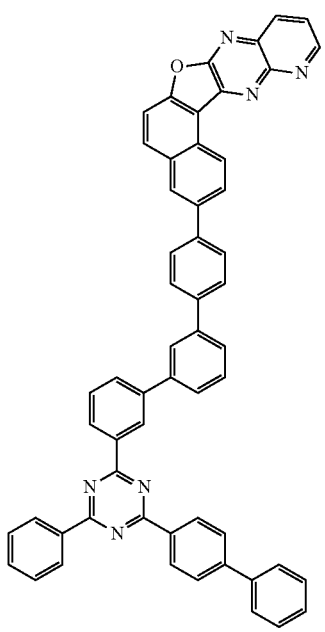
2-4-45
2-4-46
2-4-47
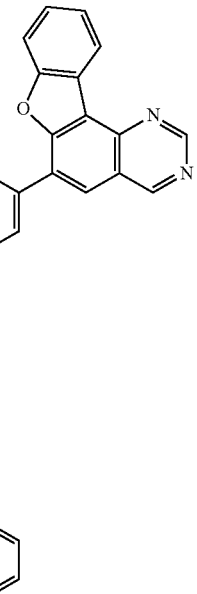

2-4-48
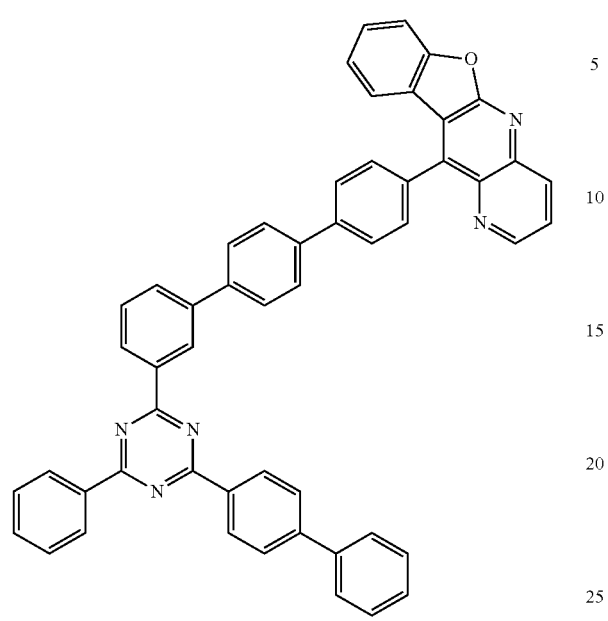
2-4-49
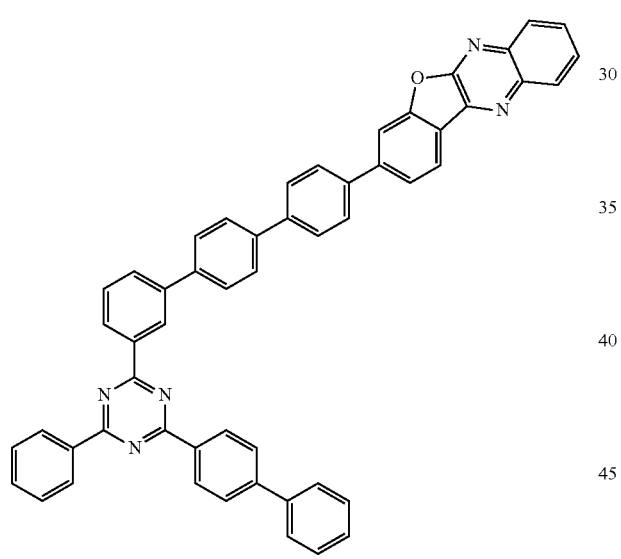
2-4-50
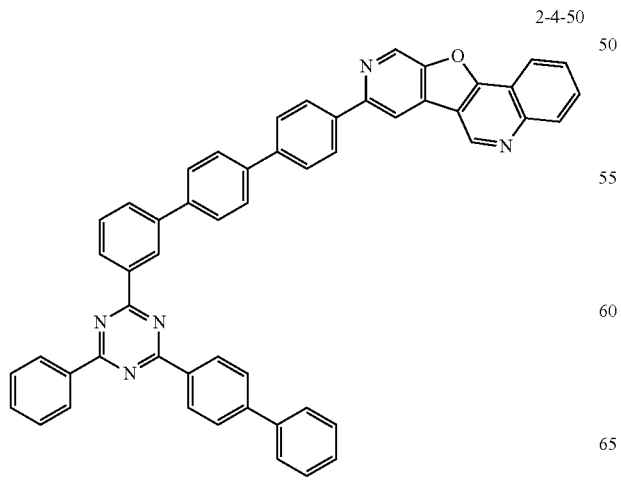
2-4-51
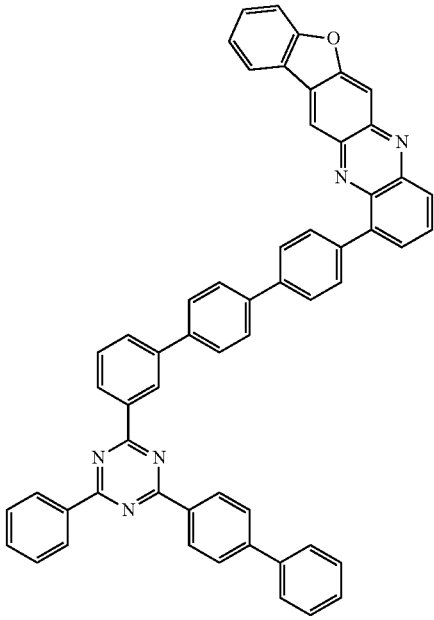
2-4-52
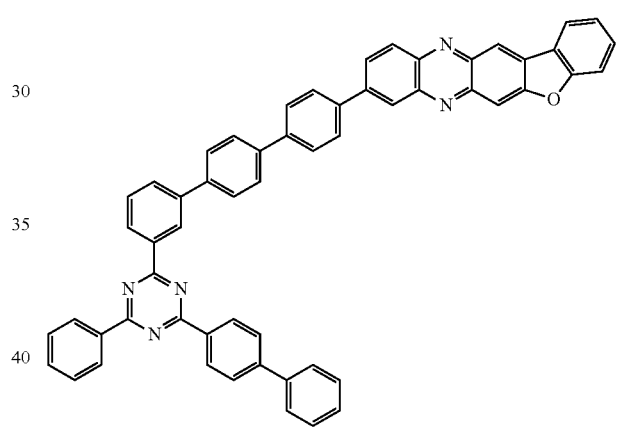
2-4-53
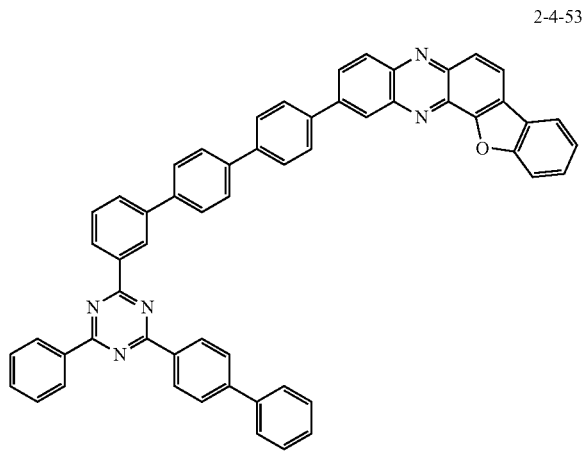

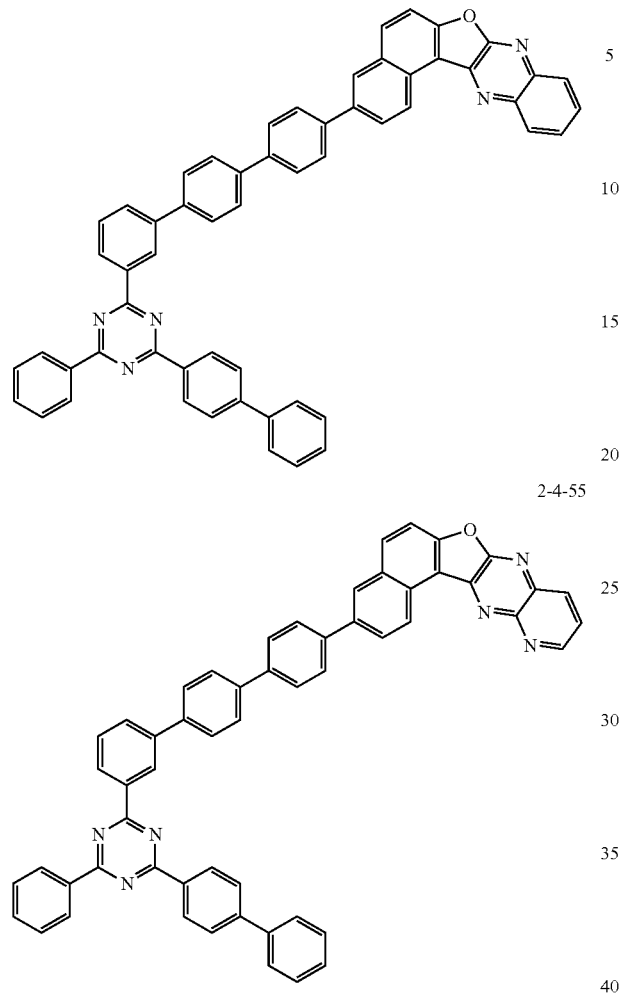
2-4-54
2-4-55
2-4-56
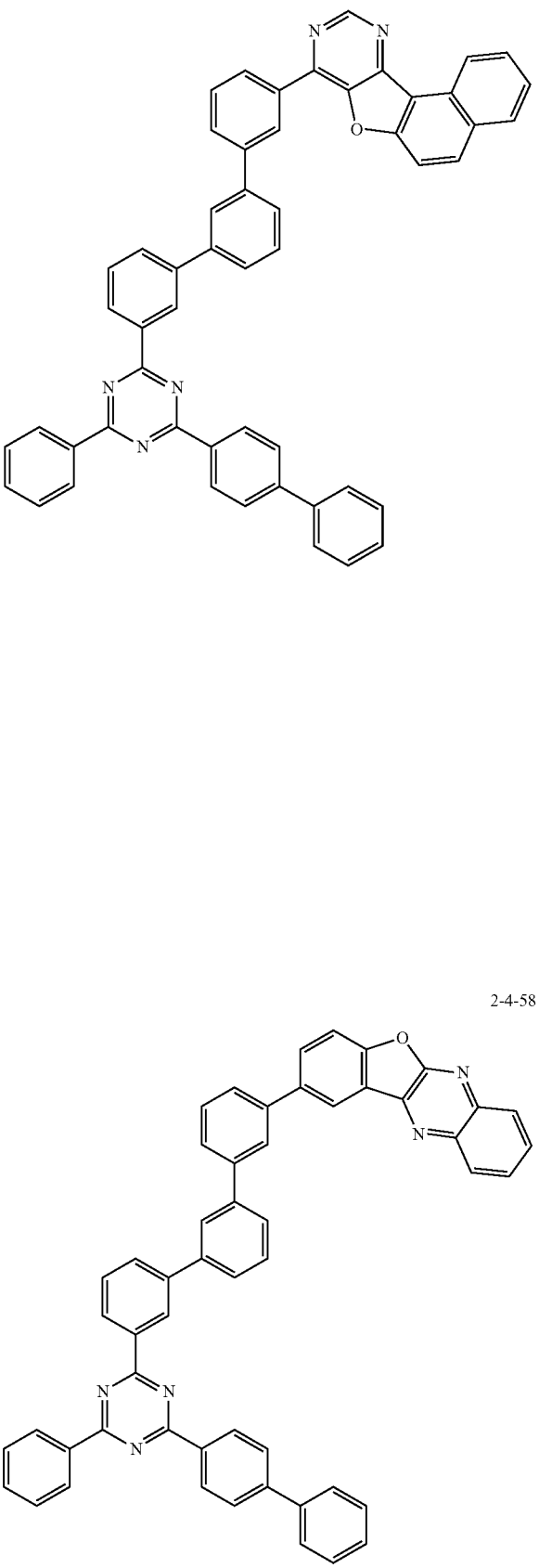
2-4-57
2-4-58

2-4-59
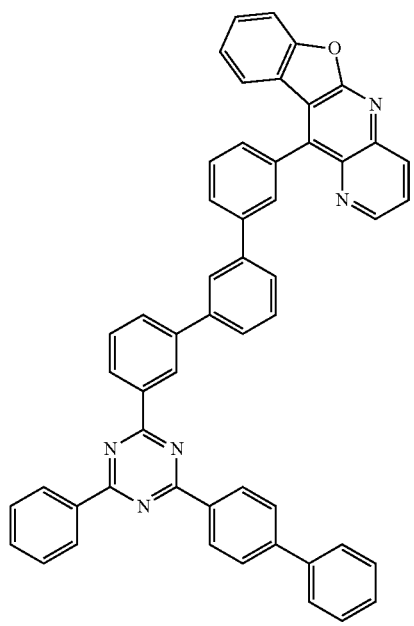
2-4-60
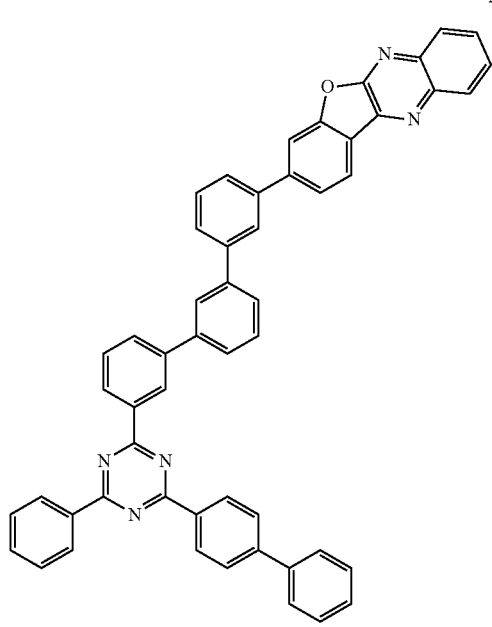
2-4-61
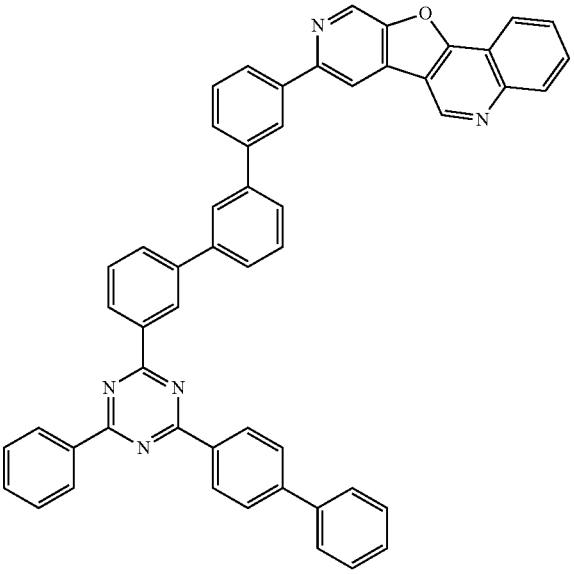
2-4-62
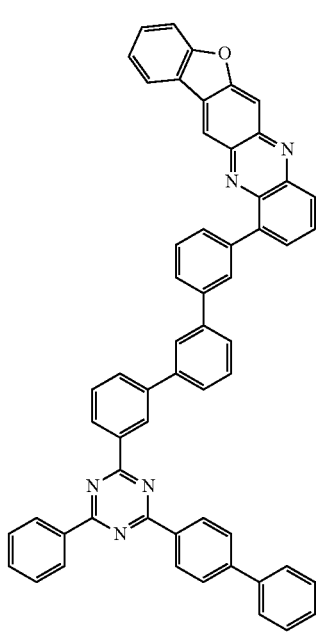

-continued
2-4-63
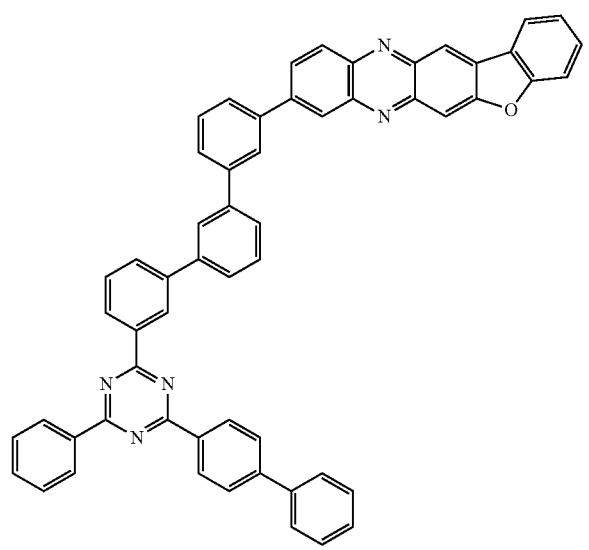
2-4-65
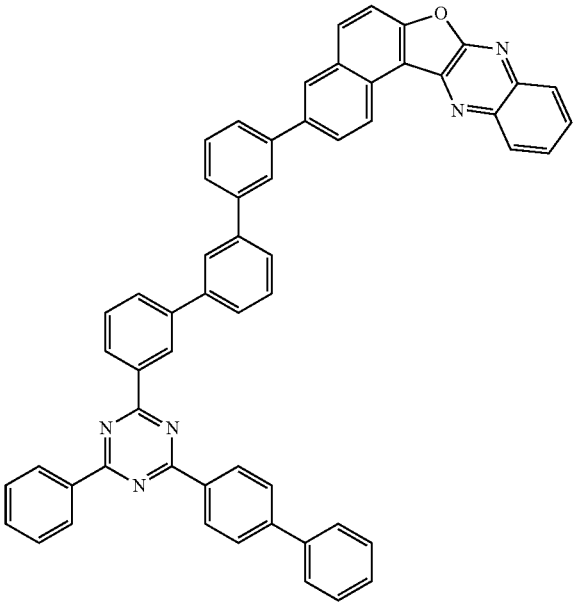
2-4-64
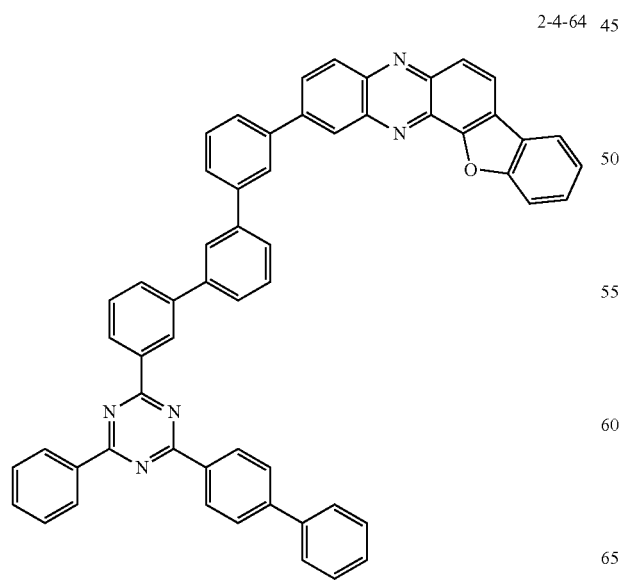
2-4-66
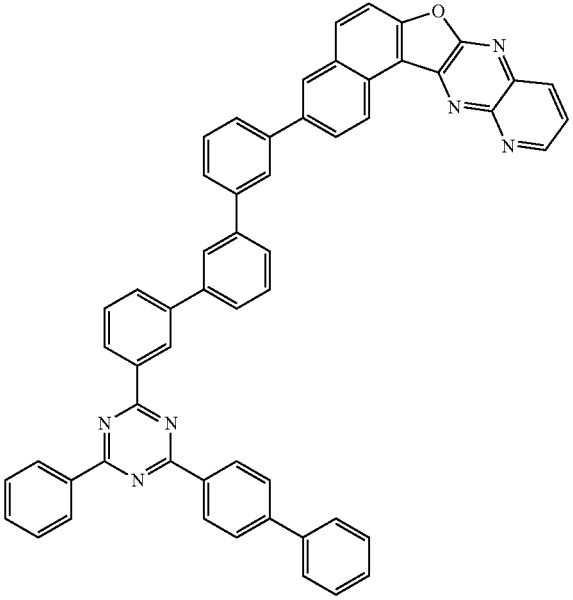

2-4-67
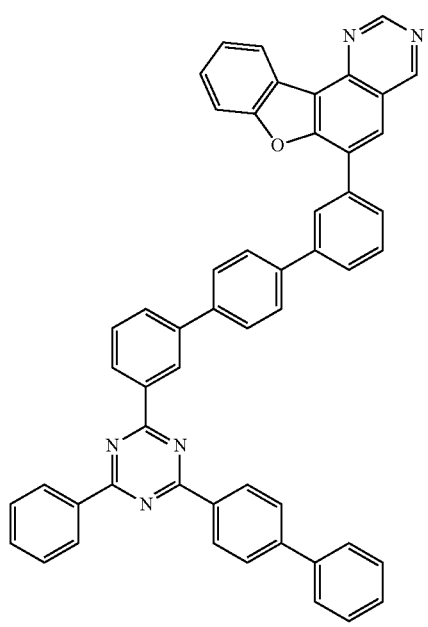
2-4-68
2-4-69
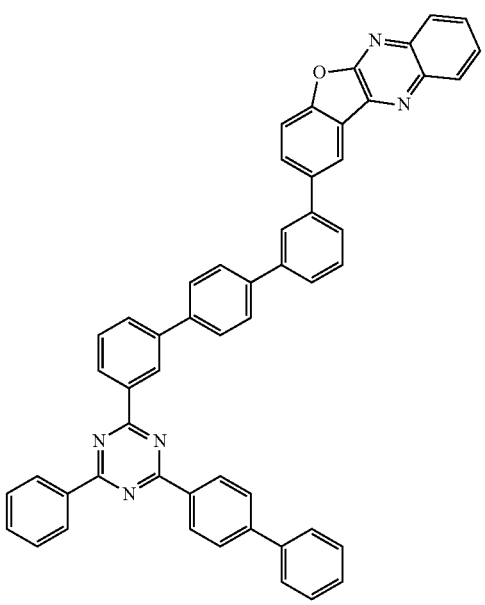
2-4-70

-continued
2-4-71
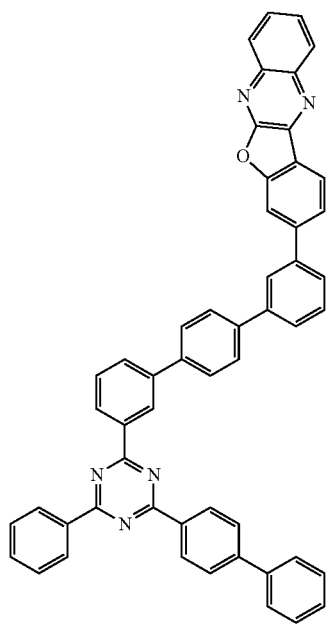
2-4-73
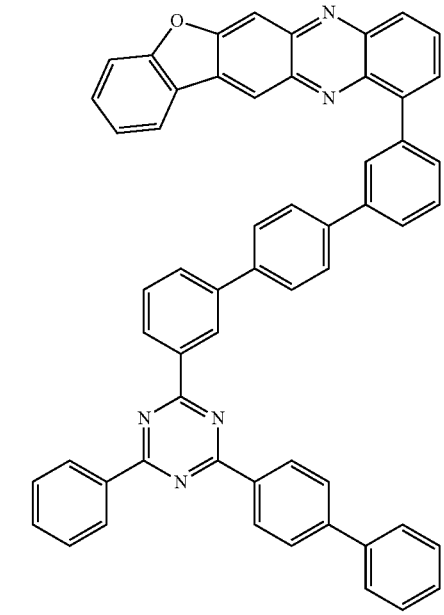
2-4-72
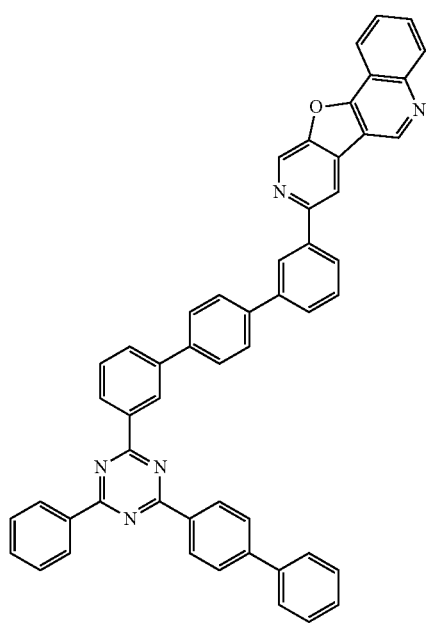
2-4-74
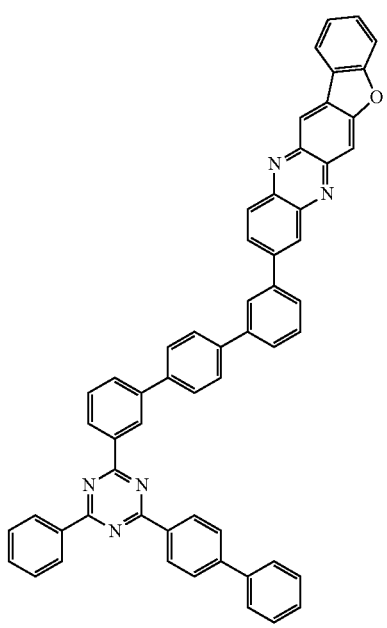

2-4-75
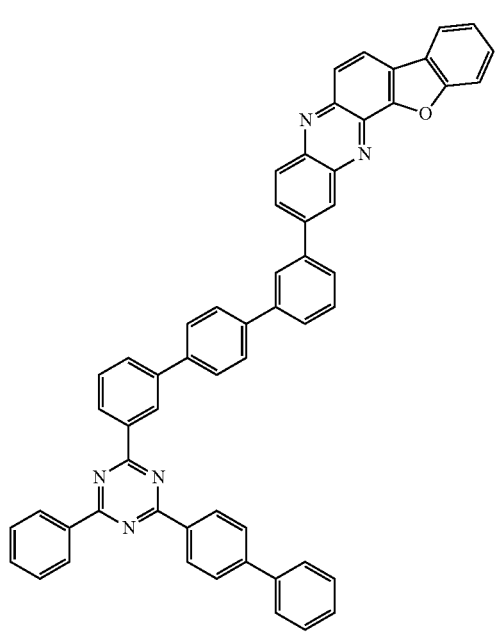
2-4-77
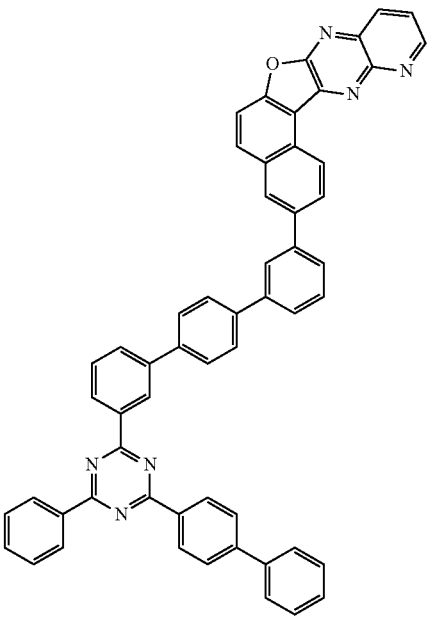
2-4-76
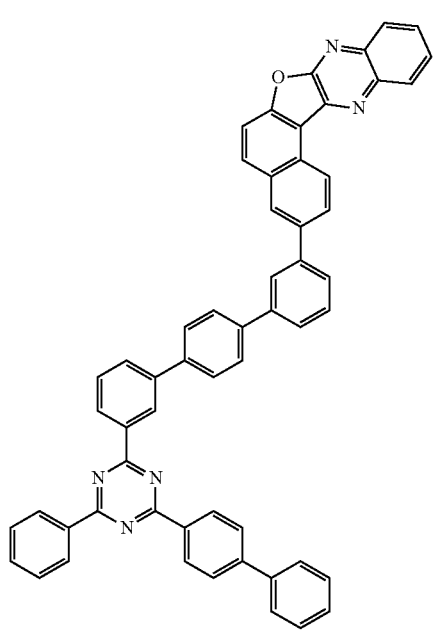
2-4-78
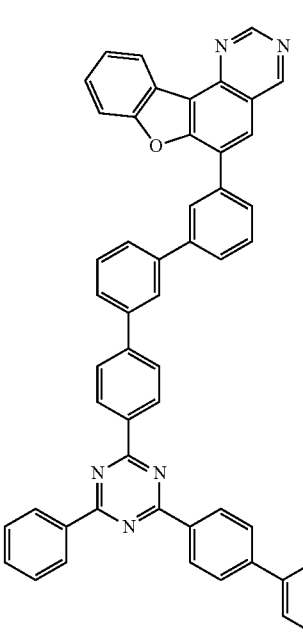

2-4-79
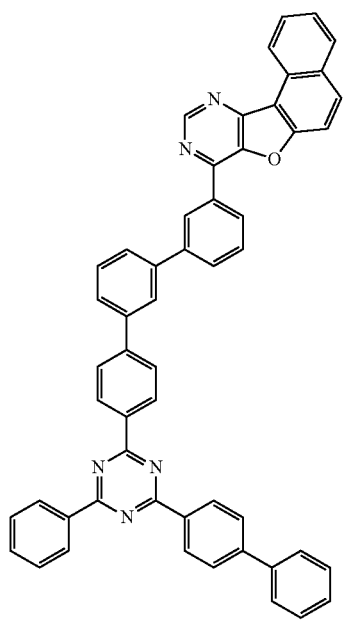
2-4-81
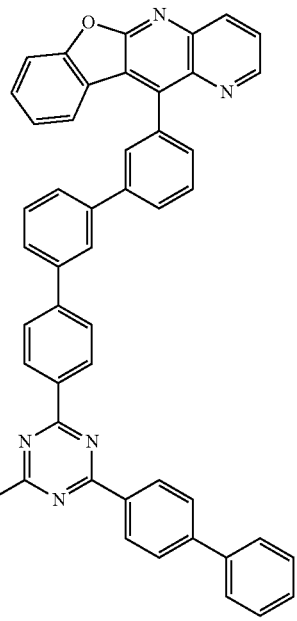
2-4-80
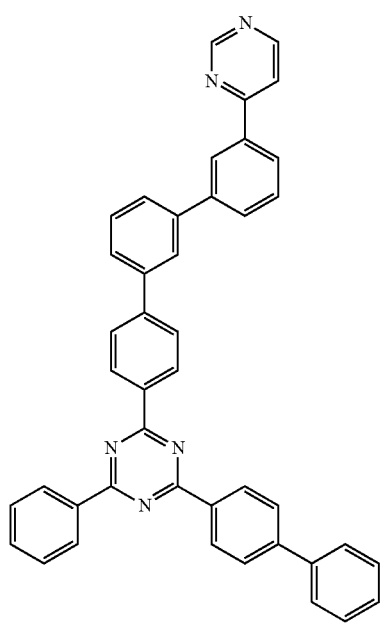
2-4-82
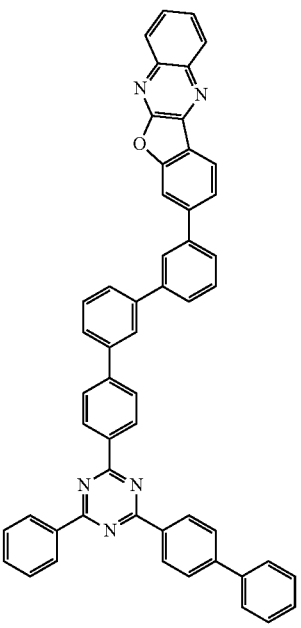

2-4-83
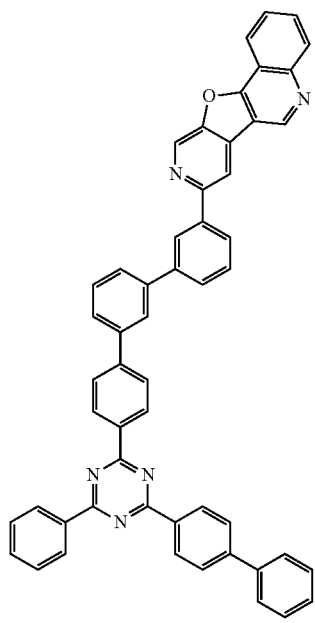
2-4-85
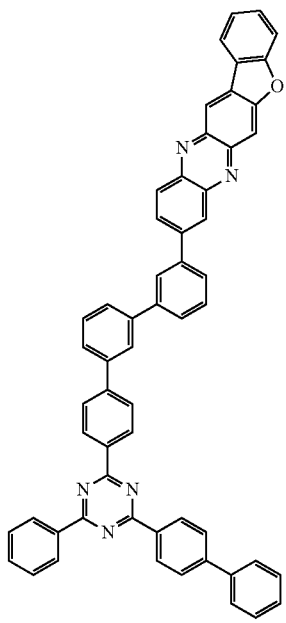
2-4-84
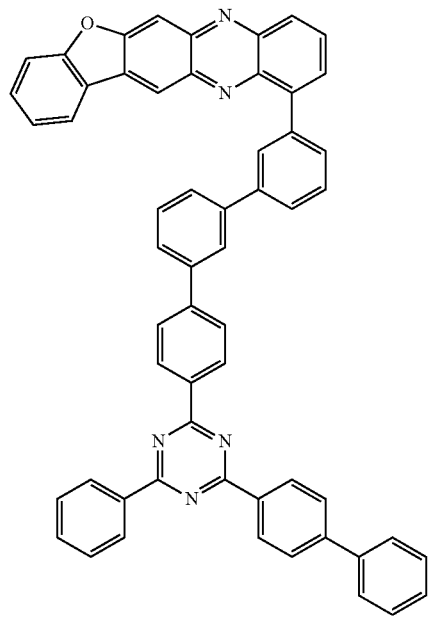
2-4-86
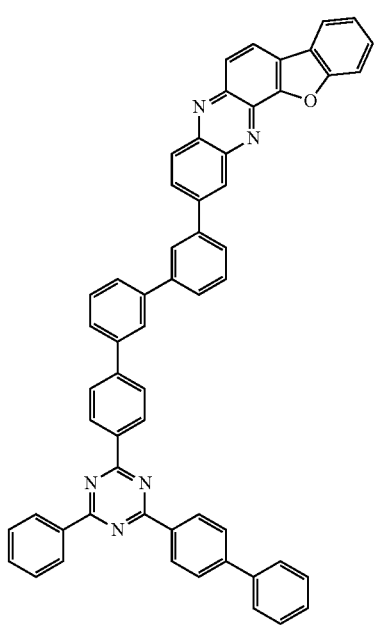

2-4-87
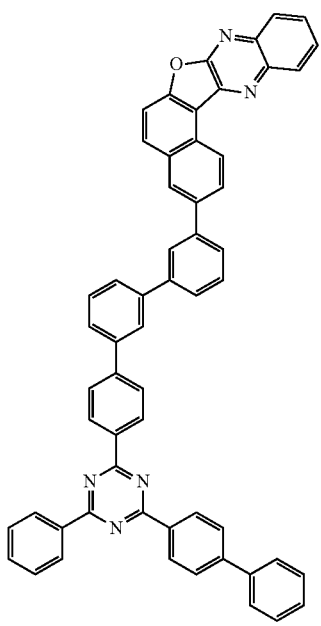
2-4-88
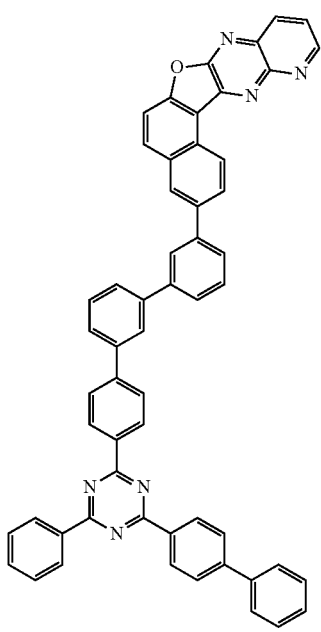
3-1-1
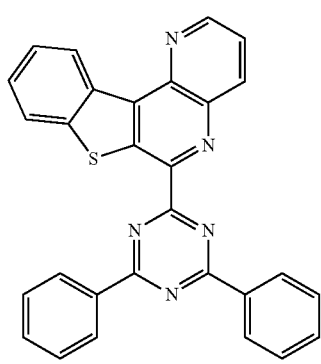
3-1-2
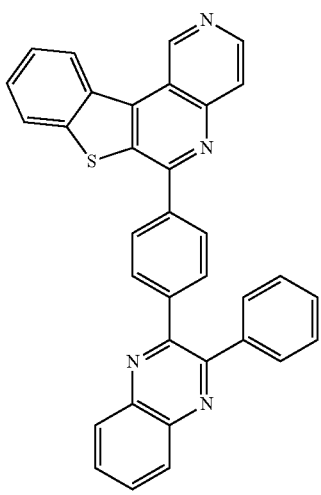
3-1-3
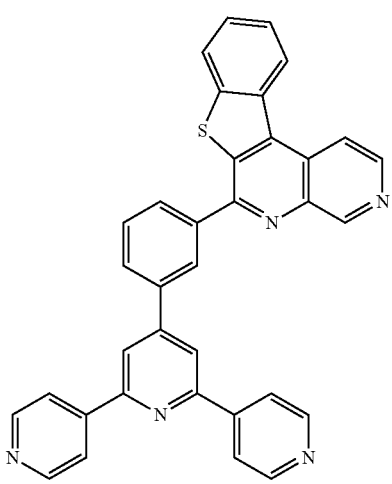
3-1-4

185
-continued
3-1-5
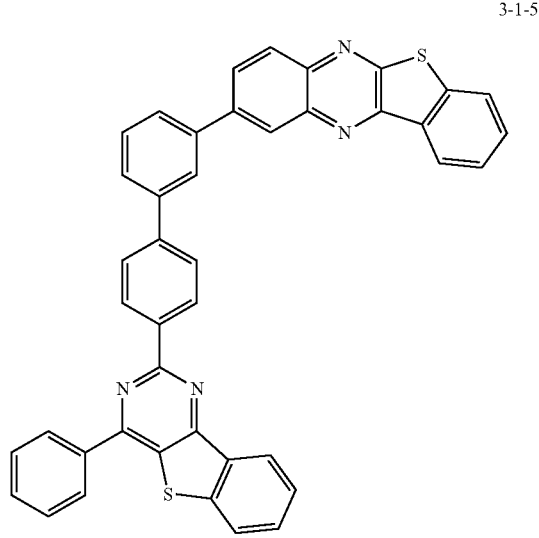
3-1-6
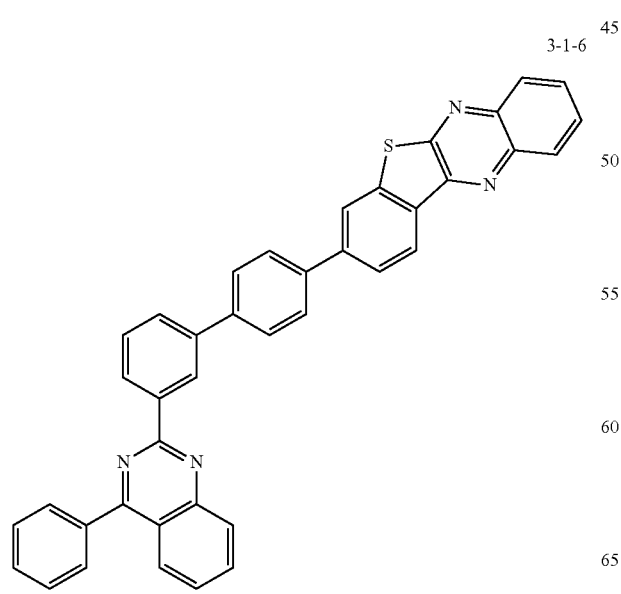
186
-continued
3-1-7
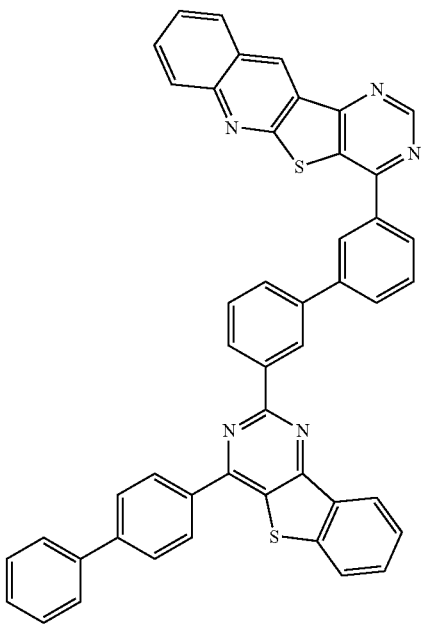
3-1-8
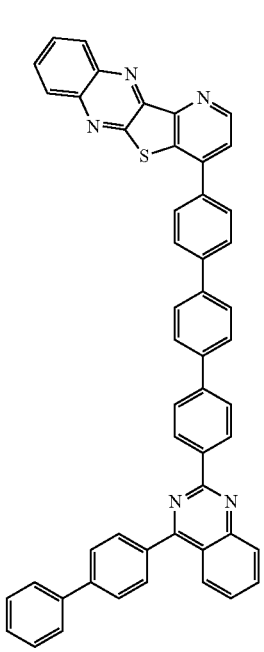

-continued
3-1-9
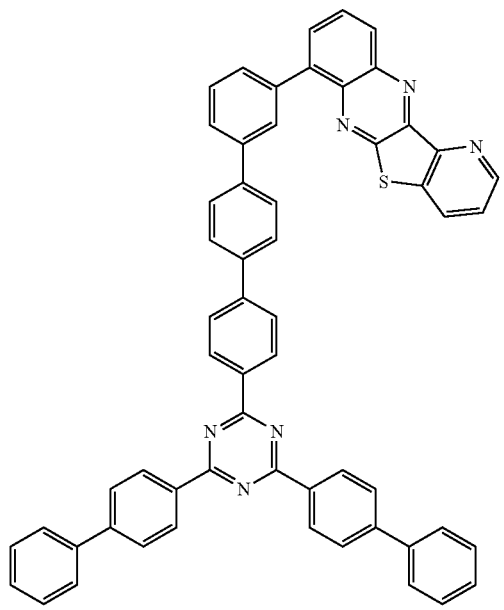
3-1-10
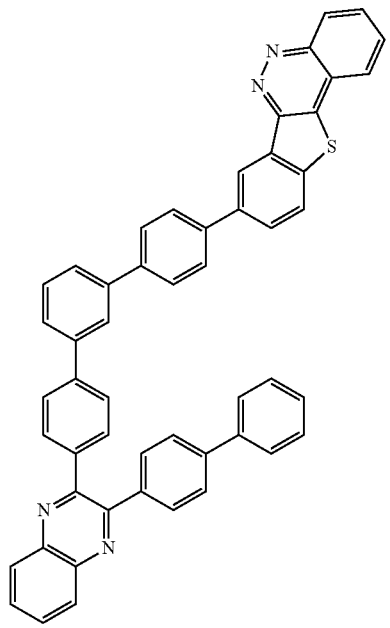
-continued
3-1-11
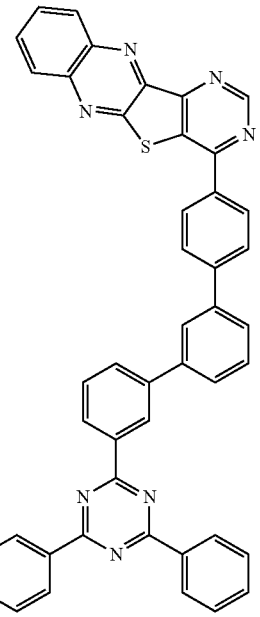
3-1-12
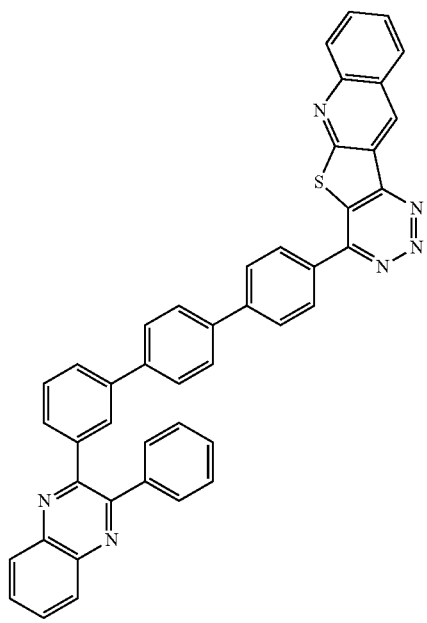

-continued
3-1-13
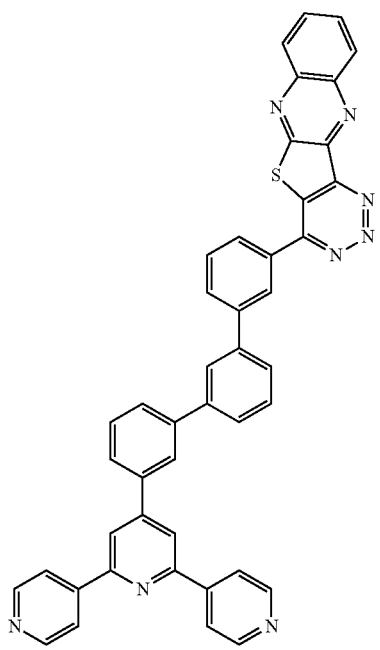
3-1-14
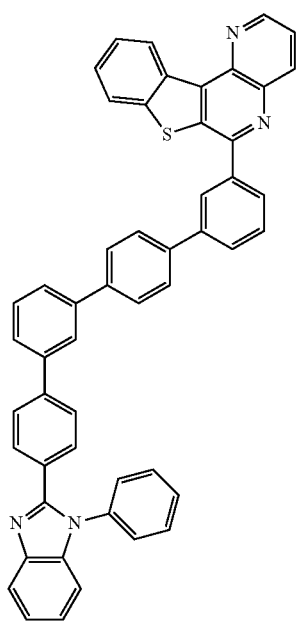
-continued
3-1-15
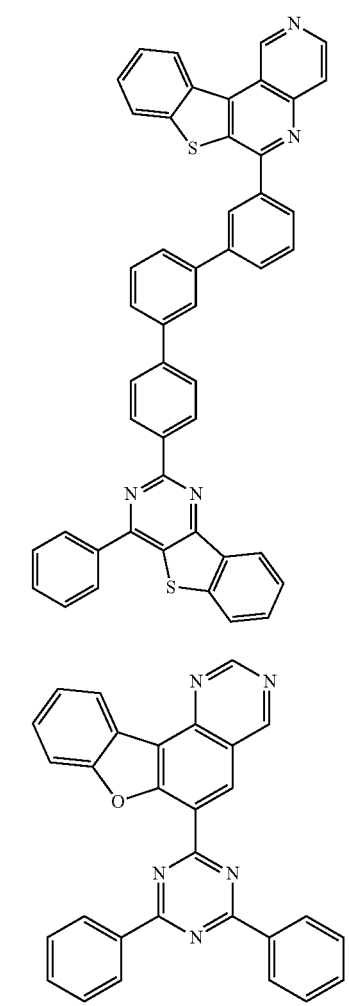
3-2-1
3-2-2
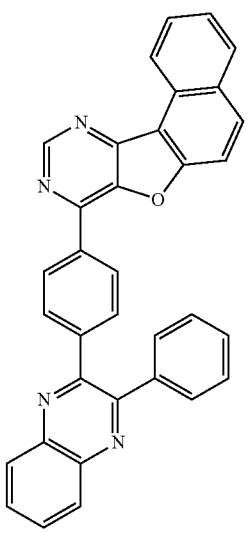

3-2-3
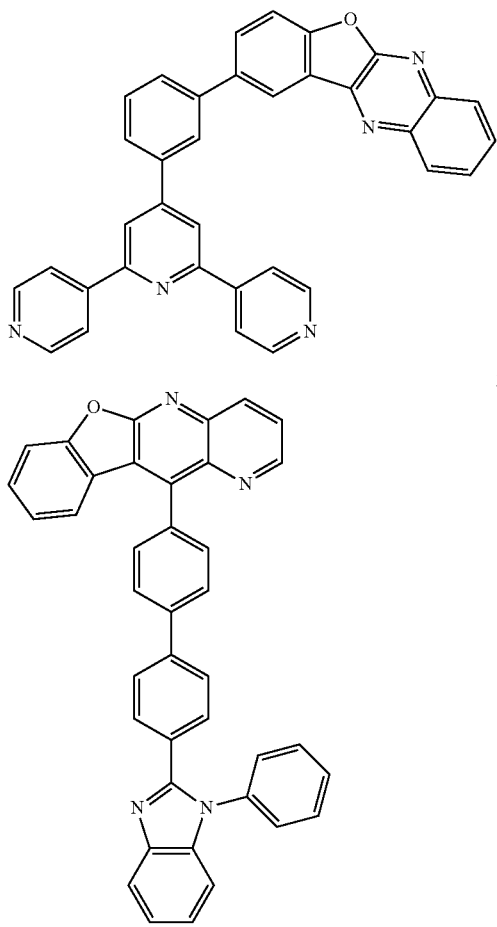
3-2-4
3-2-6
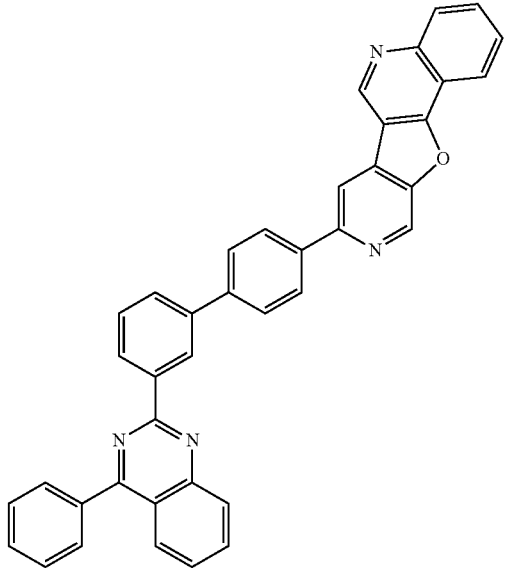
3-2-5
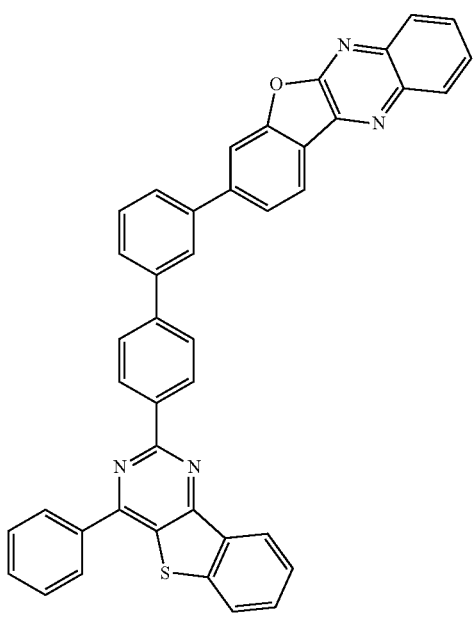
3-2-7
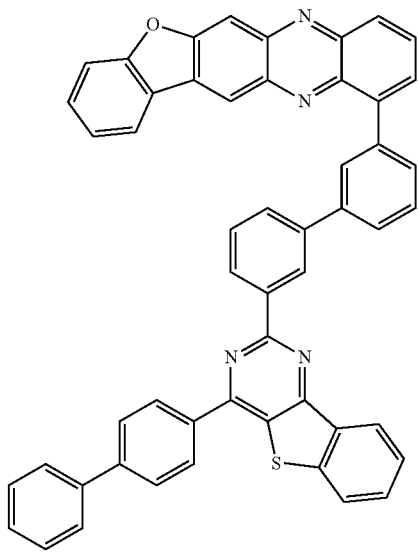

-continued
3-2-8
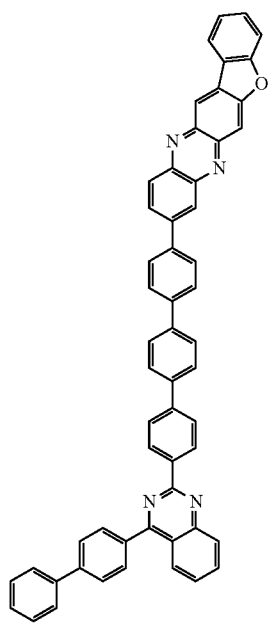
3-2-10
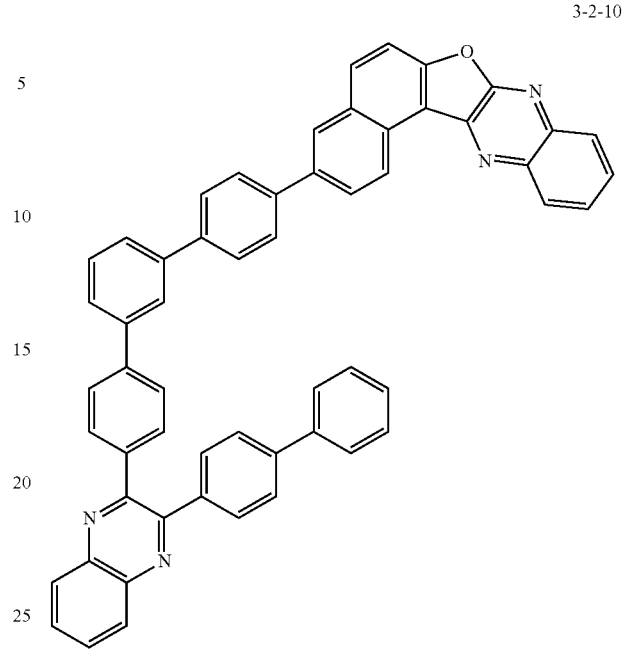
3-2-9
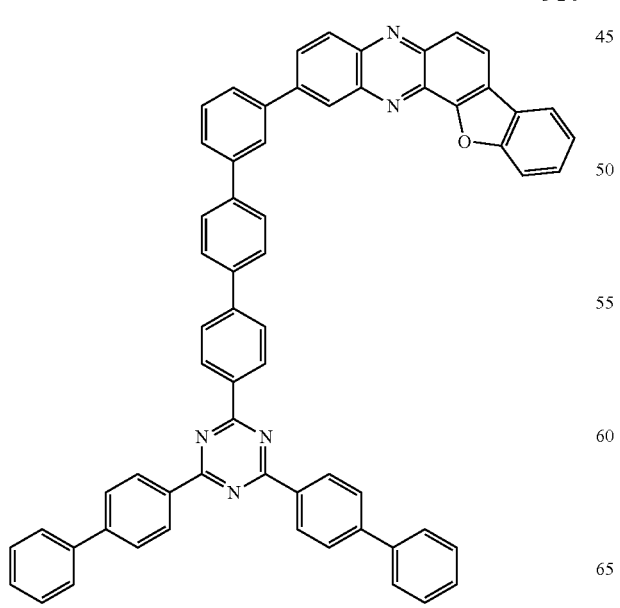
3-2-11
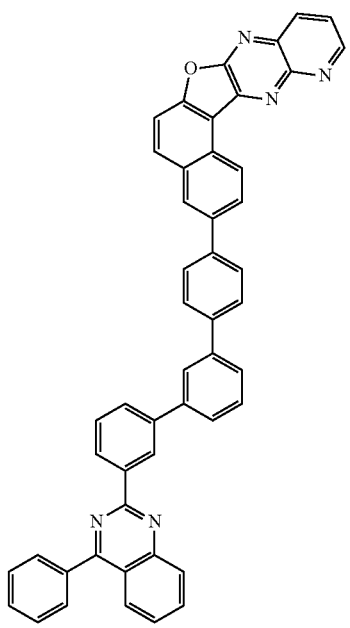

-continued
3-2-12
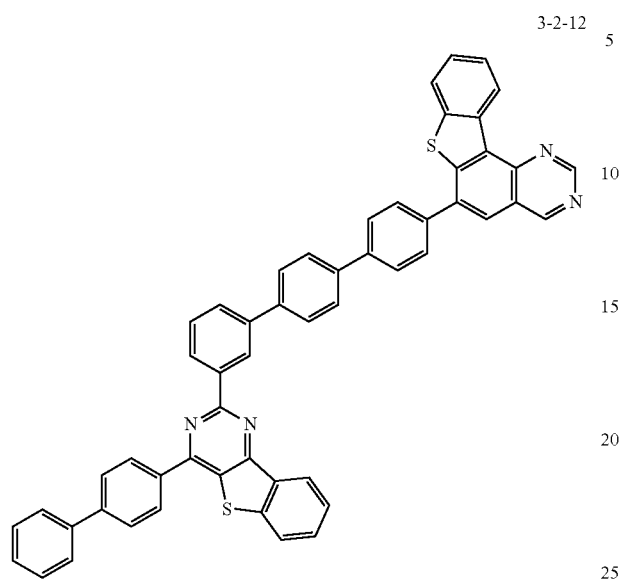
3-2-14
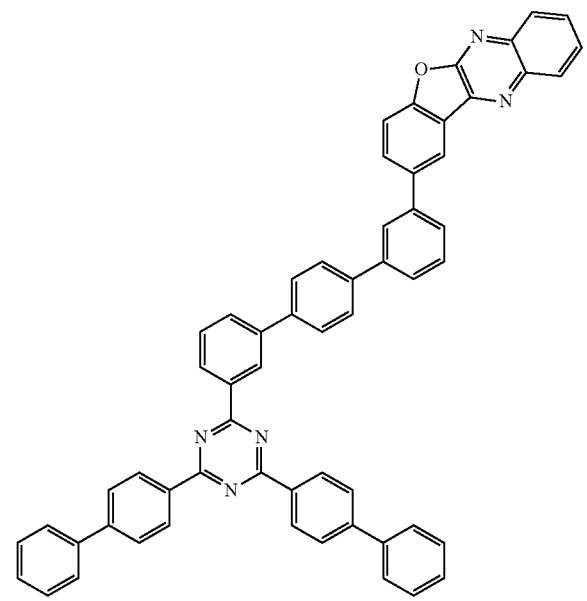
3-2-13
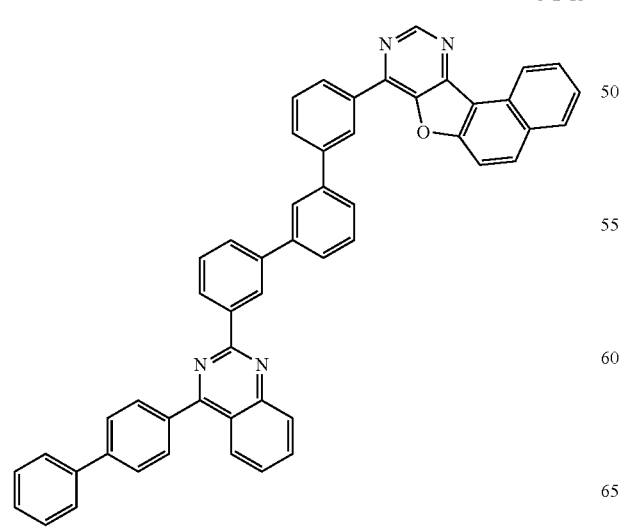
3-2-15
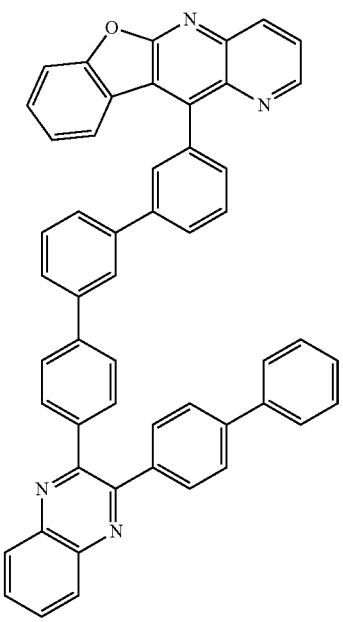

-continued

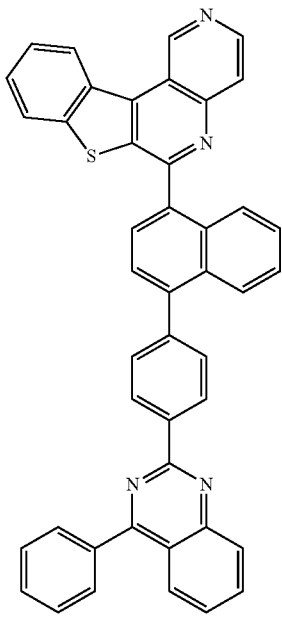

3-2-16

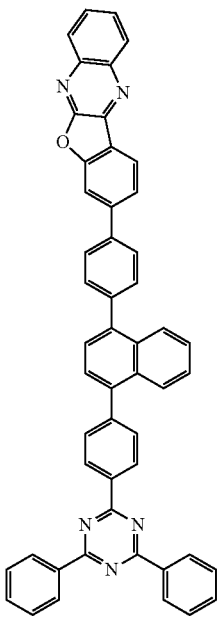

3-2-17

According to another aspect of the present invention, provided is an organic electroluminescent device comprising: a first electrode; a second electrode facing the first electrode; and an organic material layer interposed between the first electrode and the second electrode, wherein the organic material layer comprises the compound of chemical formula 1.

Furthermore, in the organic electroluminescent device, the first electrode is an anode, the second electrode is a cathode, the organic material layer comprises i) a light emitting layer, ii) a hole transport region interposed between the first electrode and the light emitting layer and including at least one of a hole injection layer, a hole transport layer, and a hole transport assisting layer, and iii) an electron transport region interposed between the light emitting layer and the second electrode and including at least one of an electron transport assisting layer, an electron transport layer and an electron injection layer, and, the electron transport region comprises the compound of chemical formula 1.

Furthermore, in the organic electroluminescent device, the electron transport layer or the electron transport assisting layer of the organic electroluminescent device comprises the compound of chemical formula 1.

According to another aspect of the present invention, there is provided a display device including the organic electroluminescent device, wherein the first electrode of the organic electroluminescent device is electrically connected to a source electrode or a drain electrode of a thin film transistor.

Hereinafter, synthesis examples of compounds represented by chemical formula 1 and manufacturing examples of organic electroluminescent devices according to the present invention will be described in detail, but the present invention is not limited to the following examples.

<Synthesis Method of Intermediate Products and FDMS Data>

(1) Synthesis of Intermediate Products for Core 1-1 to Core 1-13

The intermediate for Core 1-4 can be synthesized according to the following synthesis methods:

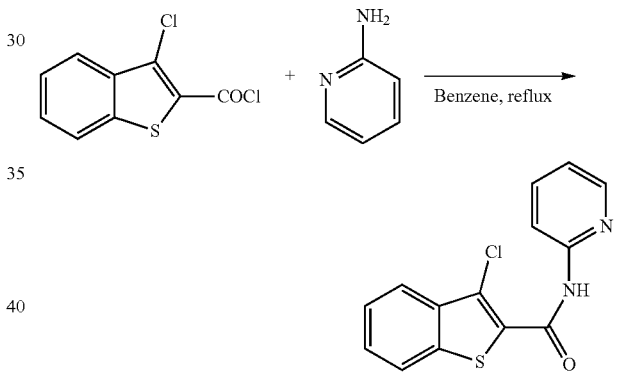

3-chlorobenzo[b]thiophene-2-carbonylchloride (15.2 g, 60.8 mmol) and 2-aminopyridine (6.2 g, 60.8 mmol) were dissolved in benzene and then triethylamine (9.4 ml, 60.8 mmol) was added and the mixture was stirred under reflux for 1 hour. Upon completion of the reaction, benzene was removed under reduced pressure, and the reaction product was extracted with MC and water, and dried using MgSO4, and concentrated. The resulting organic compound was subjected to recrystallization using ethanol to obtain 15.2 g (yield: 80%) of a product, 3-chloro-N-(pyridine-2-yl) benzo[b] thiophene-2-carboxamide.

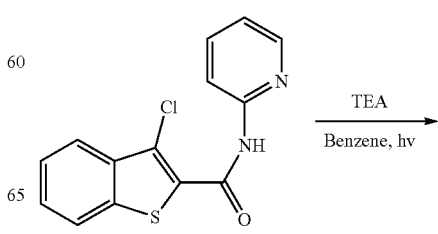

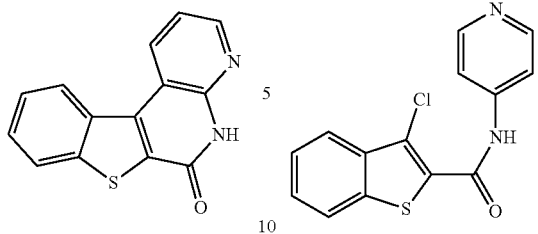

3-chloro-N-(pyridine-2-yl)benzo[b]thiophene-2-carboxamide (12.9 g, 41.6 mmol) was dissolved in benzene and stirred, and triethylamine (4.7 g, 4.64 mmol) was added dropwise, and was subjected to irradiation from a 450 watt high-pressure mercury lamp for 10 hours. When the reaction was completed, the benzene was removed by distillation under reduced pressure, and the solid was washed several times with water, and dried to obtain 9.4 g (yield: 83%) of benzothieno [2,3-c][1,8]naphthyridine-6(5H)-one.

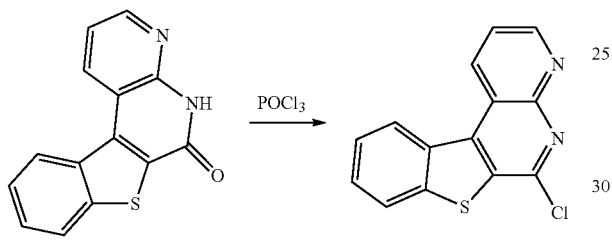

Benzothieno[2,3-c][1,8]naphthyridine-6(5H)-one (10.0 g, 33.6 mmol) was added with Phosphorous oxychloride and stirred under reflux for 4 hours. Upon completion of the reaction, Phosphorous oxychloride was removed by distillation under reduced pressure, and ice water was added thereto and stirred. Ammonium hydroxide is added dropwise to the level of pH9. The resulting brown solid was filtered and washed several times with water, and subjected to recrystallization with benzene to obtain 7.8 g (yield: 73%) of the intermediate product for Core 1-4,6-chlorobenzo[4,5]thieno[2,3-c][1,8]naphthyridine.

The intermediate product for Core 1-2 can be synthesized in the same manner as the intermediate product for Core 1-4 according to the following reaction scheme.

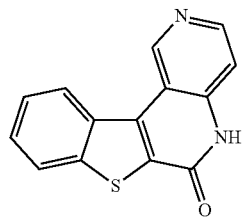

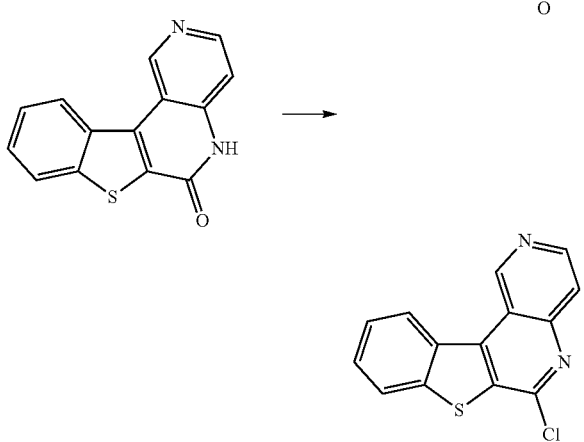

The intermediate products for Cores 1-1 and 1-3 were synthesized by obtaining the compound in the same manner as the intermediate product for Core 1-4 and then purifying the compound using M.C/methanol silicagel column chromatography. The yield for the intermediate product for Core 1-1 was 20% and the yield for the intermediate product for Core 1-3 was 70.

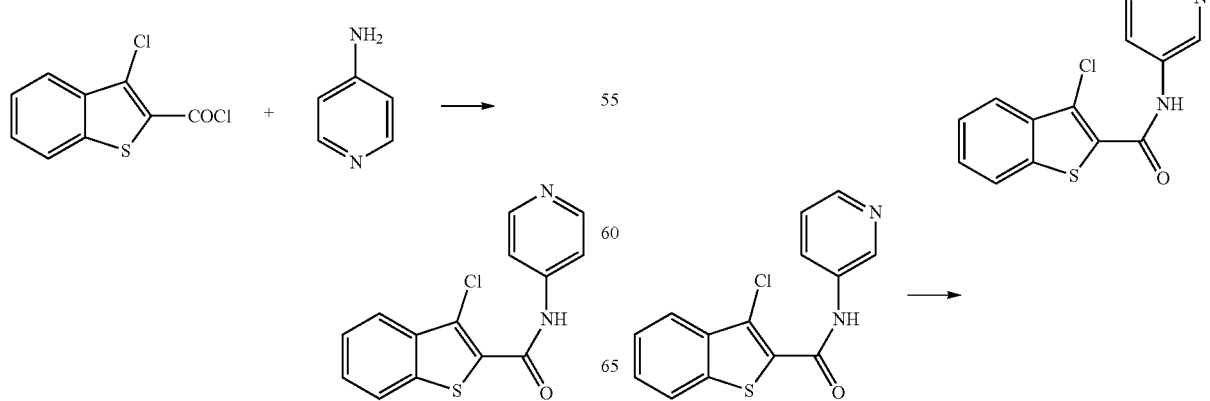

-continued

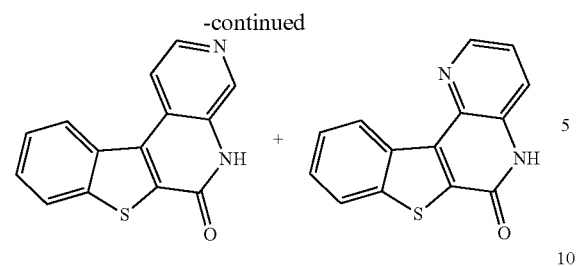

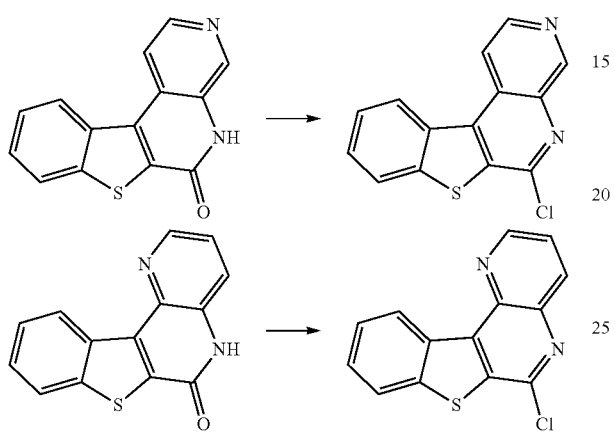

The intermediate product for Core 1-5 can be synthesized by the following reaction:

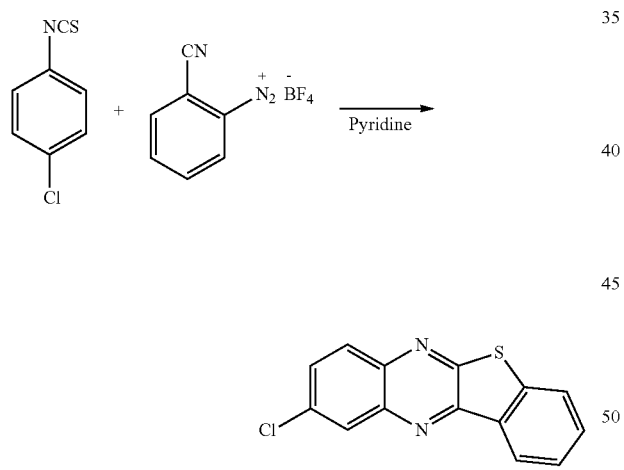

1-chloro-4-isothiocyanatobenzene (15 g, 86.4 mmol) was dissolved in pyridine, stirred, cooled to −20° C. and 2-cyanobenzenediazonium tetrafluoroborate (21.1 g, 97.27 mmol) was added dropwise over 1 hour. The temperature was maintained at −20° C. Upon completion of the reaction, the temperature was raised to room temperature and pyridine was removed under the reduced pressure. The reaction product was subjected to recrystallization using methylene chloride, filtered to remove Isothiocyanatobenzene, and washed several times with water. The resulting organic compound were purified by M.C/methanol silicagel column chromatography to obtain 9-chlorobenzo[4,5]thieno[2,3-b] quinoxaline (15 g, 62%).

The intermediate product for Core 1-6 can be synthesized by the following reaction:

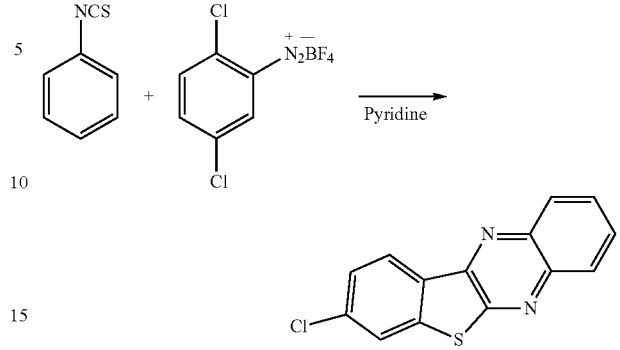

That is, isothiocyanato benzene (16.1 g, 111.4 mmol) was dissolved in pyridine, stirred, cooled to −20° C. and tetrafluoroborate (10 g, 31.8 mmol) was added dropwise over 1 hour. The temperature is maintained at −20° C. Upon completion of the reaction, the temperature is raised to room temperature and pyridine was removed under the reduced pressure. The reaction product was subjected to recrystallization using methylene chloride, filtered to remove Isothiocyanatobenzene, and washed several times with water. The resulting organic compound were purified by M.C/methanol silicagel column chromatography to obtain 6.46 g (yield: 60%) of 3-chlorobenzo [4,5]thieno[2,3-b] quinoxaline.

The intermediate product for Core 1-13 can be synthesized by the following reaction scheme:

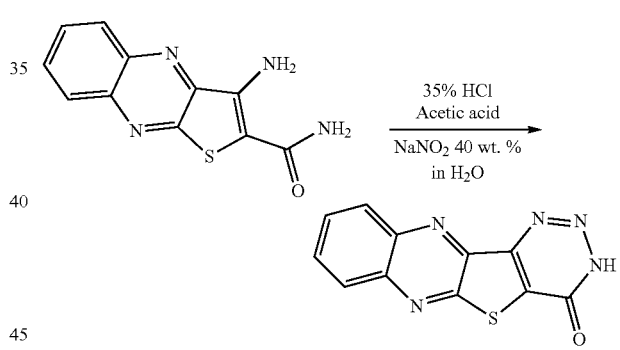

3-amino-2-carbamoyl thieno[2,3-b]quinoxaline (2.44 g, 10 mmol) and 35% HCl were mixed and stirred. Mixture of acetic acid (10 ml) and sodium nitride (20 ml) under −5° C. was slowly added dropwise and stirred for 1 hour. Upon completion of the reaction, the solid was filtered and recrystallized in acetic acid to obtain 2.08 g of [1,2,3]triazino [4',5':4,5]thieno[2,3-b]quinoxaline-4(3H)-one (yield: 80%).

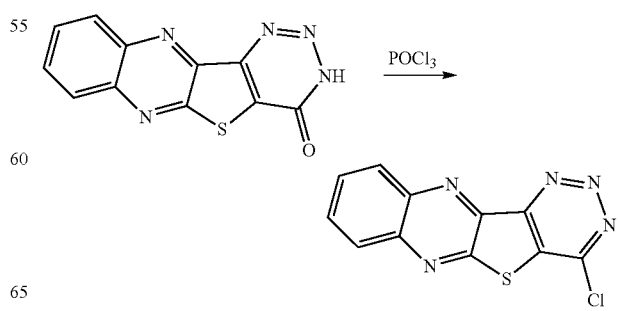

[1,2,3]triazino [4',5':4,5]thieno[2,3-b]quinoxaline-4(3H)-one (5.10 g, 20.0 mmol) was dissolved in phosphorous oxychloride (30 ml) and stirred under reflux for 3 hours. Upon completion of the reaction, the temperature was cooled to room temperature and then the reaction product was distilled under reduced pressure to remove phosphorous oxychloride and the ice water was poured. The resulting yellow solid was filtered and washed several times with water, dried, and recrystallized with ethanol to obtain 4 g of 4-chloro-[1,2,3] triazino [4',5':4,5]thieno[2,3-b]quinoxaline (yield: 72%).

The intermediate products for Cores 1-11 and 1-12 can be synthesized according to the following reaction scheme:

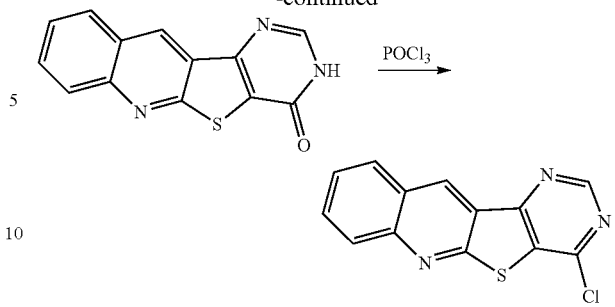

TABLE 1

| Compound | FD-MS | Compound | FD-MS |
|---|---|---|---|
| Cores 1-1~ 1-6 | Chemical Formula: C14H7ClN2S<br>Molecular Weight: 270.73<br>m/z: 270.00 (100.0%) | Cores 1-7~ 1-8 | Chemical Formula: C13H6ClN3S<br>Molecular Weight: 271.72<br>m/z: 271.00 (100.0%) |
| Cores 1-9~ 1-10 | Chemical Formula: C14H7ClN2S<br>Molecular Weight: 270.73<br>m/z: 270.00 (100.0%) | Cores 1-11~ 1-12 | Chemical Formula: C12H5ClN4S<br>Molecular Weight: 272.71<br>m/z: 271.99 (100.0%) |
| Core 1-13 | Chemical Formula: C11H4ClN5S<br>Molecular Weight: 273.70<br>m/z: 272.99 (100.0%) | | |

(2) Synthesis of Intermediate Products for Cores 2-1 to 2-13

The intermediate product for Core 2-10 can be synthesized according to the following reaction:

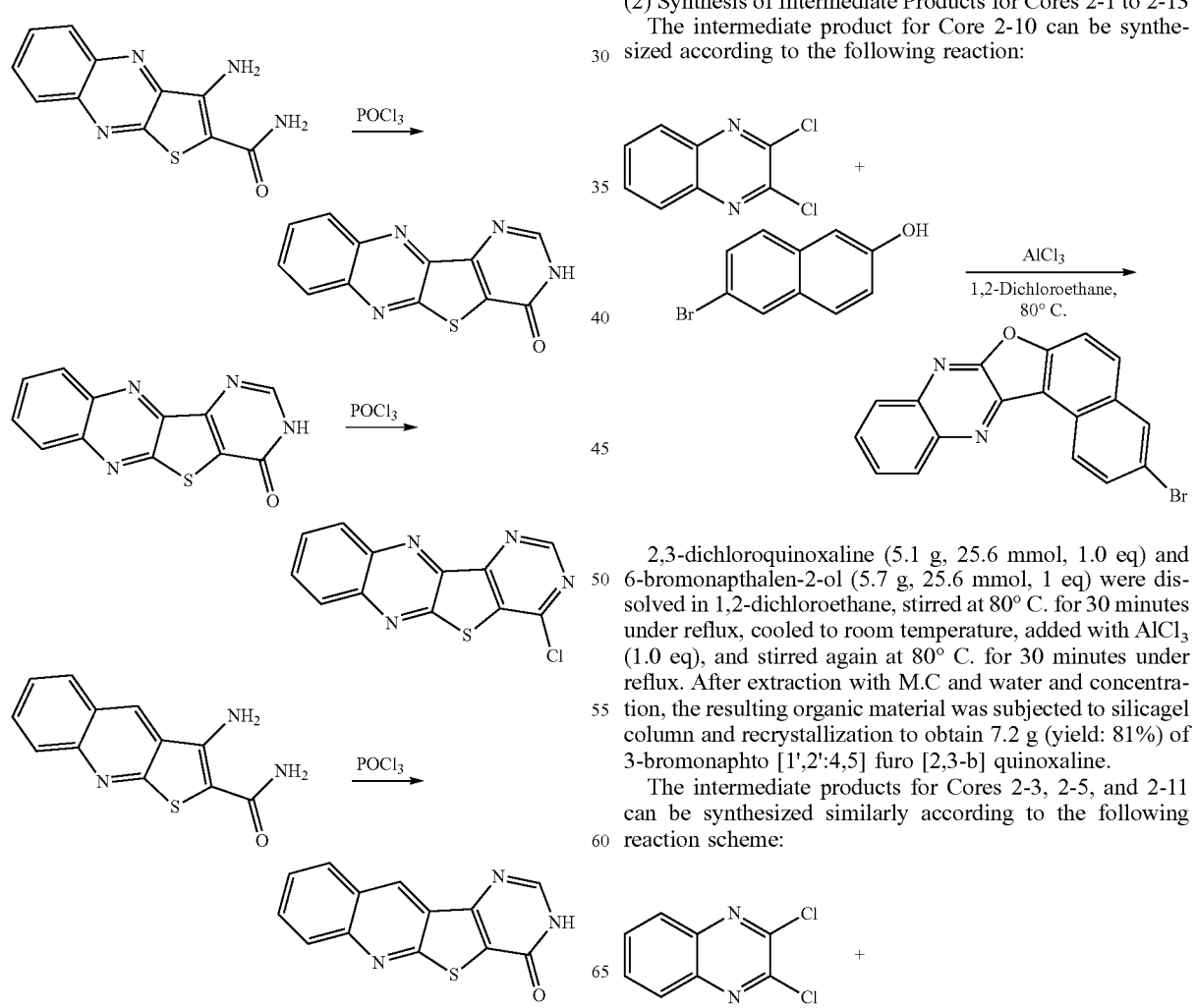

2,3-dichloroquinoxaline (5.1 g, 25.6 mmol, 1.0 eq) and 6-bromonapthalen-2-ol (5.7 g, 25.6 mmol, 1 eq) were dissolved in 1,2-dichloroethane, stirred at 80° C. for 30 minutes under reflux, cooled to room temperature, added with AlCl$_3$ (1.0 eq), and stirred again at 80° C. for 30 minutes under reflux. After extraction with M.C and water and concentration, the resulting organic material was subjected to silicagel column and recrystallization to obtain 7.2 g (yield: 81%) of 3-bromonaphto [1',2':4,5] furo [2,3-b] quinoxaline.

The intermediate products for Cores 2-3, 2-5, and 2-11 can be synthesized similarly according to the following reaction scheme:

-continued

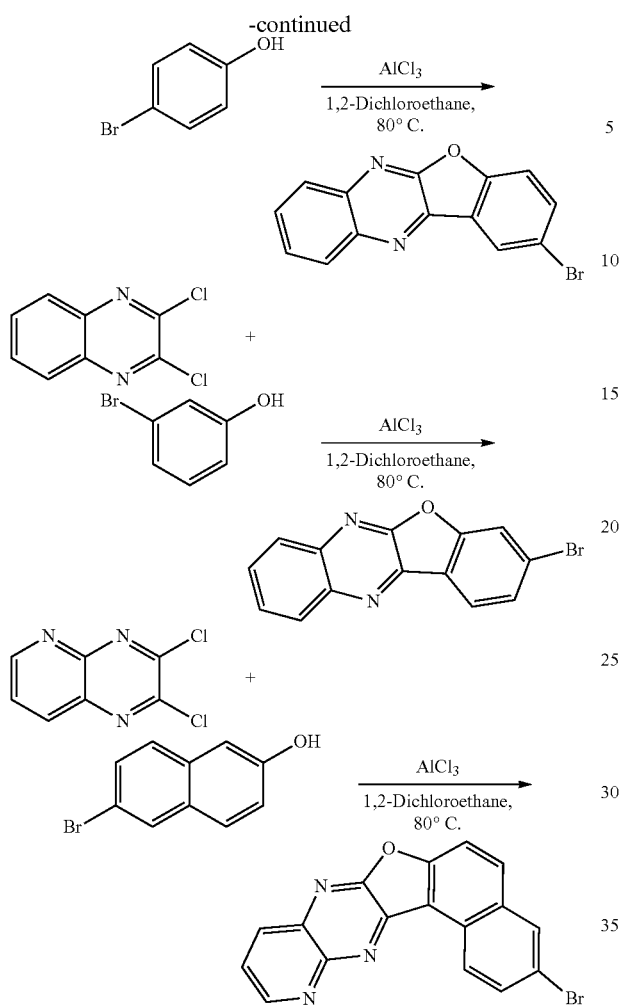

The intermediate product for Core 2-9 can be synthesized by the following synthesis scheme:

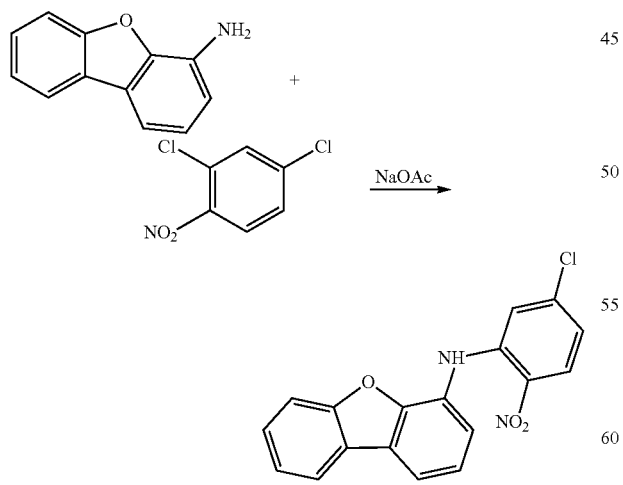

Dibenzo[b,d]furan-4-amine (32 g, 174.6 mmol) was dissolved in 2,5-dichloronitriro benzene (36 g, 187.5 mmol), added with sodium acetate (30 g, 365.75 mmol) and stirred under reflux at 210° C. for 4 hours. Upon completion of the reaction, the 2,5-dichloro-nitro benzene was removed by distillation under reduced pressure and then extracted with M.C and water. The organic layer was concentrated and recrystallized with m-ethanol to obtain 42.5 g (yield: 80%) of N-(5-chloro-2-nitrophenyl) dibenzo [b, d] furans-4-amine.

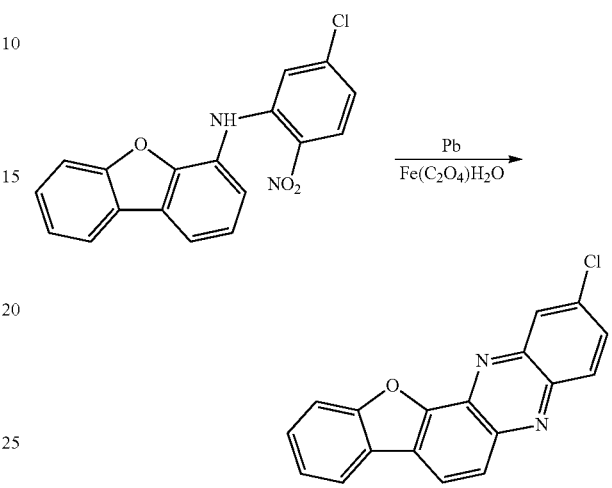

Ferrous oxylate dihydrate (6.5 g, 30.13 mmol) and granulated lead (50 g) were added to N-(5-chloro-2-nitrophenyl) dibenzo [b, d] furan-4-amine (5 g, 14.76 mmol), and stirred under reflux at 270° C. for 15 minutes. Upon completion of the reaction, the compound was separated by sublimation purification, and then recrystallized with benzene to obtain 2.4 g (yield: 54%) of 2-chlorobenzofuro [2,3-a] phenazine.

The intermediate products for Cores 2-7 and 2-8 can be synthesized similarly according to the following reaction scheme:

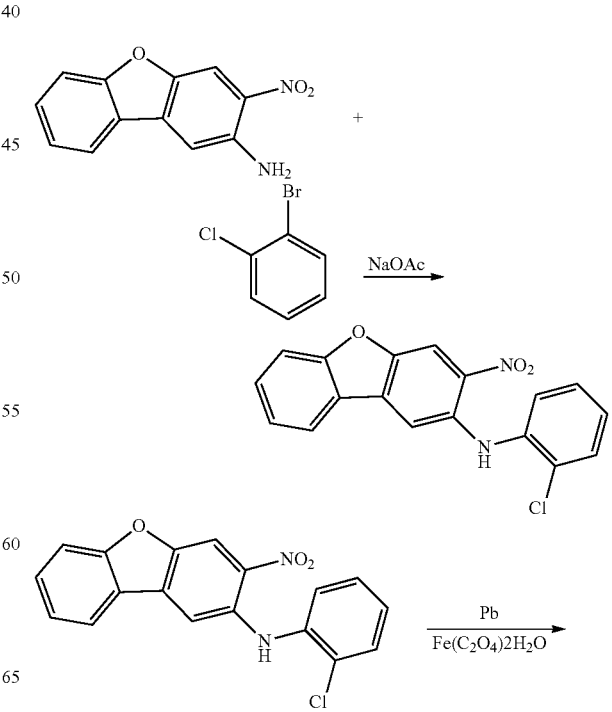

-continued

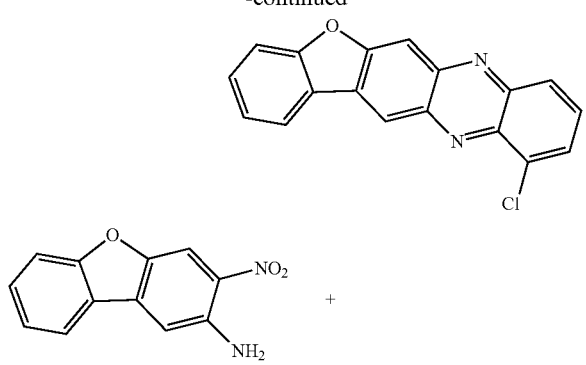

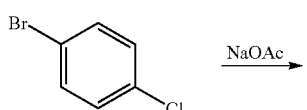

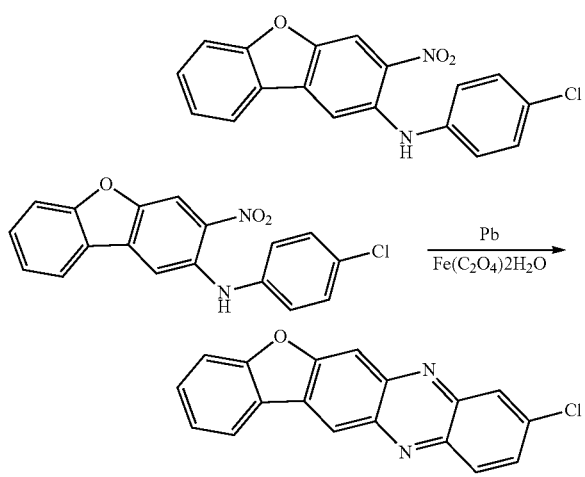

The intermediate product for Core 2-4 can be obtained according to the following synthesis scheme:

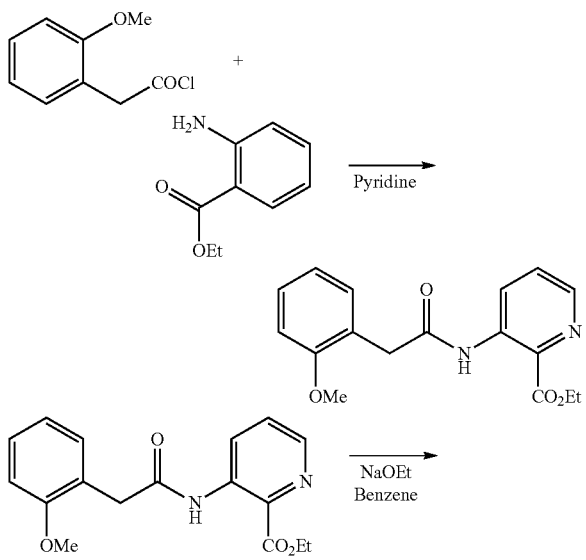

-continued

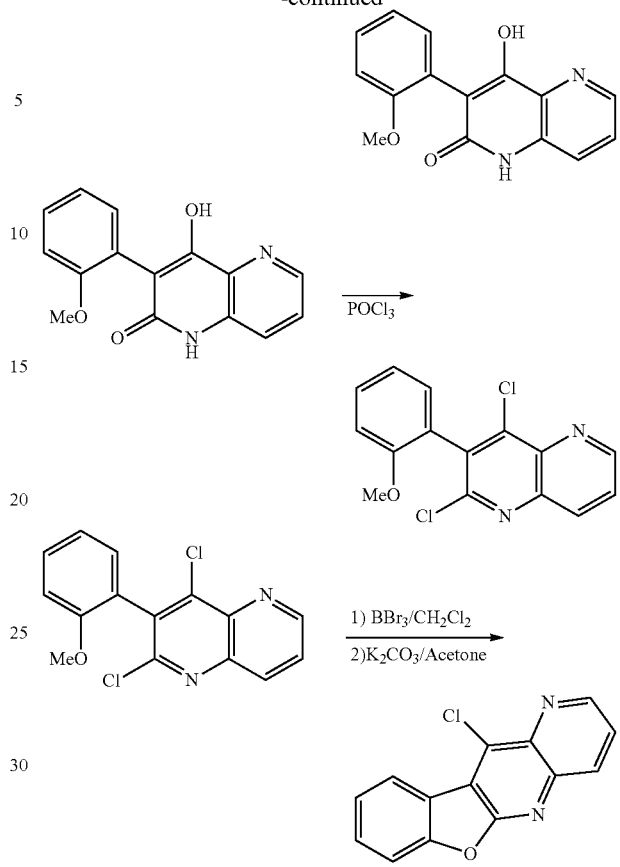

Ethyl 3-aminopicolinate (100 g, 602 mmol) and o-methoxyphenol chloride (180 g, 974.6 mmol) were dissolved in pyridine and stirred under reflux for 30 minutes. Upon completion of the reaction, the reaction mixture was cooled to room temperature and extracted with water and chloroform. The resulting orange layer was washed with water, and then dried with $MgSO_4$. The dried compound was concentrated and then subjected to silicagel column and recrystallization to obtain ethyl 3-(2-(2-methoxyphenyl) acetamido) picolinate (142 g, 75%).

Ethyl 3-(2-(2-methoxyphenyl) acetamido) picolinate (140 g, 462 mmol) and Sodium methoxide (anhydrous Ethanol and 30 g of Na metal) were dissolved in benzene and stirred under reflux for 5 hours. Upon completion of the reaction, the reaction mixture was cooled to room temperature and neutralized by adding water and acetic acid. The precipitate was recrystallized from acetic acid and ethanol to obtain colorless 4-hydroxy-3-(2-methoxyphenyl)-1,5-naphthyridine-2 (1H)-one (87.2 g, 73%).

4-hydroxy-3-(2-methoxyphenyl)-1,5-naphthyridine-2 (1H)-one (80 g, 280 mmol) was added with excess phosphoryl chloride and stirred under reflux for 6 hours. Upon completion of the reaction, water and ammonia were added after cooling, and then extracted with chloroform. The resulting organic layer was washed with brine, dried with $MgSO_4$, and concentrated. The resulting compound was purified by silicagel column to give 2,4-dichloro-3-(2-methoxyphenyl)-1,5-naphthyridine (72 g, 79%).

2,4-dichloro-3-(2-methoxyphenyl)-1,5-naphthyridine (70 g, 229 mmol) was dissolved in anhydrous dichloromethane, stirred, cooled to −78° C. and an excess of Boron tribromide dissolved in dichloromethane was added dropwise thereto.

The mixture was stirred at room temperature for 2 hours, then water was added and extracted with ethyl acetate. The resulting organic layer was dried with MgSO$_4$ and concentrated. The resulting compound was dissolved in acetone, added with K$_2$CO$_3$ and stirred at 60-70° C. for 3-4 hours. After completion of the reaction, the solvent was removed and extracted with water and chloroform. The resulting orange color layer was dried with MgSO$_4$, concentrated, and the resulting compound was purified by silica gel column to give 11-chorobenzofuro[2,3-b] [1,5]naphthyridine (39.2 g, 93%).

TABLE 2

| Compound | FD-MS | Compound | FD-MS |
| --- | --- | --- | --- |
| Cores 2-1~ 2-6 | Chemical Formula: C14H7BrN2O<br>Molecular Weight: 299.13<br>m/z: 297.97 (100.0%) | Cores 2-7~ 2-10 | Chemical Formula: C18H9ClN2O<br>Molecular Weight: 304.73<br>m/z: 304.04 (100.0%) |
| Cores 2-11 | Chemical Formula: C17H8BrN3O<br>Molecular Weight: 350.18<br>m/z: 348.99 (100.0%) | | |

(3) Synthesis of Intermediate Products for Subs

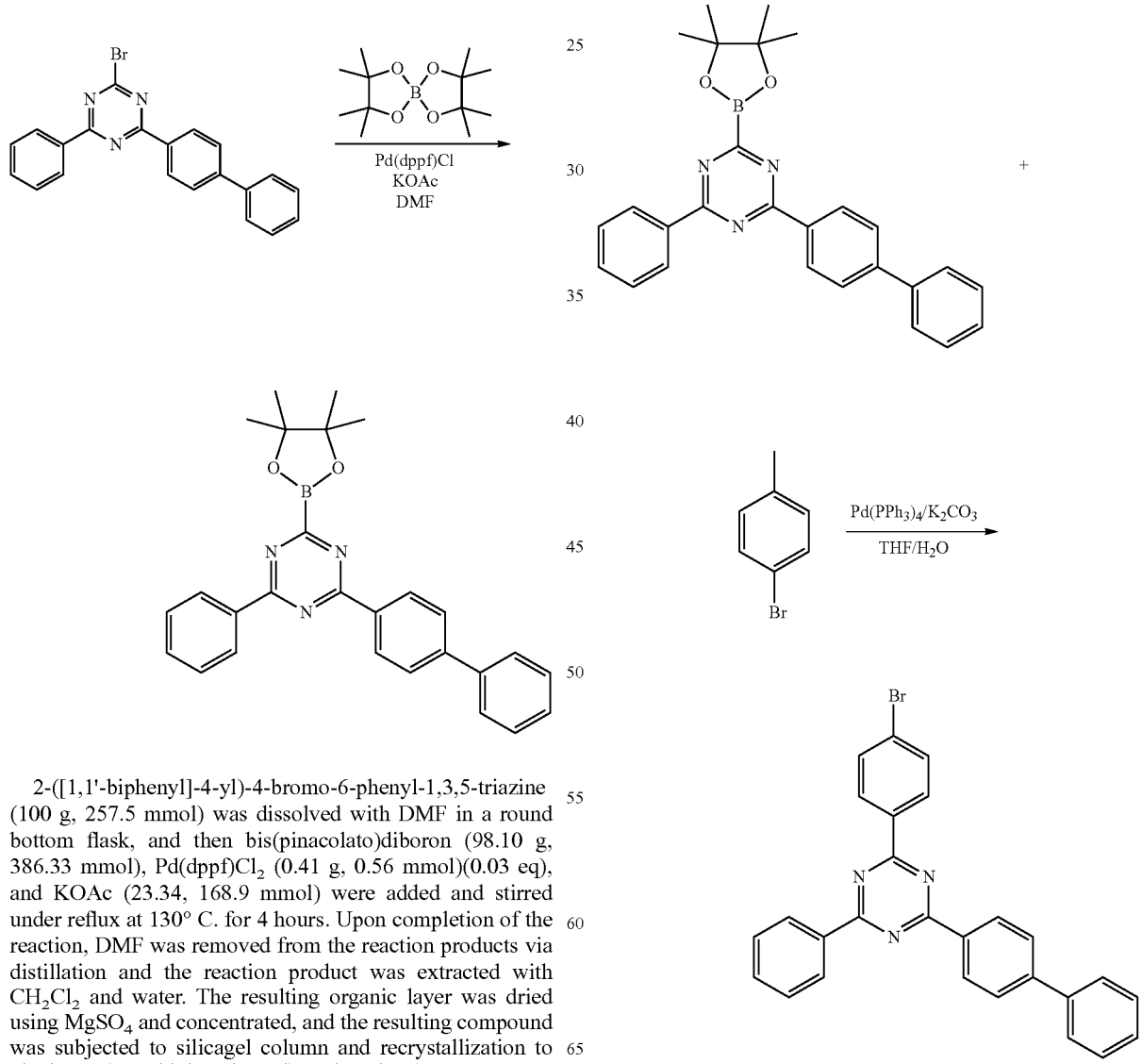

2-([1,1'-biphenyl]-4-yl)-4-bromo-6-phenyl-1,3,5-triazine (100 g, 257.5 mmol) was dissolved with DMF in a round bottom flask, and then bis(pinacolato)diboron (98.10 g, 386.33 mmol), Pd(dppf)Cl$_2$ (0.41 g, 0.56 mmol)(0.03 eq), and KOAc (23.34, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silicagel column and recrystallization to obtain 2-([1,1'-biphenyl]-4-yl)-4-phenyl-6-(4,4,5,5-tetramethyl-1,3,2-dioxaborolan-2-yl)-1,3,5-triazine (78 g, 69.9%).

2-([1,1'-biphenyl]-4-yl)-4-phenyl-6-(4,4,5,5-tetramethyl-1,3,2-dioxaborolan-2-yl)-1,3,5-triazine (50 g, 114.86 mmol) was dissolved in THF, and then 1-bromo-4-iodo benzene (38.99 g, 137.83 mmol), Pd(PPh$_3$)$_4$ (1.95 g, 1.69 mmol), K2CO3 (23.34 g, 168.9 mmol) and water were added, and stirred under reflux at 100° C. for 3 hours. Upon completion of the reaction, the organic layer was extracted with E.A. and water, and was dried using MgSO4 and concentrated. The resulting organic material was purified by silica gel column to obtain 2-([1,1'-biphenyl]-4-yl)-4-(4-bromophenyl)-6-phenyl-1,3,5-triazine (35 g, 65.6%).

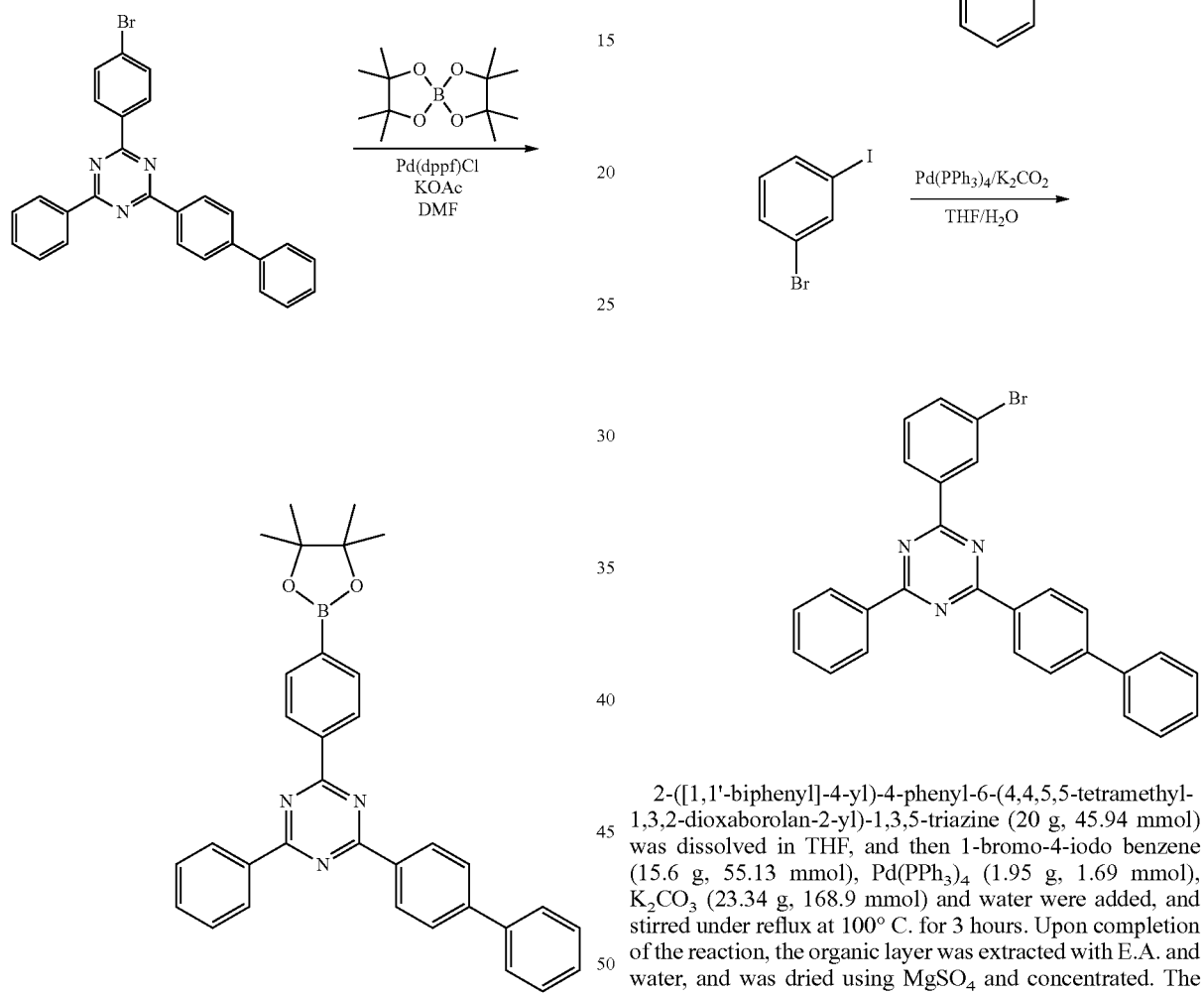

Then, 2-([1,1'-biphenyl]-4-yl)-4-(4-bromophenyl)-6-phenyl-1,3,4-triazine (50.0 g, 114.86 mmol) was dissolved with DMF in a round bottom flask, and then bis(pinacolato)diboron (48.74 g, 172.28 mmol), Pd(dppf)Cl$_2$ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silica gel column and recrystallization to obtain 2-([1,1'-biphenyl]-4-yl)-4-phenyl-6-(4-(4,4,5,5-tetramethyl-1,3,2-dioxaborolan-2-yl)phenyl)-1,3,5-triazine (40 g, 68.1%).

2-([1,1'-biphenyl]-4-yl)-4-phenyl-6-(4,4,5,5-tetramethyl-1,3,2-dioxaborolan-2-yl)-1,3,5-triazine (20 g, 45.94 mmol) was dissolved in THF, and then 1-bromo-4-iodo benzene (15.6 g, 55.13 mmol), Pd(PPh$_3$)$_4$ (1.95 g, 1.69 mmol), K$_2$CO$_3$ (23.34 g, 168.9 mmol) and water were added, and stirred under reflux at 100° C. for 3 hours. Upon completion of the reaction, the organic layer was extracted with E.A. and water, and was dried using MgSO$_4$ and concentrated. The resulting organic material was purified by silica gel column to obtain 2-([1,1'-biphenyl]-4-yl)-4-(3-bromophenyl)-6-phenyl-1,3,5-triazine (15 g, 70.3%).

213
-continued

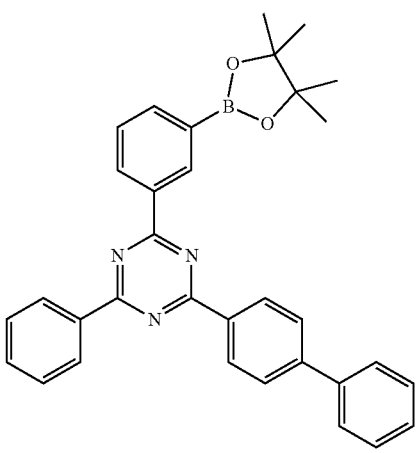

2-([1,1'-biphenyl]-4-yl)-4-(3-bromophenyl)-6-phenyl-1,3,5-triazine (10.0 g, 21.53 mmol) was dissolved with DMF in a round bottom flask, and then bis(pinacolato) diboron (9.14 g, 32.3 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(3-(4,4,5,5-tetramethyl-1,3,2-dioxaborolan-2-yl)phenyl)-1,3,5-triazine (7 g, 63.55%).

214
-continued

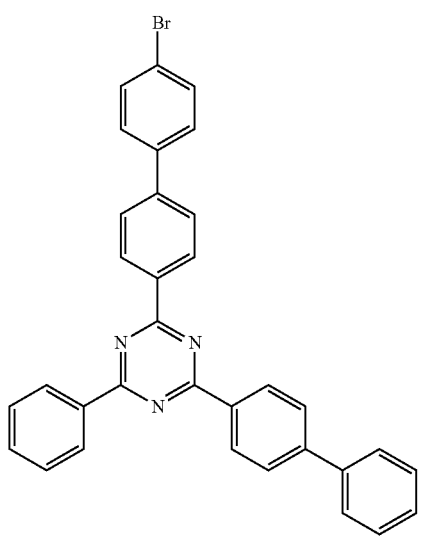

2-([1,1'-biphenyl]-4-yl)-4-phenyl-6-(4-(4,4,5,5-tetramethyl-1,3,2-dioxaborolan-2-yl)phenyl)-1,3,5-triazine (20 g, 39.1 mmol) was dissolved in THF, and then 1-bromo-4-iodo benzene (13.28 g, 46.93 mmol), Pd(PPh₃)₄ (1.95 g 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphenyl]-4-yl)-4-(4'-bromo-[1,1'-biphenyl]-4-yl)-6-phenyl-1,3,5-triazine (14 g, 66.24%).

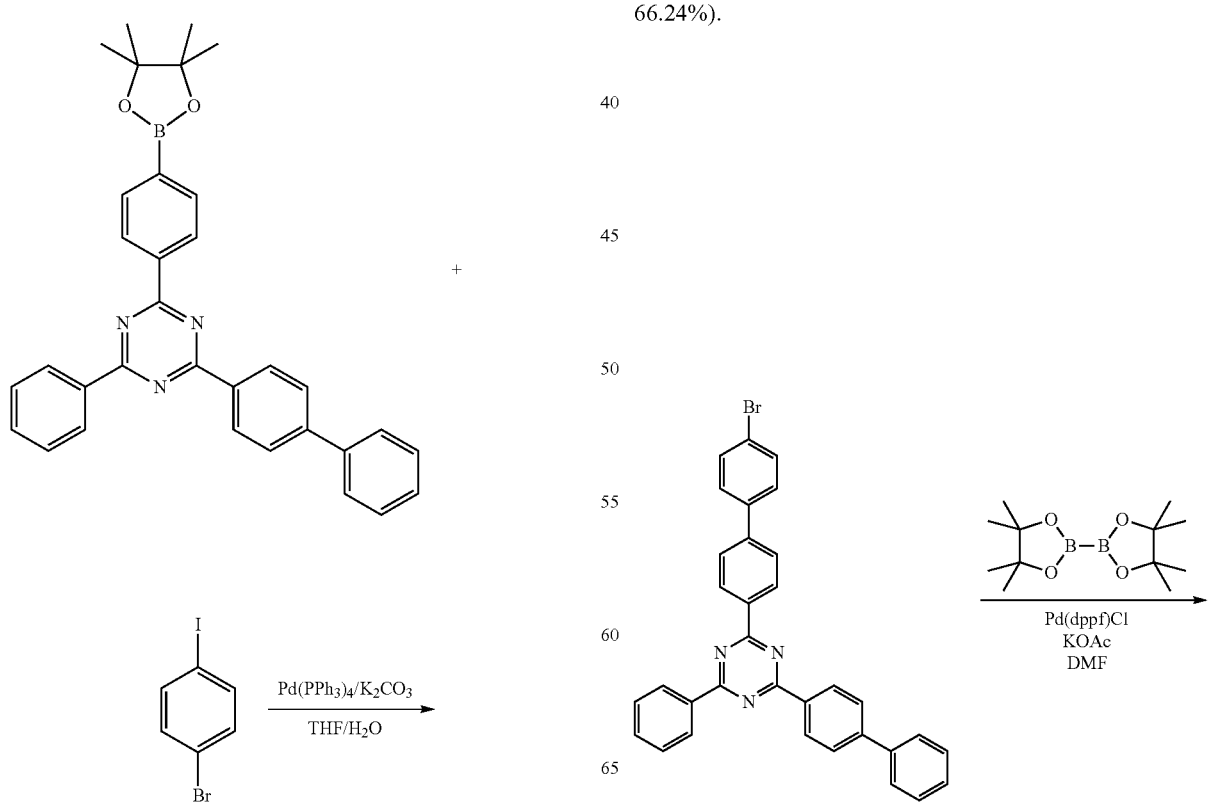

215

-continued

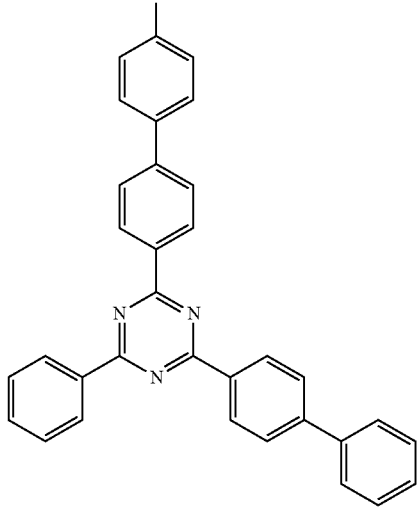

2-([1,1'-biphenyl]-4-yl)-4-(4'-bromo-[1,1'-biphenyl]-4-yl)-6-phenyl-1,3,5-triazine (10.0 g 18.5 mmol) was dissolved with DMF in around bottom flask, and then bis(pinacolato) diboron (7.05 g, 27.75 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(4'-(4,4,5,5-tetramethyl-1,3,2-dioxaborolan-2-yl)-[1,1'-biphenyl]-4-yl)-1,3,5-triazine (7 g, 64.39%).

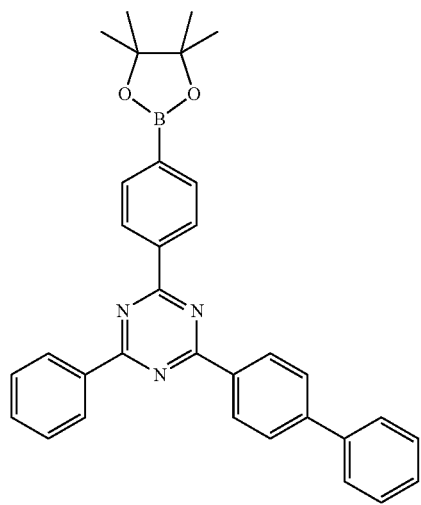

+

216

-continued

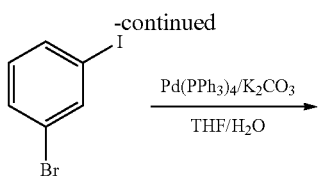

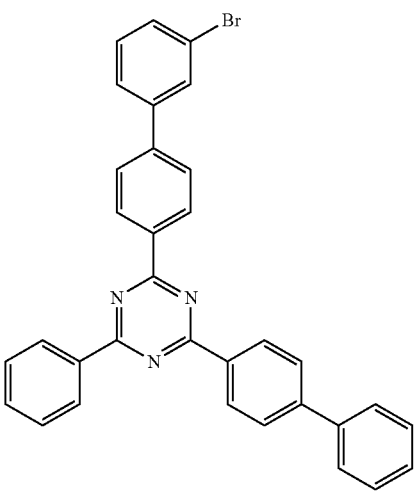

2-([1,1'-biphenyl]-4-yl)-4-phenyl-6-(4-(4,4,5,5-tetramethyl-1,3,2-dioxaborolan-2-yl) phenyl)-1,3,5-triazine (20 g, 39.11 mmol) was dissolved in THF, and then 1-bromo-3-iodo benzene (16.6 g, 58.66 mmol), Pd(PPh₃)₄ (1.95 g, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphenyl]-4-yl)-4-(3'-bromo-[1,1'-biphenyl]-4-yl)-6-phenyl-1,3,5-triazine (14 g, 66.24%).

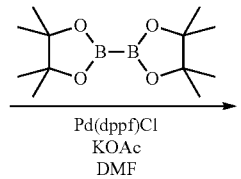

217
-continued

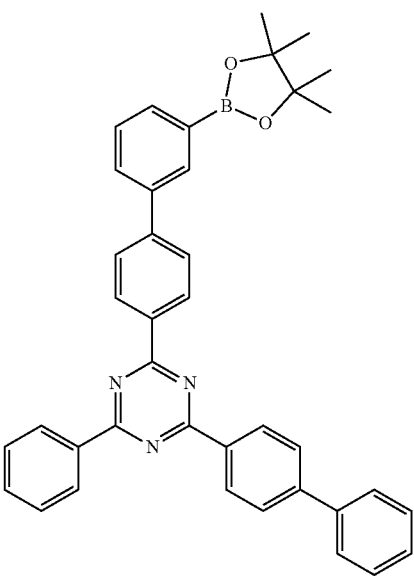

2-([1,1'-biphenyl]-4-yl-4-(3'-bromo-[1,1'-biphenyl]-4-yl)-6-phenyl-1,3,5-triazine (10.0 g, 18.5 mmol) was dissolved with DMF in around bottom flask, and then bis (pinacolato) diboron (5.64 g, 22.2 mmol), Pd(dppf)Cl₂ (1.24 g 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(3'-(4,4,5,5-tetramethyl-1,3,2-dioxaborolan-2-yl)-[1,1'-biphenyl]-4-yl)-1,3,5-triazine (7 g, 64.39%).

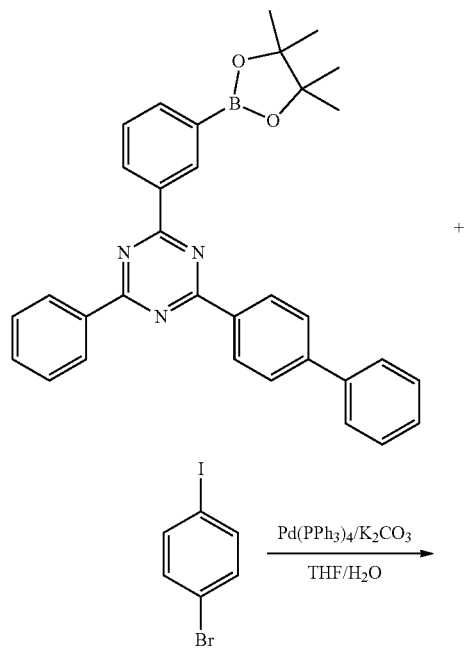

218
-continued

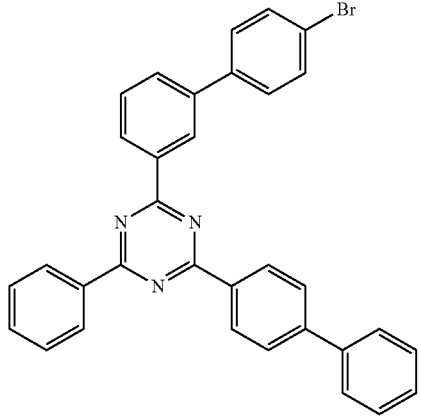

2-([1,1'-biphenyl]-4-yl)-4-phenyl-6-(3-(4,4,5,5-tetramethyl-1,3,2-dioxaborolan-2-yl)phenyl)-1,3,5-triazine (20 g 39.1 mmol) was dissolved in THF, and then 1-bromo-4-iodo benzene (13.28 g, 46.93 mmol), Pd(PPh₃)₄ (1.95 g, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO4 and concentrated. The resulting organic material was purified by silica gel column to obtain 2-([1,1'-biphenyl]-4-yl)-4-(4'-bromo-[1,1'-biphenyl]-3-yl)-6-phenyl-1,3,5-triazine (15 g, 70.97%).

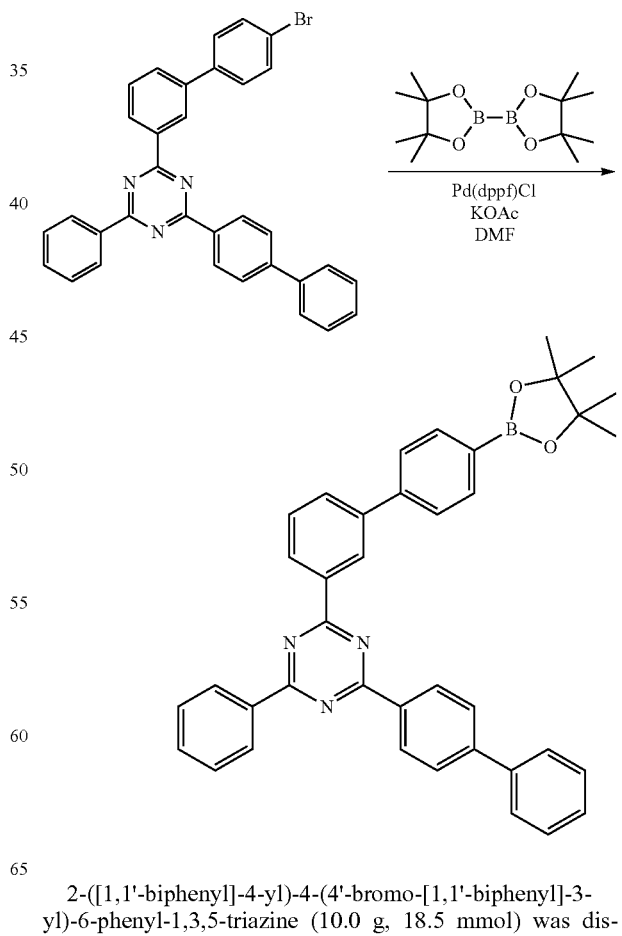

2-([1,1'-biphenyl]-4-yl)-4-(4'-bromo-[1,1'-biphenyl]-3-yl)-6-phenyl-1,3,5-triazine (10.0 g, 18.5 mmol) was dissolved with DMF in a round bottom flask, and then bis(pinacolato) diboron (7.05 g, 27.75 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(4'-(4,4,5,5-tetramethyl-1,3,2-dioxaborolan-2-yl)-[1,1'-biphenyl]-3-yl)-1,3,5-triazine (8 g, 73.59%).

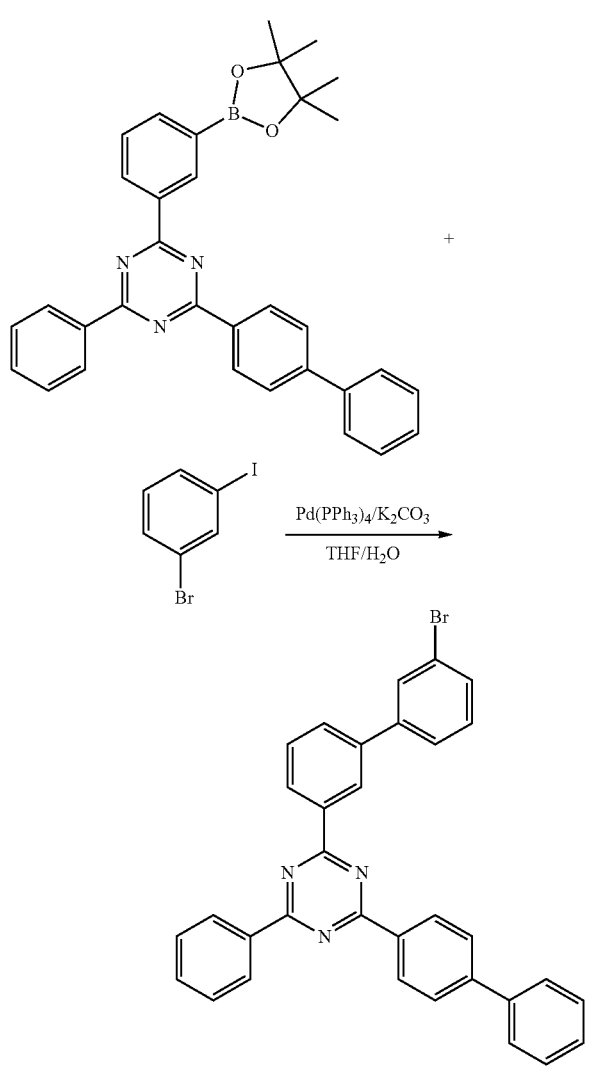

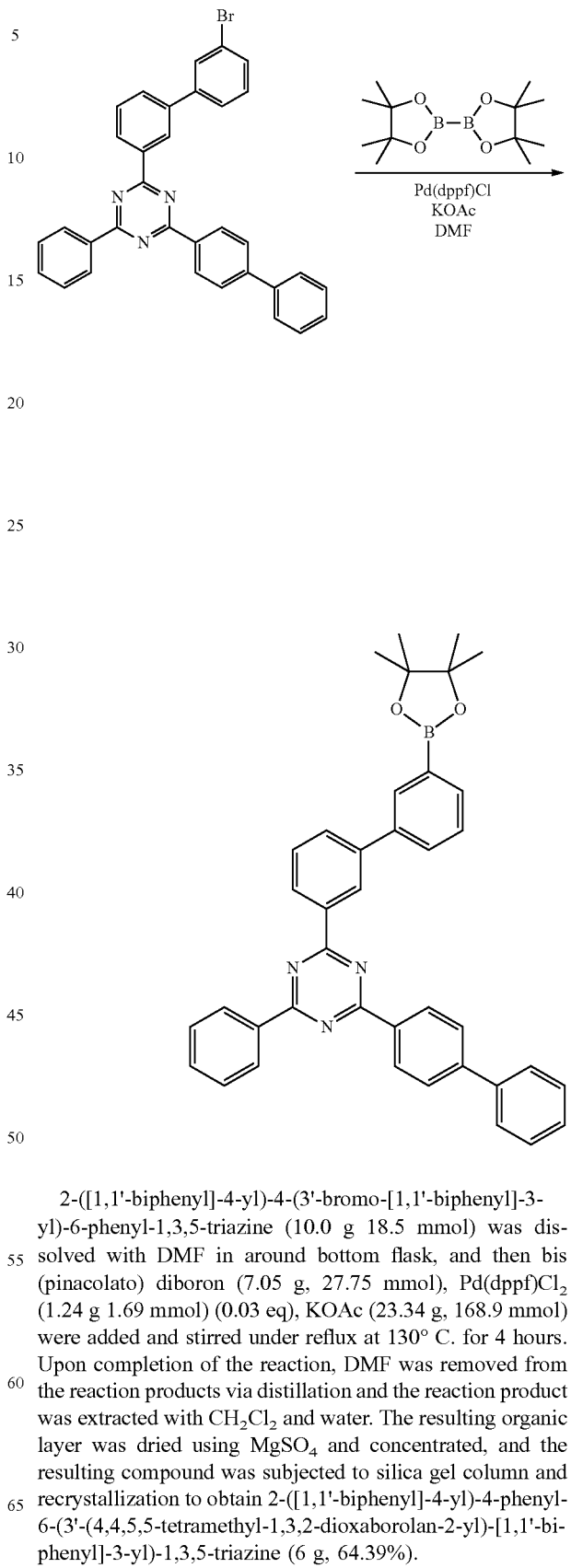

2-([1,1'-biphenyl]-4-yl)-4-phenyl-6-(3-(4,4,5,5-tetramethyl-1,3,2-dioxaborolan-2-yl) phenyl)-1,3,5-triazine (20 g, 39.11 mmol) was dissolved in THF, and then 1-bromo-3-iodo benzene (13.28 g 46.93 mmol), Pd(PPh)₄ (1.95 g, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO4 and concentrated. The resulting organic material was purified by silica gel column to obtain 2-([1,1'-biphenyl]-4-yl)-4-(3'-bromo-[1,1'-biphenyl]-3-yl)-6-phenyl-1,3,5-triazine (13 g, 61.51%).

2-([1,1'-biphenyl]-4-yl)-4-(3'-bromo-[1,1'-biphenyl]-3-yl)-6-phenyl-1,3,5-triazine (10.0 g 18.5 mmol) was dissolved with DMF in around bottom flask, and then bis(pinacolato) diboron (7.05 g, 27.75 mmol), Pd(dppf)Cl₂ (1.24 g 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(3'-(4,4,5,5-tetramethyl-1,3,2-dioxaborolan-2-yl)-[1,1'-biphenyl]-3-yl)-1,3,5-triazine (6 g, 64.39%).

nyl]-4-yl)-4-(4"-bromo-[1,1':4',1"-terphenyl]-4-yl)-6-phenyl-1,3,5-triazine (13 g, 61.93%).

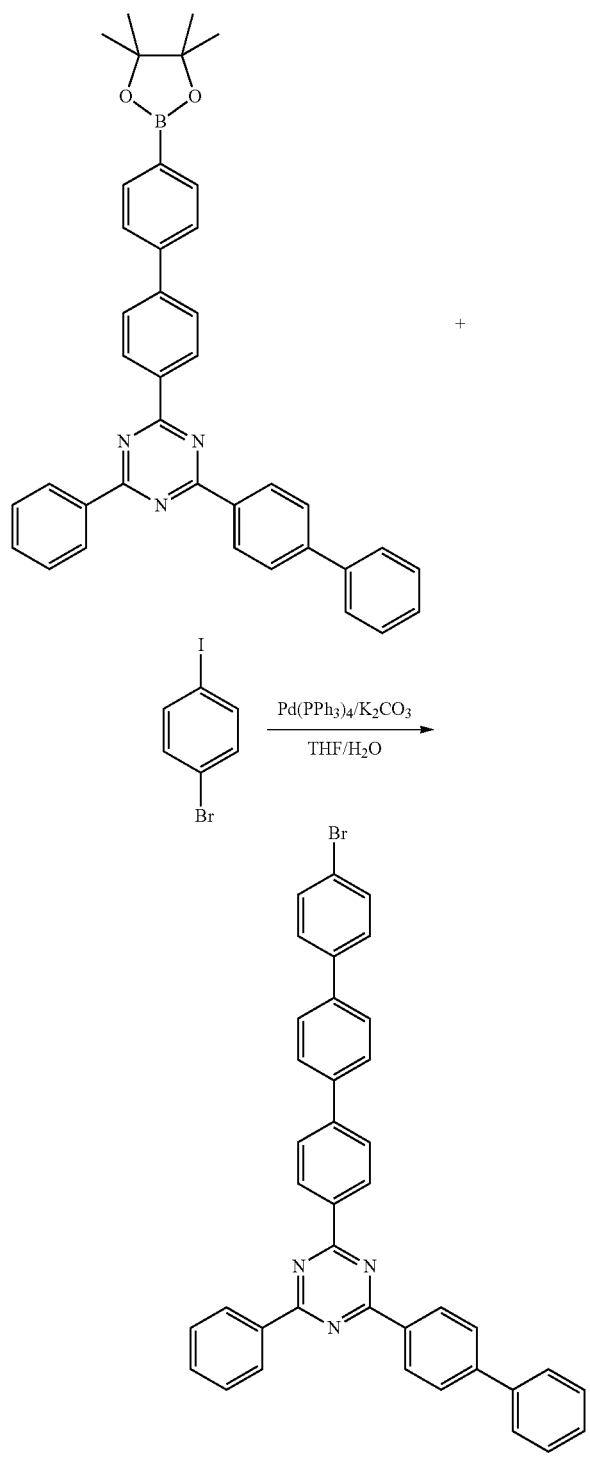

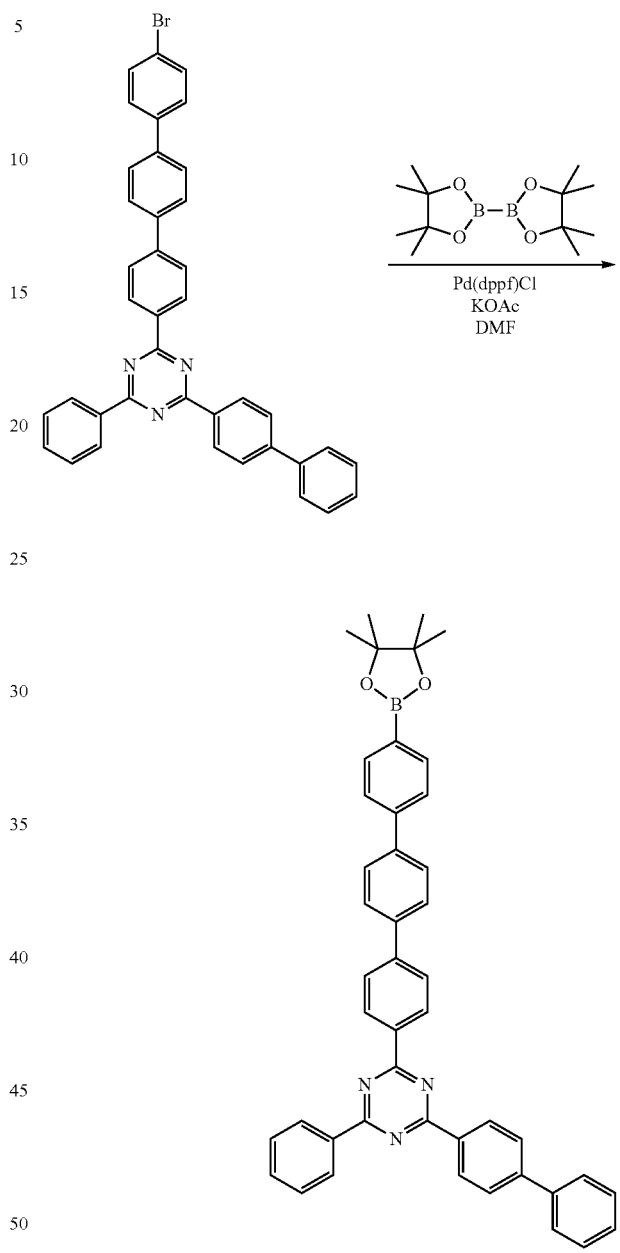

2-([1,1'-biphenyl]-4-yl)-4-phenyl-6-(4'-(4,4,5,5-tetramethyl-1,3,2-dioxaborolan-2-yl)-[1,1'-biphenyl]-4-yl)-1,3,5-triazine (20 g, 34.04 mmol) was dissolved in THF, and then 1-bromo-4-iodo benzene (11.56 g, 40.85 mmol), Pd(PPh₃)₄ (1.95 g, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphe- 2-([1,1'-biphenyl]-4-yl)-4-(4"-bromo-[1,1':4',1"-terphenyl]-4-yl)-6-phenyl-1,3,5-triazine (10.0 g, 16.22 mmol) was dissolved with DMF in a round bottom flask, and then bis(pinacolato) diboron (6.18 g, 24.33 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(4"-(4,4,5,5-tetramethyl-1,3,2-dioxaborolan-2-yl)-[1,1':4', 1"-terphenyl]-4-yl)-1,3,5-triazine (7 g, 65.03%).

223

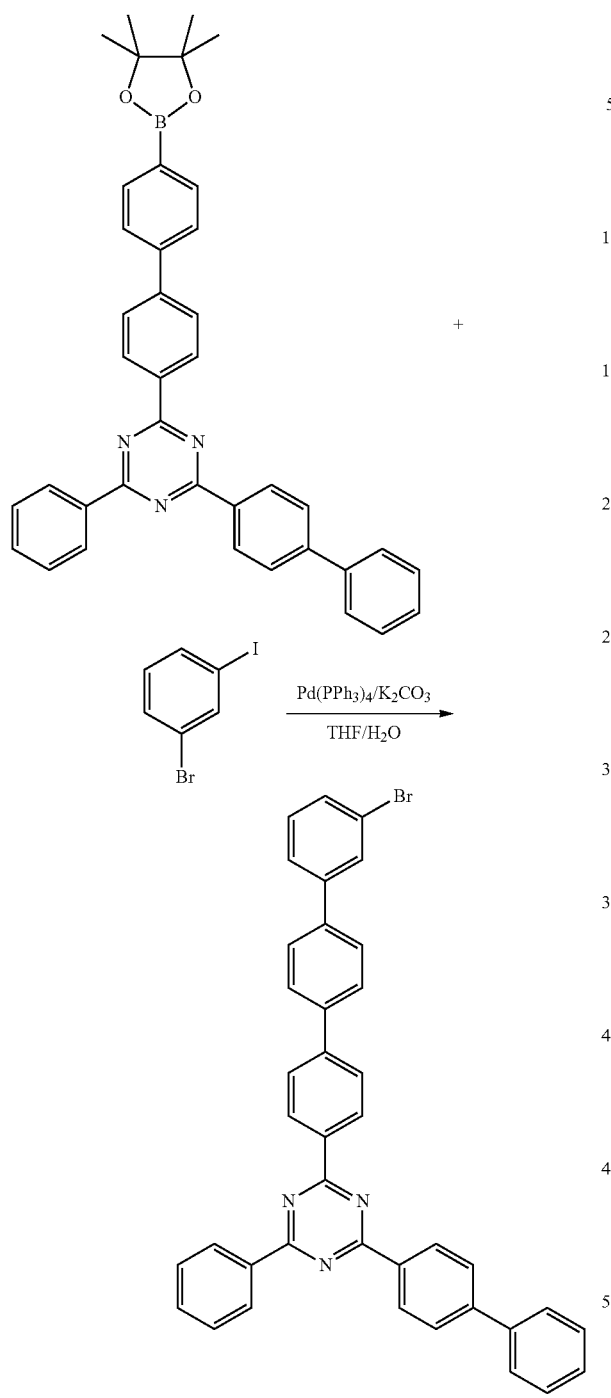

2-([1,1'-biphenyl]-4-yl)-4-phenyl-6-(4'-(4,4,5,5-tetramethyl-1,3,2-dioxaborolan-2-yl)-[1,1'-biphenyl]-4-yl)-1,3,5-triazine (20 g, 34.4 mmol) was dissolved in THF, and then 1-bromo-3-iodo benzene (11.56 g, 40.85 mmol), Pd(PPh$_3$)$_4$ (1.95 g 1.69 mmol), K$_2$CO$_3$ (23.34 g, 168.9 mmol) and water were added, and stirred under reflux at 100° C. for 3 hours. Upon completion of the reaction, the organic layer was extracted with E.A. and water, and was dried using MgSO4 and concentrated. The resulting organic material was purified by silica gel column to obtain 2-([1,1'-biphenyl]-4-yl)-4-(3"-bromo-[1,1':4',1"-terphenyl]-4-yl)-6-phenyl-1,3,5-triazine (14 g, 66.7%).

224

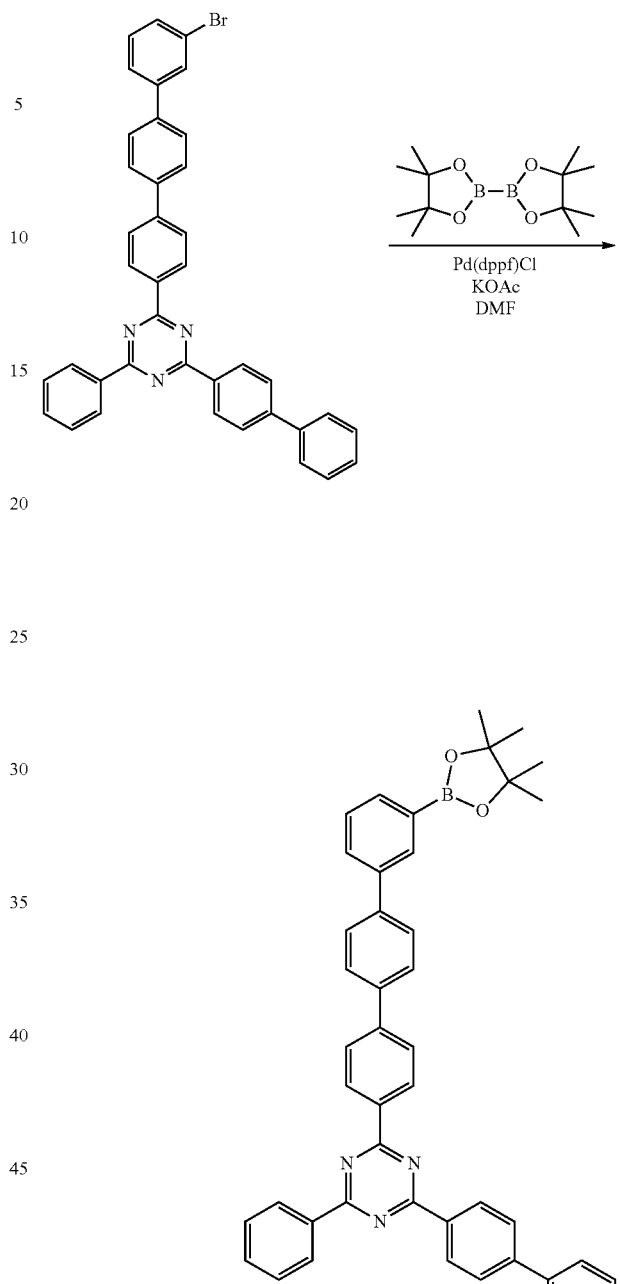

2-([1,1'-biphenyl]-4-yl)-4-(3"-bromo-[1,1':4',1"-terphenyl]-4-yl)-6-phenyl-1,3,5-triazine (10.0 g, 16.22 mmol) was dissolved with DMF in a round bottom flask, and then bis(pinacolato) diboron (6.18 g, 24.33 mmol), Pd(dppf)Cl$_2$ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silica gel column and recrystallization to obtain 2-([1,1'-biphenyl]-4-yl)-4-phenyl-6-(3"-(4,4,5,5-tetramethyl-1,3,2-dioxaborolan-2-yl)-[1,1':4',1"-terphenyl]-4-yl)-1,3,5-triazine (7 g, 65.03%).

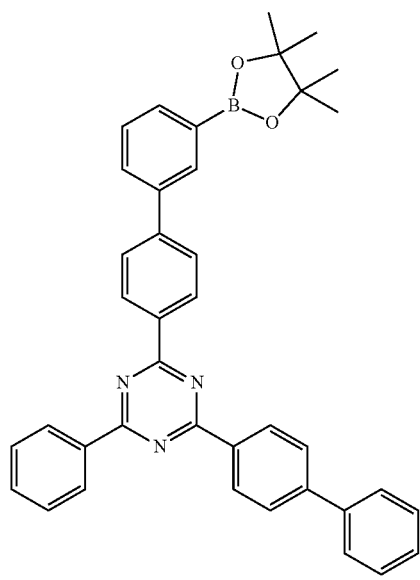

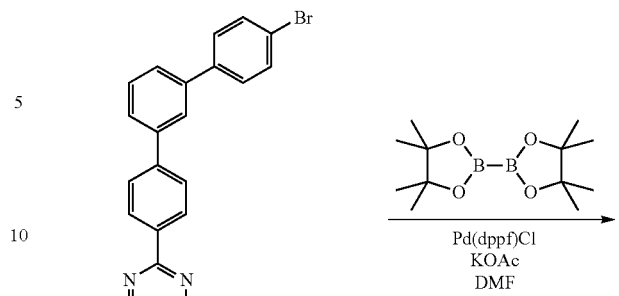

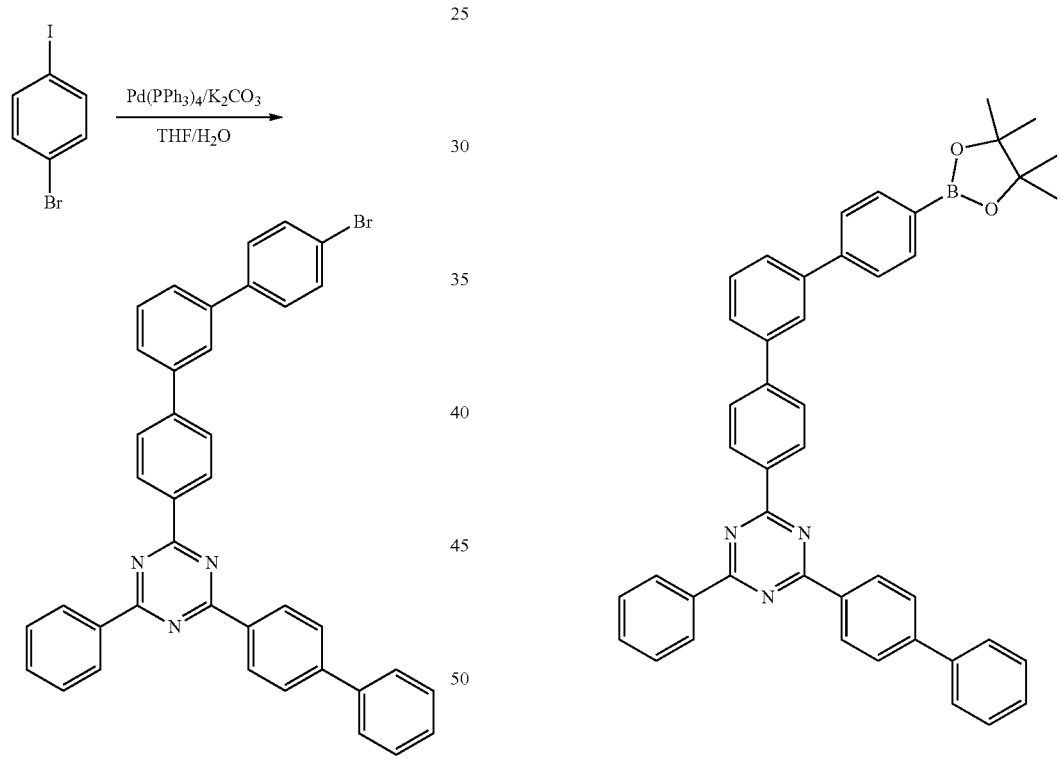

2-([1,1'-biphenyl]-4-yl)-4-phenyl-6-(3'-(4,4,5,5-tetramethyl-1,3,2-dioxaborolan-2-yl)-[1,1'-biphenyl]-4-yl)-1,3,5-triazine (20 g, 34.04 mmol) was dissolved in THF, and then 1-bromo-4-iodo benzene (11.56 g, 40.85 mmol), Pd(PPh$_3$)$_4$ (1.95 g, 1.69 mmol), K$_2$CO$_3$ (23.34 g, 168.9 mmol) and water were added, and stirred under reflux at 100° C. for 3 hours. Upon completion of the reaction, the organic layer was extracted with E.A. and water, and was dried using MgSO$_4$ and concentrated. The resulting organic material was purified by silica gel column to obtain 2-([1,1'-biphenyl]-4-yl)-4-(4"-bromo-[1,1':3',1"-terphenyl]-4-yl)-6-phenyl-1,3,5-triazine (14 g, 66.7%).

2-([1,1'-biphenyl]-4-yl)-4-(4"-bromo-[1,1':3',1"-terphenyl]-4-yl)-6-phenyl-1,3,5-triazine (10.0 g 16.22 mmol) was dissolved with DMF in around bottom flask, and then bis(pinacolato) diboron (6.18 g, 24.33 mmol), Pd(dppf)Cl$_2$ (1.24 g 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silica gel column and recrystallization to obtain 2-([1,1'-biphenyl]-4-yl)-4-phenyl-6-(4"-(4,4,5,5-tetramethyl-1,3,2-dioxaborolan-2-yl)-[1,1':3',1"-terphenyl]-4-yl)-1,3,5-triazine (7 g, 65.03%).

227

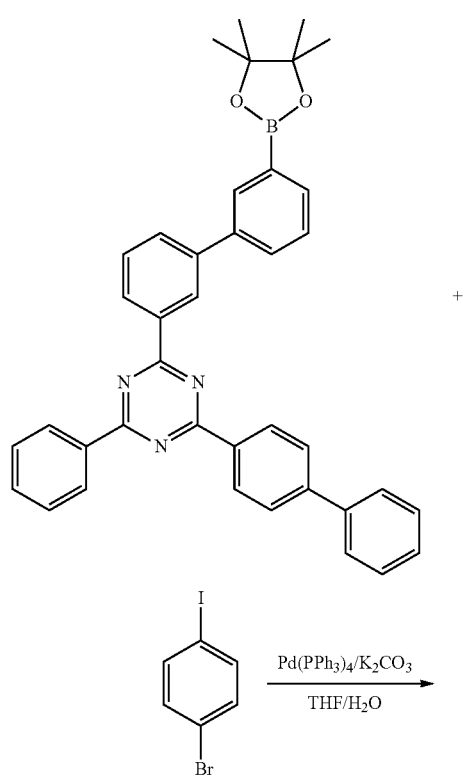

2-([1,1'-biphenyl]-4-yl)-4-phenyl-6-(3'-(4,4,5,5-tetramethyl-1,3,2-dioxaborolan-2-yl)-[1,1'-biphenyl]-3-yl)-1,3,5-triazine (20 g, 34.04 mmol) was dissolved in THF, and then 1-bromo-4-iodo benzene (11.56 g, 40.85 mmol), Pd(PPh₃)₄ (1.95 g, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphenyl]-4-yl)-4-(4"-bromo-[1,1':3',1"-terphenyl]-3-yl)-6-phenyl-1,3,5-triazine (14 g, 66.7%).

228

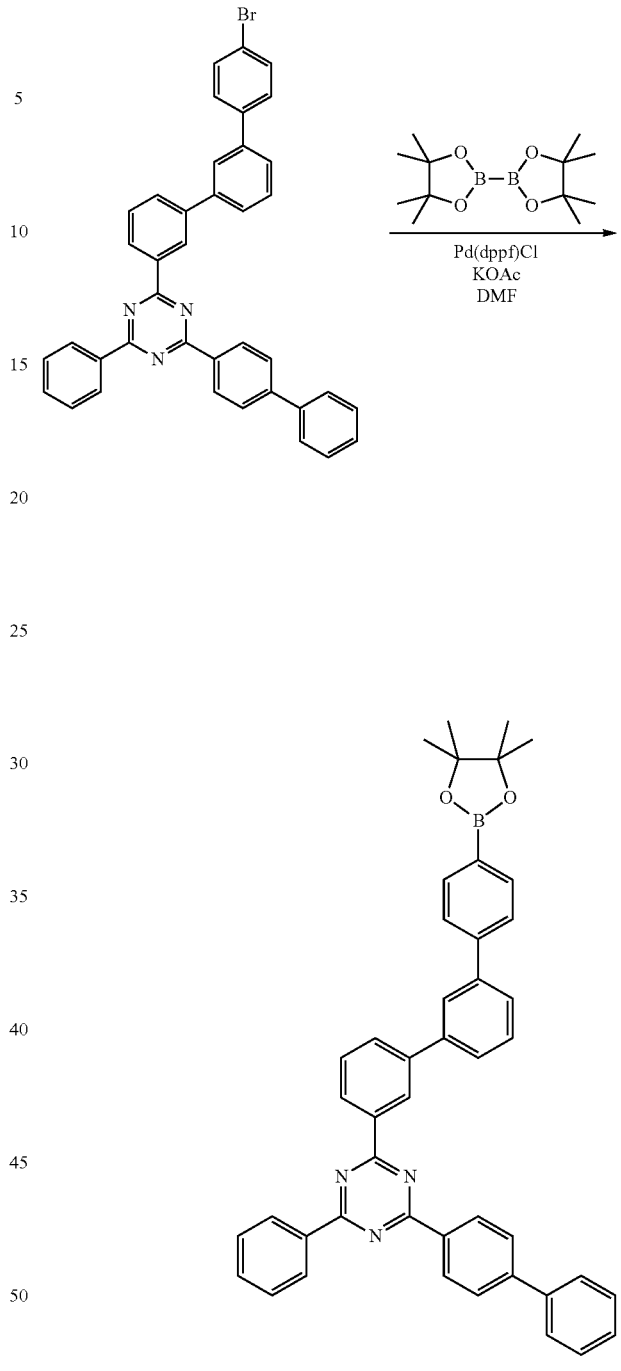

2-([1,1'-biphenyl]-4-yl)-4-(4"-bromo-[1,1':3',1"-terphenyl]-3-yl)-6-phenyl-1,3,5-triazine (10.0 g, 16.22 mmol) was dissolved with DMF in a round bottom flask, and then bis(pinacolato) diboron (6.18 g, 24.33 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(4"-(4,4,5,5-tetramethyl-1,3,2-dioxaborolan-2-yl)-[1,1':3',1"-terphenyl]-3-yl)-1,3,5-triazine (8 g, 74.32%).

229

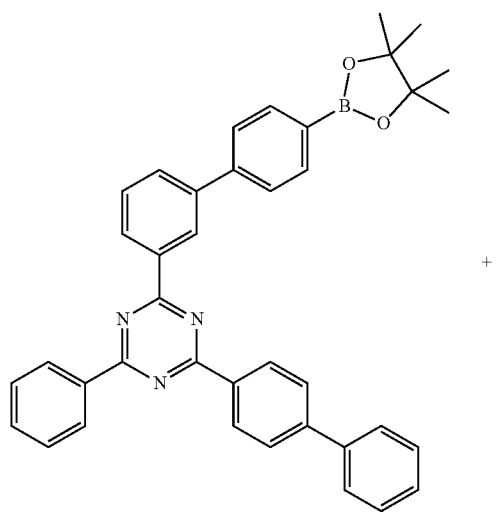

+

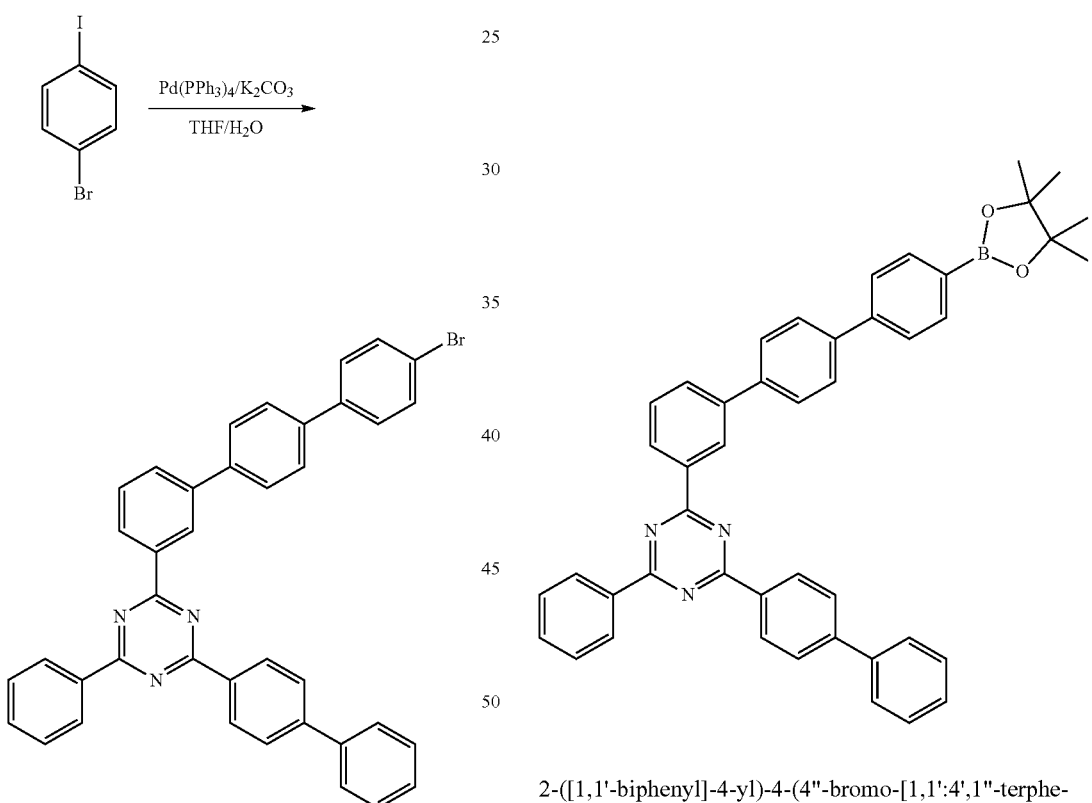

2-([1,1'-biphenyl]-4-yl)-4-phenyl-6-(4'-(4,4,5,5-tetramethyl-1,3,2-dioxaborolan-2-yl)-[1,1'-biphenyl]-3-yl)-1,3,5-triazine (20 g, 34.4 mmol) was dissolved in THF, and then 1-bromo-4-iodo benzene (11.56 g, 40.85 mmol), Pd(PPh₃)₄ (1.95 g 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphenyl]-4-yl)-4-(4"-bromo-[1,1':4',1"-terphenyl]-3-yl)-6-phenyl-1,3,5-triazine (15 g, 71.47%).

230

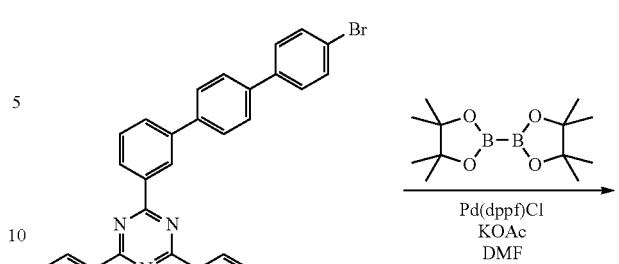

2-([1,1'-biphenyl]-4-yl)-4-(4"-bromo-[1,1':4',1"-terphenyl]-3-yl)-6-phenyl-1,3,5-triazine (10.0 g, 16.22 mmol) was dissolved with DMF in around bottom flask, and then bis(pinacolato) diboron (6.18 g, 24.33 mmol), Pd(dppf)Cl₂ (1.24 g 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(4"-(4,4,5,5-tetramethyl-1,3,2-dioxaborolan-2-yl)-[1,1':4',1"-terphenyl]-3-yl)-1,3,5-triazine (7 g, 65.03%).

231

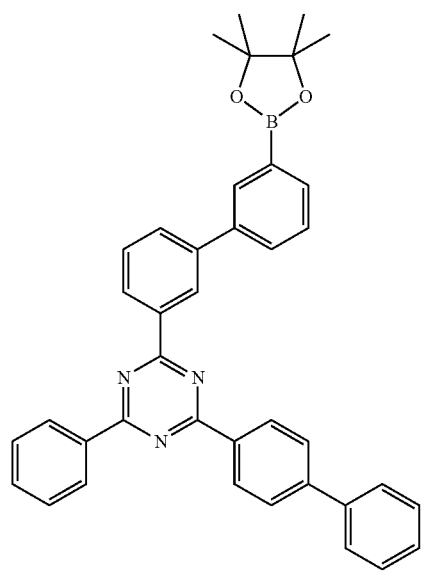

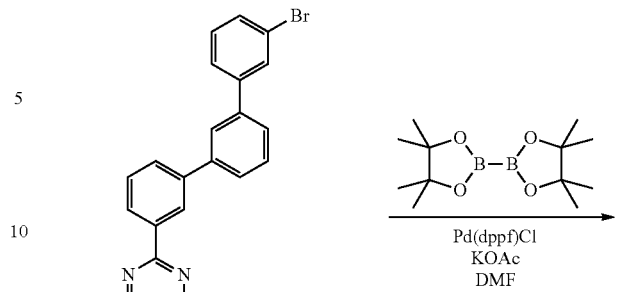

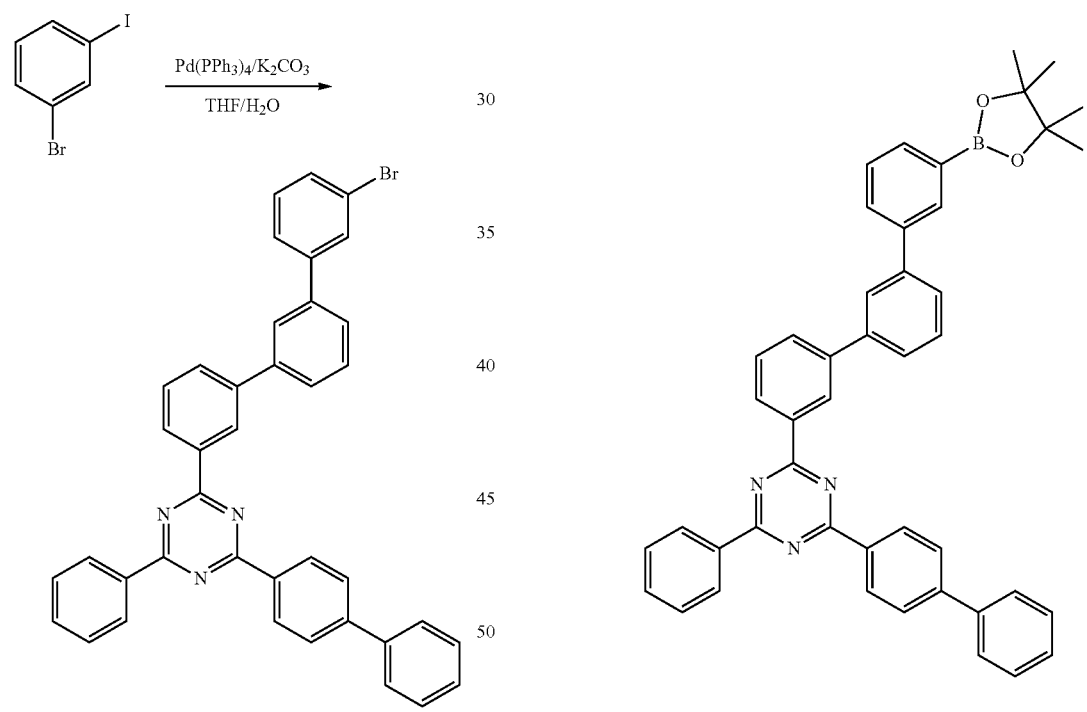

2-([1,1'-biphenyl]-4-yl)-4-phenyl-6-(3'-(4,4,5,5-tetramethyl-1,3,2-dioxaborolan-2-yl)-[1,1'-biphenyl]-3-yl)-1,3,5-triazine (20 g, 34.4 mmol) was dissolved in THF, and then 1-bromo-3-iodo benzene (11.56 g, 40.85 mmol), Pd(PPh₃)₄ (1.958, 1.69 mmol), K₂CO₃ (23.34 g, 168.9 mmol) and water were added, and stirred under reflux at 100° C. for 3 hours. Upon completion of the reaction, the organic layer was extracted with E.A. and water, and was dried using MgSO₄ and concentrated. The resulting organic material was purified by silica gel column to obtain 2-([1,1'-biphenyl]-4-yl)-4-(3"-bromo-[1,1':3',1"-terphenyl]-3-yl)-6-phenyl-1,3,5-triazine (15 g, 71.47%).

2-([1,1'-biphenyl]-4-yl)-4-(3"-bromo-[1,1':3',1"-terphenyl]-3-yl)-6-phenyl-1,3,5-triazine (10.0 g, 16.22 mmol) was dissolved with DMF in a round bottom flask, and then bis(pinacolato) diboron (6.18 g, 24.33 mmol), Pd(dppf)Cl₂ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH₂Cl₂ and water. The resulting organic layer was dried using MgSO₄ and concentrated, and the resulting compound was subjected to silica gel column and recrystallization to obtain 2-([1,1'-biphenyl]-4-yl)-4-phenyl-6-(3"-(4,4,5,5-tetramethyl-1,3,2-dioxaborolan-2-yl)-[1,1':3',1"-terphenyl]-3-yl)-1,3,5-triazine (7 g, 65.03%).

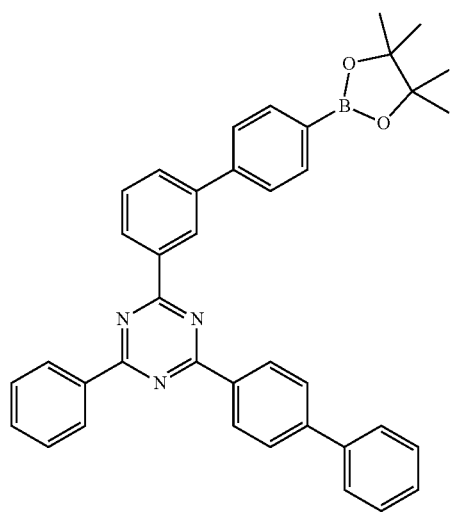

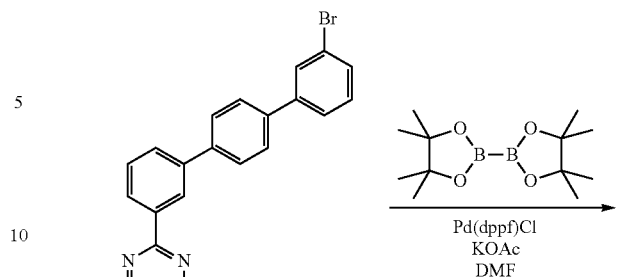

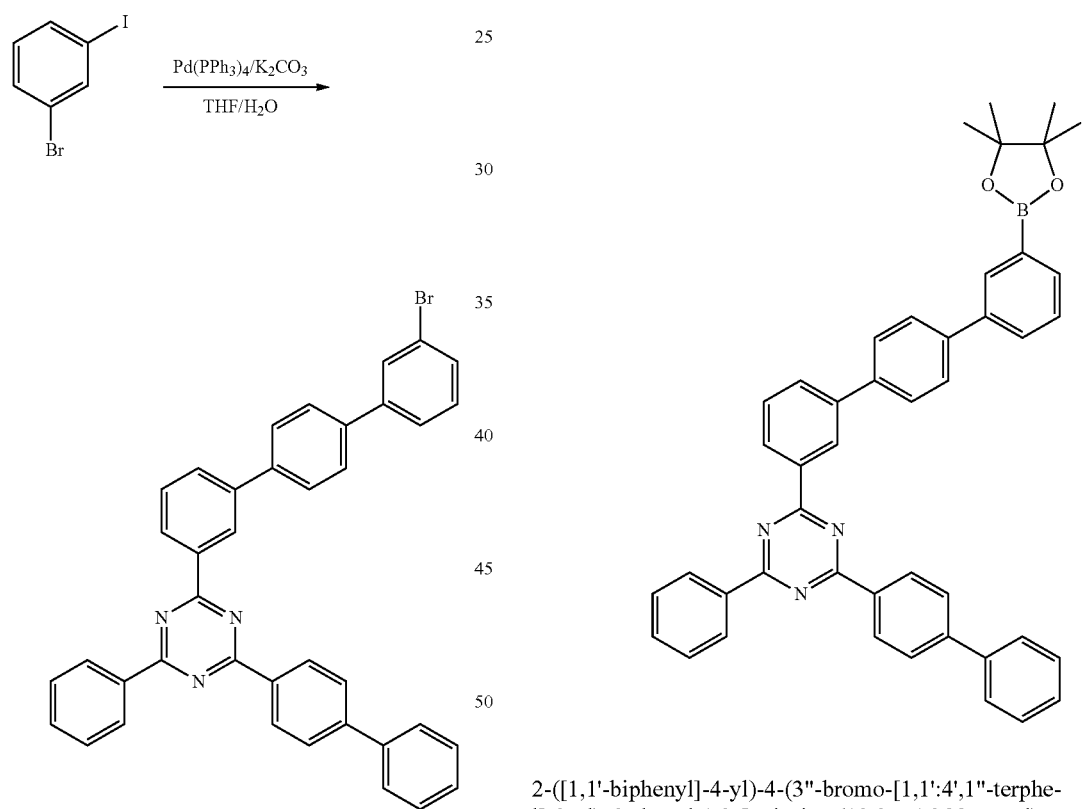

2-([1,1'-biphenyl]-4-yl)-4-phenyl-6-(4'-(4,4,5,5-tetramethyl-1,3,2-dioxaborolan-2-yl)-[1,1'-biphenyl]-3-yl)-1,3,5-triazine (20 g, 34.04 mmol) was dissolved in THF, and then 1-bromo-3-iodo benzene (11.56 g, 40.85 mmol), Pd(PPh$_3$)$_4$ (1.95 g, 1.69 mmol), K$_2$CO$_3$ (23.34 g, 168.9 mmol) and water were added, and stirred under reflux at 100° C. for 3 hours. Upon completion of the reaction, the organic layer was extracted with E.A. and water, and was dried using MgSO$_4$ and concentrated. The resulting organic material was purified by silica gel column to obtain 2-([1,1'-biphenyl]-4-yl)-4-(3"-bromo-[1,1':4',1"-terphenyl]-3-yl)-6-phenyl-1,3,5-triazine (14 g, 66.7%).

2-([1,1'-biphenyl]-4-yl)-4-(3"-bromo-[1,1':4',1"-terphenyl]-3-yl)-6-phenyl-1,3,5-triazine (10.0 g 16.22 mmol) was dissolved with DMF in around bottom flask, and then bis(pinacolato) diboron (6.18 g, 24.33 mmol), Pd(dppf)Cl$_2$ (1.24 g 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silica gel column and recrystallization to obtain 2-([1,1'-biphenyl]-4-yl)-4-phenyl-6-(3"-(4,4,5,5-tetramethyl-1,3,2-dioxaborolan-2-yl)-[1,1':4',1"-terphenyl]-3-yl)-1,3,5-triazine (7 g, 65.03%).

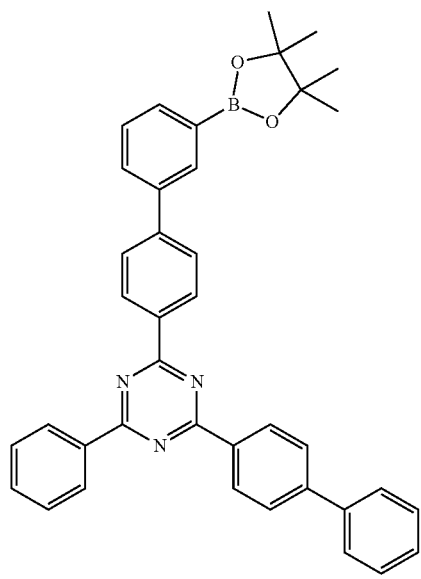

+

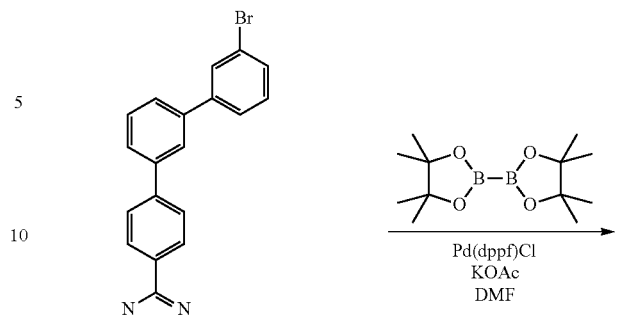

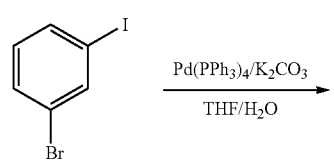

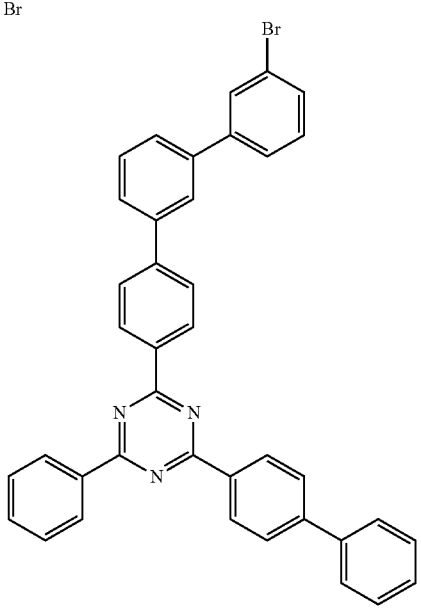

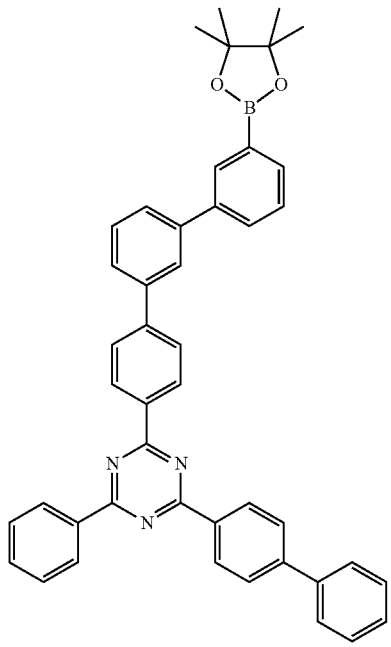

2-([1,1'-biphenyl]-4-yl)-4-phenyl-6-(3'-(4,4,5,5-tetramethyl-1,3,2-dioxaborolan-2-yl)-[1,1'-biphenyl]-4-yl)-1,3,5-triazine (20 g, 34.04 mmol) was dissolved in THF, and then 1-bromo-3-iodo benzene (11.56 g, 40.85 mmol), Pd(PPh$_3$)$_4$ (1.95 g, 1.69 mmol), K$_2$CO$_3$ (23.34 g, 168.9 mmol) and water were added, and stirred under reflux at 100° C. for 3 hours. Upon completion of the reaction, the organic layer was extracted with E.A. and water, and was dried using MgSO$_4$ and concentrated. The resulting organic material was purified by silica gel column to obtain 2-([1,1'-biphenyl]-4-yl)-4-(3"-bromo-[1,1':3',1"-terphenyl]-4-yl)-6-phenyl-1,3,5-triazine (14 g, 66.7%).

2-([1,1'-biphenyl]-4-yl)-4-(3"-bromo-[1,1':3',1"-terphenyl]-4-yl)-6-phenyl-1,3,5-triazine (10.0 g 16.22 mmol) was dissolved with DMF in around bottom flask, and then bis(pinacolato) diboron (6.18 g, 24.33 mmol), Pd(dppf)Cl$_2$ (1.24 g, 1.69 mmol) (0.03 eq), KOAc (23.34 g, 168.9 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silica gel column and recrystallization to obtain 2-([1,1'-biphenyl]-4-yl)-4-phenyl-6-(3"-(4,4,5,5-tetramethyl-1,3,2-dioxaborolan-2-yl)-[1,1':3',1"-terphenyl]-4-yl)-1,3,5-triazine (7 g, 65.03%).

Synthesis Example and FDMS Data of Final Products

(1) Synthesis Example (Compounds 1-1-1 to 1-1-13)

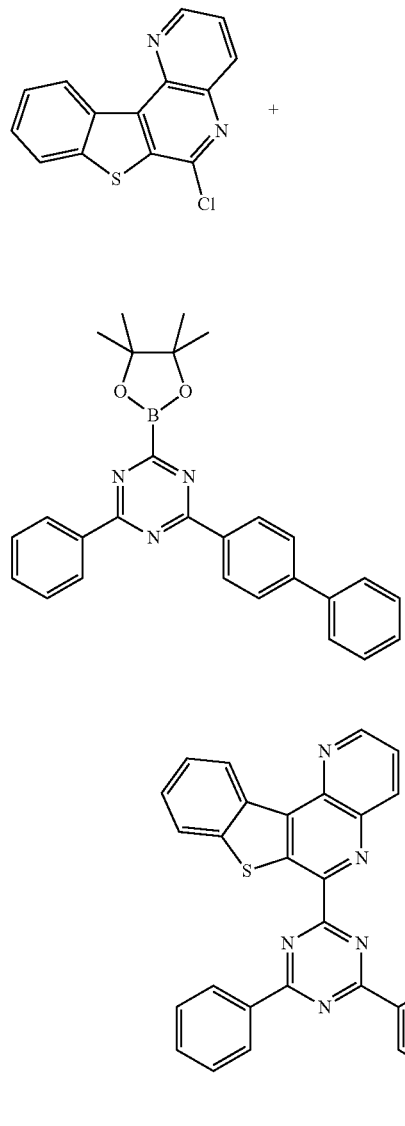

(2) Synthesis Example (Compounds 1-2-1 to 1-2-13)

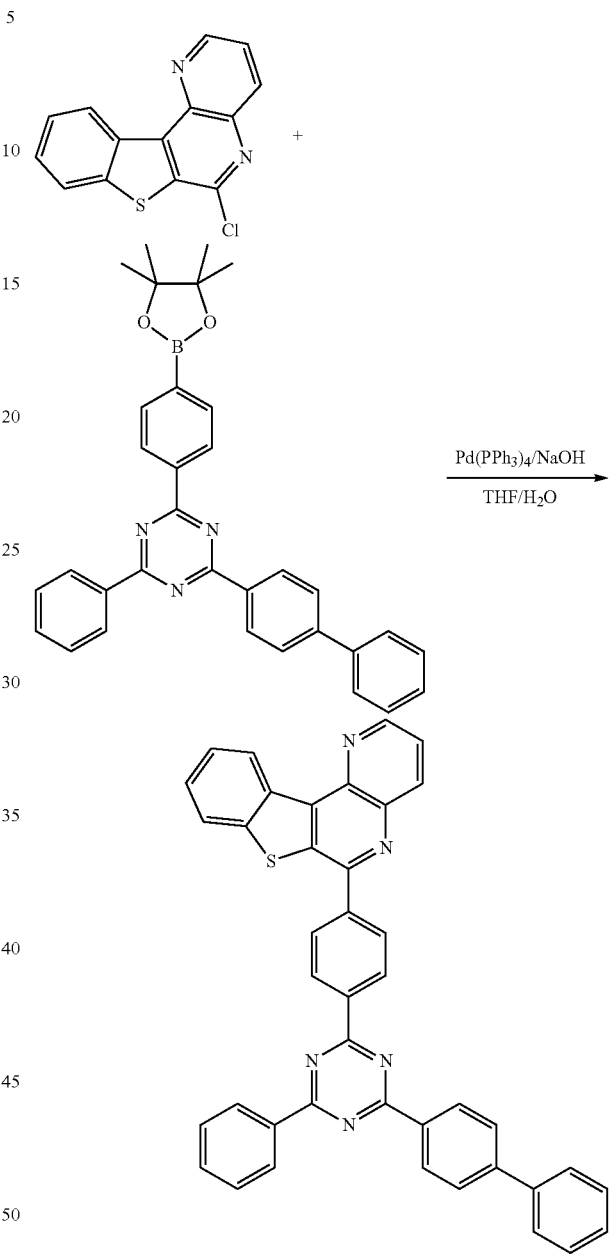

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4,4,5,5-tetramethyl-1,3,2-dioxaborolan-2-yl)-1,3,5-triazine (48.24 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 25 g (yield: 62.2%) of the final product.

Compounds 1-1-2 to 1-1-13 are synthesized by the same method as Compound 1-1-1, using Cores 1-2 to 1-13.

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4-(4,4,5,5-tetramethyl-1,3,2-dioxaborolan-2-yl)phenyl)-1,3,5-triazine (56.67 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 30 g (yield: 65.5%) of the final product.

Compounds 1-2-2 to 1-2-13 are synthesized by the same method as Compound 1-2-1 using Cores 1-2 to 1-13.

(3) Synthesis Example (Compounds 1-2-14 to 1-2-26)

(4) Synthesis Example (Compounds 1-3-1 to 1-3-13)

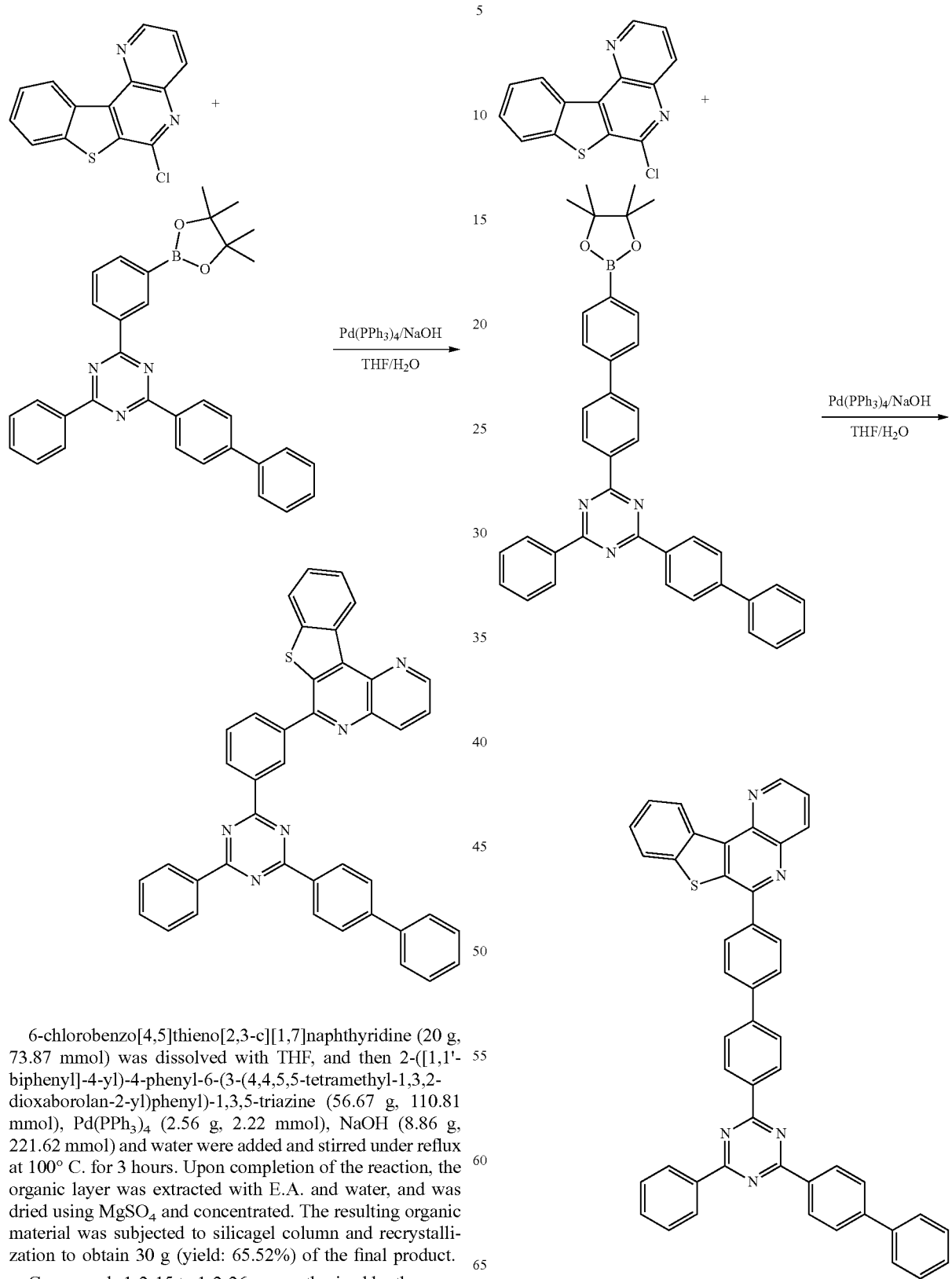

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3-(4,4,5,5-tetramethyl-1,3,2-dioxaborolan-2-yl)phenyl)-1,3,5-triazine (56.67 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 30 g (yield: 65.52%) of the final product.

Compounds 1-2-15 to 1-2-26 are synthesized by the same method as Compound 1-2-14 using Cores 1-2 to 1-13.

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4'-(4,4,5,5-tetramethyl-1,3,2-dioxaborolan-2-yl)-[1,1'-biphenyl]-4-yl)-1,3,5-triazine (65.11 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 33 g (yield: 64.2%) of the final product.

Compounds 1-3-2 to 1-3-13 are synthesized by the same method as Compound 1-3-1 using Cores 1-2 to 1-13.

(5) Synthesis Example (Compounds 1-3-14 to 1-3-26)

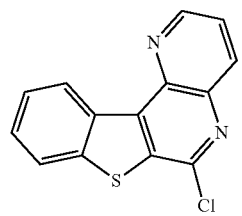
+

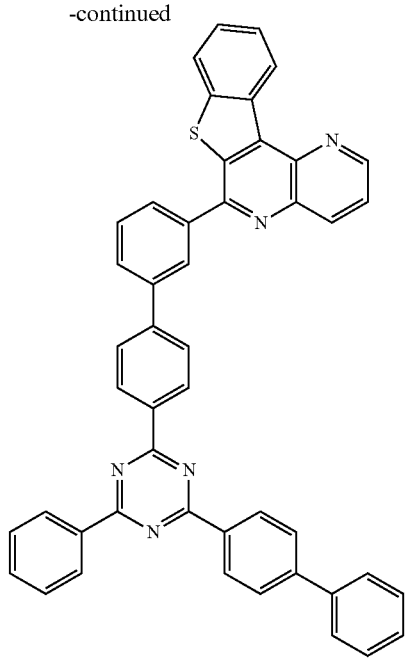

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3'-(4,4,5,5-tetramethyl-1,3,2-dioxaborolan-2-yl)-[1,1'-biphenyl]-4-yl)-1,3,5-triazine (65.11 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 35 g (yield: 68%) of the final product.

Compounds 1-3-15 to 1-3-26 are synthesized by the same method as Compound 1-3-14 using Cores 1-2 to 1-13.

(6) Synthesis Example (Compounds 1-3-27 to 1-3-39)

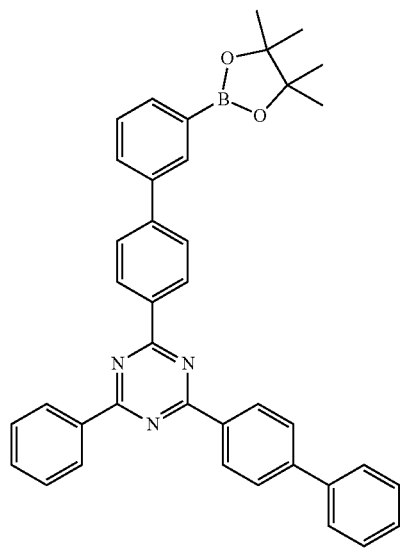
Pd(PPh₃)₄/NaOH
THF/H₂O
→

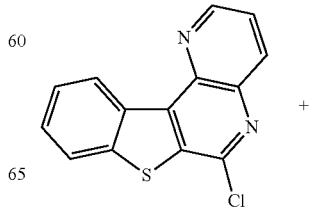
+

(7) Synthesis Example (Compounds 1-3-40 to 1-3-52)

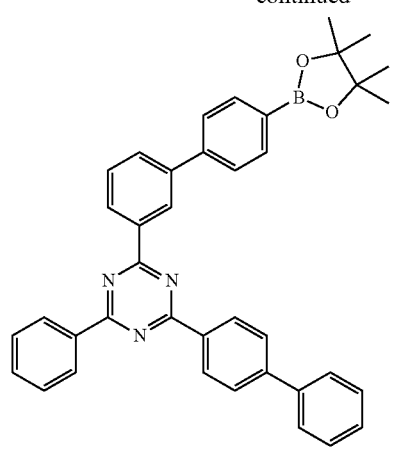

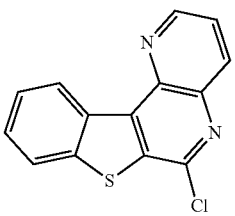

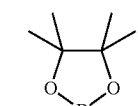

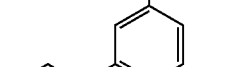

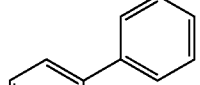

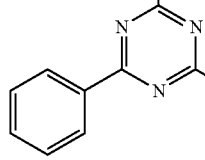

6-chlorobenzo[4,5]thieno[2,3-c][1,7]naphthyridine (20 g, mmol) was dissolved with THF, and then 2-([1,1'-biphenyl]-4-yl)-4-phenyl-6-(4'-(4,4,5,5-tetramethyl-1,3,2-dioxaborolan-2-yl)-[1,1'-biphenyl]-3-yl)-1,3,5-triazine (65.11 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 32 g (yield: 62.25%) of the final product.

Compounds 1-3-28 to 1-3-39 are synthesized by the same method as Compound 1-3-27 using Cores 1-2 to 1-13.

245

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3'-(4,4,5,5-tetramethyl-1,3,2-dioxaborolan-2-yl)-[1,1'-biphenyl]-3-yl)-1,3,5-triazine (65.11 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 34 g (yield: 66.1%) of the final product.

Compounds 1-3-41 to 1-3-52 are synthesized by the same method as Compound 1-3-40, using Cores 1-2 to 1-13.

(8) Synthesis Example (Compounds 1-4-1 to 1-4-13)

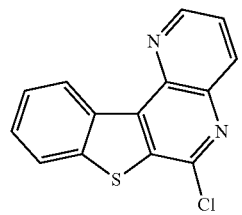

+

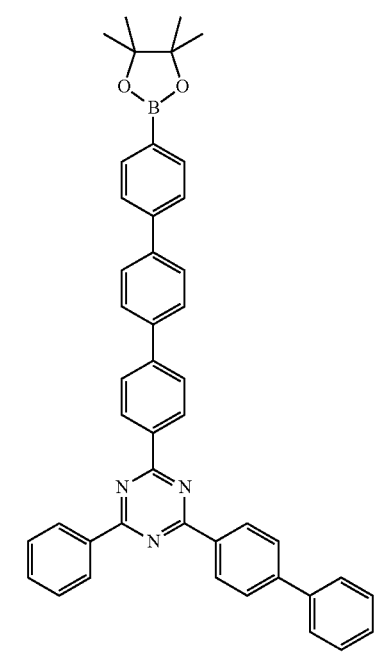

Pd(PPh₃)₄/NaOH
―――――――――→
THF/H₂O

246

-continued

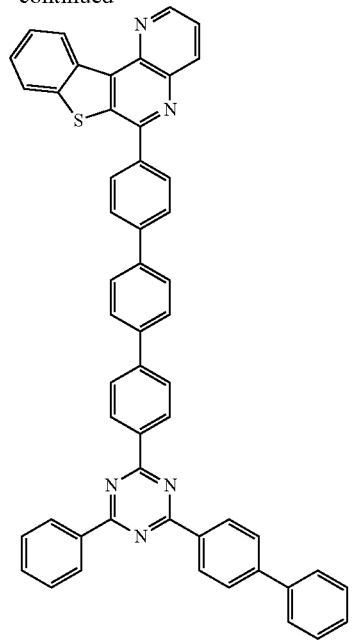

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4''-(4,4,5,5-tetramethyl-1,3,2-dioxaborolan-2-yl)-[1,1':4',1''-terphenyl]-4-yl)-1,3,5-triazine (73.54 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 35 g (yield: 61.37%) of the final product.

Compounds 1-4-2 to 1-4-13 are synthesized by the same method as Compound 1-4-1 using Cores 1-2 to 1-13.

(9) Synthesis Example (Compounds 1-4-14 to 1-4-26)

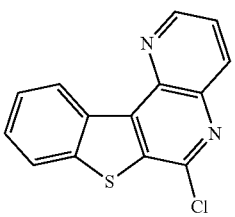

+

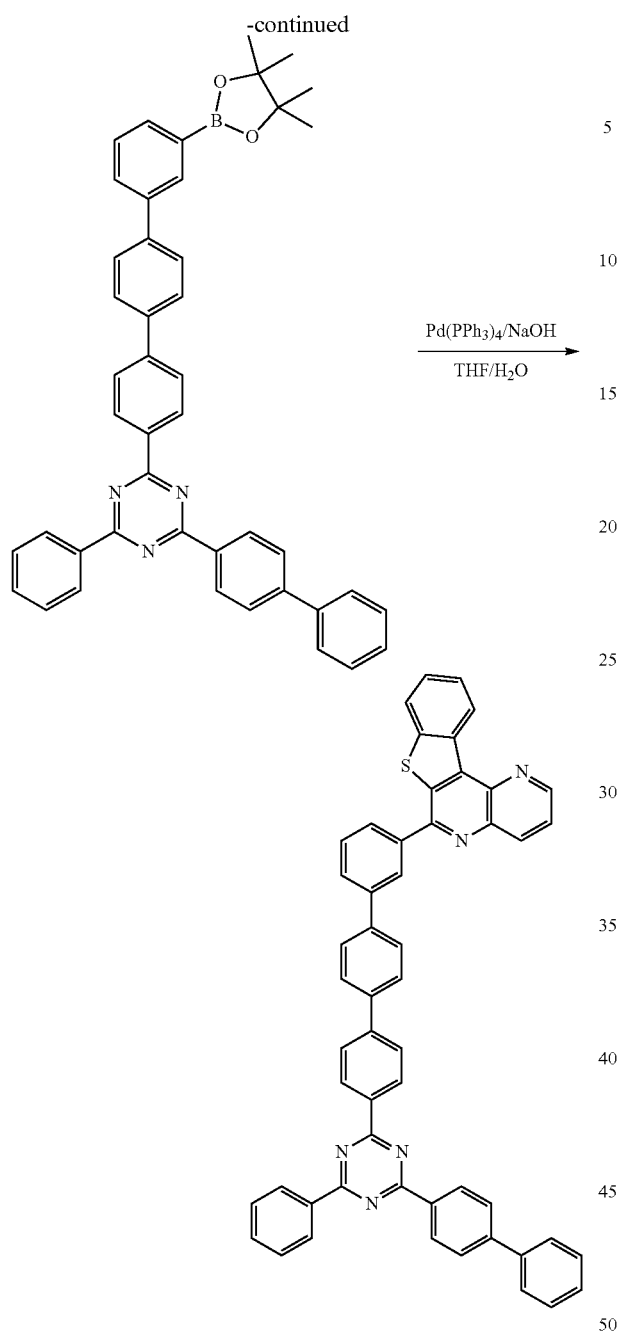

(10) Synthesis Example (Compounds 1-4-27 to 1-4-39)

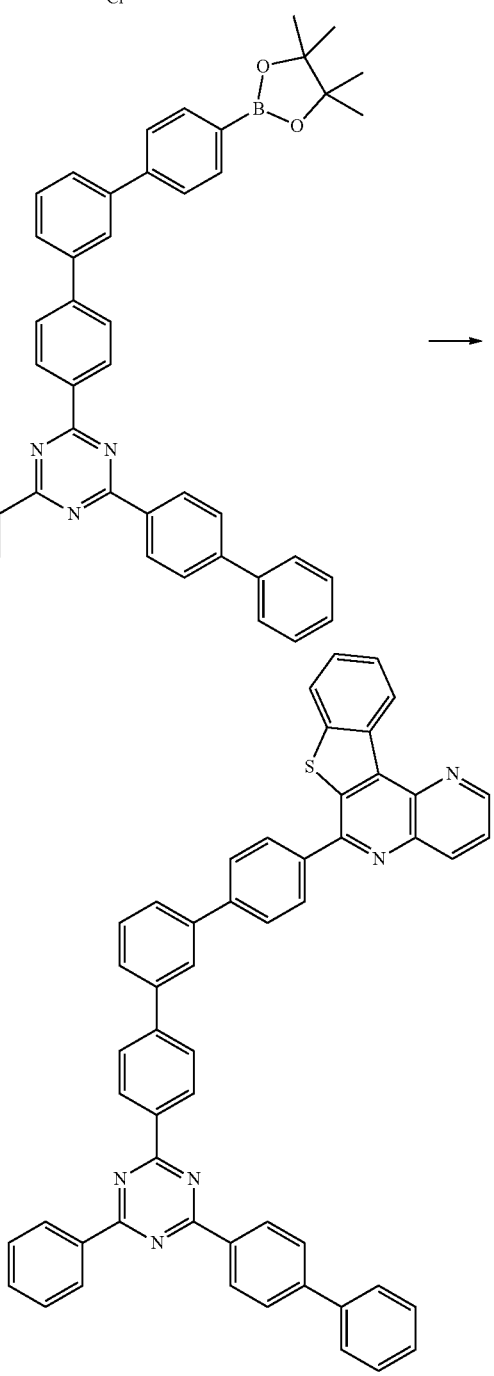

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1':4',1"-terphenyl]-4-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 37 g (yield: 64.88%) of the final product.

Compounds 1-4-15 to 1-4-26 are synthesized by the same method as Compound 1-4-14 using Cores 1-2 to 1-13.

249

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4"-(4,4,5,5-tetramethyl-1,3,2-dioxaborolan-2-yl)-[1,1':3',1"-terphenyl]-4-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 39 g (yield: 68.4%) of the final product.

Compounds 1-4-28 to 1-4-39 are synthesized by the same method as Compound 1-4-27 using Cores 1-2 to 1-13.

(11) Synthesis Example (Compounds 1-4-40 to 1-4-52)

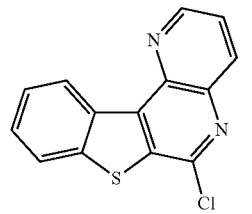

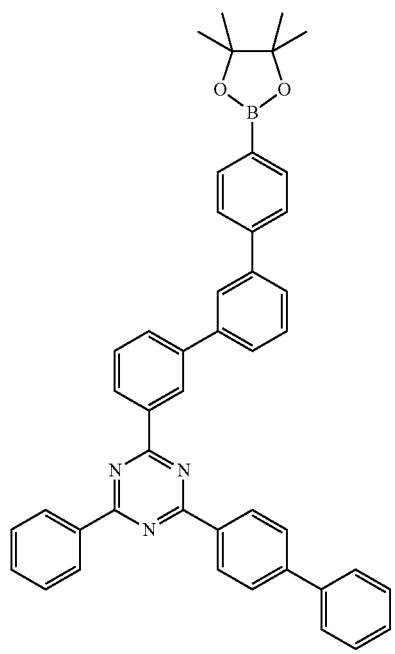

250

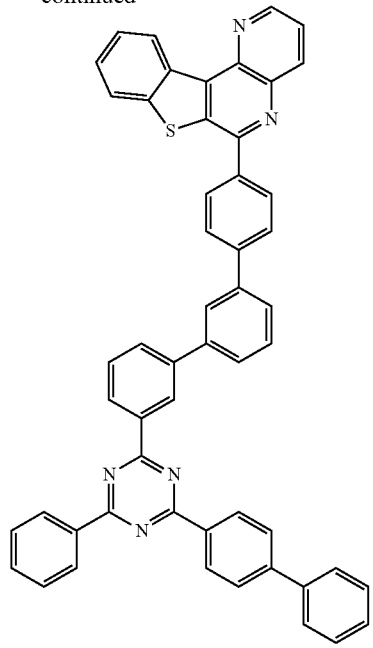

6-chlorobenzo[4,5]thieno[2,3-c][1,7]naphthyridine (20 g 73.87 mmol) was dissolved with THF, and then 2-([1,1'-biphenyl]-4-yl)-4-phenyl-6-(4"-(4,4,5,5-tetramethyl-1,3,2-dioxaborolan-2-yl)-[1,1':3',1"-terphenyl]-3-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 39 g (yield: 68.38%) of the final product.

Compounds 1-4-41 to 1-4-52 are synthesized by the same method as Compound 1-4-40, using Cores 1-2 to 1-13.

(12) Synthesis Example (Compounds 1-4-53 to 1-4-65)

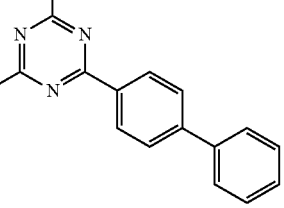

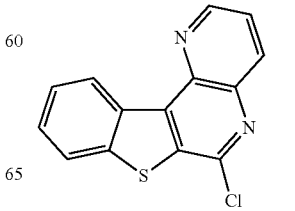

(13) Synthesis Example (Compounds 1-4-66 to 1-4-78)

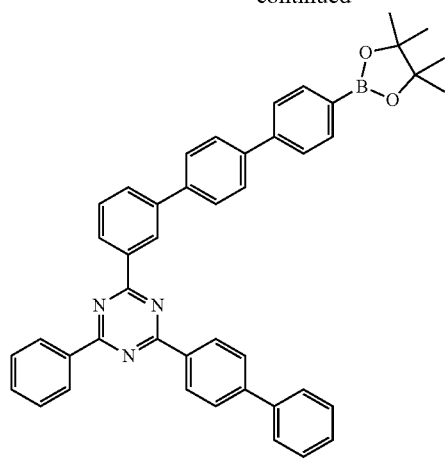

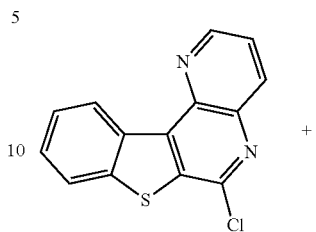

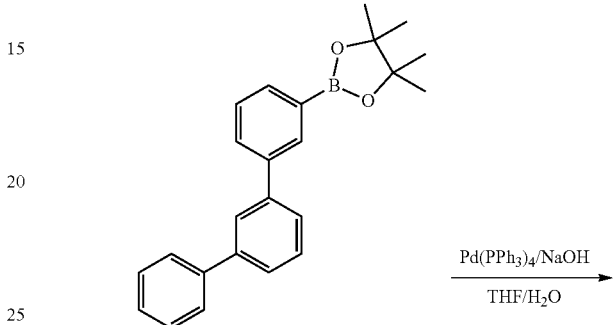

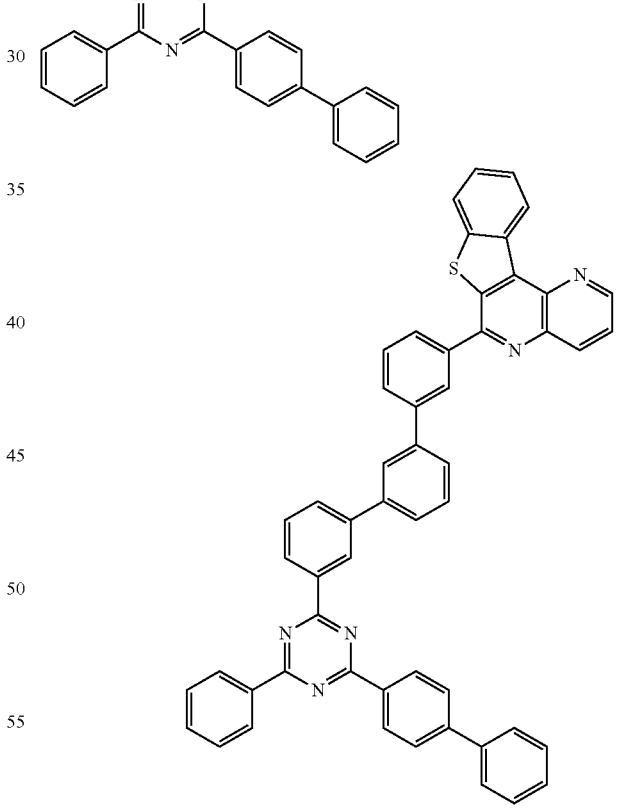

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(4"-(4,4,5,5-tetramethyl-1,3,2-dioxaborolan-2-yl)-[1,1':4',1"-terphenyl]-3-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 36 g (yield: 63.13%) of the final product.

Compounds 1-4-54 to 1-4-65 are synthesized by the same method as Compound 1-4-53, using Cores 1-2 to 1-13.

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1':3',1"-terphenyl]-3-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 36 g (yield: 63.13%) of the final product.

Compounds 1-4-67 to 1-4-78 are synthesized by the same method as Compound 1-4-66, using Cores 1-2 to 1-13.

(14) Synthesis Example (Compounds 1-4-79 to 1-4-91)

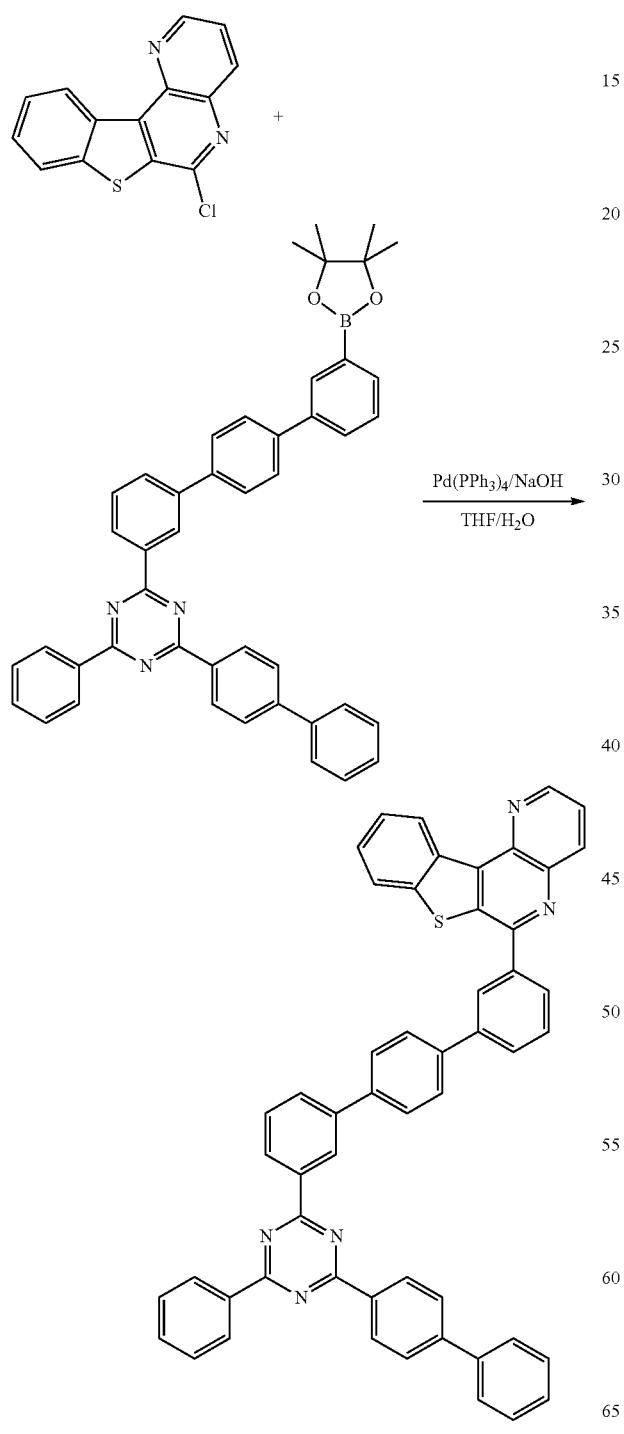

6-chlorobenzo[4,5]thieno[2,3-c][1,7]naphthyridine (20 g, 73.87 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1':4',1"-terphenyl]-3-yl)-1,3,5-triazine (73.54 g, 110.81 mmol), Pd(PPh₃)₄ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 37 g (yield: 64.88%) of the final product.

Compounds 1-4-80 to 1-4-91 are synthesized by the same method as Compound 1-4-79, using Cores 1-2 to 1-13.

(15) Synthesis Example (Compounds 1-4-92 to 1-4-104)

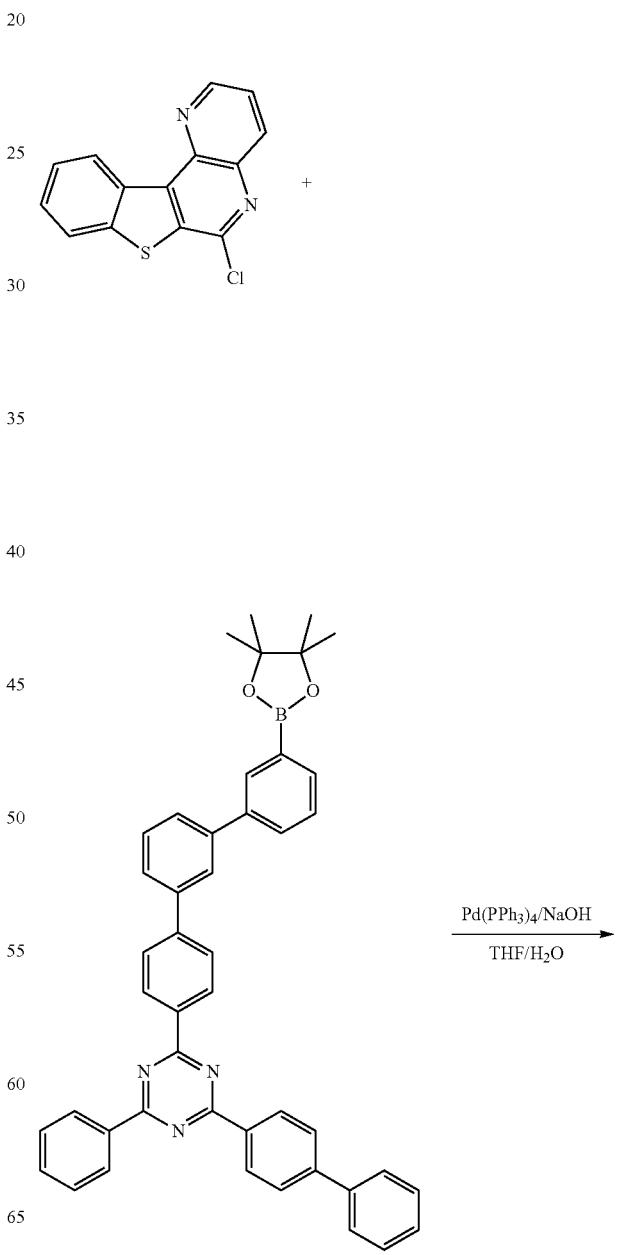

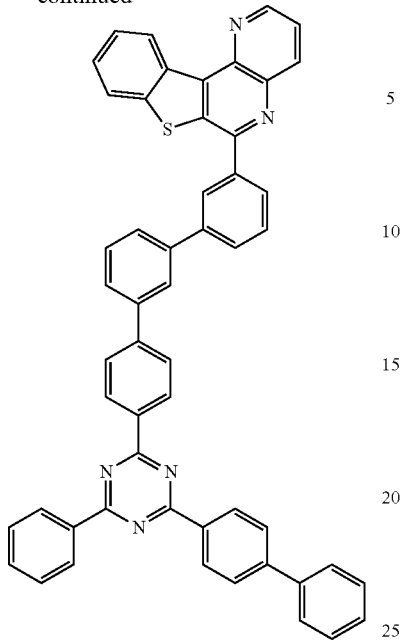

6-chlorobenzo[4,5]thieno[2,3-c][1,7]naphthyridine (20 g, 110.81 mmol) was dissolved with THF, and then 2-([1,1'-biphenyl]-4-yl)-4-phenyl-6-(3''-(4,4,5,5-tetramethyl-1,3,2-dioxaborolan-2-yl)-[1,1':3',1''-terphenyl]-4-yl)-1,3,5-triazine (73.54 g, 110.81 mmol), Pd(PPh$_3$)$_4$ (2.56 g, 2.22 mmol), NaOH (8.86 g, 221.62 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 37 g (yield: 64.88%) of the final product.

Compounds 1-4-93 to 1-4-104 are synthesized by the same method as Compound 1-4-92, using Cores 1-2 to 1-13.

TABLE 3

| Compound | FD-MS | Compound | FD-MS |
| --- | --- | --- | --- |
| 1-1-1~1-1-6, 1-1-9, 1-1-10 | Chemical Formula: C35H21N5S Molecular Weight: 543.65 m/z: 543.15 (100.0%) | 1-1-7, 1-1-8 | Chemical Formula: C34H20N6S Molecular Weight: 544.64 m/z: 544.15 (100.0%) |
| 1-1-11, 1-1-12 | Chemical Formula: C33H19N7S Molecular Weight: 545.62 m/z: 545.14 (100.0%) | 1-1-13 | Chemical Formula: C32H18N8S Molecular Weight: 546.61 m/z: 546.14 (100.0%) |
| 1-2-1~1-2-6, 1-2-9, 1-2-10 | Chemical Formula: C41H25N5S Molecular Weight: 619.75 m/z: 619.18 (100.0%) | 1-2-7, 1-2-8 | Chemical Formula: C40H24N6S Molecular Weight: 620.73 m/z: 620.18 (100.0%) |
| 1-2-11, 1-2-12 | Chemical Formula: C39H23N7S Molecular Weight: 621.72 m/z: 621.17 (100.0%) | 1-2-13 | Chemical Formula: C38H22N8S Molecular Weight: 622.71 m/z: 622.17 (100.0%) |
| 1-2-14~1-2-19, 1-2-22, 1-2-23 | Chemical Formula: C41H25N5S Molecular Weight: 619.75 m/z: 619.18 (100.0%) | 1-2-20, 1-2-21 | Chemical Formula: C40H24N6S Molecular Weight: 620.73 m/z: 620.18 (100.0%) |
| 1-2-24, 1-2-25 | Chemical Formula: C39H23N7S Molecular Weight: 621.72 m/z: 621.17 (100.0%) | 1-2-26 | Chemical Formula: C38H22N8S Molecular Weight: 622.71 m/z: 622.17 (100.0%) |
| 1-3-1~1-3-6, 1-3-9, 1-3-10 | Chemical Formula: C47H29N5S Molecular Weight: 695.84 m/z: 695.21 (100.0%) | 1-3-7, 1-3-8 | Chemical Formula: C46H28N6S Molecular Weight: 696.83 m/z: 696.21 (100.0%) |
| 1-3-11, 1-3-12 | Chemical Formula: C45H27N7S Molecular Weight: 697.82 m/z: 697.20 (100.0%) | 1-3-13 | Chemical Formula: C44H26N8S Molecular Weight: 698.81 m/z: 698.20 (100.0%) |
| 1-3-14~1-3-19, 1-3-22, 1-3-23 | Chemical Formula: C47H29N5S Molecular Weight: 695.84 m/z: 695.21 (100.0%) | 1-3-20, 1-3-21 | Chemical Formula: C46H28N6S Molecular Weight: 696.83 m/z: 696.21 (100.0%) |

TABLE 3-continued

| Compound | FD-MS | Compound | FD-MS |
|---|---|---|---|
| 1-3-24, 1-3-25 | Chemical Formula: C45H27N7S<br>Molecular Weight: 697.82<br>m/z: 697.20 (100.0%) | 1-3-26 | Chemical Formula: C44H26N8S<br>Molecular Weight: 698.81<br>m/z: 698.20 (100.0%) |
| 1-3-27~1-3-32, 1-3-35, 1-3-36 | Chemical Formula: C47H29N5S<br>Molecular Weight: 695.84<br>m/z: 695.21 (100.0%) | 1-3-33, 1-3-34 | Chemical Formula: C46H28N6S<br>Molecular Weight: 696.83<br>m/z: 696.21 (100.0%) |
| 1-3-37, 1-3-38 | Chemical Formula: C45H27N7S<br>Molecular Weight: 697.82<br>m/z: 697.20 (100.0%) | 1-3-39 | Chemical Formula: C44H26N8S<br>Molecular Weight: 698.81<br>m/z: 698.20 (100.0%) |
| 1-3-40~1-3-45, 1-3-48, 1-3-49 | Chemical Formula: C47H29N5S<br>Molecular Weight: 695.84<br>m/z: 695.21 (100.0%) | 1-3-46, 1-3-47 | Chemical Formula: C46H28N6S<br>Molecular Weight: 696.83<br>m/z: 696.21 (100.0%) |
| 1-3-50, 1-3-51 | Chemical Formula: C45H27N7S<br>Molecular Weight: 697.82<br>m/z: 697.20 (100.0%) | 1-3-52 | Chemical Formula: C44H26N8S<br>Molecular Weight: 698.81<br>m/z: 698.20 (100.0%) |
| 1-4-1~1-4-6, 1-4-9, 1-4-10 | Chemical Formula: C53H33N5S<br>Molecular Weight: 771.94<br>m/z: 771.25 (100.0%) | 1-4-7, 1-4-8 | Chemical Formula: C52H32N6S<br>Molecular Weight: 772.93<br>m/z: 772.24 (100.0%) |
| 1-4-11, 1-4-12 | Chemical Formula: C51H31N7S<br>Molecular Weight: 773.92<br>m/z: 773.24 (100.0%) | 1-4-13 | Chemical Formula: C50H30N8S<br>Molecular Weight: 774.91<br>m/z: 774.23 (100.0%) |
| 1-4-14~1-4-19, 1-4-22, 1-4-23 | Chemical Formula: C53H33N5S<br>Molecular Weight: 771.94<br>m/z: 771.25 (100.0%) | 1-4-20, 1-4-21 | Chemical Formula: C52H32N6S<br>Molecular Weight: 772.93<br>m/z: 772.24 (100.0%) |
| 1-4-24, 1-4-25 | Chemical Formula: C51H31N7S<br>Molecular Weight: 773.92<br>m/z: 773.24 (100.0%) | 1-4-26 | Chemical Formula: C50H30N8S<br>Molecular Weight: 774.91<br>m/z: 774.23 (100.0%) |
| 1-4-27~1-4-32, 1-4-35, 1-4-36 | Chemical Formula: C53H33N5S<br>Molecular Weight: 771.94<br>m/z: 771.25 (100.0%) | 1-4-33, 1-4-34 | Chemical Formula: C52H32N6S<br>Molecular Weight: 772.93<br>m/z: 772.24 (100.0%) |
| 1-4-37, 1-4-38 | Chemical Formula: C51H31N7S<br>Molecular Weight: 773.92<br>m/z: 773.24 (100.0%) | 1-4-39 | Chemical Formula: C50H30N8S<br>Molecular Weight: 774.91<br>m/z: 774.23 (100.0%) |
| 1-4-40~1-4-45, 1-4-48, 1-4-49 | Chemical Formula: C53H33N5S<br>Molecular Weight: 771.94<br>m/z: 771.25 (100.0%) | 1-4-46, 1-4-47 | Chemical Formula: C52H32N6S<br>Molecular Weight: 772.93<br>m/z: 772.24 (100.0%) |
| 1-4-50, 1-4-51 | Chemical Formula: C51H31N7S<br>Molecular Weight: 773.92<br>m/z: 773.24 (100.0%) | 1-4-52 | Chemical Formula: C50H30N8S<br>Molecular Weight: 774.91<br>m/z: 774.23 (100.0%) |
| 1-4-53~1-4-58, 1-4-61, 1-4-62 | Chemical Formula: C53H33N5S<br>Molecular Weight: 771.94<br>m/z: 771.25 (100.0%) | 1-4-59, 1-4-60 | Chemical Formula: C52H32N6S<br>Molecular Weight: 772.93<br>m/z: 772.24 (100.0%) |
| 1-4-63, 1-4-64 | Chemical Formula: C51H31N7S<br>Molecular Weight: 773.92<br>m/z: 773.24 (100.0%) | 1-4-65 | Chemical Formula: C50H30N8S<br>Molecular Weight: 774.91<br>m/z: 774.23 (100.0%) |
| 1-4-66~1-4-71, 1-4-74, 1-4-75 | Chemical Formula: C53H33N5S<br>Molecular Weight: 771.94<br>m/z: 771.25 (100.0%) | 1-4-72, 1-4-73 | Chemical Formula: C52H32N6S<br>Molecular Weight: 772.93<br>m/z: 772.24 (100.0%) |
| 1-4-76, 1-4-77 | Chemical Formula: C51H31N7S<br>Molecular Weight: 773.92<br>m/z: 773.24 (100.0%) | 1-4-78 | Chemical Formula: C50H30N8S<br>Molecular Weight: 774.91<br>m/z: 774.23 (100.0%) |
| 1-4-79~1-4-84, 1-4-87, 1-4-88 | Chemical Formula: C53H33N5S<br>Molecular Weight: 771.94<br>m/z: 771.25 (100.0%) | 1-4-85, 1-4-86 | Chemical Formula: C52H32N6S<br>Molecular Weight: 772.93<br>m/z: 772.24 (100.0%) |
| 1-4-89, 1-4-90 | Chemical Formula: C51H31N7S<br>Molecular Weight: 773.92<br>m/z: 773.24 (100.0%) | 1-4-91 | Chemical Formula: C50H30N8S<br>Molecular Weight: 774.91<br>m/z: 774.23 (100.0%) |
| 1-4-92~1-4-97, 1-4-100, 1-4-101 | Chemical Formula: C53H33N5S<br>Molecular Weight: 771.94<br>m/z: 771.25 (100.0%) | 1-4-98, 1-4-99 | Chemical Formula: C52H32N6S<br>Molecular Weight: 772.93<br>m/z: 772.24 (100.0%) |
| 1-4-102, 1-4-103 | Chemical Formula: C51H31N7S<br>Molecular Weight: 773.92<br>m/z: 773.24 (100.0%) | 1-4-104 | Chemical Formula: C50H30N8S<br>Molecular Weight: 774.91<br>m/z: 774.23 (100.0%) |

(16) Synthesis Example (Compounds 2-1-1 to 2-1-11)

(17) Synthesis Example (Compounds 2-2-1 to 2-2-11)

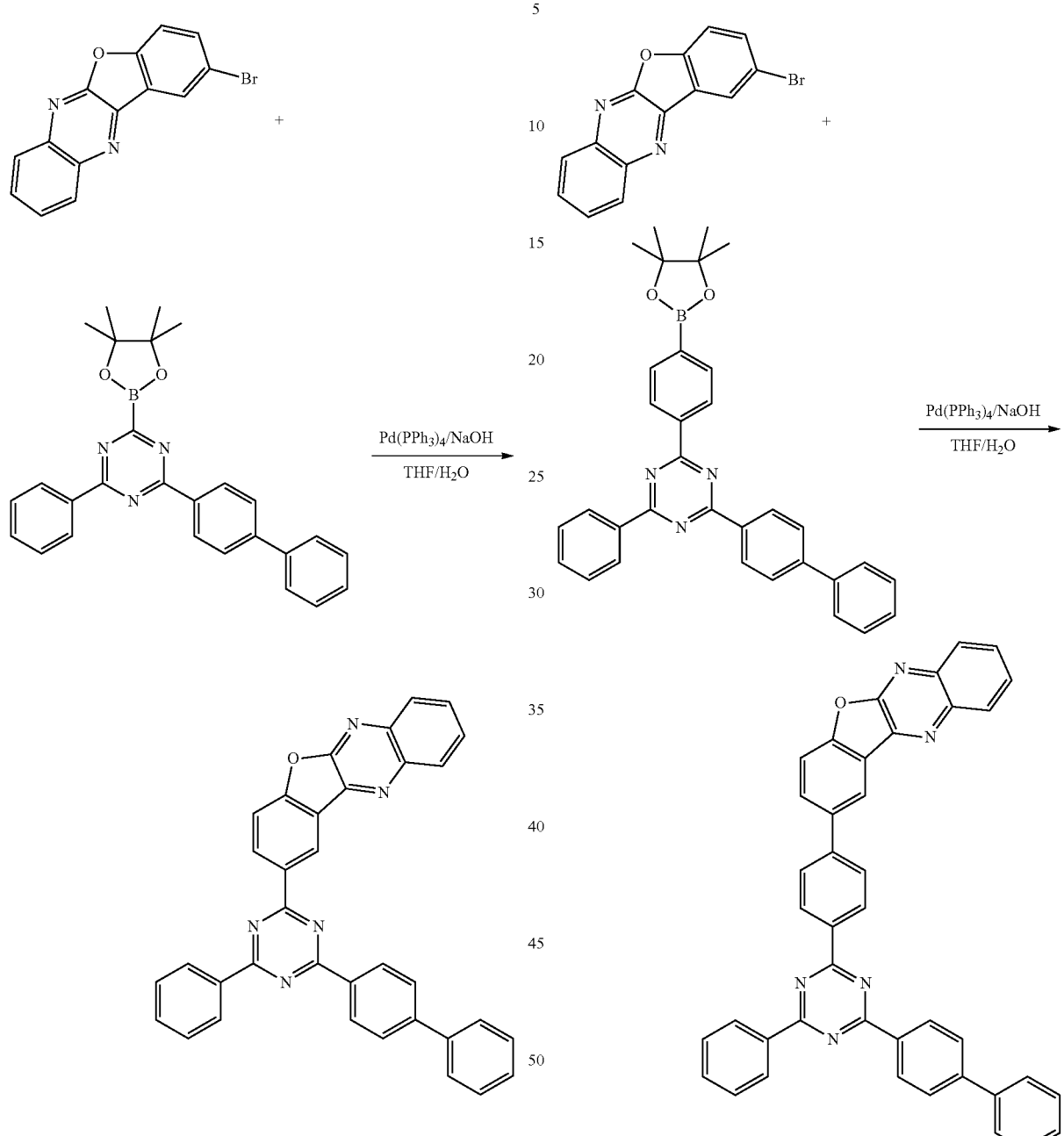

2-bromobenzofuro[2,3-b]quinoxaline (20 g 66.6 mmol) was dissolved with THF, and then 2-([1,1'-biphenyl]-4-yl)-4-phenyl-6-(4,4,5,5-tetramethyl-1,3,2-dioxaborolan-2-yl)-1,3,5-triazine (43.66 g, 100.29 mmol), Pd(PPh$_3$)$_4$ (1.95 g 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 25 g (yield: 70.9%) of the final product.

Compounds 2-1-1 to 2-1-2 and 2-1-4 to 2-1-11 can be synthesized by the same method as Compound 2-1-3, using Cores 2-1 to 2-11.

2-bromobenzofuro[2,3-b]quinoxaline (20 g, 66.86 mmol) was dissolved with THF, and then 2-([1,1'-biphenyl]-4-yl)-4-phenyl-6-(4-(4,4,5,5-tetramethyl-1,3,2-dioxaborolan-2-yl)phenyl)-1,3,5-triazine (51.29 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 26 g (yield: 64.4%) of the final product.

Compounds 2-2-1 to 2-2-2 and 2-2-4 to 2-2-11 can be synthesized by the same method as Compound 2-2-3 using Cores 2-1 to 2-11.

(18) Synthesis Example (Compounds 2-2-12 to 2-2-22)

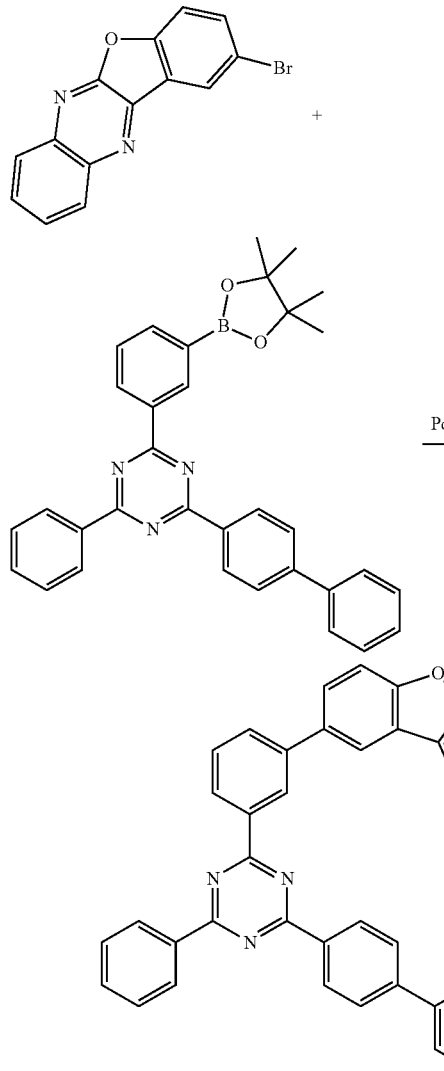

2-bromobenzofuro[2,3-b]quinoxaline (20 g, 66.6 mmol) was dissolved with THF, and then 2-([1,1'-biphenyl]-4-yl)-4-phenyl-6-(3-(4,4,5,5-tetramethyl-1,3,2-dioxaborolan-2-yl)phenyl)-1,3,5-triazine (51.29 g, 100.29 mmol), Pd(PPh$_3$)$_4$ (1.95 g 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 27 g (yield: 66.8%) of the final product.

Compounds 2-2-12 to 2-2-13 and 2-2-15 to 2-2-22 can be synthesized by the same method as Compound 2-2-14 using Cores 2-1 to 2-11.

(19) Synthesis Example (Compounds 2-3-1 to 2-3-11)

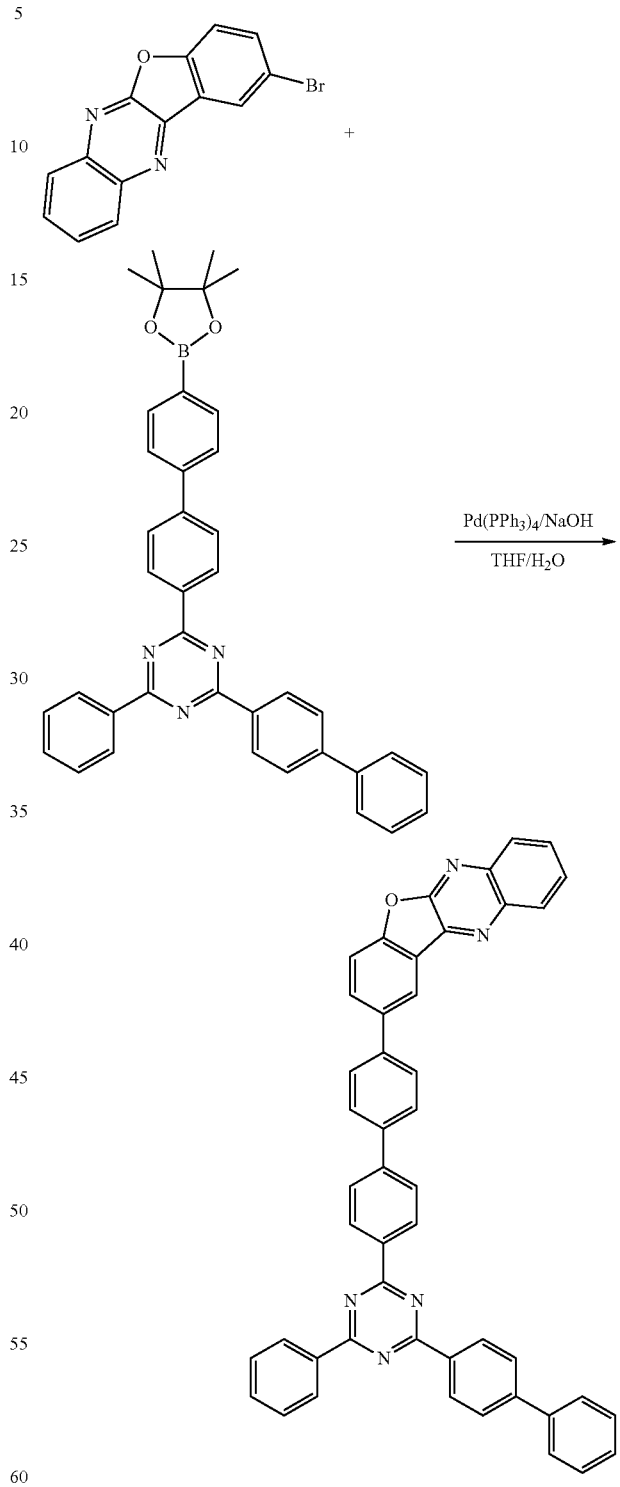

2-bromobenzofuro[2,3-b]quinoxaline (20 g, 66.6 mmol) was dissolved with THF, and then 2-([1,1'-biphenyl]-4-yl)-4-phenyl-6-(4'-(4,4,5,5-tetramethyl-1,3,2-dioxaborolan-2-yl)-[1,1'-biphenyl]-4-yl)-1,3,5-triazine (58.92 g, 100.29 mmol), Pd(PPh$_3$)$_4$ (1.95 g, 1.69 mmol), NaOH (6.76 g 168.9 mmol) and water were added and stirred under reflux at 100°

C. for 3 hours. Upon completion of the reaction, the organic layer was extracted with E.A. and water, and was dried using MgSO$_4$ and concentrated. The resulting organic material was subjected to silicagel column and recrystallization to obtain 30 g (yield: 66%) of the final product.

Compounds 2-3-1 to 2-3-2 and 2-3-4 to 2-3-11 can be synthesized by the same method as Compound 2-3-3 using Cores 2-1 to 2-11.

(20) Synthesis Example (Compounds 2-3-12 to 2-3-22)

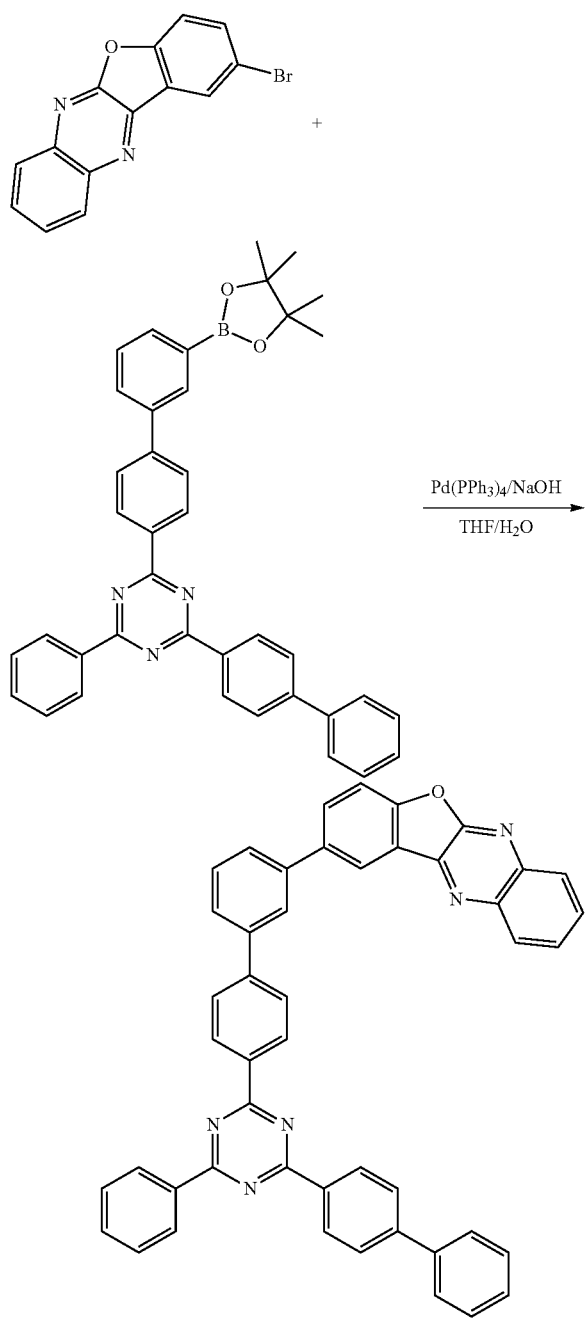

2-bromobenzofuro[2,3-b]quinoxaline (20 g, 66.86 mmol) was dissolved with THF, and then 2-([1,1'-biphenyl]-4-yl)-4-phenyl-6-(3'-(4,4,5,5-tetramethyl-1,3,2-dioxaborolan-2-yl)-[1,1'-biphenyl]-4-yl)-1,3,5-triazine (58.92 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 31 g (yield: 68.2%) of the final product.

Compounds 2-3-12 to 2-3-13 and 2-3-15 to 2-3-22 can be synthesized by the same method as Compound 2-3-14, using Cores 2-1 to 2-11.

(21) Synthesis Example (Compounds 2-3-23 to 2-3-33)

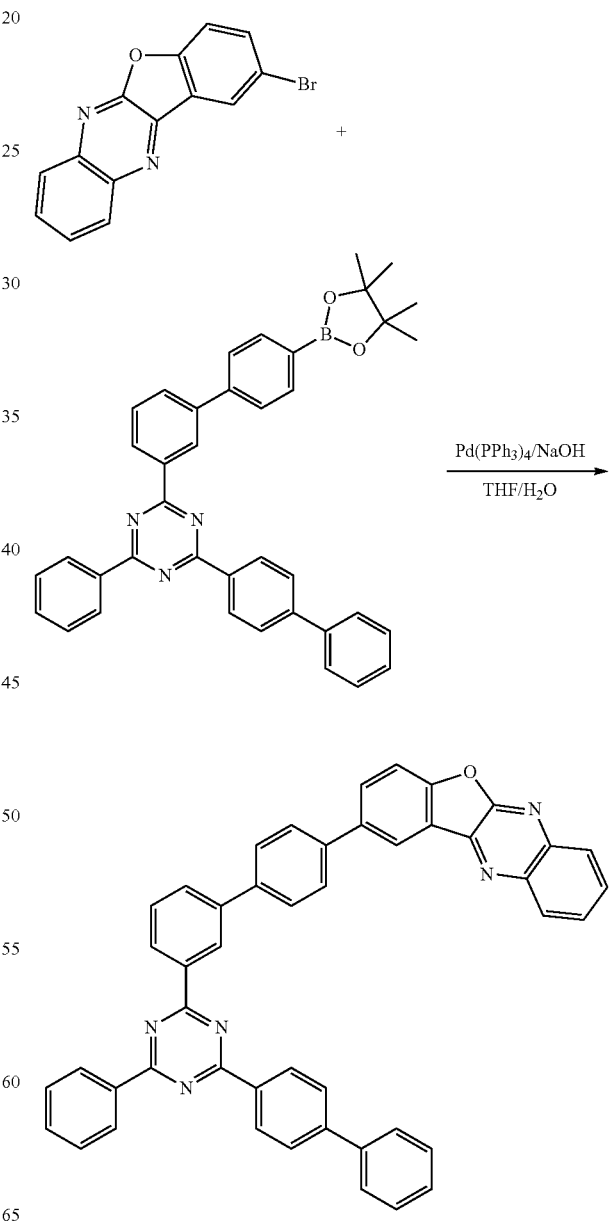

2-bromobenzofuro[2,3-b]quinoxaline (20 g, 66.86 mmol) was dissolved with THF, and then 2-([1,1'-biphenyl]-4-yl)-4-phenyl-6-(4'-(4,4,5,5-tetramethyl-1,3,2-dioxaborolan-2-yl)-[1,1'-biphenyl]-3-yl)-1,3,5-triazine (58.92 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 28 g (yield: 61.6%) of the final product.

Compounds 2-3-23 to 2-3-24 and 2-3-26 to 2-3-33 can be synthesized by the same method as Compound 2-3-25, using Cores 2-1 to 2-11.

(22) Synthesis Example (Compounds 2-3-34 to 2-3-44)

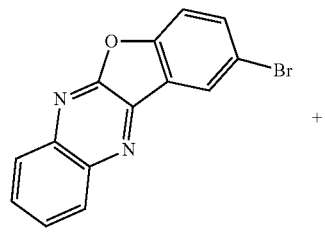

+

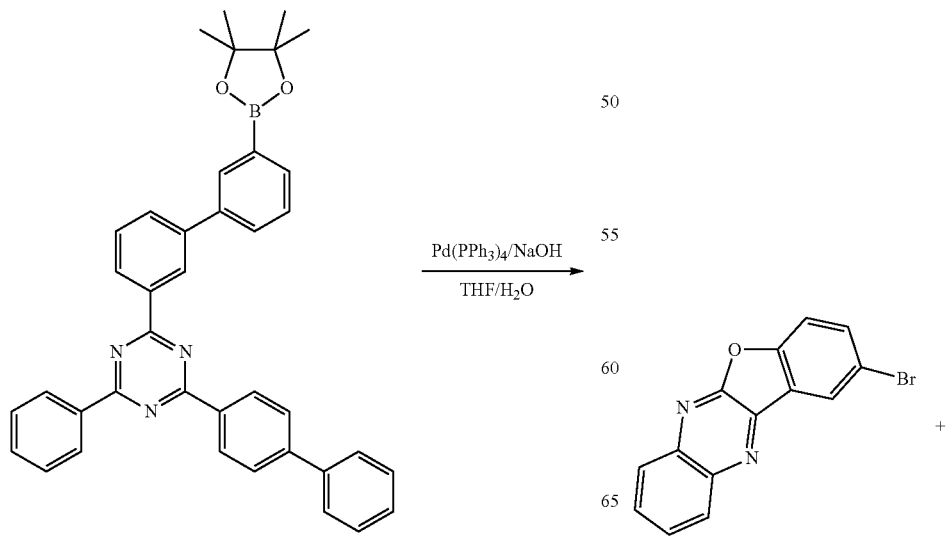

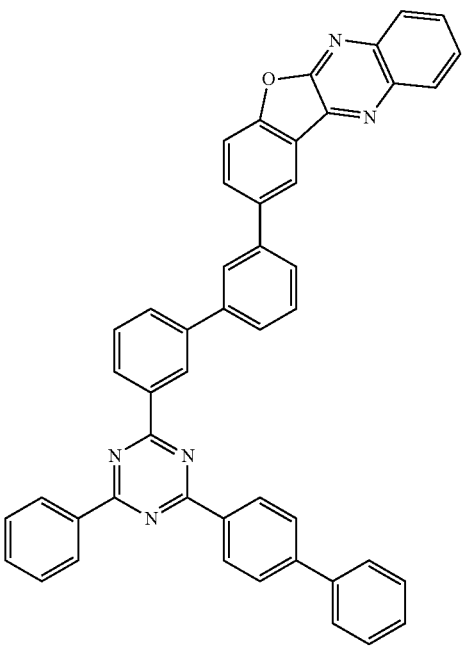

2-bromobenzofuro[2,3-b]quinoxaline (20 g, 66.86 mmol) was dissolved with THF, and then 2-([1,1'-biphenyl]-4-yl)-4-phenyl-6-(3'-(4,4,5,5-tetramethyl-1,3,2-dioxaborolan-2-yl)-[1,1'-biphenyl]-3-yl)-1,3,5-triazine (58.92 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 29 g (yield: 63.8%) of the final product.

Compounds 2-3-34 to 2-3-35 and 2-3-37 to 2-3-44 can be synthesized by the same method as Compound 2-3-36, using Cores 2-1 to 2-11.

(23) Synthesis Example (Compounds 2-4-1 to 2-4-11)

-continued

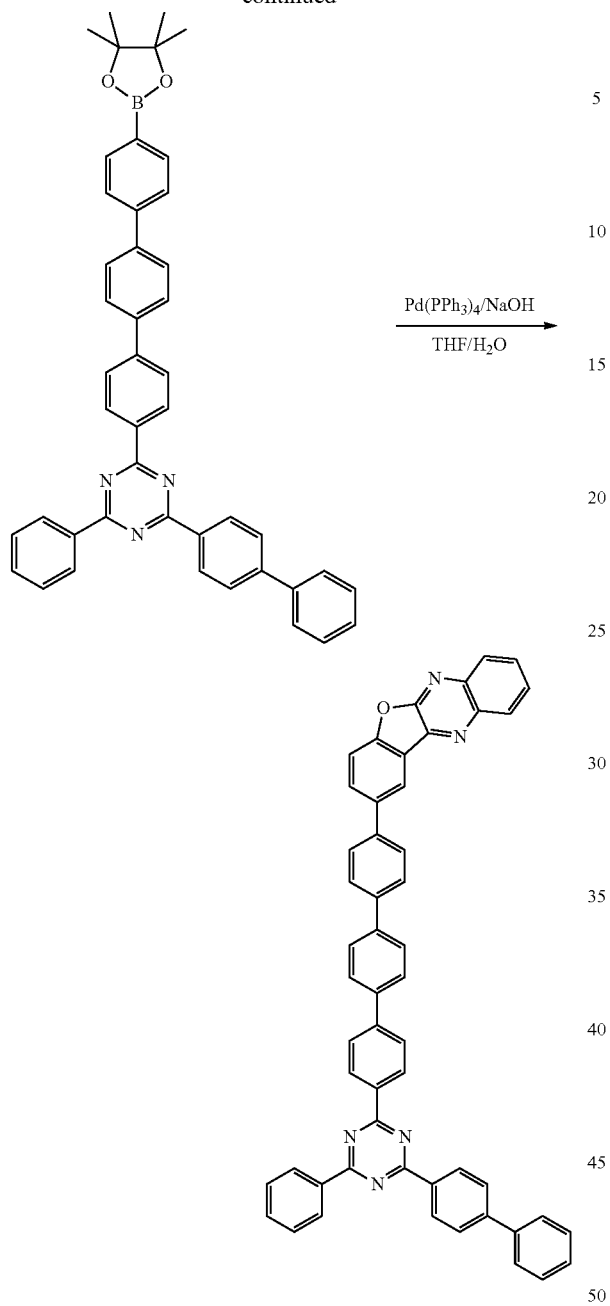

(24) Synthesis Example (Compounds 2-4-12 to 2-4-22)

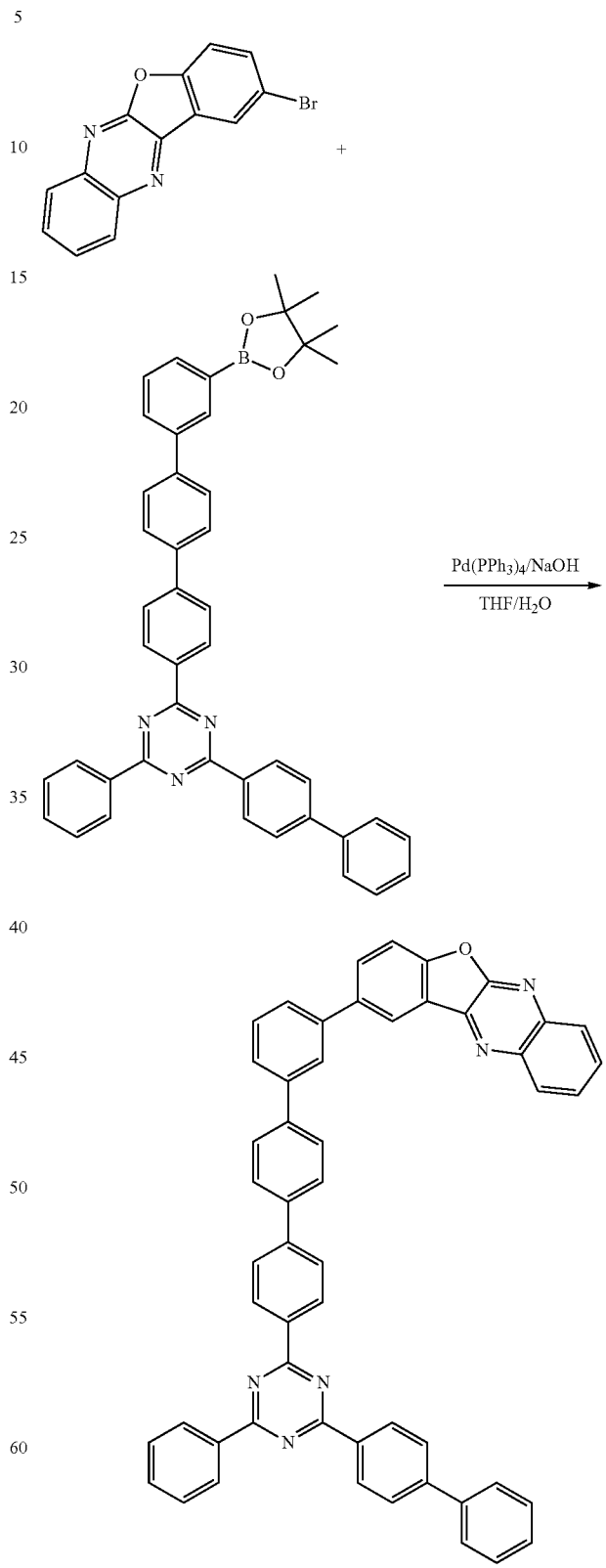

2-bromobenzofuro[2,3-b]quinoxaline (20 g, 66.86 mmol) was dissolved with THF, and then 2-([1,1'-biphenyl]-4-yl)-4-phenyl-6-(4''-(4,4,5,5-tetramethyl-1,3,2-dioxaborolan-2-yl)-[1,1': 4',1''-terphenyl]-4-yl)-1,3,5-triazine (66.56 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 33 g (yield: 65.3%) of the final product.

Compounds 2-4-1 to 2-4-2 and 2-4-4 to 2-4-11 can be synthesized by the same method as Compound 2-4-3 using Cores 2-1 to 2-11.

2-bromobenzofuro[2,3-b]quinoxaline (20 g, 66.86 mmol) was dissolved with THF, and then 2-([1,1'-biphenyl]-4-yl)-4-phenyl-6-(3''-(4,4,5,5-tetramethyl-1,3,2-dioxaborolan-2-yl)-[1,1': 4',1''-terphenyl]-4-yl)-1,3,5-triazine (66.56 g, 100.29 mmol), Pd(PPh$_3$)$_4$ (1.95 g, 1.69 mmol), NaOH (6.76 g 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 34 g (yield: 67.3%) of the final product.

Compounds 2-4-12 to 2-4-13 and 2-4-15 to 2-4-22 can be synthesized by the same method as Compound 2-4-14, using cores 2-1 to 2-11.

(25) Synthesis Example (Compounds 2-4-23 to 2-4-33)

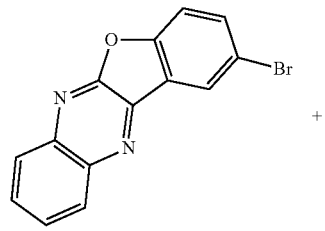

+

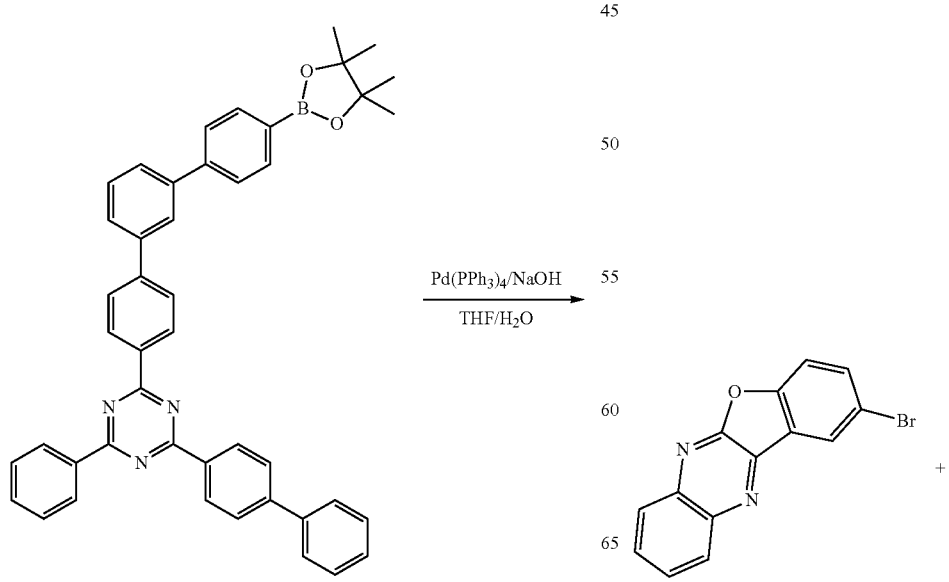

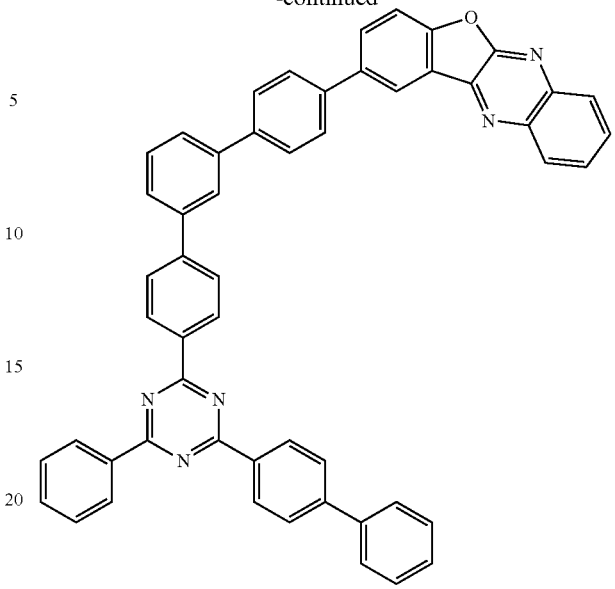

2-bromobenzofuro[2,3-b]quinoxaline (20 g, 66.86 mmol) was dissolved with THF, and then 2-([1,1'-biphenyl]-4-yl)-4-phenyl-6-(4''-(4,4,5,5-tetramethyl-1,3,2-dioxaborolan-2-yl)-[1,1': 3',1''-terphenyl]-4-yl)-1,3,5-triazine (66.56 g, 100.29 mmol), Pd(PPh$_3$)$_4$ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 35 g (yield: 69.3%) of the final product.

Compounds 2-4-23 to 2-4-24 and 2-4-26 to 2-4-33 can be synthesized by the same method as Compound 2-4-25, using Cores 2-1 to 2-11.

(26) Synthesis Example (Compounds 2-4-34 to 2-4-44)

(27) Synthesis Example (Compounds 2-4-45 to 2-4-55)

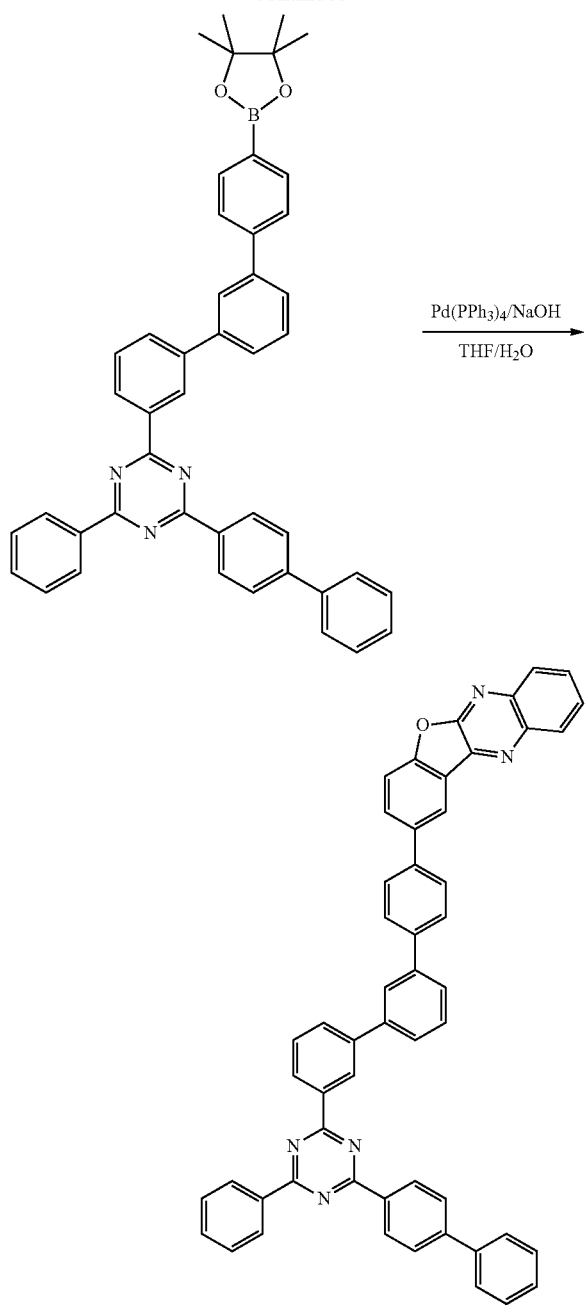
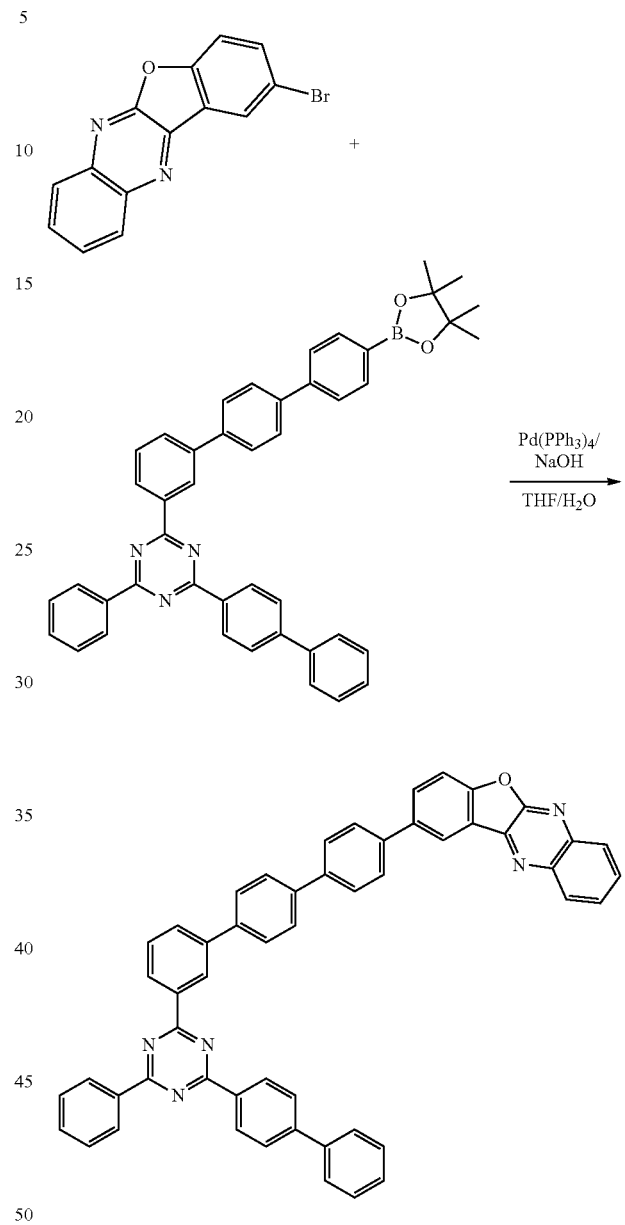

2-bromobenzofuro[2,3-b]quinoxaline (20 g, 66.86 mmol) was dissolved with THF, and 2-([1,1'-biphenyl]-4-yl)-4-phenyl-6-(4''-(4,4,5,5-tetramethyl-1,3,2-dioxaborolan-2-yl)-[1,1':3',1''-terphenyl]-3-yl)-1,3,5-triazine (66.56 g, 100.29 mmol), Pd(PPh₃)₄ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 32 g (yield: 63.3%) of the final product.

Compounds 2-4-34 to 2-4-35 and 2-4-37 to 2-4-44 can be synthesized by the same method as Compound 2-4-36, using Cores 2-1 to 2-11.

2-bromobenzofuro[2,3-b]quinoxaline (20 g, 66.86 mmol) was dissolved with THF, and then 2-([1,1'-biphenyl]-4-yl)-4-phenyl-6-(4''-(4,4,5,5-tetramethyl-1,3,2-dioxaborolan-2-yl)-[1,1':  4',1'''-terphenyl]-3-yl)-1,3,5-triazine (66.56 g, 100.29 mmol), Pd(PPh₃)₄ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 33 g (yield: 65.3%) of the final product.

Compounds 2-4-45 to 2-4-46 and 2-4-48 to 2-4-55 can be synthesized by the same method as Compound 2-4-47, using Cores 2-1 to 2-11.

(28) Synthesis Example (Compounds 2-4-56 to 2-4-66)

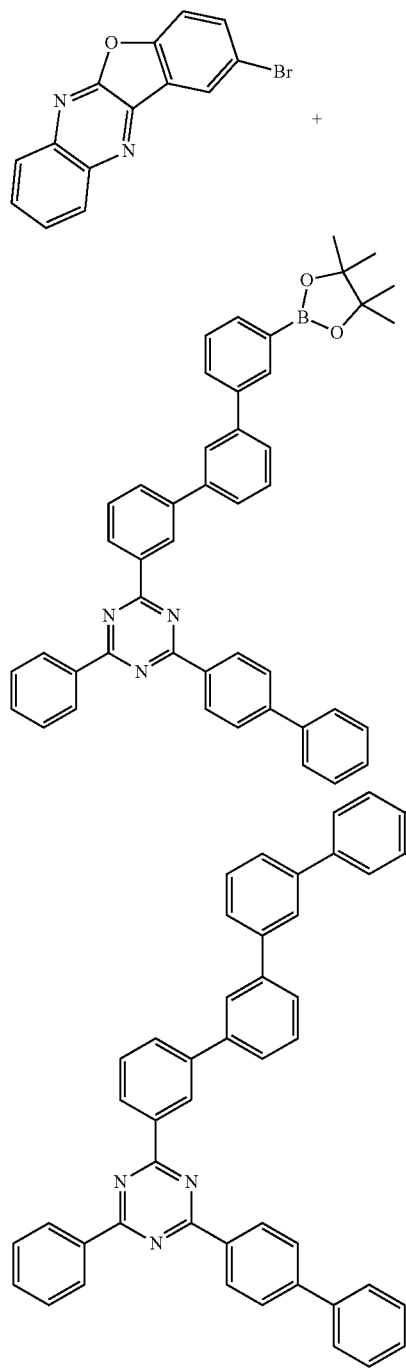

2-bromobenzofuro[2,3-b]quinoxaline (20 g, 66.6 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1': 3',1"-terphenyl]-3-yl)-1,3,5-triazine (66.56 g, 100.29 mmol), Pd(PPh₃)₄ (1.95 g 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 34 g (yield: 67.3%) of the final product.

Compounds 2-4-56 to 2-4-57 and 2-4-59 to 2-4-66 can be synthesized by the same method as Compound 2-4-58, using Cores 2-1 to 2-11.

(29) Synthesis Example (Compounds 2-4-67 to 2-4-77)

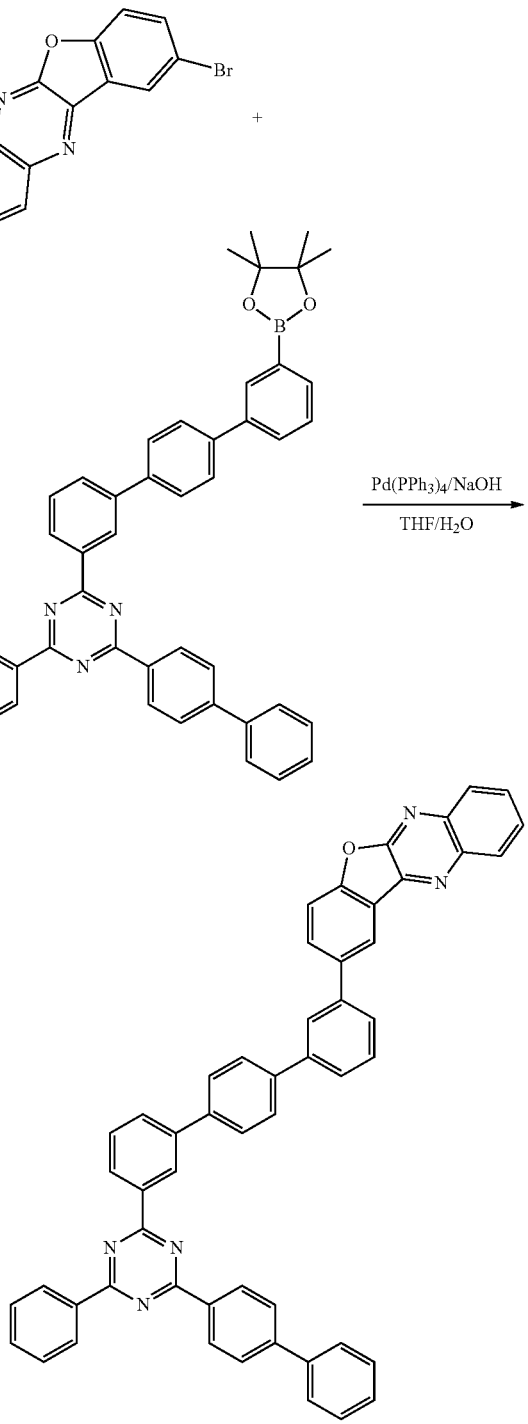

2-bromobenzofuro[2,3-b]quinoxaline (2 g, 66.6 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1': 4',1"-terphenyl]-3-yl)-1,3,5-triazine (66.56 g, 100.29 mmol), Pd(PPh₃)₄ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 33 g (yield: 65.3%) of the final product.

Compounds 2-4-67 to 2-4-68 and 2-4-70 to 2-4-77 can be synthesized by the same method as Compound 2-4-69, using Cores 2-1 to 2-11.

(30) Synthesis Example (Compounds 2-4-78 to 2-4-88)

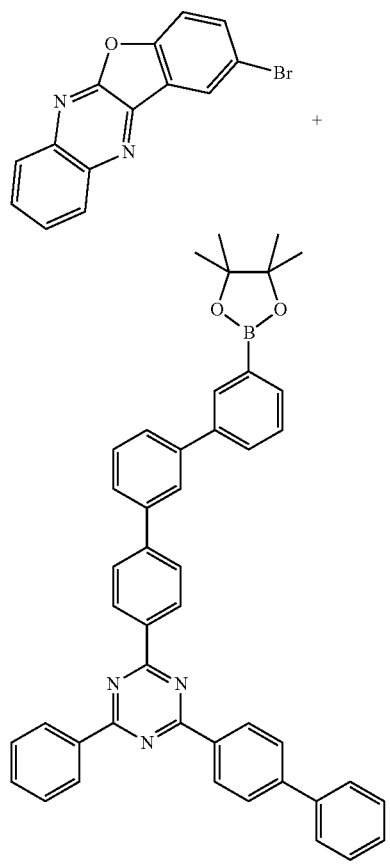

Pd(PPh₃)₄/NaOH
THF/H₂O

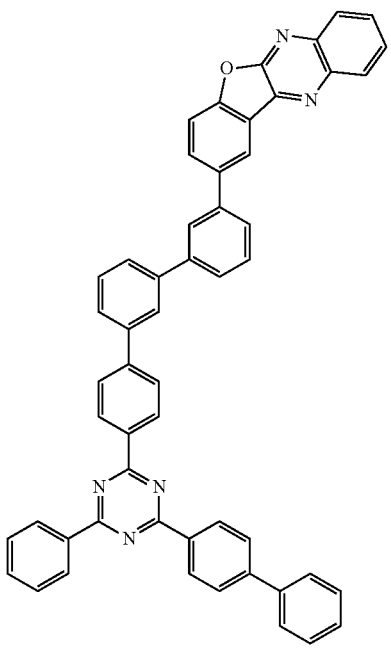

2-bromobenzofuro[2,3-b]quinoxaline (20 g, 66.6 mmol) was dissolved with THF, and then 2-([1,1'-biphenyl]-4-yl)-4-phenyl-6-(3"-(4,4,5,5-tetramethyl-1,3,2-dioxaborolan-2-yl)-[1,1': 3',1"-terphenyl]-4-yl)-1,3,5-triazine (66.56 g, 100.29 mmol), Pd(PPh₃)₄ (1.95 g, 1.69 mmol), NaOH (6.76 g, 168.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 35 g (yield: 69.3%) of the final product.

Compounds 2-4-78 to 2-4-79 and 2-4-81 to 2-4-88 can be synthesized by the same method as Compound 2-4-80, using Cores 2-1 to 2-11.

TABLE 4

| Compound | FD-MS | Compound | FD-MS |
| --- | --- | --- | --- |
| 2-1-1~ 2-1-6 | Chemical Formula: C35H21N5O Molecular Weight: 527.59 m/z: 527.17 (100.0%) | 2-1-7~ 2-1-10 | Chemical Formula: C39H23N5O Molecular Weight: 577.65 m/z: 577.19 (100.0%) |
| 2-1-11 | Chemical Formula: C38H22N6O Molecular Weight: 578.64 m/z: 578.19 (100.0%) | 2-2-1~ 2-2-6 | Chemical Formula: C41H25N5O Molecular Weight: 603.69 m/z: 603.21 (100.0%) |
| 2-2-7~ 2-2-10 | Chemical Formula: C45H27N5O Molecular Weight: 653.75 m/z: 653.22 (100.0%) | 2-2-11 | Chemical Formula: C44H26N6O Molecular Weight: 654.73 m/z: 654.22 (100.0%) |

TABLE 4-continued

| Compound | FD-MS | Compound | FD-MS |
| --- | --- | --- | --- |
| 2-2-12~ 2-2-17 | Chemical Formula: C41H25N5O<br>Molecular Weight: 603.69<br>m/z: 603.21 (100.0%) | 2-2-18~ 2-2-21 | Chemical Formula: C45H27N5O<br>Molecular Weight: 653.75<br>m/z: 653.22 (100.0%) |
| 2-2-22 | Chemical Formula: C44H26N6O<br>Molecular Weight: 654.73<br>m/z: 654.22 (100.0%) | 2-3-1~ 2-3-6 | Chemical Formula: C47H29N5O<br>Molecular Weight: 679.78<br>m/z: 679.24 (100.0%) |
| 2-3-7~ 2-3-10 | Chemical Formula: C51H31N5O<br>Molecular Weight: 729.84<br>m/z: 729.25 (100.0%) | 2-3-11 | Chemical Formula: C50H30N6O<br>Molecular Weight: 730.83<br>m/z: 730.25 (100.0%) |
| 2-3-12~ 2-3-17 | Chemical Formula: C47H29N5O<br>Molecular Weight: 679.78<br>m/z: 679.24 (100.0%) | 2-3-18~ 2-3-21 | Chemical Formula: C51H31N5O<br>Molecular Weight: 729.84<br>m/z: 729.25 (100.0%) |
| 2-3-22 | Chemical Formula: C50H30N6O<br>Molecular Weight: 730.83<br>m/z: 730.25 (100.0%) | 2-3-23~ 2-3-28 | Chemical Formula: C47H29N5O<br>Molecular Weight: 679.78<br>m/z: 679.24 (100.0%) |
| 2-3-29~ 2-3-32 | Chemical Formula: C51H31N5O<br>Molecular Weight: 729.84<br>m/z: 729.25 (100.0%) | 2-3-33 | Chemical Formula: C50H30N6O<br>Molecular Weight: 730.83<br>m/z: 730.25 (100.0%) |
| 2-3-34~ 2-3-39 | Chemical Formula: C47H29N5O<br>Molecular Weight: 679.78<br>m/z: 679.24 (100.0%) | 2-3-40~ 2-3-43 | Chemical Formula: C51H31N5O<br>Molecular Weight: 729.84<br>m/z: 729.25 (100.0%) |
| 2-3-44 | Chemical Formula: C50H30N6O<br>Molecular Weight: 730.83<br>m/z: 730.25 (100.0%) | 2-4-1~ 2-4-6 | Chemical Formula: C53H33N5O<br>Molecular Weight: 755.88<br>m/z: 755.27 (100.0%) |
| 2-4-7~ 2-4-10 | Chemical Formula: C57H35N5O<br>Molecular Weight: 805.94<br>m/z: 805.28 (100.0%) | 2-4-11 | Chemical Formula: C56H34N6O<br>Molecular Weight: 806.93<br>m/z: 806.28 (100.0%) |
| 2-4-12~ 2-4-17 | Chemical Formula: C53H33N5O<br>Molecular Weight: 755.88<br>m/z: 755.27 (100.0%) | 2-4-18~ 2-4-21 | Chemical Formula: C57H35N5O<br>Molecular Weight: 805.94<br>m/z: 805.28 (100.0%) |
| 2-4-22 | Chemical Formula: C56H34N6O<br>Molecular Weight: 806.93<br>m/z: 806.28 (100.0%) | 2-4-23~ 2-4-28 | Chemical Formula: C53H33N5O<br>Molecular Weight: 755.88<br>m/z: 755.27 (100.0%) |
| 2-4-29~ 2-4-32 | Chemical Formula: C57H35N5O<br>Molecular Weight: 805.94<br>m/z: 805.28 (100.0%) | 2-4-33 | Chemical Formula: C56H34N6O<br>Molecular Weight: 806.93<br>m/z: 806.28 (100.0%) |
| 2-4-34~ 2-4-39 | Chemical Formula: C53H33N5O<br>Molecular Weight: 755.88<br>m/z: 755.27 (100.0%) | 2-4-40~ 2-4-43 | Chemical Formula: C57H35N5O<br>Molecular Weight: 805.94<br>m/z: 805.28 (100.0%) |
| 2-4-44 | Chemical Formula: C56H34N6O<br>Molecular Weight: 806.93<br>m/z: 806.28 (100.0%) | 2-4-45~ 2-4-50 | Chemical Formula: C53H33N5O<br>Molecular Weight: 755.88<br>m/z: 755.27 (100.0%) |
| 2-4-51~ 2-4-54 | Chemical Formula: C57H35N5O<br>Molecular Weight: 805.94<br>m/z: 805.28 (100.0%) | 2-4-55 | Chemical Formula: C56H34N6O<br>Molecular Weight: 806.93<br>m/z: 806.28 (100.0%) |
| 2-4-56~ 2-4-61 | Chemical Formula: C53H33N5O<br>Molecular Weight: 755.88<br>m/z: 755.27 (100.0%) | 2-4-62~ 2-4-65 | Chemical Formula: C57H35N5O<br>Molecular Weight: 805.94<br>m/z: 805.28 (100.0%) |
| 2-4-66 | Chemical Formula: C56H34N6O<br>Molecular Weight: 806.93<br>m/z: 806.28 (100.0%) | 2-4-67~ 2-4-72 | Chemical Formula: C53H33N5O<br>Molecular Weight: 755.88<br>m/z: 755.27 (100.0%) |
| 2-4-73~ 2-4-76 | Chemical Formula: C57H35N5O<br>Molecular Weight: 805.94<br>m/z: 805.28 (100.0%) | 2-4-77 | Chemical Formula: C56H34N6O<br>Molecular Weight: 806.93<br>m/z: 806.28 (1000%) |
| 2-4-78~ 2-4-83 | Chemical Formula: C53H33N5O<br>Molecular Weight: 755.88<br>m/z: 755.27 (100.0%) | 2-4-84~ 2-4-87 | Chemical Formula: C57H35N5O<br>Molecular Weight: 805.94<br>m/z: 805.28 (100.0%) |
| 2-4-88 | Chemical Formula: C56H34N6O<br>Molecular Weight: 806.93<br>m/z: 806.28 (100.0%) | | |

(31) Synthesis Example (Compounds 3-1-1 to 3-2-17)

The synthesis method of compound 3-1-1 is described below with reference to the following synthesis formula.

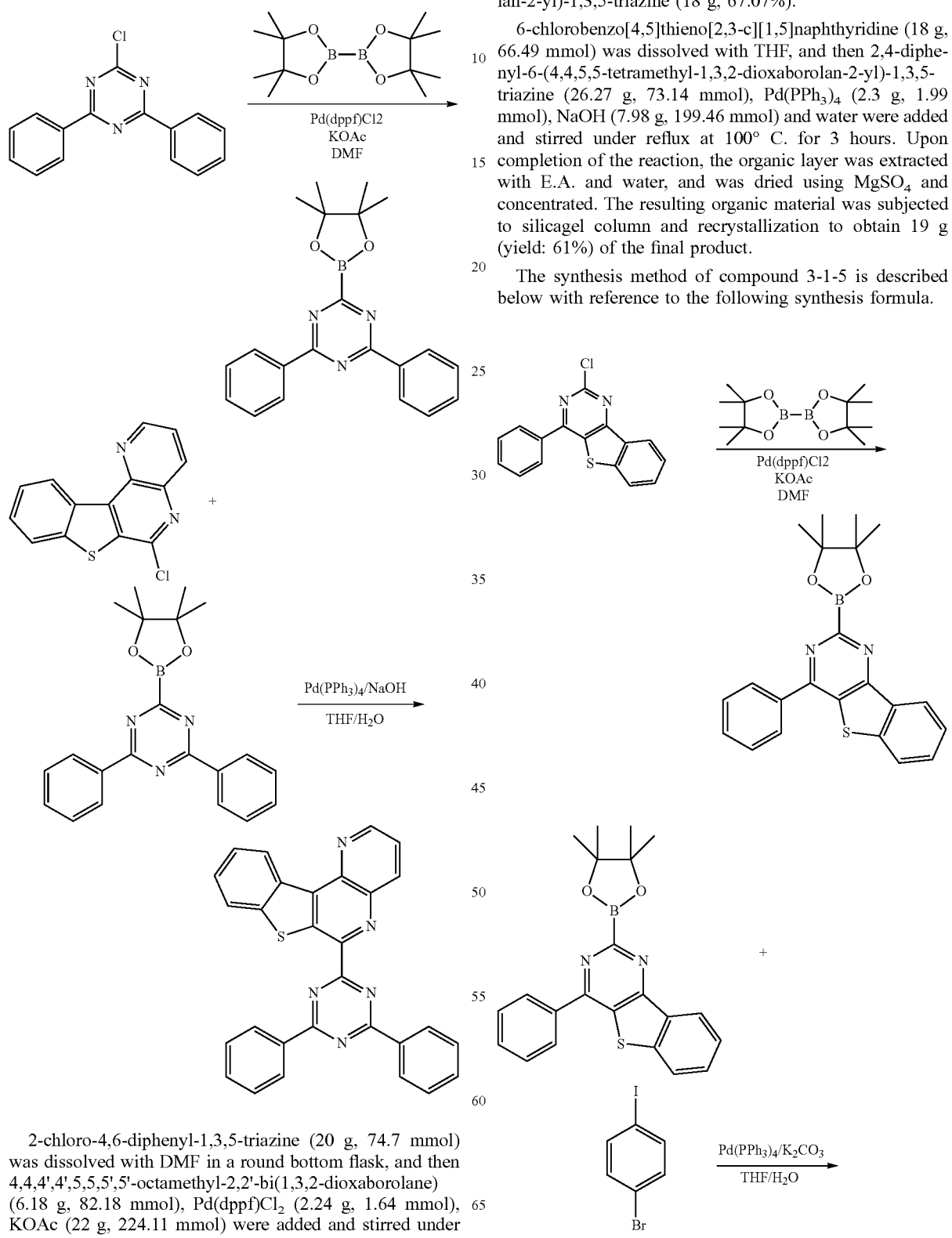

2-chloro-4,6-diphenyl-1,3,5-triazine (20 g, 74.7 mmol) was dissolved with DMF in a round bottom flask, and then 4,4,4',4',5,5,5',5'-octamethyl-2,2'-bi(1,3,2-dioxaborolane) (6.18 g, 82.18 mmol), Pd(dppf)Cl$_2$ (2.24 g, 1.64 mmol), KOAc (22 g, 224.11 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-diphenyl-6-(4,4,5,5-tetramethyl-1,3,2-dioxaborolan-2-yl)-1,3,5-triazine (18 g, 67.07%).

6-chlorobenzo[4,5]thieno[2,3-c][1,5]naphthyridine (18 g, 66.49 mmol) was dissolved with THF, and then 2,4-diphenyl-6-(4,4,5,5-tetramethyl-1,3,2-dioxaborolan-2-yl)-1,3,5-triazine (26.27 g, 73.14 mmol), Pd(PPh$_3$)$_4$ (2.3 g, 1.99 mmol), NaOH (7.98 g, 199.46 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 19 g (yield: 61%) of the final product.

The synthesis method of compound 3-1-5 is described below with reference to the following synthesis formula.

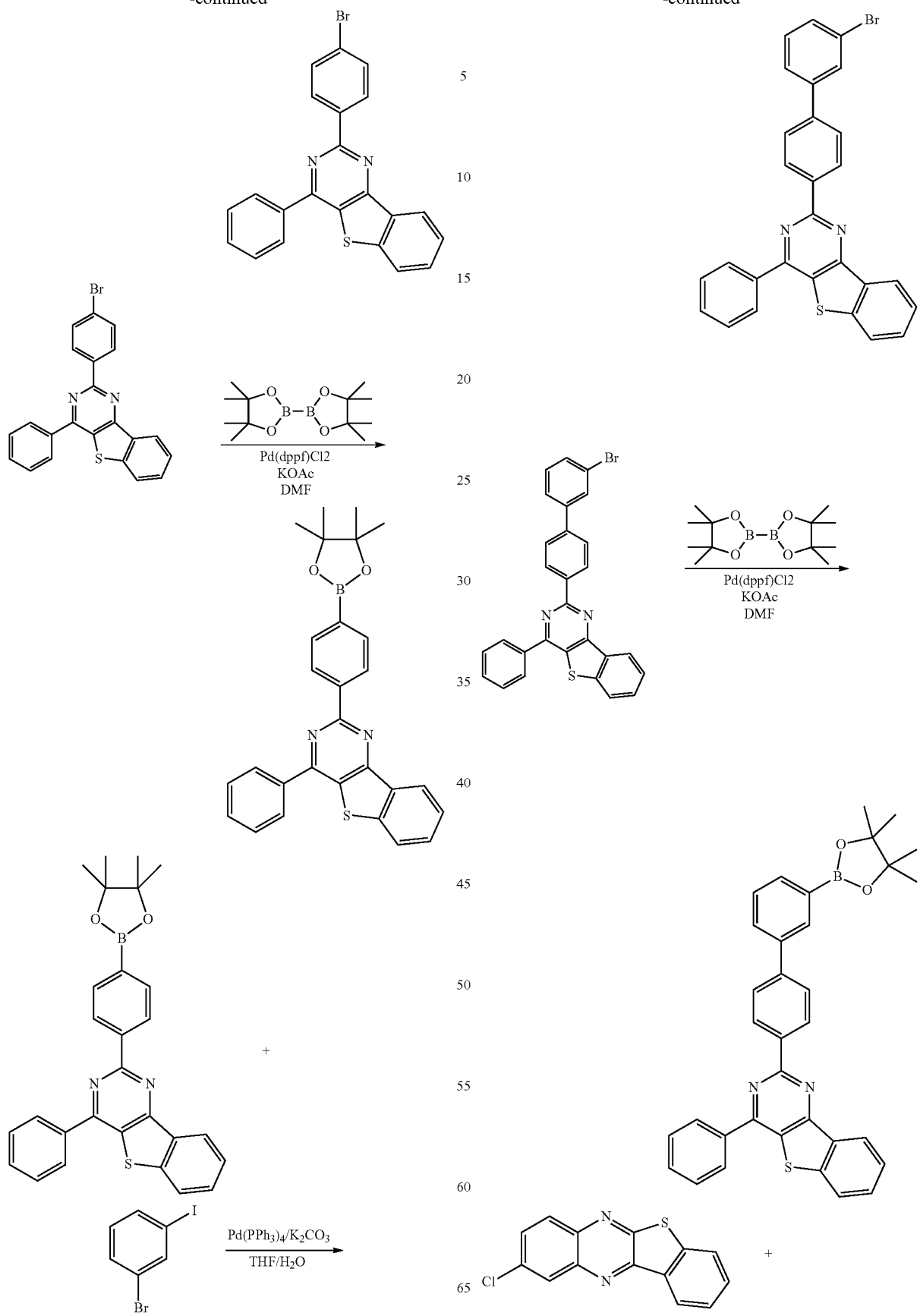

-continued

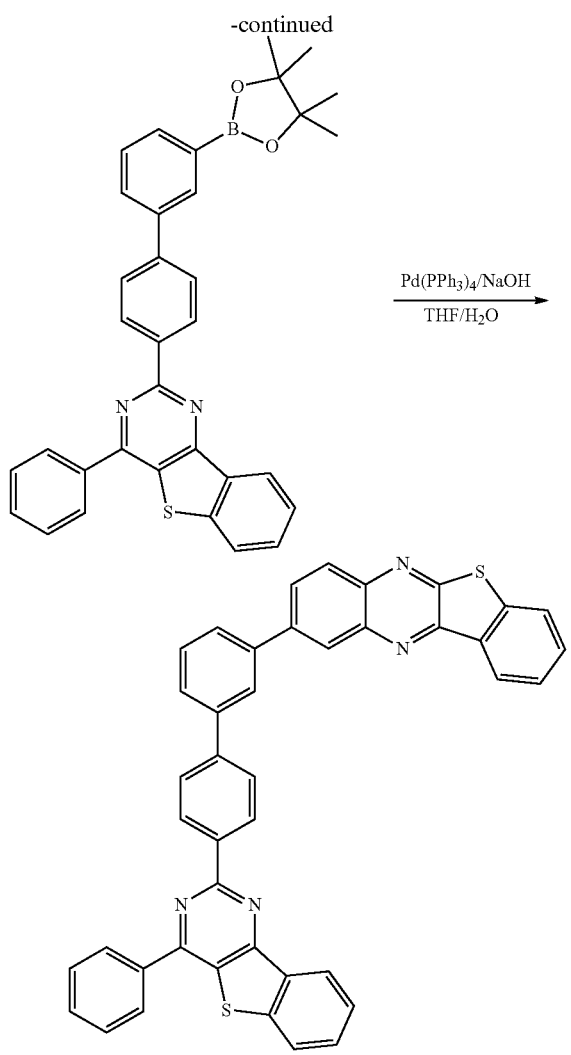

2-chloro-4-phenylbenzo[4,5]thieno[3,2-d]pyrimidine (20 g 67.39 mmol) was dissolved with DMF in a round bottom flask, and then 4,4',4',4',5,5,5',5'-octamethyl-2,2'-bi(1,3,2-dioxaborolane) (6.18 g, 74.13 mmol), Pd(dppf)Cl$_2$ (1.48 g, 2.02 mmol), KOAc (19.84 g, 202.18 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(4,4,5,5-tetramethyl-1,3,2-dioxaborolan-2-yl)benzo[4,5]thieno[3,2-d]pyrimidine (18 g, 67.07%).

4-phenyl-2-(4,4,5,5-tetramethyl-1,3,2-dioxaborolan-2-yl)benzo[4,5]thieno[3,2-d]pyrimidine (18 g, 46.36 mmol) was dissolved with THF, and then 1-bromo-4-iodobenzene (14.43 g 50.99 mmol), Pd(PPh$_3$)$_4$ (1.61 g, 1.39 mmol), K$_2$CO$_3$ (5.56 g, 139.07 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2-(4-bromophenyl)-4-phenylbenzo [4,5]thieno [3,2-d]pyrimidine (13 g, 67.2%).

2-(4-bromophenyl)-4-phenylbenzo[4,5]thieno[3,2-d]pyrimidine (13 g, 31.15 mmol) was dissolved with DMF in a round bottom flask, and then 4,4,4',4',5,5,5',5'-octamethyl-2,2'-bi(1,3,2-dioxaborolane) (8.7 g, 34.27 mmol), Pd(dppf)Cl$_2$ (0.68 g, 0.93 mmol), KOAc (9.17 g, 93.45 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(4-(4,4,5,5-tetramethyl-1,3,2-dioxaborolan-2-yl)phenyl)benzo[4,5]thieno[3,2-d]pyrimidine (10 g, 69.12%).

Repeatedly, 4-phenyl-2-(4-(4,4,5,5-tetramethyl-1,3,2-dioxaborolan-2-yl)phenyl)benzo[4,5]thieno[3,2-d]pyrimidine (10 g, 21.53 mmol) was dissolved with THF, and then 1-bromo-3-iodobenzene (14.43 g, 23.69 mmol), Pd(PPh$_3$)$_4$ (0.75 g, 0.65 mmol), K$_2$CO$_3$ (8.93 g, 64.6 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 4-phenyl-2-(4-(4,4,5,5-tetramethyl-1,3,2-dioxaborolan-2-yl)phenyl)benzo[4,5]thieno[3,2-d]pyrimidine (7.5 g, 70.58%).

4-phenyl-2-(4-(4,4,5,5-tetramethyl-1,3,2-dioxaborolan-2-yl)phenyl)benzo[4,5]thieno[3,2-d]pyrimidine (7.5 g, 15.2 mmol) was dissolved with DMF in a round bottom flask, and then 4,4,4',4',5,5,5',5'-octamethyl-2,2'-bi(1,3,2-dioxaborolane) (4.25 g, 16.72 mmol), Pd(dppf)Cl$_2$ (0.33 g, 0.46 mmol), KOAc (4.48 g, 45.6 mmol) were added and stirred under reflux at 130° C. for 4 hours. Upon completion of the reaction, DMF was removed from the reaction products via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(3'-(4,4,5,5-tetramethyl-1,3,2-dioxaborolan-2-yl)-[1,1'-biphenyl]-4-yl)benzo[4,5]thieno[3,2-d]pyrimidine (5 g, 60.86%).

9-chlorobenzo[4,5]thieno[2,3-b]quinoxaline (15 g, 55.41 mmol) was dissolved with THF, and then 4-phenyl-2-(3'-(4,4,5,5-tetramethyl-1,3,2-dioxaborolan-2-yl)-[1,1'-biphenyl]-4-yl)benzo [4,5]thieno[3,2-d]pyrimidine (32.94 g, 60.95 mmol), Pd(PPh$_3$)$_4$ (1.92 g, 1.66 mmol), NaOH (6.65 g, 166.22 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 25 g (Yield: 69.54%) of the final product.

The synthesis method of compound 3-1-7 is described below with reference to the following synthesis formula.

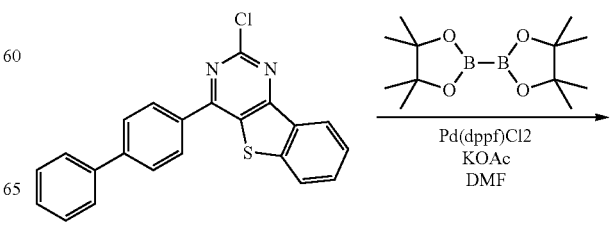

285
286
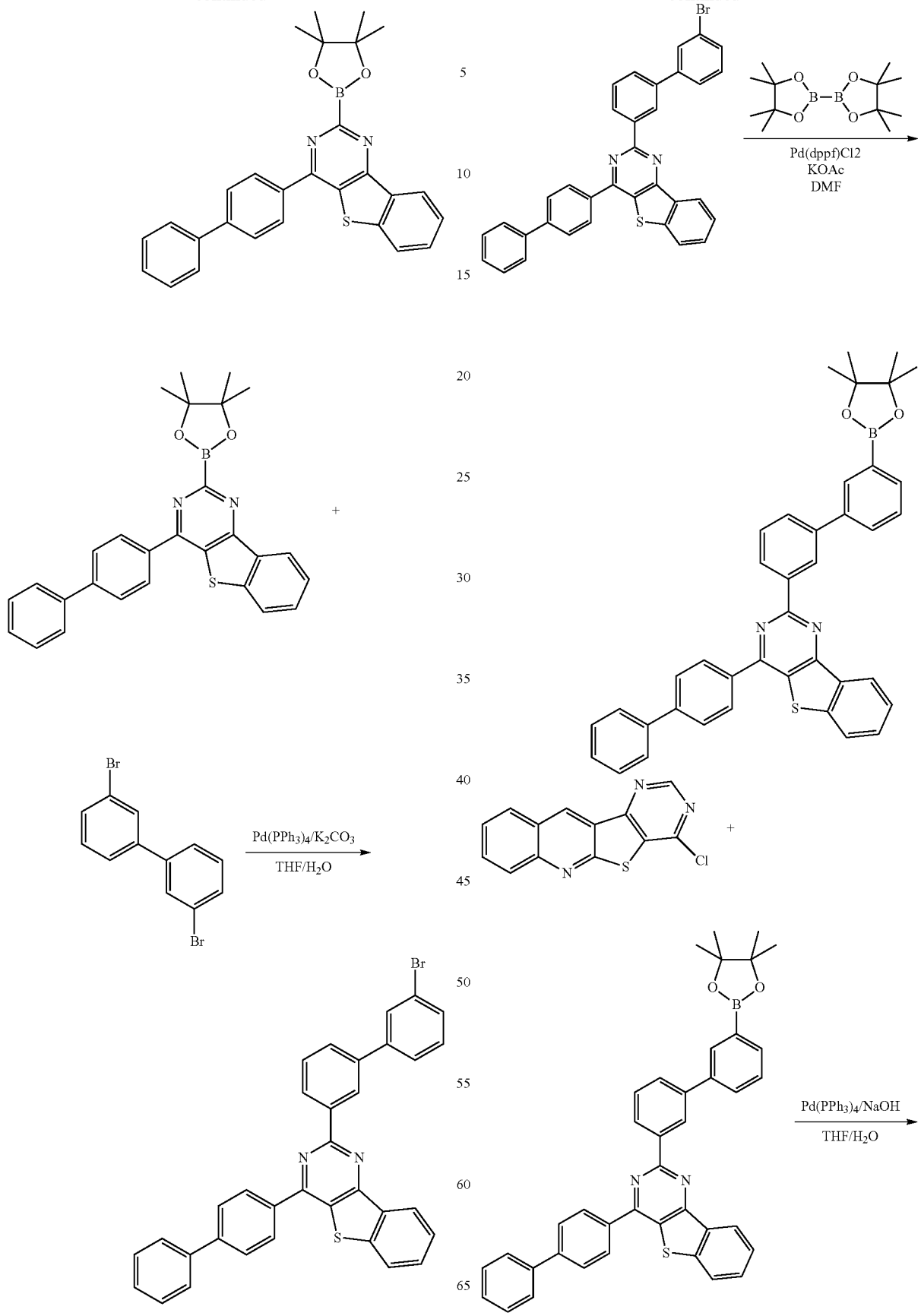

-continued

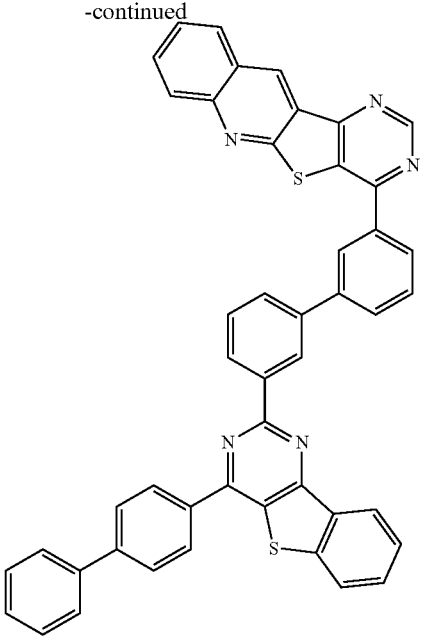

4-([1,1'-biphenyl]-4-yl)-2-chlorobenzo[4,5]thieno[3,2-d]pyrimidine (20 g, 53.64 mmol) was dissolved with DMF in around bottom flask, and then 4,4,4',4',5,5,5',5'-octamethyl-2,2'-bi(1,3,2-dioxaborolane) (14.98 g, 59 mmol), Pd(dppf)Cl₂ (1.18 g, 1.61 mmol), KOAc (15.79 g, 160.91 mmol) were added and stirred under reflux at 130° C. for 4 hours. Upon completion of the reaction, DMF was removed from the reaction product via distillation and the reaction product was extracted with $CH_2Cl_2$ and water. The resulting organic layer was dried using $MgSO_4$ and concentrated, and the resulting compound was subjected to silicagel column and recrystallization to obtain 4-([1,1'-biphenyl]-4-yl)-2-(4,4,5,5-tetramethyl-1,3,2-dioxaborolan-2-yl)benzo[4,5]thieno[3,2-d]pyrimidine (17.5 g, 70.25%).

4-([1,1'-biphenyl]-4-yl)-2-(4,4,5,5-tetramethyl-1,3,2-dioxaborolan-2-yl)benzo[4,5]thieno[3,2-d]pyrimidine (17.5 g, 37.68 mmol) was dissolved with THF, and then 3,3'-dibromo-1,1'-biphenyl (12.93 g, 41.45 mmol), Pd(PPh₃)₄ (1.31 g, 1.13 mmol), K₂CO₃ (15.62 g, 113.05 mmol) and water were added and stirred under reflux at 100° C. for 3 hours. Upon completion of the reaction, the organic layer was extracted with E.A. and water, and was dried using $MgSO_4$ and concentrated. The resulting organic material was subjected to silicagel column to obtain 4-([1,1'-biphenyl]-4-yl)-2-(3'-bromo-[1,1'-biphenyl]-3-yl)benzo[4,5]thieno[3,2-d]pyrimidine (15 g, 69.89%).

4-([1,1'-biphenyl]-4-yl)-2-(3'-bromo-[1,1'-biphenyl]-3-yl)benzo[4,5]thieno[3,2-d]pyrimidine (15 g, 26.34 mmol) was dissolved with DMF in a round bottom flask, and then 4,4,4',4',5,5,5',5'-octamethyl-2,2'-bi(1,3,2-dioxaborolane) (7.36 g, 28.97 mmol), Pd(dppf)Cl₂ (0.58 g, 0.79 mmol), KOAc (7.76 g, 79.01 mmol) were added and stirred under reflux at 130° C. for 4 hours. Upon completion of the reaction, DMF was removed from the reaction product via distillation and the reaction product was extracted with $CH_2Cl_2$ and water. The resulting organic layer was dried using $MgSO_4$ and concentrated, and the resulting compound was subjected to silicagel column and recrystallization to obtain 4-([1,1'-biphenyl]-4-yl)-2-(3'-(4,4,5,5-tetramethyl-1,3,2-dioxaborolan-2-yl)-[1,1'-biphenyl]-3-yl)benzo[4,5]thieno[3,2-d]pyrimidine (11 g, 67.7%).

4-chloropyrimido[4',5':4,5]thieno[2,3-b]quinoline (15 g, 55.2 mmol) was dissolved with THF, and then 4-([1,1'-biphenyl]-4-yl)-2-(3'-(4,4,5,5-tetramethyl-1,3,2-dioxaborolan-2-yl)-[1,1'-biphenyl]-3-yl)benzo[4,5]thieno[3,2-d]pyrimidine (37.44 g, 60.72 mmol), Pd(PPh₃)₄ (1.91 g, 1.66 mmol), NaOH (6.62 g, 165.61 mmol) and water were added and stirred under reflux at 100° C. for 3 hours. Upon completion of the reaction, the organic layer was extracted with E.A. and water, and was dried using $MgSO_4$ and concentrated. The resulting organic material was subjected to silicagel column and recrystallization to obtain 25 g (Yield: 62.38%) of the final product.

The synthesis method of compound 3-1-9 is described below with reference to the following synthesis formula.

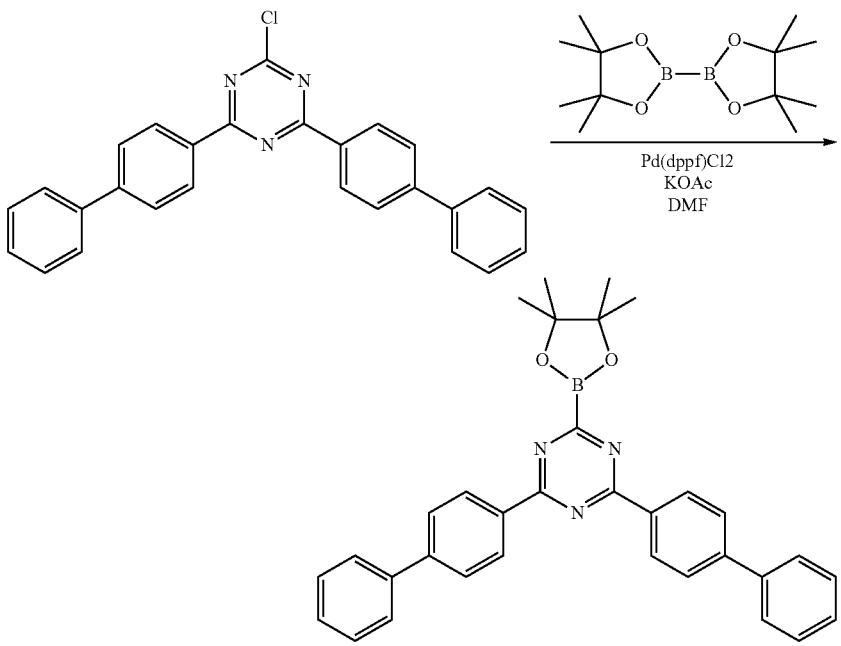

-continued
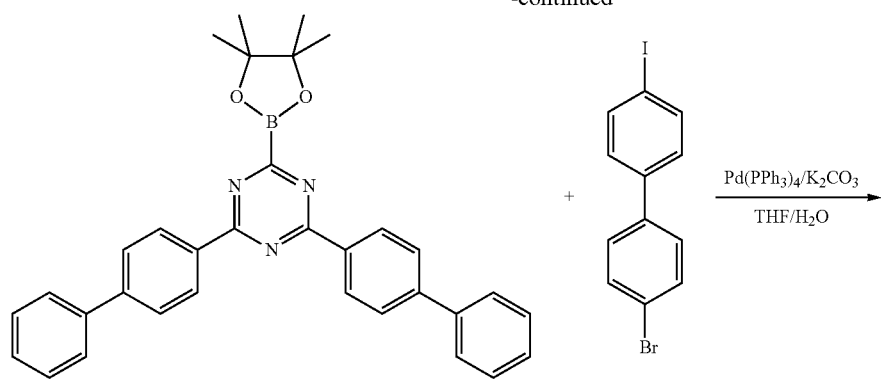
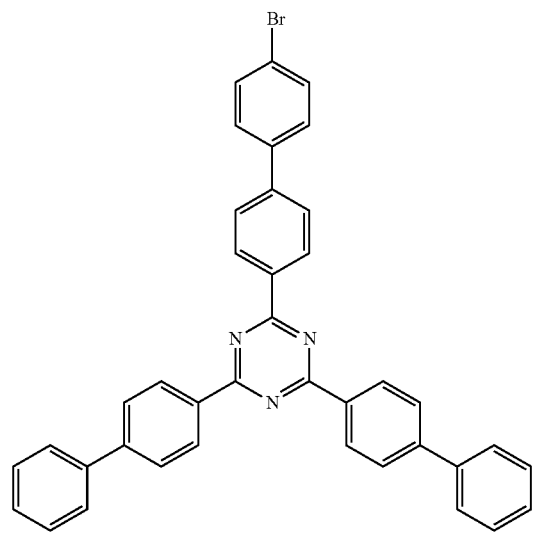
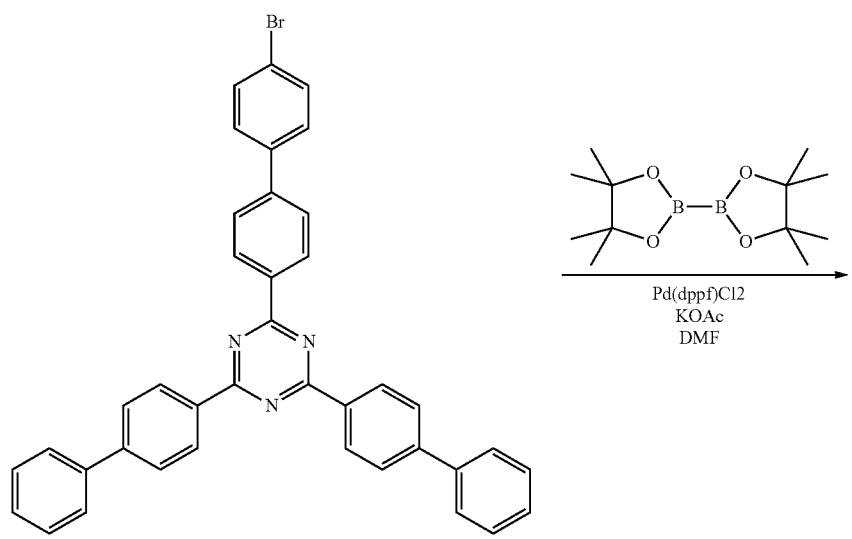

-continued
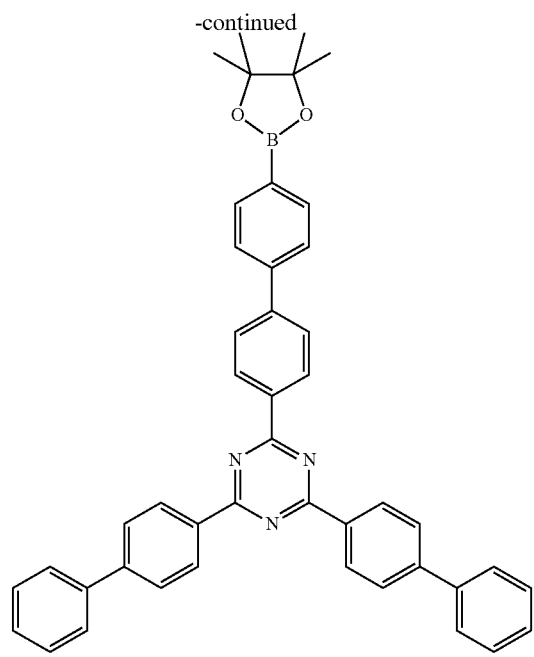
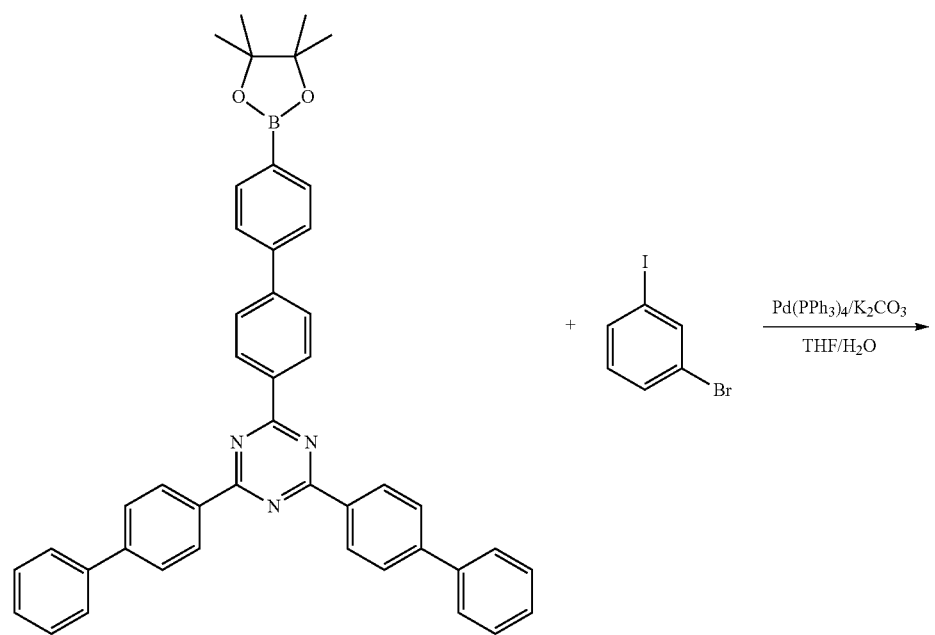

-continued
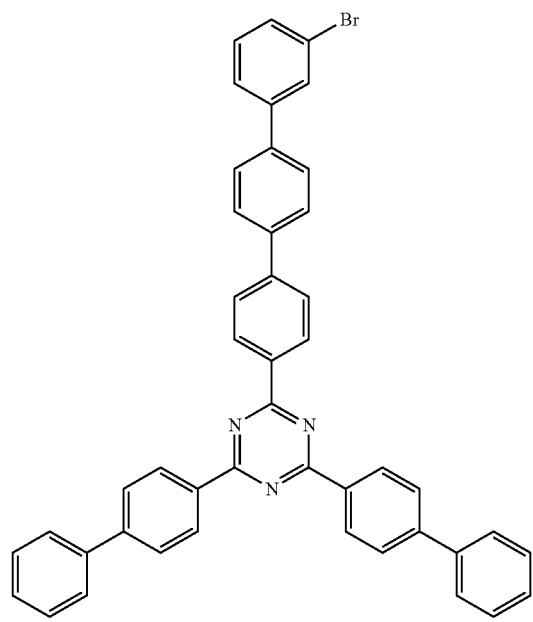
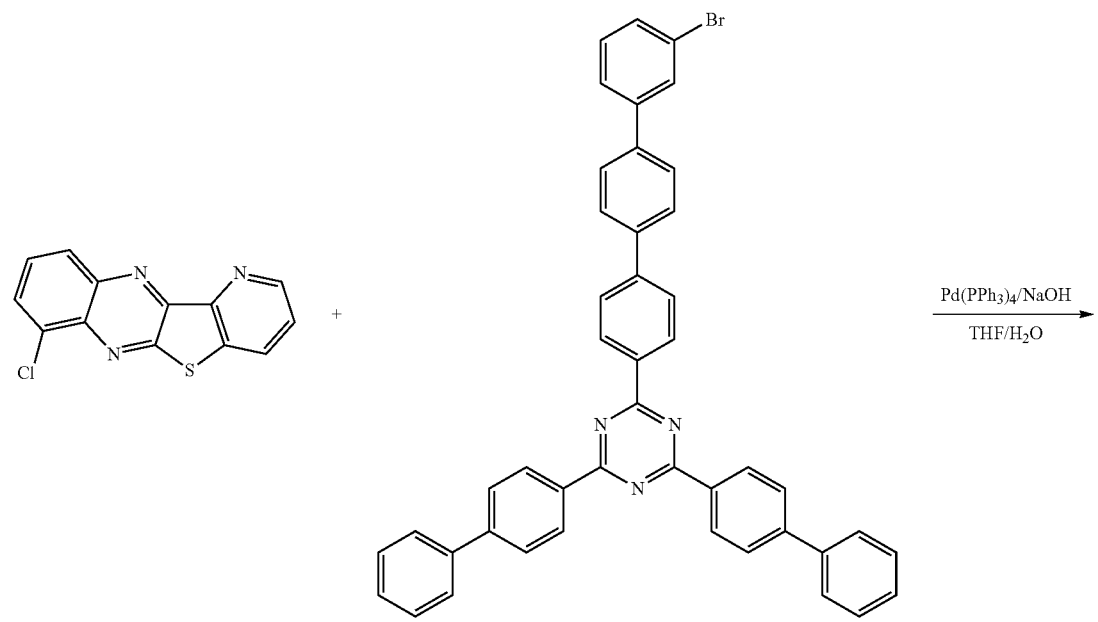

-continued

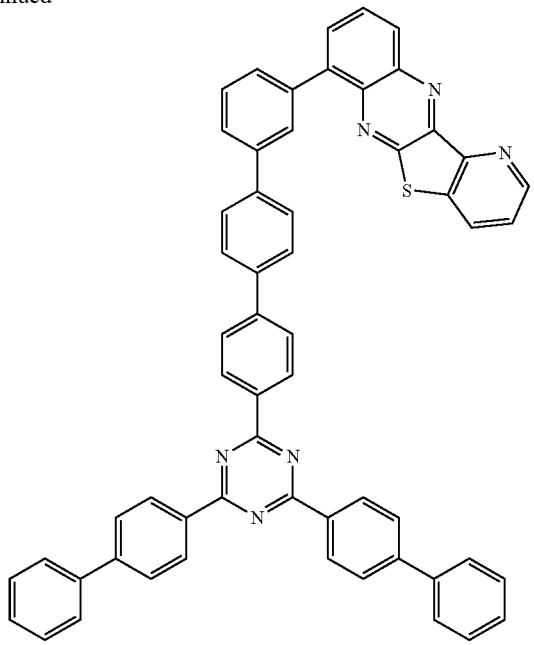

2,4-di([1,1'-biphenyl]-4-yl)-6-chloro-1,3,5-triazine (20 g, 47.63 mmol) was dissolved with DMF in a round bottom flask, and then 4,4,4',4',5,5,5',5'-octamethyl-2,2'-bi(1,3,2-dioxaborolane) (13.3 g, 52.39 mmol), Pd(dppf)Cl$_2$ (1.05 g, 1.43 mmol), KOAc (14.02 g, 142.89 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-di([1,1'-biphenyl]-4-yl)-6-(4,4,5,5-tetramethyl-1,3,2-dioxaborolan-2-yl)-1,3,5-triazine (17 g, 69.78%).

2,4-di([1,1'-biphenyl]-4-yl)-6-(4,4,5,5-tetramethyl-1,3,2-dioxaborolan-2-yl)-1,3,5-triazine (17 g, 33.24 mmol) was dissolved with THF, and then 4-bromo-4'-iodo-1,1'-biphenyl (13.13 g, 36.56 mmol), Pd(PPh$_3$)$_4$ (1.15 g, 1 mmol), K$_2$CO$_3$ (13.78 g, 99.72 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2,4-di([1,1'-biphenyl]-4-yl)-6-(4'-bromo-[1,1'-biphenyl]-4-yl)-1,3,5-triazine (14 g, 68.31%).

2,4-di([1,1'-biphenyl]-4-yl)-6-(4'-bromo-[1,1'-biphenyl]-4-yl)-1,3,5-triazine (14 g, 22.71 mmol) was dissolved with DMF in a round bottom flask, and then 4,4,4',4',5,5,5',5'-octamethyl-2,2'-bi(1,3,2-dioxaborolane)(6.34 g, 24.98 mmol), Pd(dppf)Cl$_2$ (0.5 g, 0.68 mmol), KOAc (6.69 g, 68.12 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-di([1,1'-biphenyl]-4-yl)-6-(4'-(4,4,5,5-tetramethyl-1,3,2-dioxaborolan-2-yl)-[1,1'-biphenyl]-4-yl)-1,3,5-triazine (10 g, 66.36%).

2,4-di([1,1'-biphenyl]-4-yl)-6-(4'-(4,4,5,5-tetramethyl-1,3,2-dioxaborolan-2-yl)-[1,1'-biphenyl]-4-yl)-1,3,5-triazine (10 g, 15.07 mmol) was dissolved with THF, and then 1-bromo-3-iodobenzene (4.69 g, 16.58 mmol), Pd(PPh$_3$)$_4$ (0.52 g, 0.45 mmol), K$_2$CO$_3$ (6.25 g, 45.21 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2,4-di([1,1'-biphenyl]-4-yl)-6-(3"-bromo-[1,1':4',1"-terphenyl]-4-yl)-1,3,5-triazine (7 g, 68.32%).

7-chloropyrido[2',3':4,5]thieno[2,3-b]quinoxaline (10 g, 36.8 mmol) was dissolved with THF, and then 2,4-di([1,1'-biphenyl]-4-yl)-6-(3"-bromo-[1,1':4',1"-terphenyl]-4-yl)-1,3,5-triazine (27.53 g, 40.48 mmol), Pd(PPh$_3$)$_4$ (1.28 g, 1.1 mmol), NaOH (4.42 g, 110.41 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 20 g (yield: 64%) of the final product.

The synthesis method of compound 3-1-13 is described below with reference to the following synthesis formula.

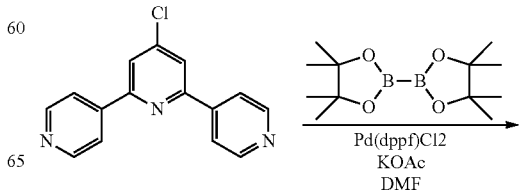

297
-continued
298
-continued
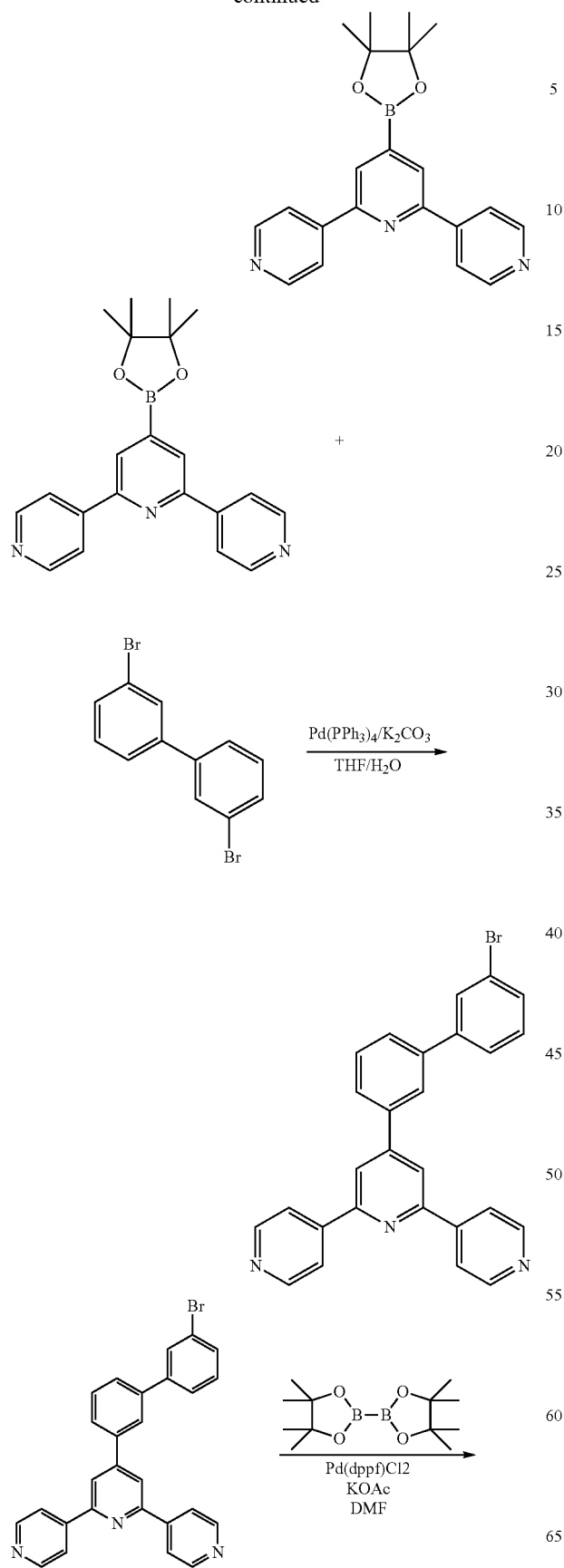
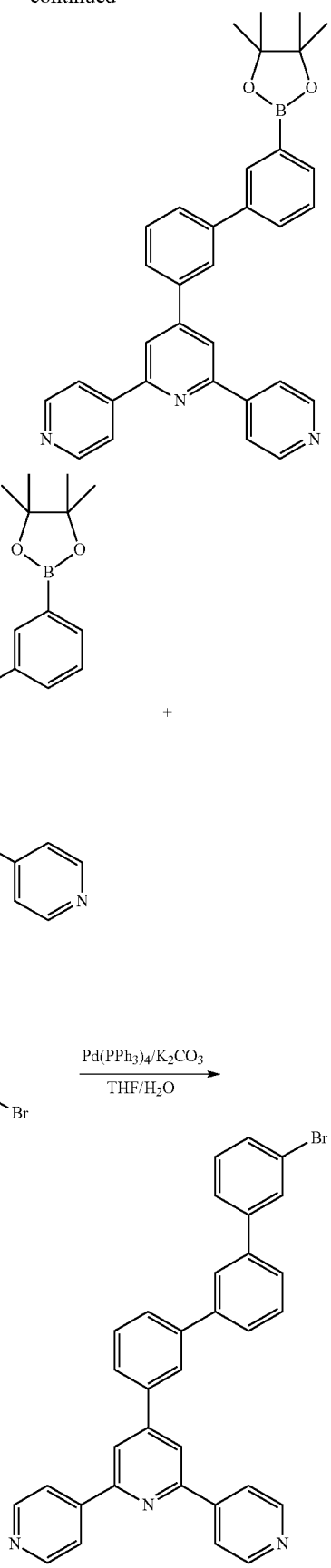

-continued

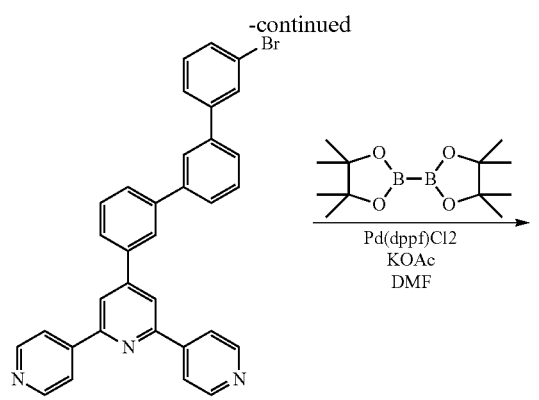

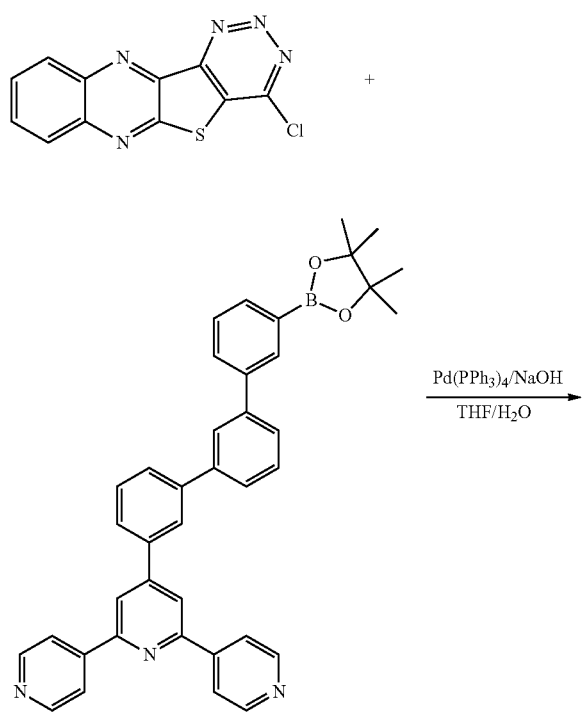

-continued

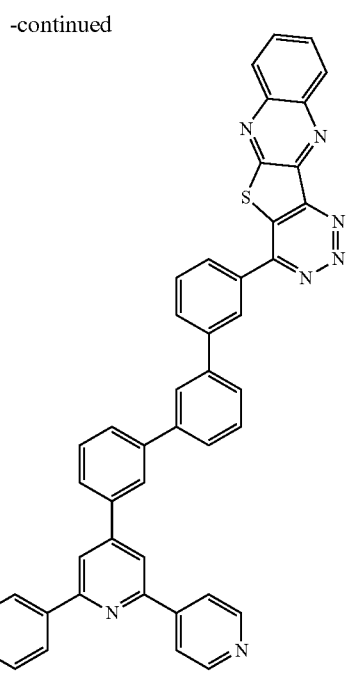

4'-chloro-4,2': 6',4"-terpyridine (20 g, 74.7 mmol) was dissolved with DMF in a round bottom flask, and then 4,4,4',4',5,5,5',5'-octamethyl-2,2'-bi(1,3,2-dioxaborolane) (20.87 g, 82.18 mmol), Pd(dppf)Cl$_2$ (1.64 g, 2.24 mmol), KOAc (22 g, 224.11 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4'-(4,4,5,5-tetramethyl-1,3,2-dioxaborolan-2-yl)-4,2': 6',4"-terpyridine (18 g, 67.07%).

4'-(4,4,5,5-tetramethyl-1,3,2-dioxaborolan-2-yl)-4,2': 6',4"-terpyridine (18 g, 50.11 mmol) was dissolved with THF, and then 3,3'-dibromo-1,1'-biphenyl (17.2 g, 55.12 mmol), Pd(PPh$_3$)$_4$ (1.74 g, 1.5 mmol), K$_2$CO$_3$ (20.77 g, 150.32 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 4'-(3'-bromo-[1,1'-biphenyl]-3-yl)-4,2': 6',4"-terpyridine (16 g, 68.76%).

4'-(3'-bromo-[1,1'-biphenyl]-3-yl)-4,2': 6',4"-terpyridin (16 g, 34.46 mmol) was dissolved with DMF in a round bottom flask, and then 4,4,4',4',5,5,5',5'-octamethyl-2,2'-bi (1,3,2-dioxaborolane) (9.62 g, 37.9 mmol), Pd(dppf)Cl$_2$ (0.76 g, 1.03 mmol), KOAc (10.15 g, 103.37 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4'-(3"-bromo-[1,1': 3',1"-terphenyl]-3-yl)-4,2': 6',4"-terpyridine (12 g, 68.09%).

4'-(3'-(4,4,5,5-tetramethyl-1,3,2-dioxaborolan-2-yl)-[1,1'-biphenyl]-3-yl)-4,2': 6',4"-terpyridine (12 g, 23.46 mmol) was dissolved with THF, and then 1-bromo-3-iodobenzene (7.3 g, 25.81 mmol), Pd(PPh₃)₄ (0.81 g, 0.7 mmol), K₂CO₃ (2.82 g, 70.39 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column to obtain 4'-(3'-bromo-[1,1'-biphenyl]-3-yl)-4,2': 6',4"-terpyridine (9 g, 70.97%).

4'-(3"-bromo-[1,1': 3',1"-terphenyl]-3-yl)-4,2': 6',4"-terpyridine (9 g, 16.65 mmol) was dissolved with DMF in a round bottom flask, and then 4,4,4',4',5,5,5',5'-octamethyl-2,2'-bi(1,3,2-dioxaborolane) (4.65 g, 18.32 mmol), Pd(dppf)Cl₂ (0.37 g, 0.5 mmol), KOAc (4.9 g, 49.96 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4'-(3"-(4,4,5,5-tetramethyl-1,3,2-dioxaborolan-2-yl)-[1,1': 3',1"-terphenyl]-3-yl)-4,2': 6',4"-terpyridine (6.5 g, 66.43%).

4-chloro-[1,2,3]triazino[4',5':4,5]thieno[2,3-b]quinoxaline (10 g, 36.54 mmol) was dissolved with THF, and then 4'-(3"-(4,4,5,5-tetramethyl-1,3,2-dioxaborolan-2-yl)-[1,1': 3',1"-terphenyl]-3-yl)-4,2': 6',4"-terpyridine (23.61 g, 40.19 mmol), Pd(PPh₃)₄ (1.27 g, 1.1 mmol), NaOH (4.38 g, 109.61 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 16 g (yield: 62.7%) of the final product.

The synthesis method of compound 3-1-15 is described below with reference to the following synthesis formula.

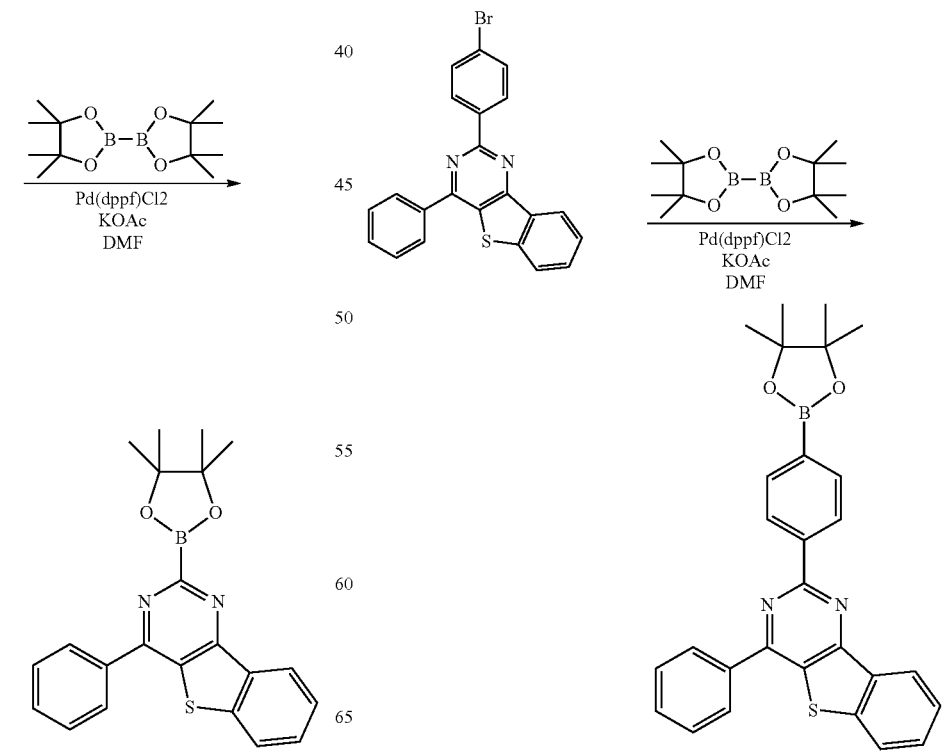

303
-continued
304
-continued
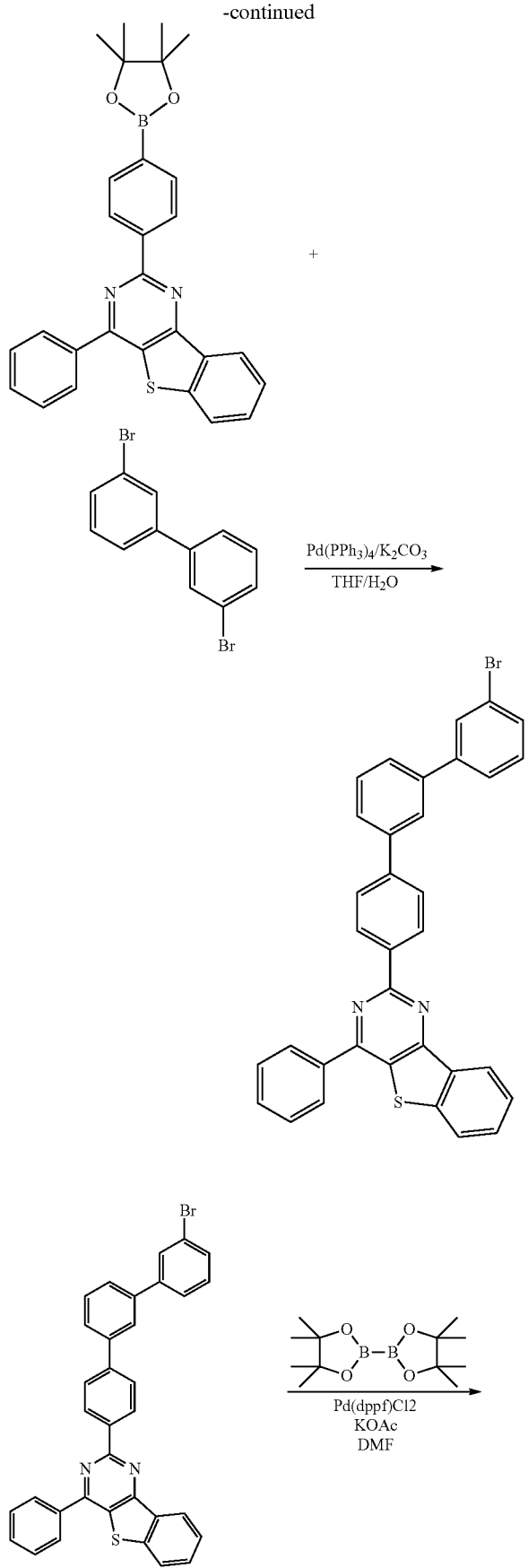
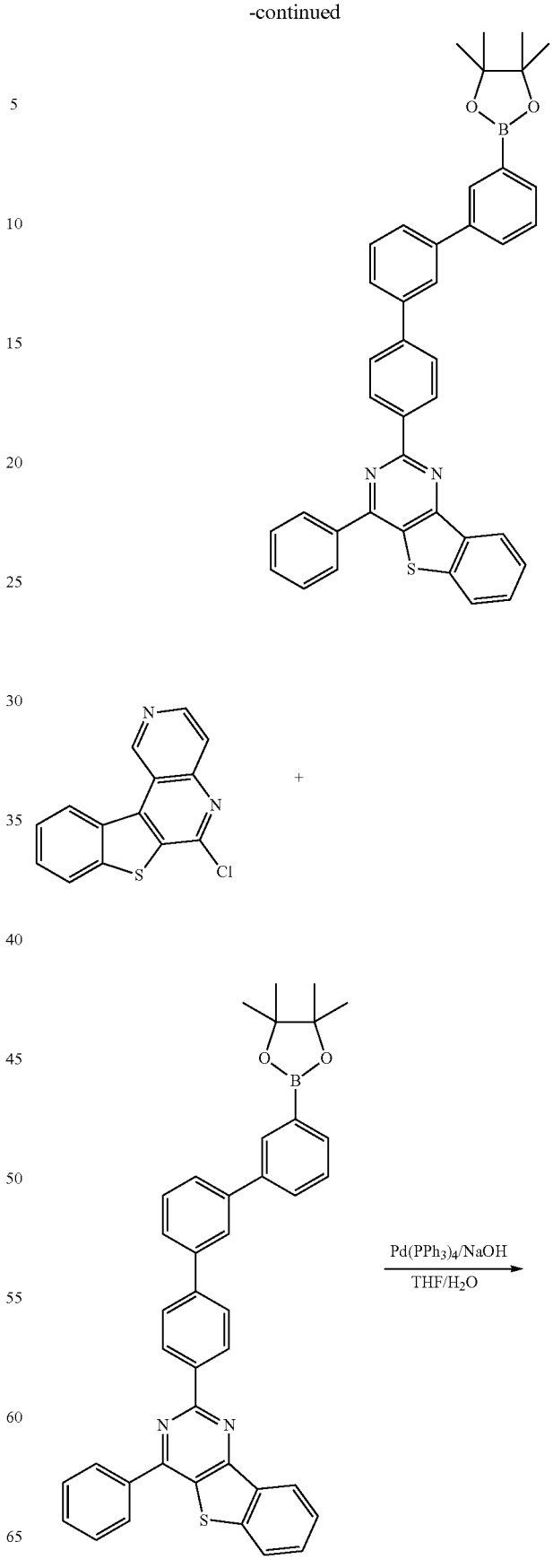

-continued

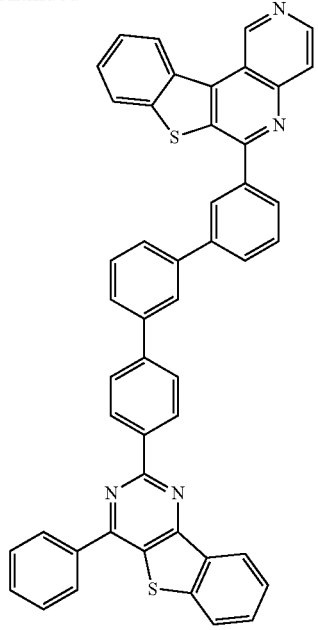

2-chloro-4-phenylbenzo[4,5]thieno[3,2-d]pyrimidine (20 g, 67.39 mmol) was dissolved with DMF in a round bottom flask, and then 4,4,4',4',5,5,5',5'-octamethyl-2,2'-bi(1,3,2-dioxaborolane) (18.82 g, 74.13 mmol), Pd(dppf)Cl$_2$ (1.48 g, 2.02 mmol), KOAc (19.84 g, 202.18 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(4,4,5,5-tetramethyl-1,3,2-dioxaborolan-2-yl)benzo[4,5] thieno[3,2-d]pyrimidine (18 g, 68.78%).

Intermediate product 4-phenyl-2-(4,4,5,5-tetramethyl-1,3,2-dioxaborolan-2-yl)benzo[4,5]thieno[3,2-d]pyrimidine (18 g, 46.36 mmol) was dissolved with THF, and then 1-bromo-4-iodobenzene (14.43 g, 50.99 mmol), Pd(PPh$_3$)$_4$ (1.61 g, 1.39 mmol), K$_2$CO$_3$ (5.56 g, 139.07 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2-(4-bromophenyl)-4-phenylbenzo[4,5] thieno[3,2-d]pyrimidine (13 g, 67.19%).

Repeatedly, 2-(4-bromophenyl)-4-phenylbenzo[4,5]thieno[3,2-d]pyrimidine (13 g, 31.15 mmol) was dissolved with DMF in a round bottom flask, and then 4,4,4',4',5,5,5',5'-octamethyl-2,2'-bi(1,3,2-dioxaborolane) (8.7 g, 34.27 mmol), Pd(dppf)Cl$_2$ (0.68 g, 0.93 mmol), KOAc (9.17 g, 93.45 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(4-(4,4,5,5-tetramethyl-1,3,2-dioxaborolan-2-yl)phenyl) benzo[4,5]thieno[3,2-d]pyrimidine (10 g, 69.12%).

4-phenyl-2-(4-(4,4,5,5-tetramethyl-1,3,2-dioxaborolan-2-yl)phenyl)benzo[4,5]thieno [3,2-d]pyrimidine (10 g, 21.53 mmol) was dissolved with THF, and then 3,3'-dibromo-1,1'-biphenyl (7.39 g, 23.69 mmol), Pd(PPh$_3$)$_4$ (0.75 g, 0.65 mmol), K$_2$CO$_3$ (8.93 g, 64.6 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2-(3"-bromo-[1,1': 3',1"-terphenyl]-4-yl)-4-phenylbenzo[4,5]thieno[3,2-d]pyrimidine (8.5 g, 69.3%).

2-(3"-bromo-[1,1': 3',1"-terphenyl]-4-yl)-4-phenylbenzo[4,5]thieno[3,2-d]pyrimidine (8.5 g, 14.92 mmol) was dissolved with DMF in a round bottom flask, and then 4,4,4',4',5,5,5',5'-octamethyl-2,2'-bi(1,3,2-dioxaborolane)(4.17 g, 16.42 mmol), Pd(dppf)Cl$_2$ (0.33 g, 0.45 mmol), KOAc (4.39 g, 44.77 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(3"-(4,4,5,5-tetramethyl-1,3,2-dioxaborolan-2-yl)-[1,1': 3',1"-terphenyl]-4-yl)benzo[4,5]thieno[3,2-d] pyrimidine (6 g, 65.19%).

6-chlorobenzo[4,5]thieno[2,3-c][1,6]naphthyridine (10 g, 36.94 mmol) was dissolved with THF, and then 4-phenyl-2-(3"-(4,4,5,5-tetramethyl-1,3,2-dioxaborolan-2-yl)-[1,1': 3',1"-terphenyl]-4-yl)benzo[4,5]thieno[3,2-d]pyrimidine (25.05 g, 40.63 mmol), Pd(PPh$_3$)$_4$ (1.28 g, 1.11 mmol), NaOH (4.43 g, 110.81 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 17 g (yield: 63.5%) of the final product.

The synthesis method of compound 3-2-4 is described below with reference to the following synthesis formula.

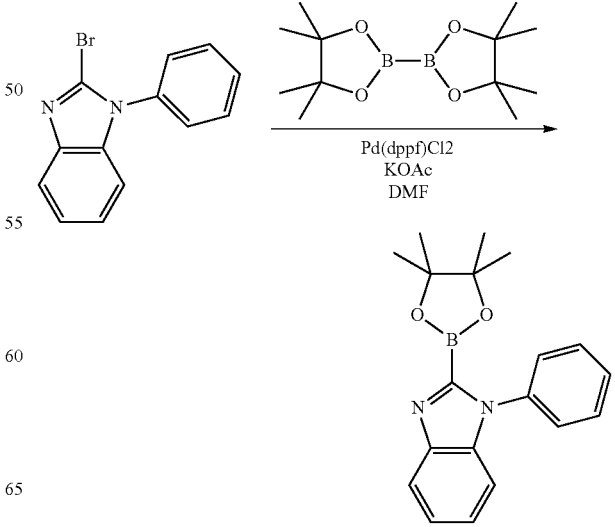

307
-continued
308
-continued
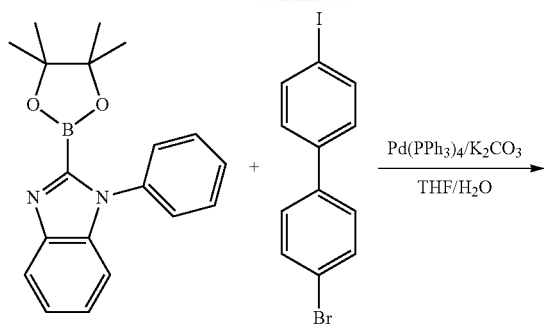
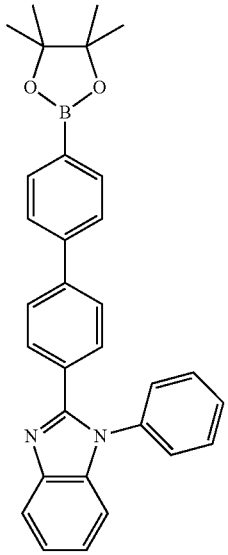
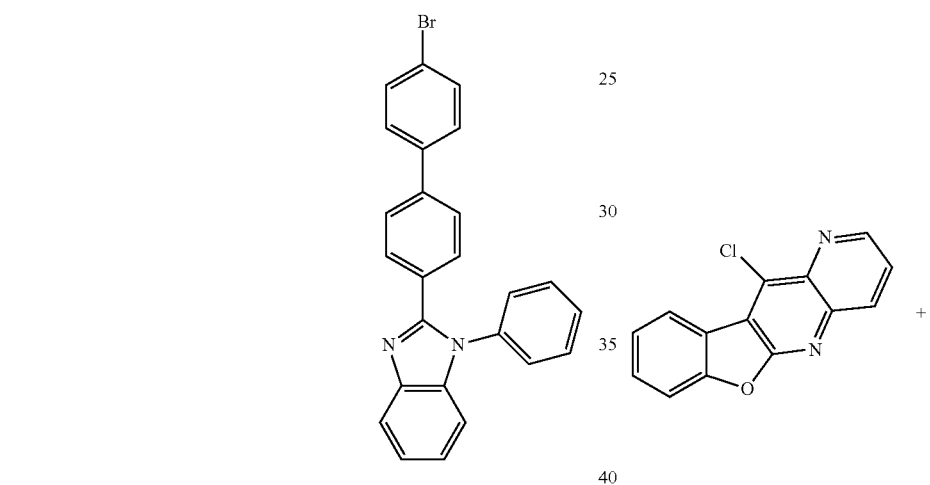
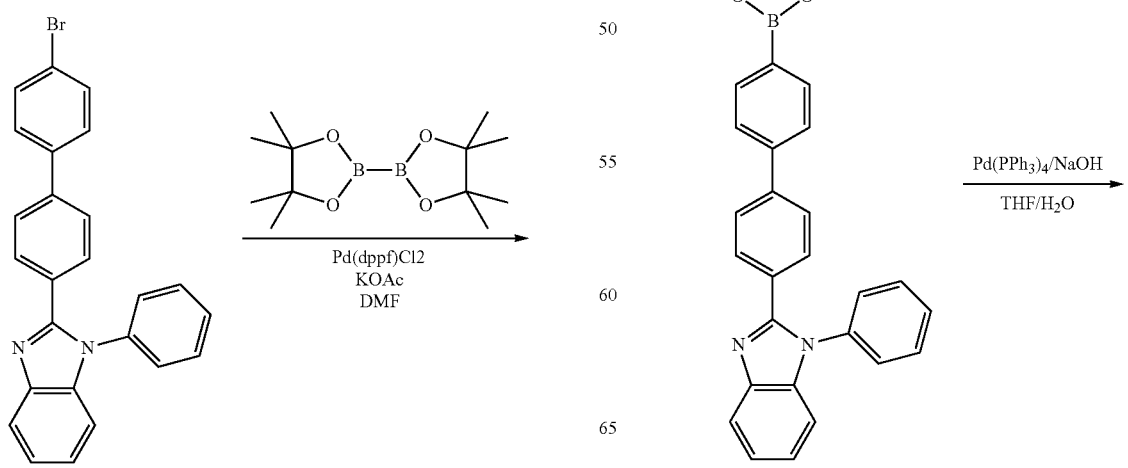

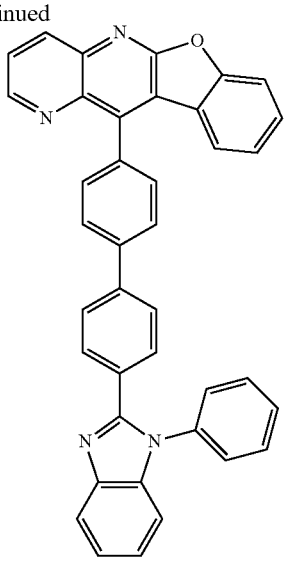

2-bromo-1-phenyl-1H-benzo[d]imidazole (100 g 366.12 mmol) was dissolved with DMF in around bottom flask, and then bis(pinacolato)diboron (139.46 g, 549.1 mmol), Pd(dppf)Cl₂ (8.04 g, 10.98 mmol), KOAc (107.8 g, 1.1 mol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 1-phenyl-2-(4,4,5,5-tetramethyl-1,3,2-dioxaborolan-2-yl)-1H-benzo[d]imidazole (76.2 g, 65%).

1-phenyl-2-(4,4,5,5-tetramethyl-1,3,2-dioxaborolan-2-yl)-1H-benzo[d]imidazole (60 g, 187.38 mmol) was dissolved with THF, and then 4-bromo-4'-iodo-1,1'-biphenyl (80.72 g, 224.86 mmol), Pd(PPh₃)₄ (6.5 g, 5.62 mmol), K₂CO₃ (77.68 g, 562.14 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column to obtain 2-(4'-bromo-[1,1'-biphenyl]-4-yl)-1-phenyl-1H-benzo[d] imidazole (52.6 g, 66%).

2-(4'-bromo-[1,1'-biphenyl]-4-yl)-1-phenyl-1H-benzo[d]imidazole (50 g, 117.55 mmol) was dissolved with DMF in a round bottom flask, and then bis(pinacolato)diboron (44.78 g, 176.33 mmol), Pd(dppf)Cl₂ (2.58 g, 3.53 mmol), KOAc (34.6 g, 352.68 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 1-phenyl-2-(4'-(4,4,5,5-tetramethyl-1,3,2-dioxaborolan-2-yl)-[1,1'-biphenyl]-4-yl)-1H-benzo[d]imidazole (36.1 g, 65%).

11-chlorobenzofuro[2,3-b][1,5]naphthyridine (20 g, 78.53 mmol) was dissolved with THF, and then 1-phenyl-2-(4'-(4,4,5,5-tetramethyl-1,3,2-dioxaborolan-2-yl)-[1,1'-biphenyl]-4-yl)-1H-benzo[d] imidazole (55.65 g, 117.8 mmol), Pd(PPh₃)₄ (2.72 g, 2.36 mmol), NaOH (9.42 g, 235.6 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 28.8 g (yield: 65%) of the final product.

The synthesis method of compound 3-2-8 is described below with reference to the following synthesis formula.

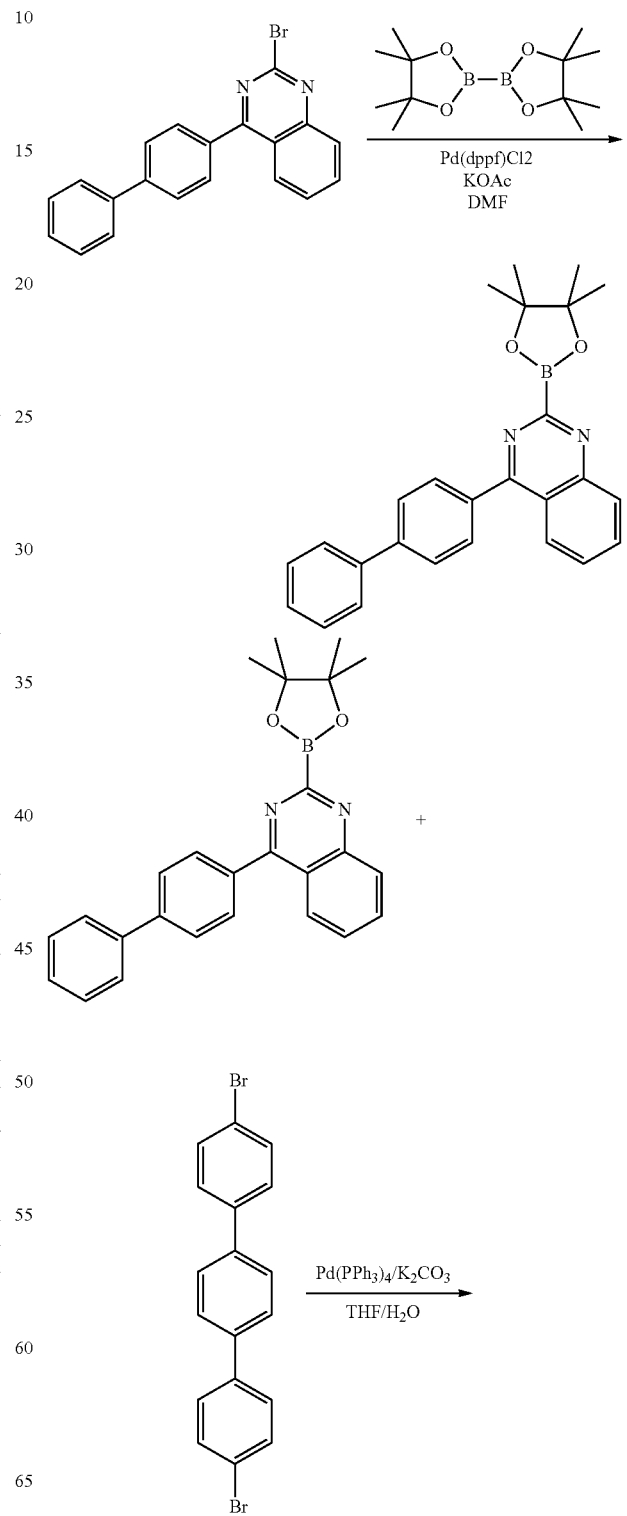

311
-continued
312
-continued
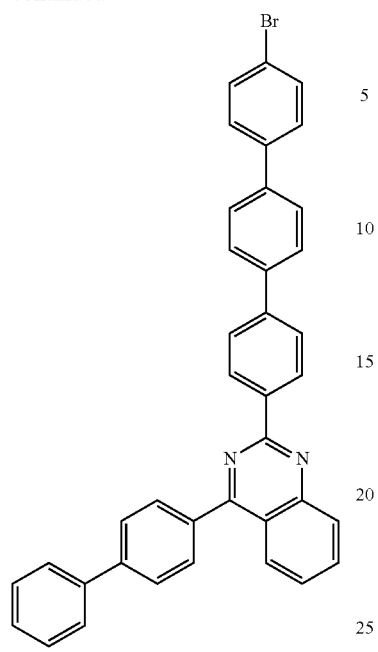
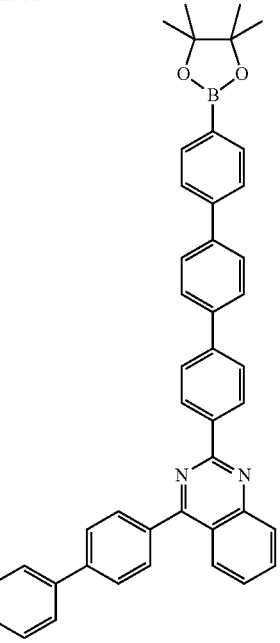
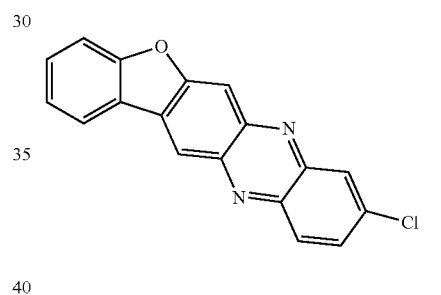
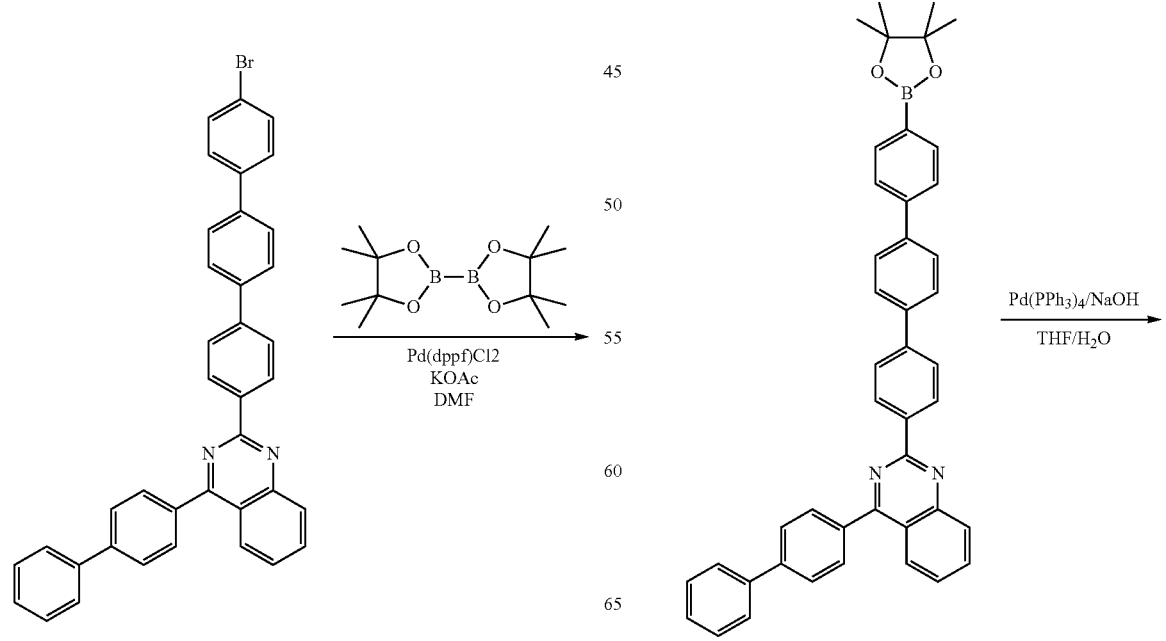

313
-continued

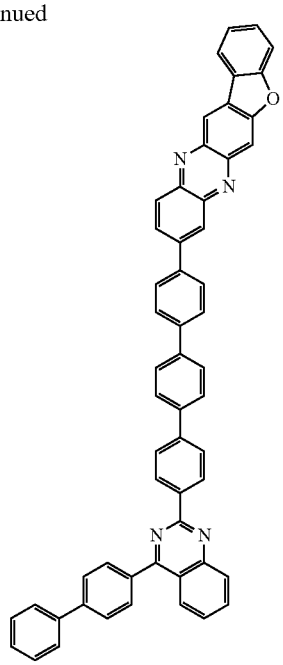

4-([1,1'-biphenyl]-4-yl)-2-bromoquinazoline (100 g, 276.82 mmol) was dissolved with DMF in a round bottom flask, and then bis(pinacolato)diboron (105.45 g, 415.24 mmol), Pd(dppf)Cl₂ (6.08 g, 8.3 mmol), KOAc (81.5 g, 830.47 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4-([1,1'-biphenyl]-4-yl)-2-(4,4,5,5-tetramethyl-1,3,2-dioxaborolan-2-yl)quinazoline (74.6 g, 66%).

4-([1,1'-biphenyl]-4-yl)-2-(4,4,5,5-tetramethyl-1,3,2-dioxaborolan-2-yl)quinazoline (70 g, 171.44 mmol) was dissolved with THF, and then 4,4"-dibromo-1,1':4',1"-terphenyl (79.84 g, 205.73 mmol), Pd(PPh₃)₄ (5.94 g, 5.14 mmol), K₂CO₃ (71.08 g, 514.32 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column to obtain 4-([1,1'-biphenyl]-4-yl)-2-(4"-bromo-[1,1':4',1"-terphenyl]-4-yl)quinazoline (66.7 g, 66%).

4-([1,1'-biphenyl]-4-yl)-2-(4"-bromo-[1,1':4',1"-terphenyl]-4-yl)quinazoline (60 g, 101.77 mmol) was dissolved with DMF in a round bottom flask, and then bis(pinacolato)diboron (38.77 g, 152.66 mmol), Pd(dppf)Cl₂ (2.23 g, 3.05 mmol), KOAc (29.96 g, 305.32 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4-([1,1'-biphenyl]-4-yl)-2-(4"-(4,4,5,5-tetramethyl-1,3,2-dioxaborolan-2-yl)-[1,1':4',1"-terphenyl]-4-yl)quinazoline (42.4 g, 65.5%).

9-chlorobenzofuro[2,3-b]phenazine (20 g, 65.63 mmol) was dissolved with THF, and then 4-([1,1'-biphenyl]-4-yl)-

314

2-(4"-(4,4,5,5-tetramethyl-1,3,2-dioxaborolan-2-yl)-[1,1':4',1"-terphenyl]-4-yl)quinazoline (62.67 g, 98.45 mmol), Pd(PPh₃)₄ (2.28 g, 1.97 mmol), NaOH (7.88 g, 196.9 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 34.7 g (yield: 68%) of the final product.

The synthesis method of compound 3-2-11 is described below with reference to the following synthesis formula.

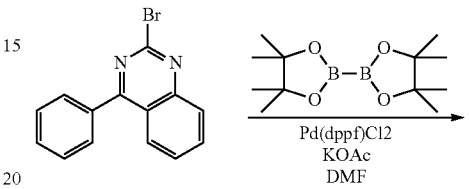

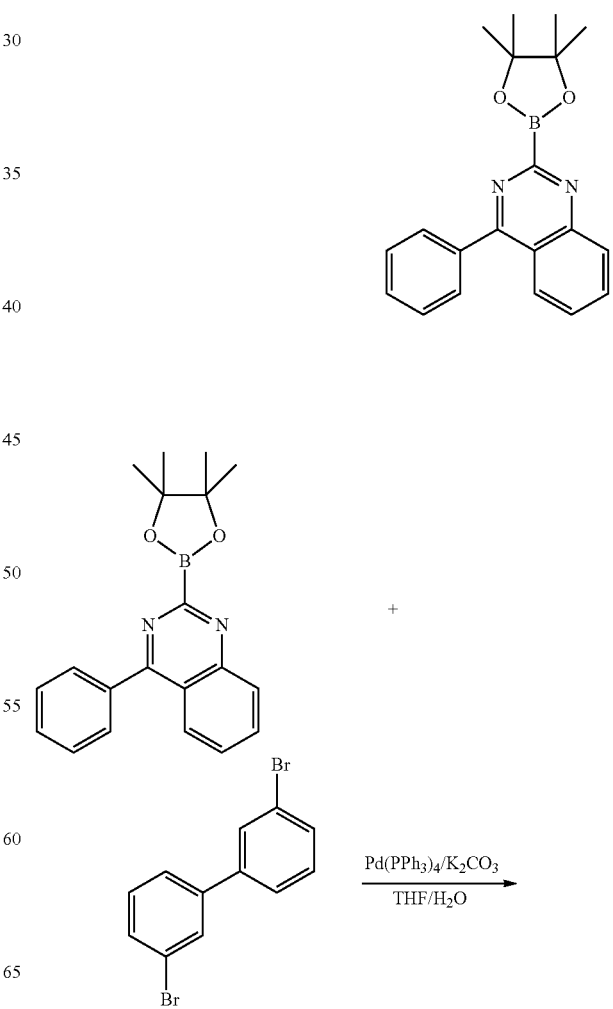

315
-continued
316
-continued
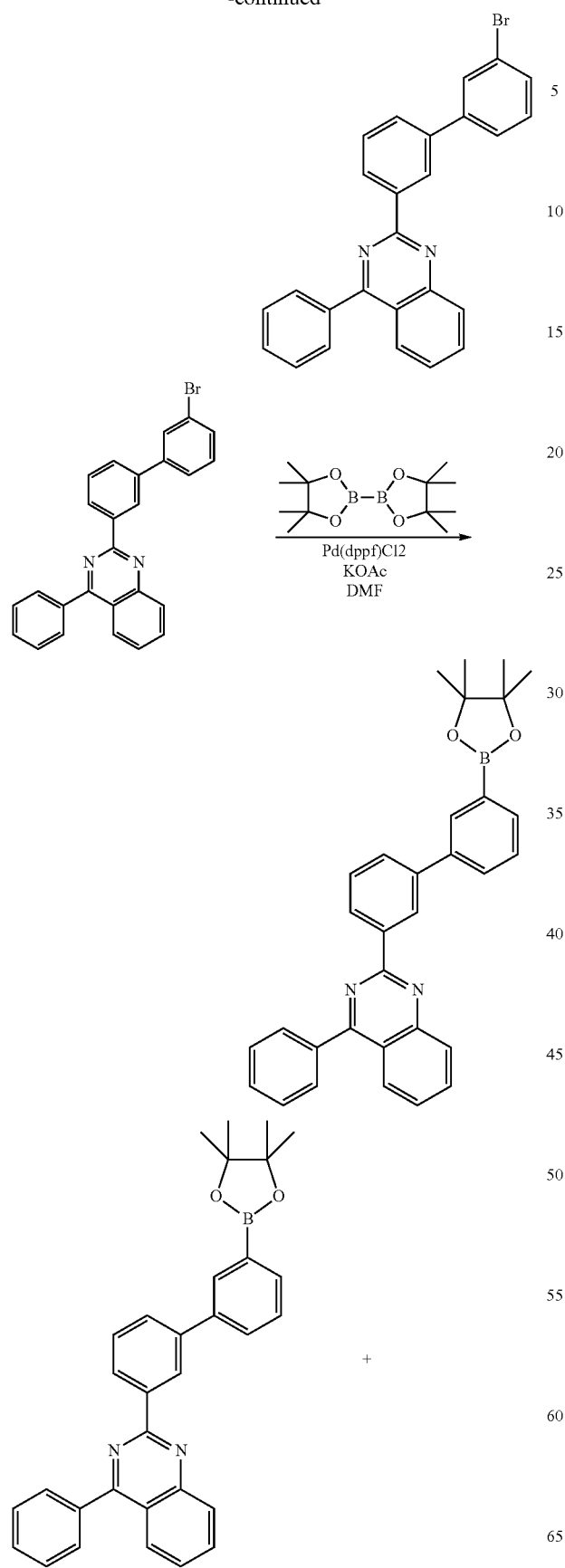
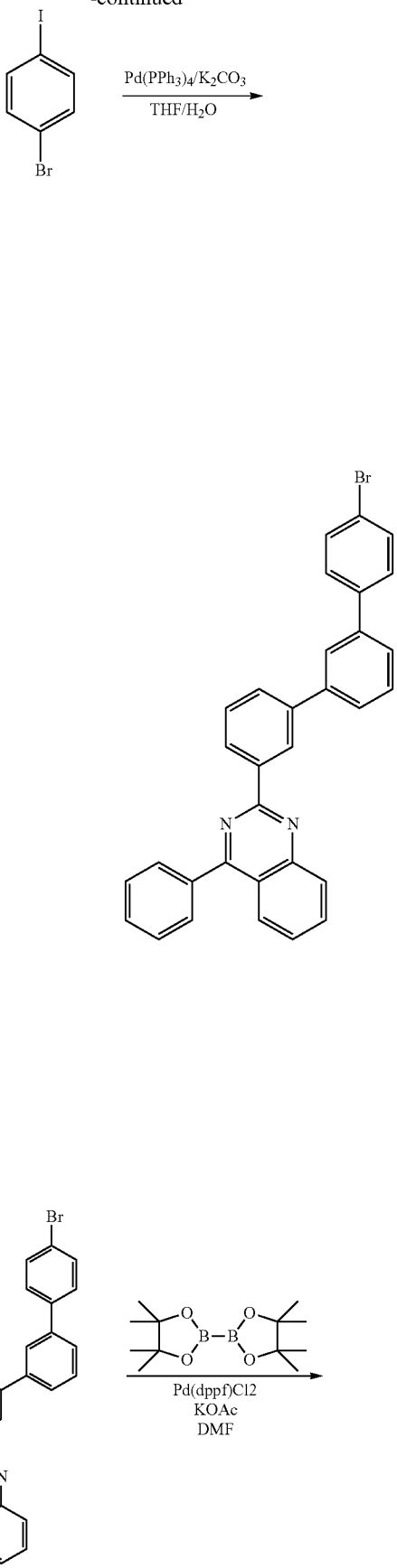

317
-continued

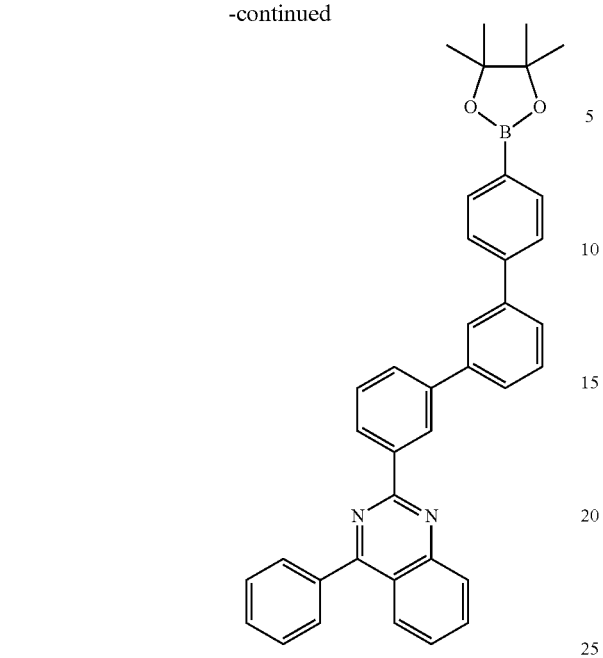

+

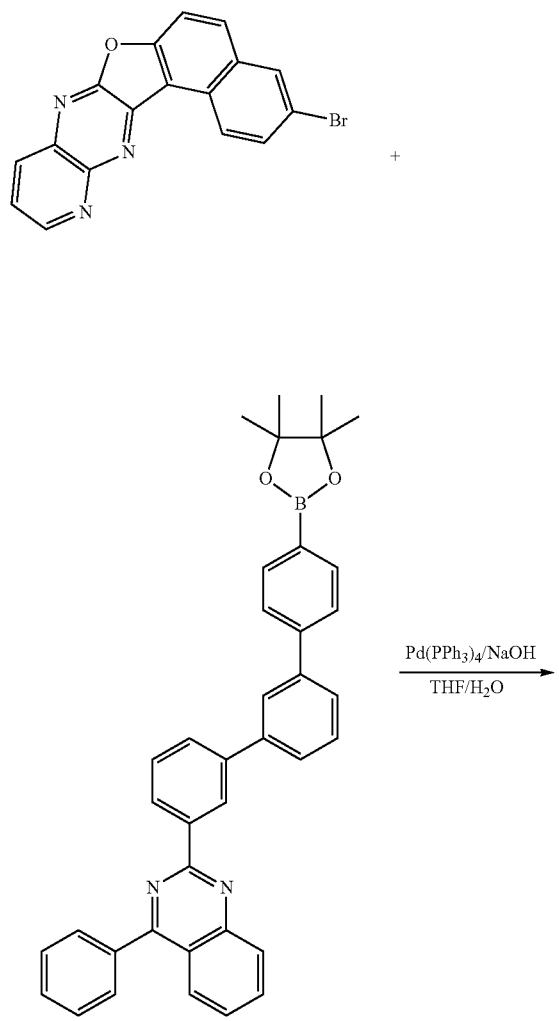

318
-continued

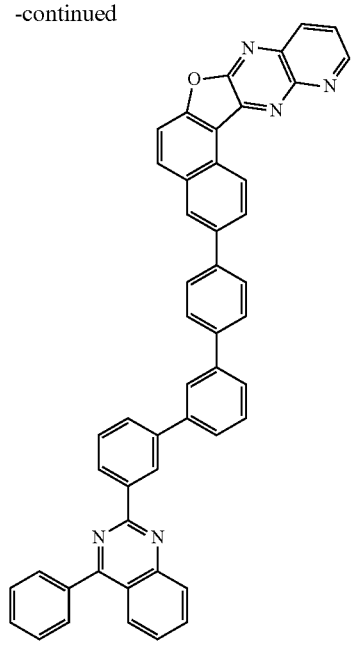

2-bromo-4-phenylquinazoline (100 g, 350.7 mmol) was dissolved with DMF in a round bottom flask, and then bis(pinacolato)diboron (133.59 g, 526.06 mmol), Pd(dppf)Cl$_2$ (7.7 g, 10.52 mmol), KOAc (103.25 g, 1.1 mol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(4,4,5,5-tetramethyl-1,3,2-dioxaborolan-2-yl) quinazoline (75.7 g, 65%).

4-phenyl-2-(4,4,5,5-tetramethyl-1,3,2-dioxaborolan-2-yl) quinazoline (70 g, 210.71 mmol) was dissolved with THF, and then 3,3'-dibromo-1,1'-biphenyl (78.89 g, 252.85 mmol), Pd(PPh$_3$)$_4$ (7.3 g, 6.32 mmol), K$_2$CO$_3$ (87.36 g, 632.13 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2-(3'-bromo-[1,1'-biphenyl]-3-yl)-4-phenylquinazoline (62.7 g, 68%).

2-(3'-bromo-[1,1'-biphenyl]-3-yl)-4-phenylquinazoline (60 g, 137.19 mmol) was dissolved with DMF in a round bottom flask, and then bis(pinacolato)diboron (52.26 g, 205.79 mmol), Pd(dppf)Cl$_2$ (3.01 g, 4.12 mmol), KOAc (40.39 g, 411.58 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-phenyl-2-(3'-(4,4,5,5-tetramethyl-1,3,2-dioxaborolan-2-yl)-[1,1'-biphenyl]-3-yl)quinazoline (42.5 g, 64%).

4-phenyl-2-(3'-(4,4,5,5-tetramethyl-1,3,2-dioxaborolan-2-yl)-[1,1'-biphenyl]-3-yl) quinazoline (40 g, 82.57 mmol) was dissolved with THF, and then 1-bromo-4-iodobenzene (28.03 g, 99.09 mmol), Pd(PPh$_3$)$_4$ (2.86 g, 2.48 mmol), K$_2$CO$_3$ (34.24 g, 247.72 mmol) and water were added and stirred under reflux at 100° C. for 3 hours. Upon completion of the reaction, the organic layer was extracted with E.A. and water, and was dried using $MgSO_4$ and concentrated. The resulting organic material was subjected to silicagel column to obtain 2-(4"-bromo-[1,1':3',1"-terphenyl]-3-yl)-4-phenylquinazoline (27.6 g, 65%).

2-(4"-bromo-[1,1':3',1"-terphenyl]-3-yl)-4-phenylquinazoline (27.6 g, 53.76 mmol) was dissolved with DMF in a round bottom flask, and then bis(pinacolato)diboron (20.48 g, 80.63 mmol), Pd(dppf)Cl$_2$ (0.18 g, 1.61 mmol), KOAc (15.83 g, 161.27 mmol) were added and stirred under reflux at 130° C. for 4 hours. Upon completion of the reaction, DMF was removed from the reaction product via distillation and the reaction product was extracted with $CH_2Cl_2$ and water. The resulting organic layer was dried using $MgSO_4$ and concentrated, and the resulting compound was subjected to silicagel column and recrystallization to obtain 4-phenyl-2-(4"-(4,4,5,5-tetramethyl-1,3,2-dioxaborolan-2-yl)-[1,1':3',1"-terphenyl]-3-yl)quinazoline (19 g, 63%).

3-bromonaphtho[1',2':4,5]furo[2,3-b]pyrido[2,3-e]pyrazine (20 g, 57.11 mmol) was dissolved with THF, and then 4-phenyl-2-(4"-(4,4,5,5-tetramethyl-1,3,2-dioxaborolan-2-yl)-[1,1':3',1"-terphenyl]-3-yl)quinazoline (48.02 g, 85.67 mmol), Pd(PPh$_3$)$_4$ (1.98 g, 1.71 mmol), NaOH (6.85 g, 171.34 mmol) and water were added and stirred under reflux at 100° C. for 3 hours. Upon completion of the reaction, the organic layer was extracted with E.A. and water, and was dried using $MgSO_4$ and concentrated. The resulting organic material was subjected to silicagel column and recrystallization to obtain 26.9 g (yield: 67%) of the final product.

The synthesis method of compound 3-2-12 is described below with reference to the following synthesis formula.

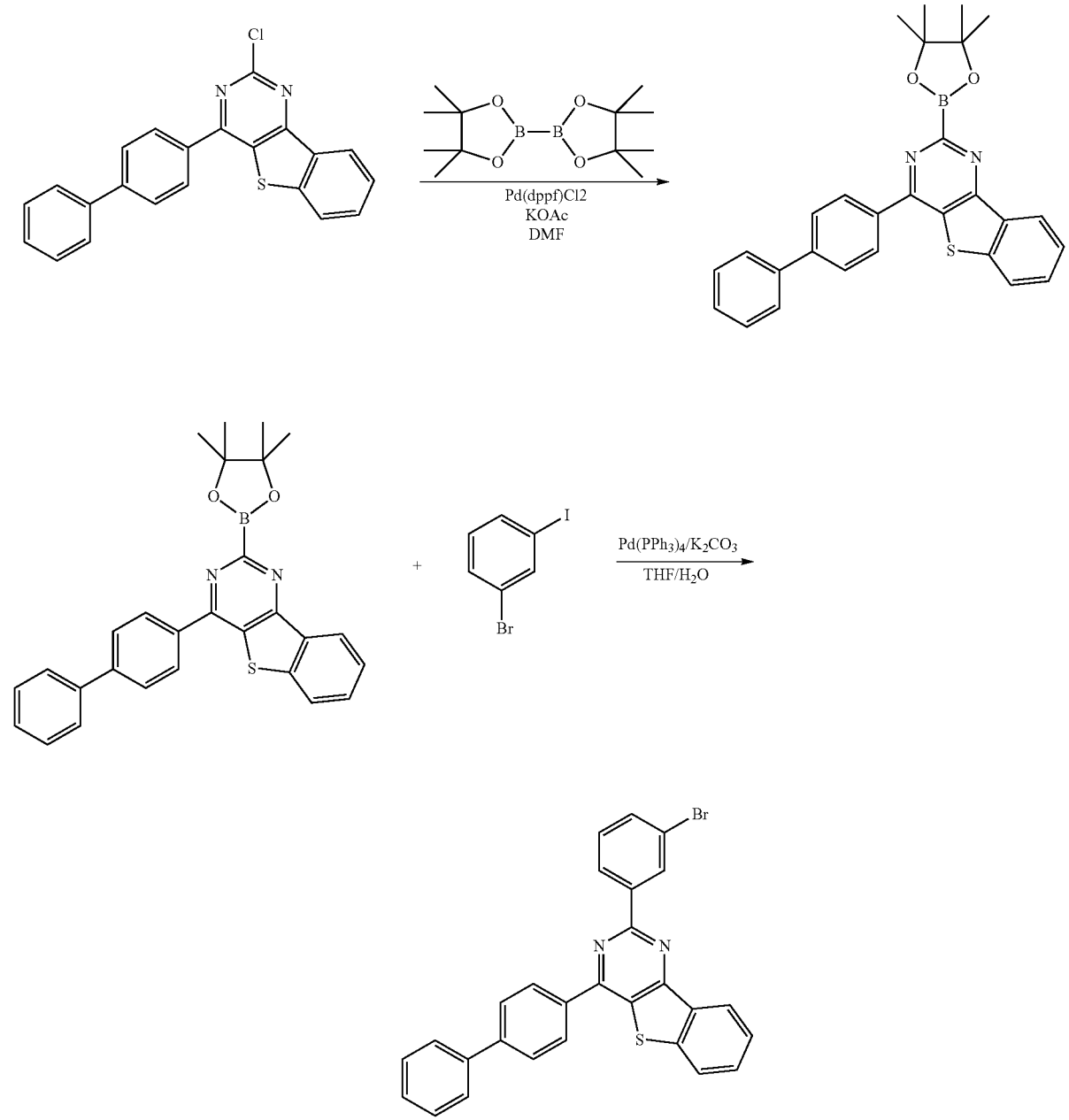

321
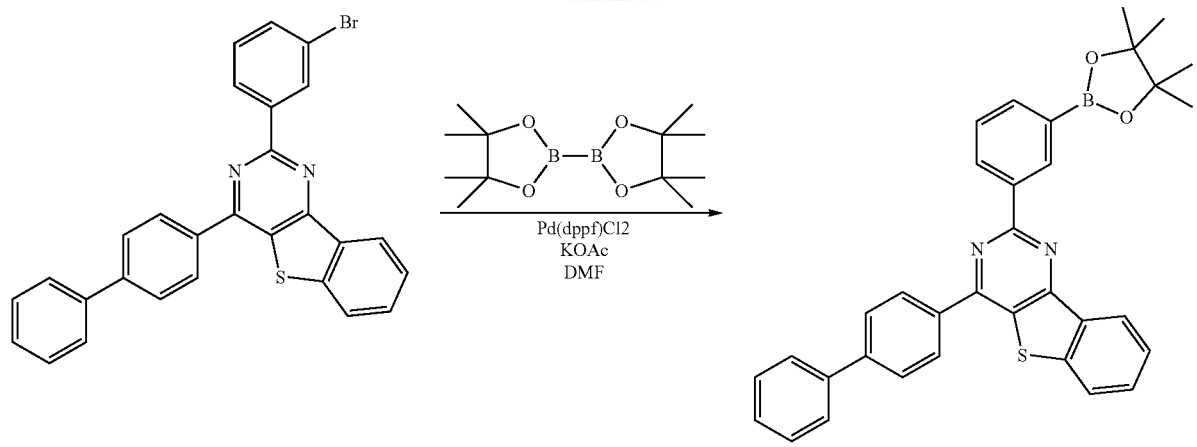
322
-continued
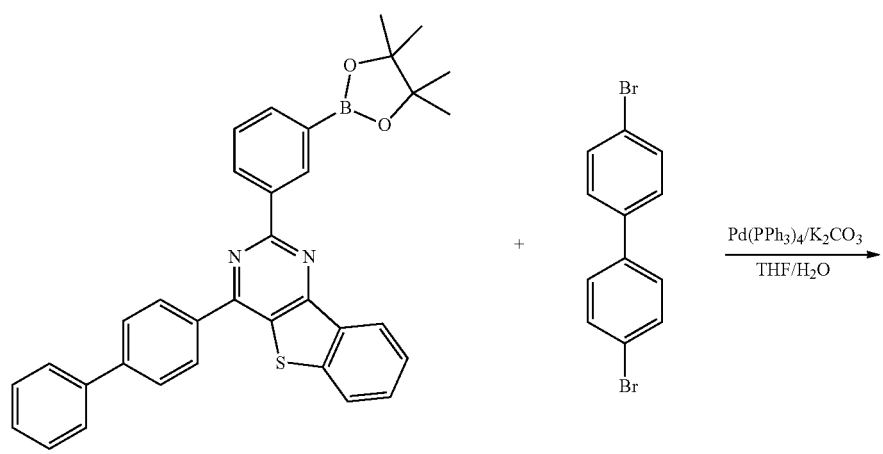
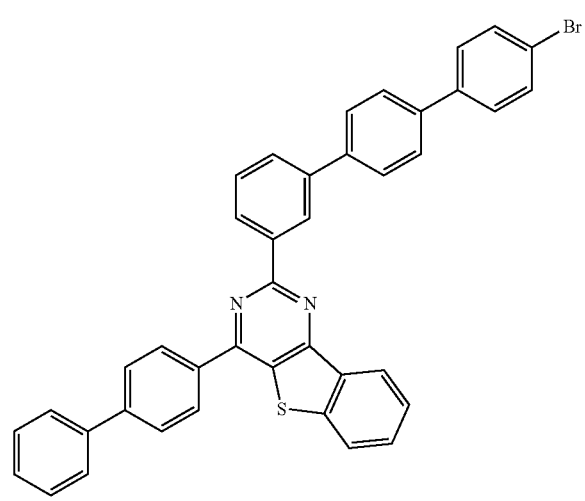

-continued
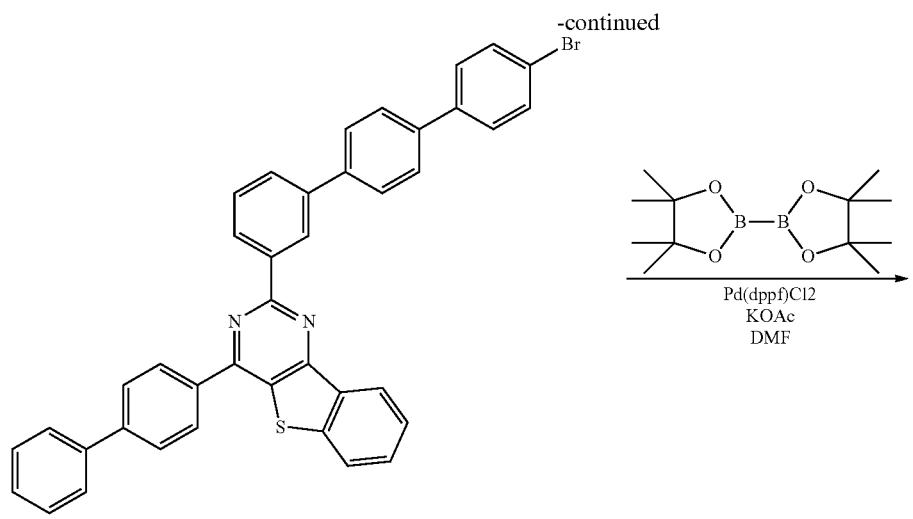
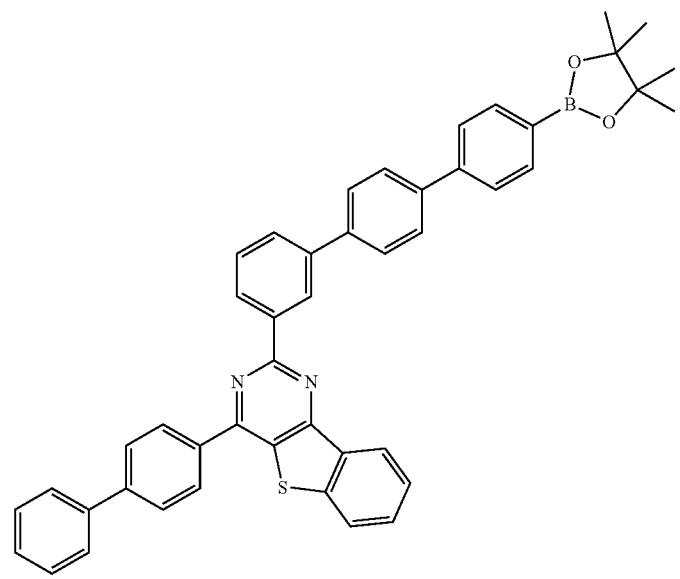
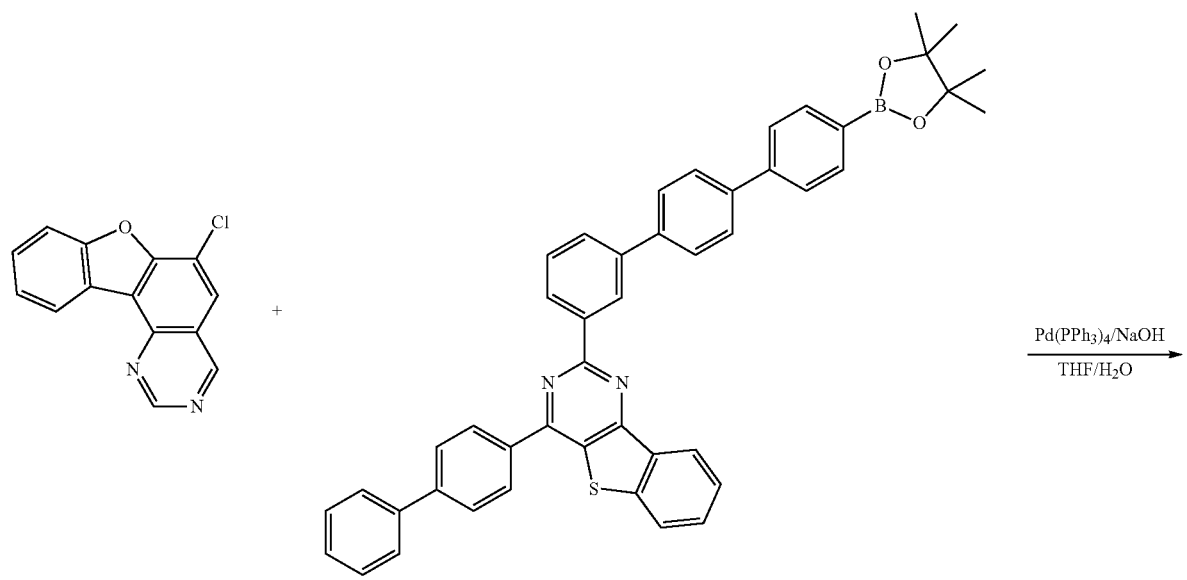

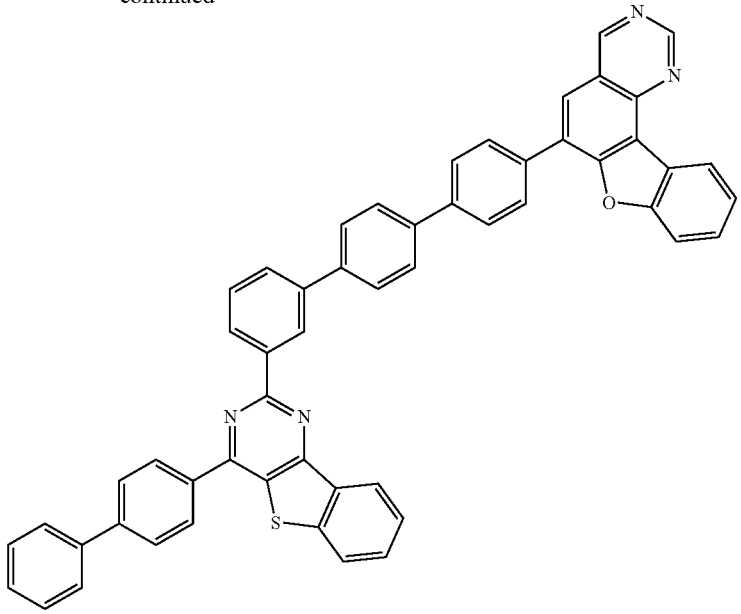

4-([1,1'-biphenyl]-4-yl)-2-chlorobenzo[4,5]thieno[3,2-d]pyrimidine (100 g, 268.19 mmol) was dissolved with DMF in around bottom flask, and then bis(pinacolato) diboron (102.16 g, 402.28 mmol), Pd(dppf)Cl$_2$ (5.89 g, 8.05 mmol), KOAc (78.96 g, 804.57 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-([1,1'-biphenyl]-4-yl)-2-(4,4,5,5-tetramethyl-1,3,2-dioxaborolan-2-yl)benzo[4,5]thieno[3,2-d]pyrimidine (79.7 g, 64%).

4-([1,1'-biphenyl]-4-yl)-2-(4,4,5,5-tetramethyl-1,3,2-dioxaborolan-2-yl)benzo[4,5]thieno[3,2-d]pyrimidine (70 g, 150.74 mmol) was dissolved with THF, and then 1-bromo-3-iodobenzene (51.17 g, 180.88 mmol), Pd(PPh$_3$)$_4$ (5.23 g, 4.52 mmol), K$_2$CO$_3$ (62.49 g, 452.21 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 4-([1,1'-biphenyl]-4-yl)-2-(3-bromophenyl)benzo[4,5]thieno[3,2-d]pyrimidine (49.1 g, 66%).

4-([1,1'-biphenyl]-4-yl)-2-(3-bromophenyl)benzo[4,5]thieno[3,2-d]pyrimidine (49 g, 99.31 mmol) was dissolved with DMF in a round bottom flask, and then bis(pinacolato) diboron (37.83 g, 148.96 mmol), Pd(dppf)Cl$_2$ (2.18 g, 2.98 mmol), KOAc (29.24 g, 297.92 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-([1,1'-biphenyl]-4-yl)-2-(3-(4,4,5,5-tetramethyl-1,3,2-dioxaborolan-2-yl)phenyl)benzo[4,5] thieno[3,2-d]pyrimidine (19.8 g, 64%).

4-([1,1'-biphenyl]-4-yl)-2-(3-(4,4,5,5-tetramethyl-1,3,2-dioxaborolan-2-yl)phenyl)benzo [4,5]thieno[3,2-d]pyrimidine (19 g, 35.15 mmol) was dissolved with THF, and then 4,4'-dibromo-1,1'-biphenyl (13.16 g, 42.18 mmol), Pd(PPh$_3$)$_4$ (1.22 g, 1.05 mmol), K$_2$CO$_3$ (14.57 g, 105.46 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 4-([1,1'-biphenyl]-4-yl)-2-(4"-bromo-[1,1':4',1"-terphenyl]-3-yl)benzo[4,5]thieno[3,2-d]pyrimidine (14.8 g, 65%).

4-([1,1'-biphenyl]-4-yl)-2-(4"-bromo-[1,1':4',1"-terphenyl]-3-yl)benzo[4,5]thieno[3,2-d]pyrimidine (14 g, 21.68 mmol) was dissolved with DMF in a round bottom flask, and then bis(pinacolato)diboron (8.26 g, 32.53 mmol), Pd(dppf)Cl$_2$ (0.48 g, 0.65 mmol), KOAc (6.38 g, 65.05 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 4-([1,1'-biphenyl]-4-yl)-2-(4"-(4,4,5,5-tetramethyl-1,3,2-dioxaborolan-2-yl)-[1,1':4',1"-terphenyl]-3-yl)benzo[4,5]thieno[3,2-d]pyrimidine (10.2 g, 68%).

6-chlorobenzofuro[2,3-h]quinazoline (20 g, 78.53 mmol) was dissolved with THF, and then 4-([1,1'-biphenyl]-4-yl)-2-(4"-(4,4,5,5-tetramethyl-1,3,2-dioxaborolan-2-yl)-[1,1':4',1"-terphenyl]-3-yl)benzo[4,5]thieno[3,2-d]pyrimidine (81.6 g, 117.8 mmol), Pd(PPh$_3$)$_4$ (2.72 g, 2.36 mmol), NaOH (9.42 g, 235.6 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 42.5 g (yield: 69%) of the final product.

The synthesis method of compound 3-2-14 is described below with reference to the following synthesis formula.

327 328
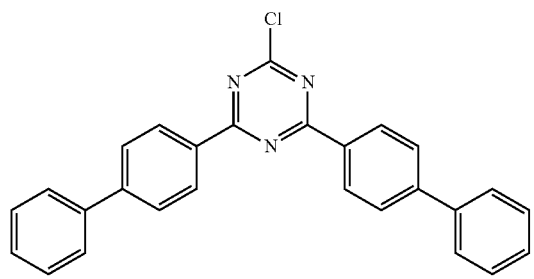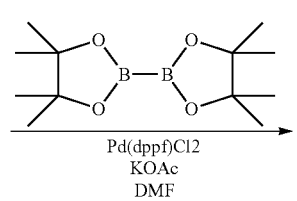
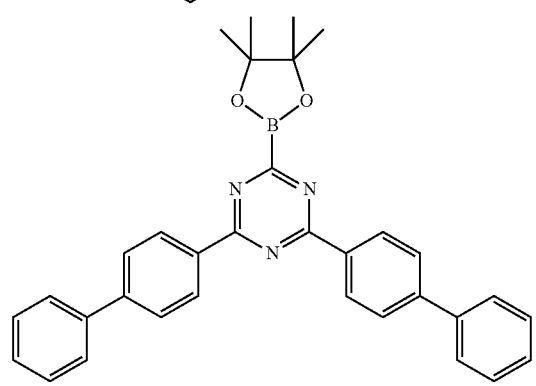
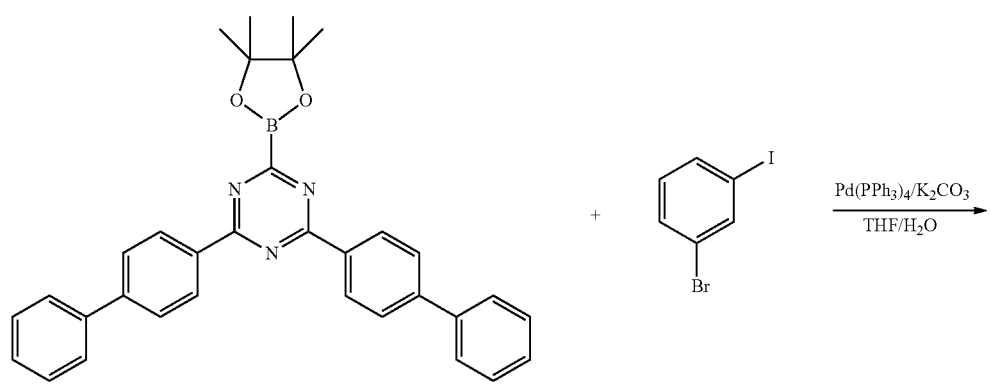
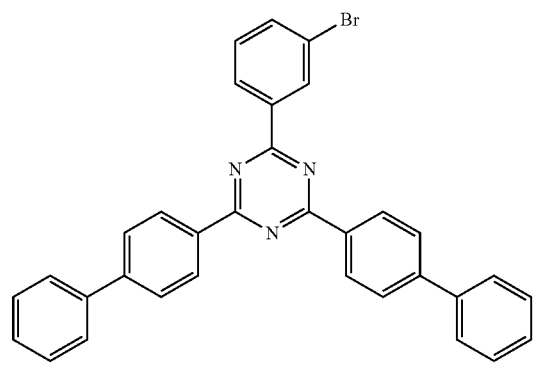

-continued
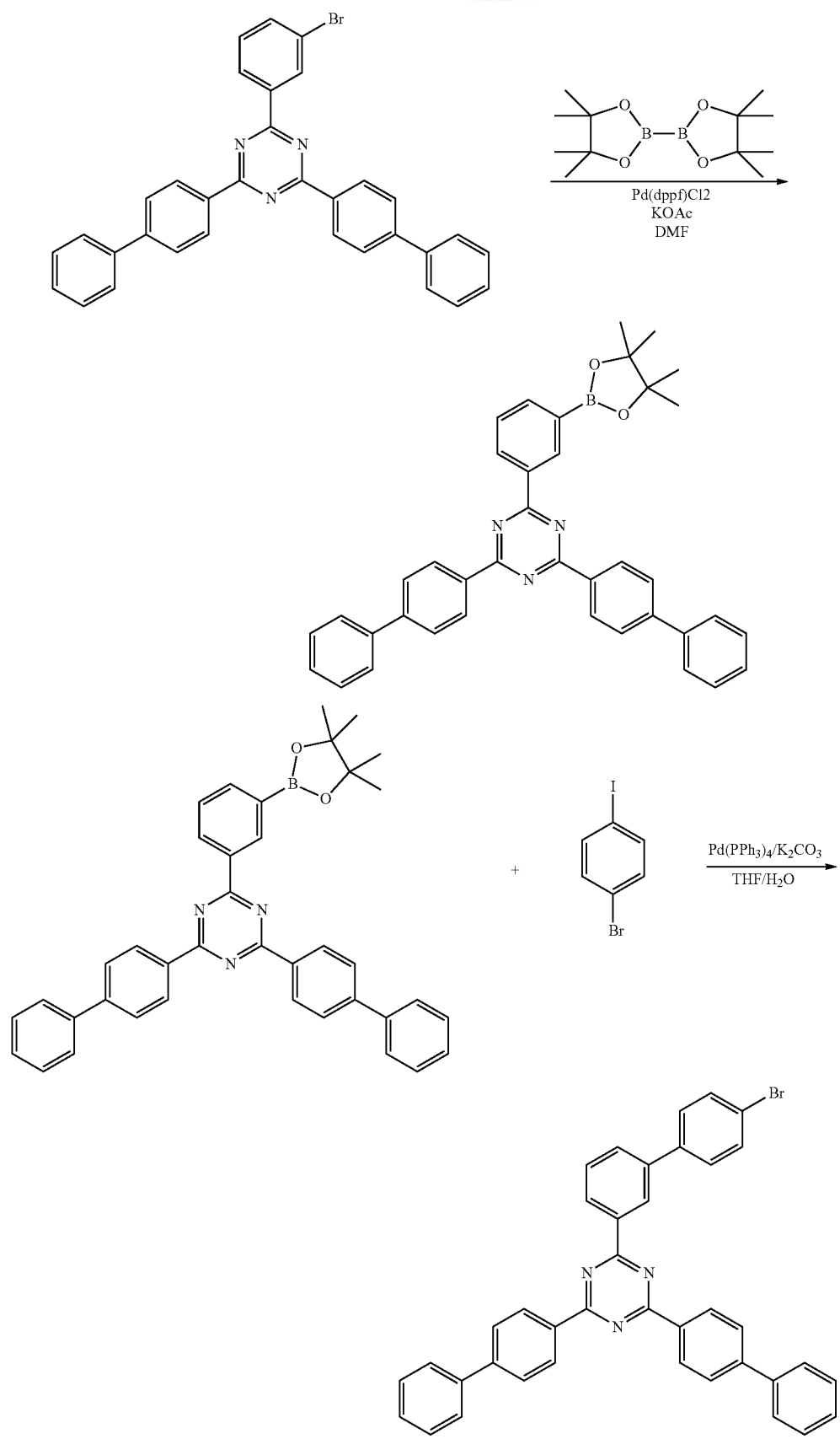

-continued
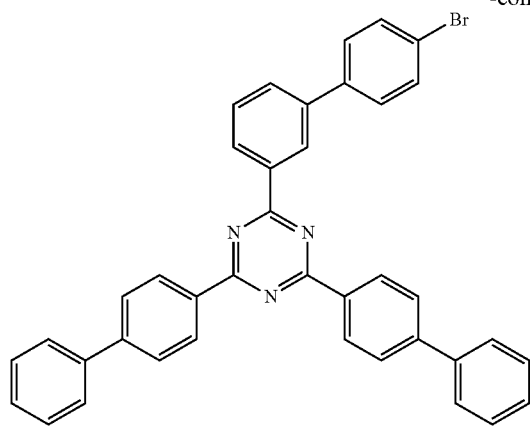 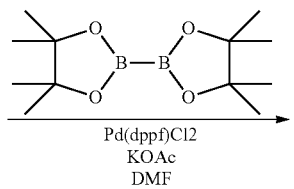
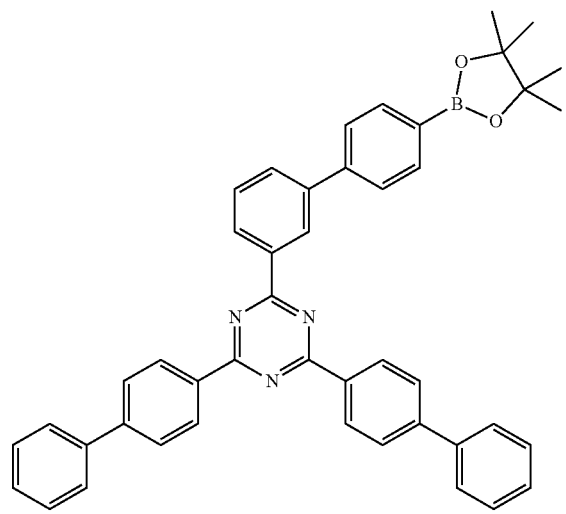
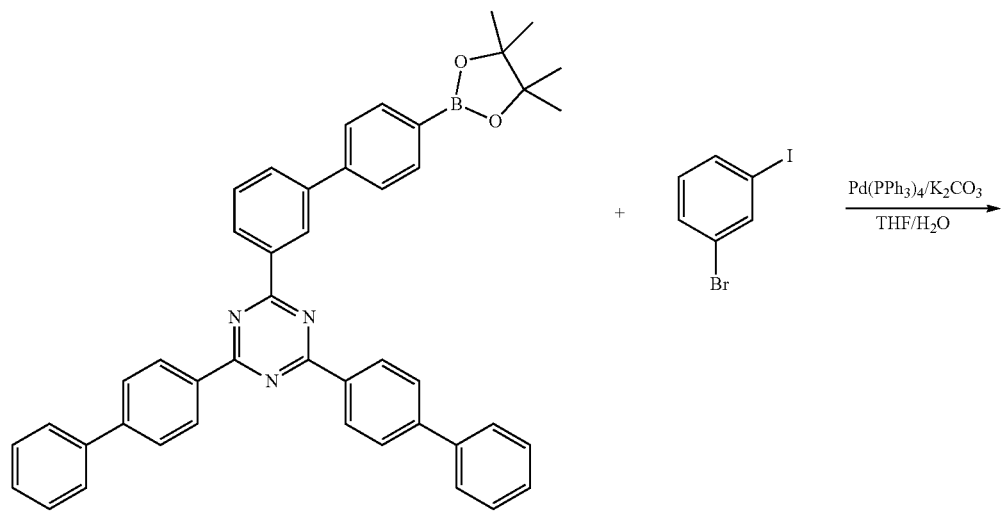

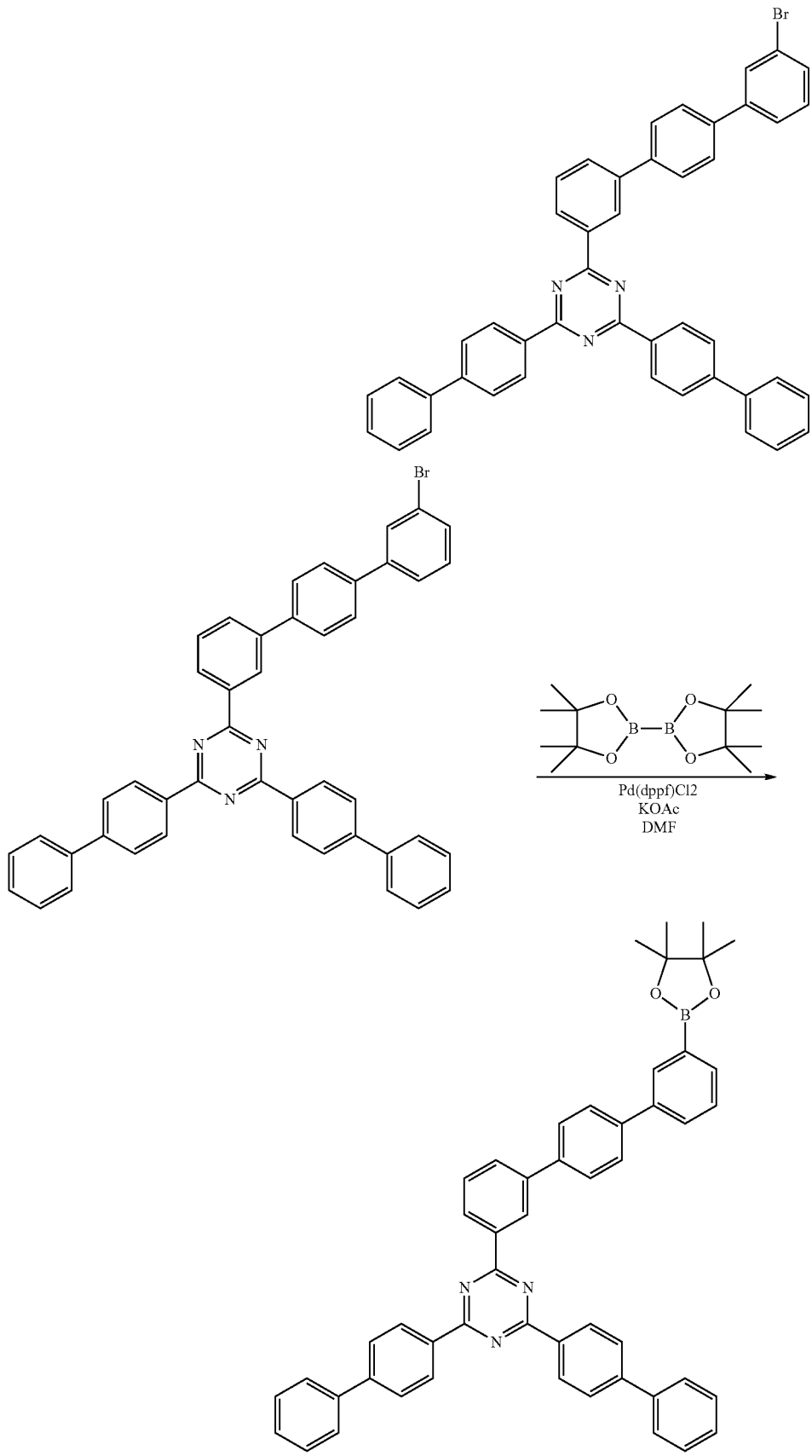

-continued

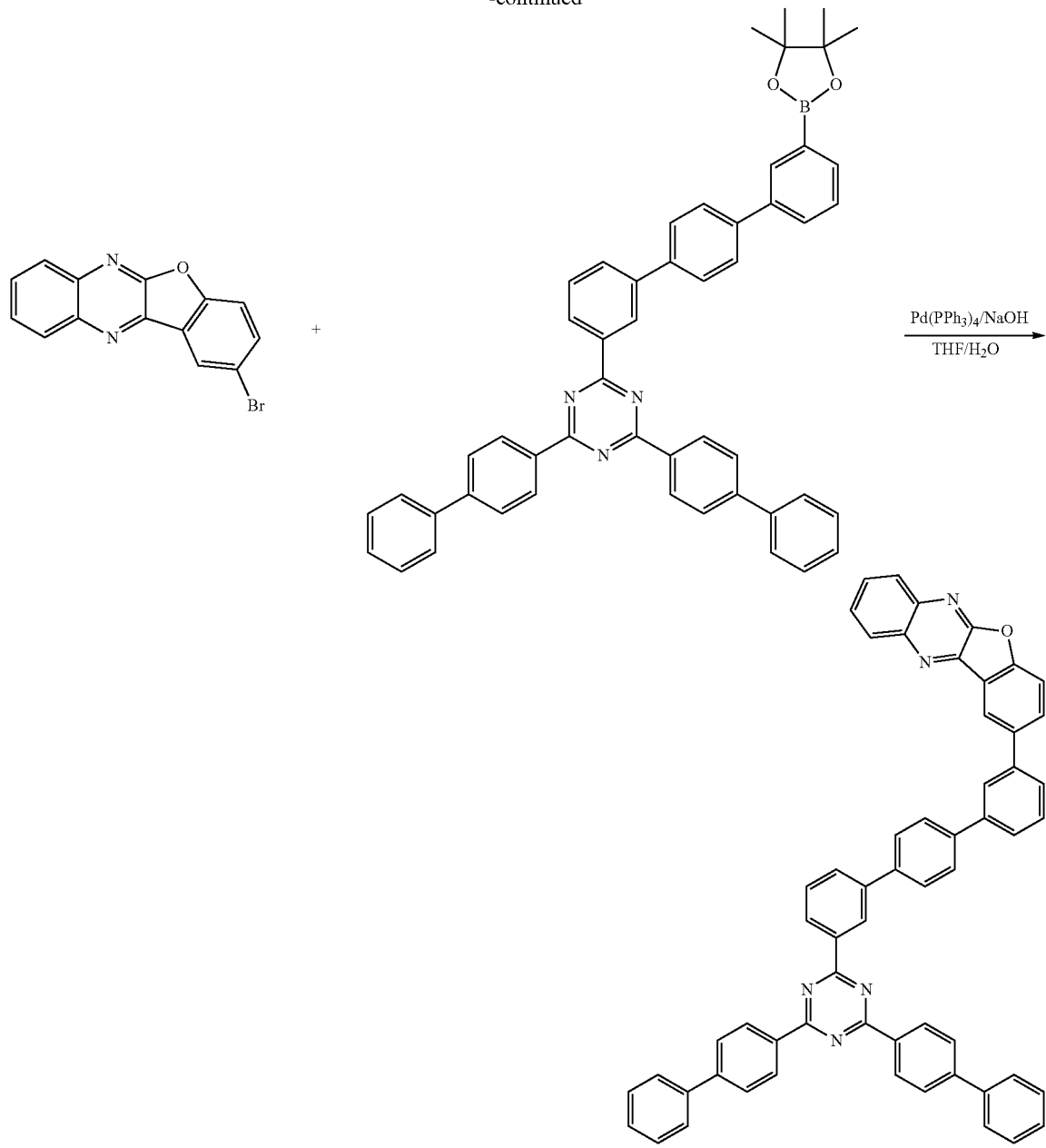

2,4-di([1,1'-biphenyl]-4-yl)-6-chloro-1,3,5-triazine (100 g, 238.15 mmol) was dissolved with DMF in a round bottom flask, and then bis(pinacolato)diboron (90.71 g, 357.22 mmol), Pd(dppf)Cl$_2$ (5.23 g, 7.14 mmol), KOAc (70.12 g, 714.44 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-di([1,1'-biphenyl]-4-yl)-6-(4,4,5,5-tetramethyl-1,3,2-dioxaborolan-2-yl)-1,3,5-triazine (77 g, 64%).

2,4-di([1,1'-biphenyl]-4-yl)-6-(4,4,5,5-tetramethyl-1,3,2-dioxaborolan-2-yl)-1,3,5-triazine (70 g, 136.87 mmol) was dissolved with THF, and then 1-bromo-3-iodobenzene (51.24 g, 164.25 mmol), Pd(PPh$_3$)$_4$ (4.74 g, 4.11 mmol), K$_2$CO$_3$ (56.75 g, 410.61 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2,4-di([1,1'-biphenyl]-4-yl)-6-(3-bromophenyl)-1,3,5-triazine (48.8 g, 66%).

2,4-di([1,1'-biphenyl]-4-yl)-6-(3-bromophenyl)-1,3,5-triazine (45 g, 83.26 mmol) was dissolved with DMF in a round bottom flask, and then bis(pinacolato)diboron (31.72 g, 124.89 mmol), Pd(dppf)Cl$_2$ (1.83 g, 2.50 mmol), KOAc (24.51 g, 249.79 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column to obtain 2,4-di([1,1'-biphenyl]-4-yl)-6-(3-(4,4,5,5-tetramethyl-1,3,2-dioxaborolan-2-yl)phenyl)-1,3,5-triazine (31.3 g, 64%).

2,4-di([1,1'-biphenyl]-4-yl)-6-(3-(4,4,5,5-tetramethyl-1,3,2-dioxaborolan-2-yl)phenyl)-1,3,5-triazine (30 g, 51.06 mmol) was dissolved with THF, and then 1-bromo-4-iodobenzene (17.33 g, 61.27 mmol), Pd(PPh$_3$)$_4$ (1.77 g, 1.53 mmol), K$_2$CO$_3$ (21.17 g, 153.18 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2,4-di([1,1'-biphenyl]-4-yl)-6-(4'-bromo-[1,1'-biphenyl]-3-yl)-1,3,5-triazine (20.5 g, 65%).

2,4-di([1,1'-biphenyl]-4-yl)-6-(4'-bromo-[1,1'-biphenyl]-3-yl)-1,3,5-triazine (20 g, 32.44 mmol) was dissolved with DMF in a round bottom flask, and then bis(pinacolato)diboron (12.36 g, 48.66 mmol), Pd(dppf)Cl$_2$ (0.71 g, 0.97 mmol), KOAc (9.55 g, 97.31 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-di([1,1'-biphenyl]-4-yl)-6-(4'-(4,4,5,5-tetramethyl-1,3,2-dioxaborolan-2-yl)-[1,1'-biphenyl]-3-yl)-1,3,5-triazine (14.6 g, 68%).

2,4-di([1,1'-biphenyl]-4-yl)-6-(4'-(4,4,5,5-tetramethyl-1,3,2-dioxaborolan-2-yl)-[1,1'-biphenyl]-3-yl)-1,3,5-triazine (14 g, 21.1 mmol) was dissolved with THF, and then 1-bromo-3-iodobenzene (7.16 g, 25.32 mmol), Pd(PPh$_3$)$_4$ (0.73 g, 0.63 mmol), K$_2$CO$_3$ (8.75 g, 63.29 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column to obtain 2,4-di([1,1'-biphenyl]-4-yl)-6-(3"-bromo-[1,1':4',1"-terphenyl]-3-yl)-1,3,5-triazine (9.5 g, 65%).

2,4-di([1,1'-biphenyl]-4-yl)-6-(3"-bromo-[1,1':4',1"-terphenyl]-3-yl)-1,3,5-triazine (9 g, 12.99 mmol) was dissolved with DMF in a round bottom flask, and then bis(pinacolato)diboron (4.95 g, 19.49 mmol), Pd(dppf)Cl$_2$ (0.29 g, 0.39 mmol), KOAc (3.83 g, 38.98 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-di([1,1'-biphenyl]-4-yl)-6-(3"-(4,4,5,5-tetramethyl-1,3,2-dioxaborolan-2-yl)-[1,1':4',1"-terphenyl]-3-yl)-1,3,5-triazine (6.5 g, 68%).

6-chlorobenzofuro[2,3-h]quinazoline (20 g, 66.86 mmol) was dissolved with THF, and then 2,4-di([1,1'-biphenyl]-4-yl)-6-(3"-(4,4,5,5-tetramethyl-1,3,2-dioxaborolan-2-yl)-[1,1':4',1"-terphenyl]-3-yl)-1,3,5-triazine (74.19 g, 100.29 mmol), Pd(PPh$_3$)$_4$ (2.32 g, 2.01 mmol), NaOH (8.02 g, 200.58 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 38.4 g (yield: 69%) of the final product.

The synthesis method of compound 3-2-16 is described below with reference to the following synthesis formula.

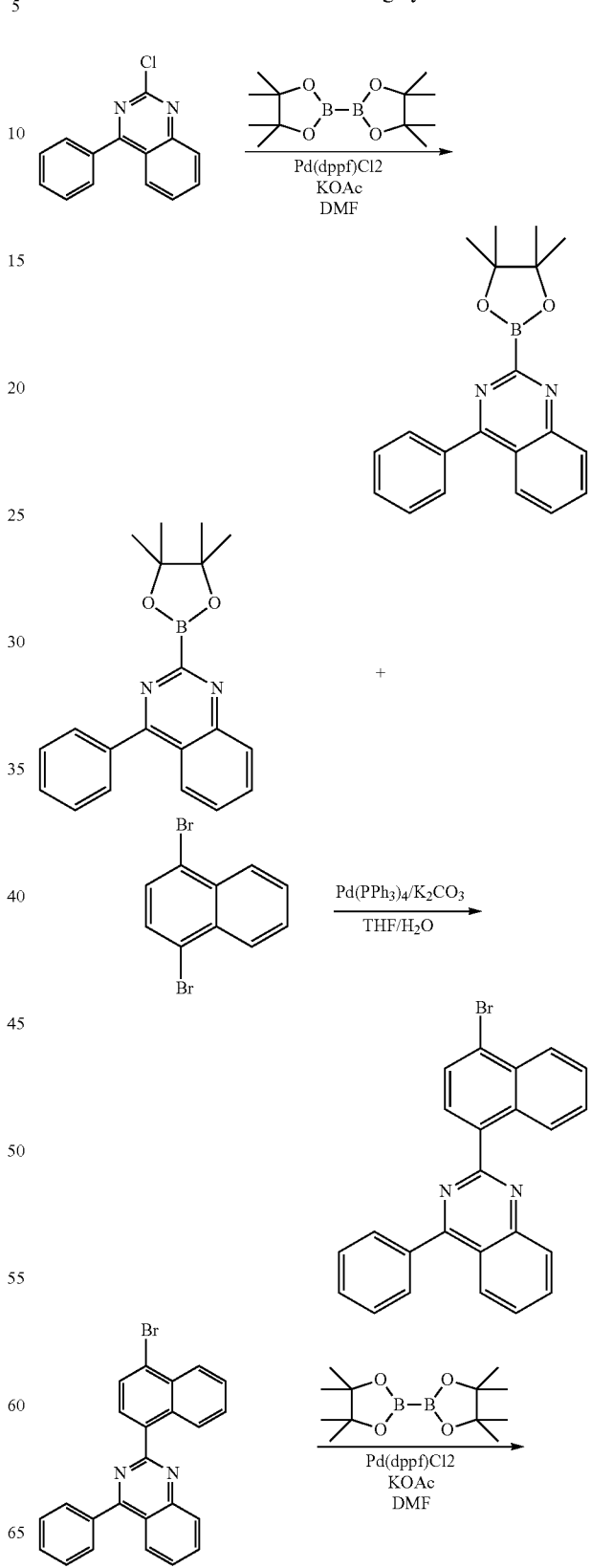

339
-continued
340
-continued
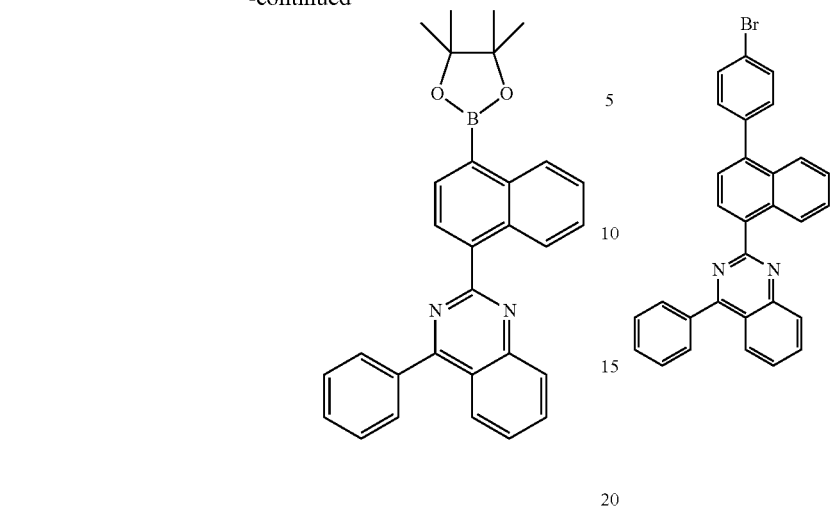
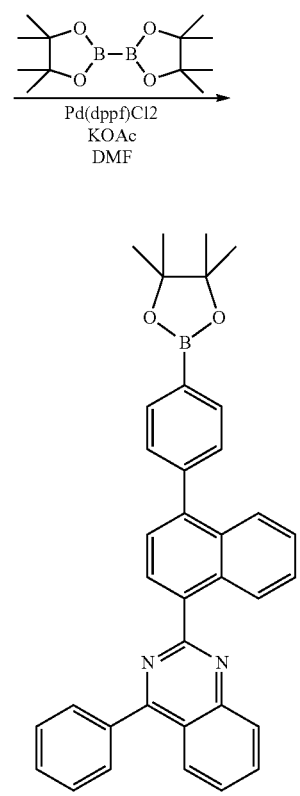
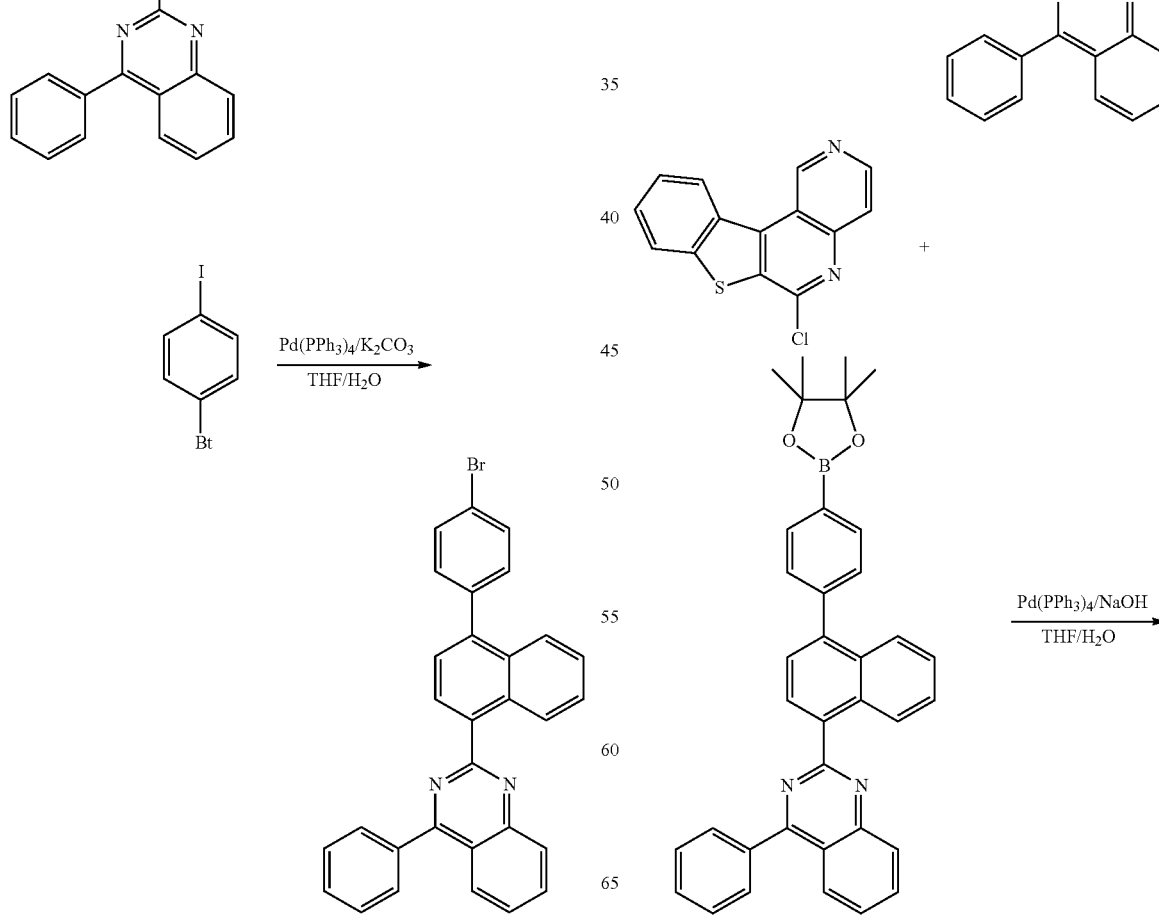

-continued

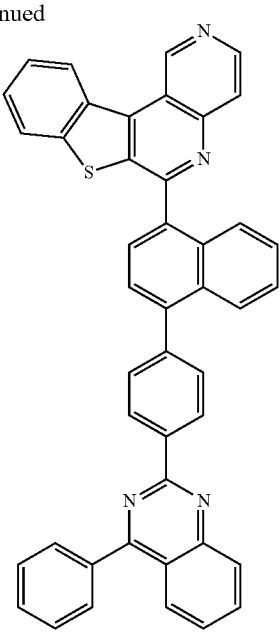

2-chloro-4-phenylquinazoline (20 g, 83.9 mmol) was dissolved with DMF in around bottom flask, and then 4,4,4',4',5,5,5',5'-octamethyl-2,2'-bi(1,3,2-dioxaborolane) (23.21 g, 91.4 mmol), Pd(dppf)Cl₂ (1.82 g, 2.49 mmol), KOAc (24.47 g, 249.28 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4-phenyl-2-(4,4,5,5-tetramethyl-1,3,2-dioxaborolan-2-yl)quinazoline (19 g, 68.82%).

4-phenyl-2-(4,4,5,5-tetramethyl-1,3,2-dioxaborolan-2-yl)quinazoline (19 g, 57.19 mmol) was dissolved with THF, and then 1,4-dibromonaphthalene (19.63 g, 62.91 mmol), Pd(PPh₃)₄ (1.98 g, 1.72 mmol), K₂CO₃ (23.71 g, 171.58 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column to obtain 2-(4-bromonaphthalen-1-yl)-4-phenylquinazoline (16 g, 68.01%).

2-(4-bromonaphthalen-1-yl)-4-phenylquinazoline (16 g, 38.9 mmol) was dissolved with DMF in a round bottom flask, and then 4,4,4',4',5,5,5',5'-octamethyl-2,2'-bi(1,3,2-dioxaborolane) (10.87 g, 42.79 mmol), Pd(dppf)Cl₂ (0.85 g, 1.17 mmol), KOAc (11.45 g, 116.7 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4-phenyl-2-(4-(4,4,5,5-tetramethyl-1,3,2-dioxaborolan-2-yl)naphthalen-1-yl)quinazoline (12 g, 67.29%).

4-phenyl-2-(4-(4,4,5,5-tetramethyl-1,3,2-dioxaborolan-2-yl)naphthalen-1-yl)quinazoline (12 g, 26.18 mmol) was dissolved with THF, and then 1-bromo-4-iodobenzene (8.15 g, 28.8 mmol), Pd(PPh₃)₄ (0.91 g, 0.79 mmol), K₂CO₃ (10.85 g, 78.54 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column to obtain 2-(4-(4-bromophenyl)naphthalen-1-yl)-4-phenylquinazoline (8 g, 62.69%).

2-(4-(4-bromophenyl)naphthalen-1-yl)-4-phenylquinazoline (8 g, 16.41 mmol) was dissolved with DMF in a round bottom flask, and then 4,4,4',4',5,5,5',5'-octamethyl-2,2'-bi(1,3,2-dioxaborolane) (4.58 g, 18.05 mmol), Pd(dppf)Cl₂ (0.36 g, 0.49 mmol), KOAc (4.83 g, 49.24 mmol) were added and stirred under reflux at 130° C. for 4 hours. Upon completion of the reaction, DMF was removed from the reaction product via distillation and the reaction product was extracted with CH₂Cl₂ and water. The resulting organic layer was dried using MgSO₄ and concentrated, and the resulting compound was subjected to silicagel column and recrystallization to obtain 4-phenyl-2-(4-(4-(4,4,5,5-tetramethyl-1,3,2-dioxaborolan-2-yl)phenyl)naphthalen-1-yl)quinazoline (6 g, 68.39%).

6-chlorobenzo[4,5]thieno[2,3-c][1,6]naphthyridine (15 g, 55.41 mmol) was dissolved with THF, and then 4-phenyl-2-(4-(4-(4,4,5,5-tetramethyl-1,3,2-dioxaborolan-2-yl)phenyl)naphthalen-1-yl)quinazoline (32.57 g, 60.95 mmol), Pd(PPh₃)₄ (1.92 g, 1.66 mmol), NaOH (6.65 g, 166.22 mmol) and water were added and stirred under reflux at 100° C. for 3 hours. Upon completion of the reaction, the organic layer was extracted with E.A. and water, and was dried using MgSO₄ and concentrated. The resulting organic material was subjected to silicagel column and recrystallization to obtain 24 g (yield: 67.38%) of the final product.

The synthesis method of compound 3-2-17 is described below with reference to the following synthesis formula.

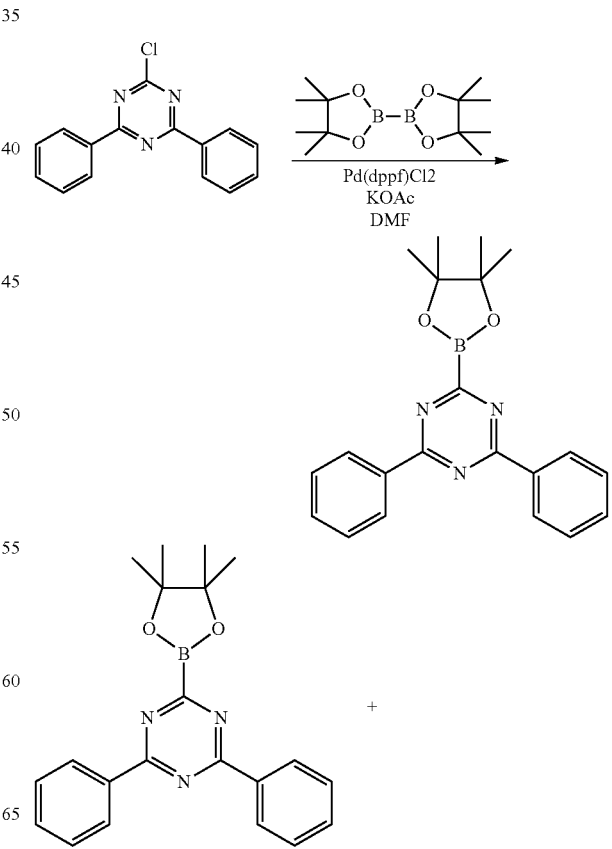

343
-continued
344
-continued
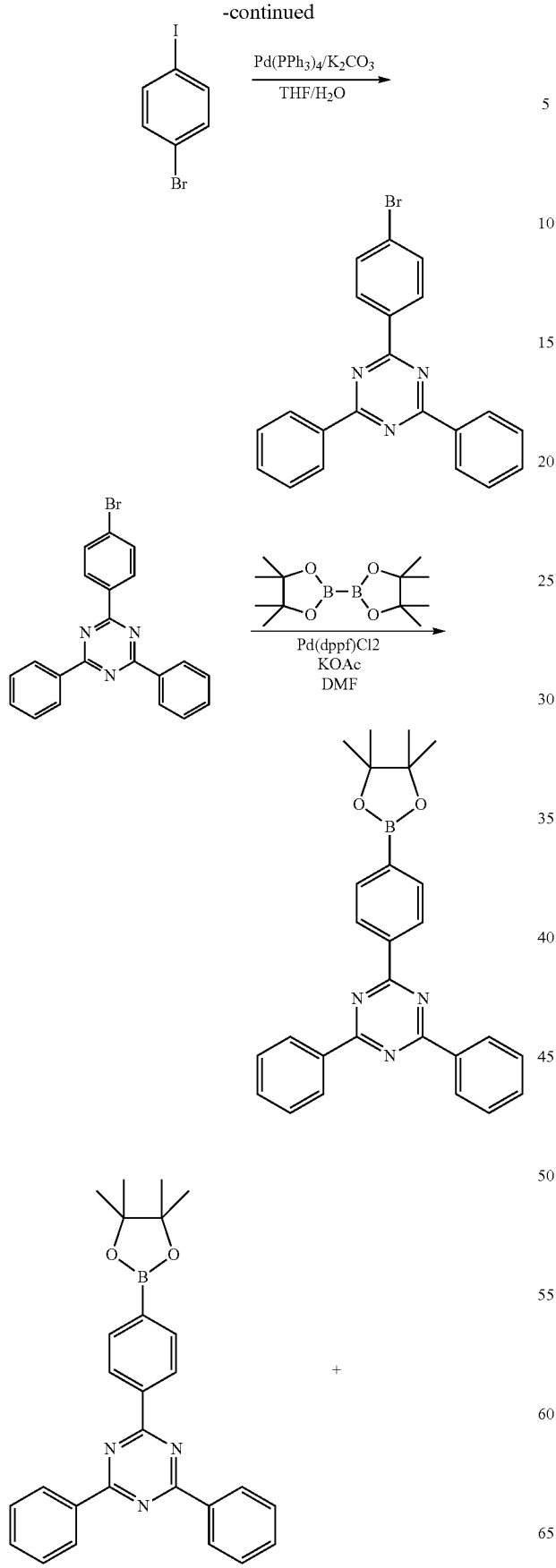
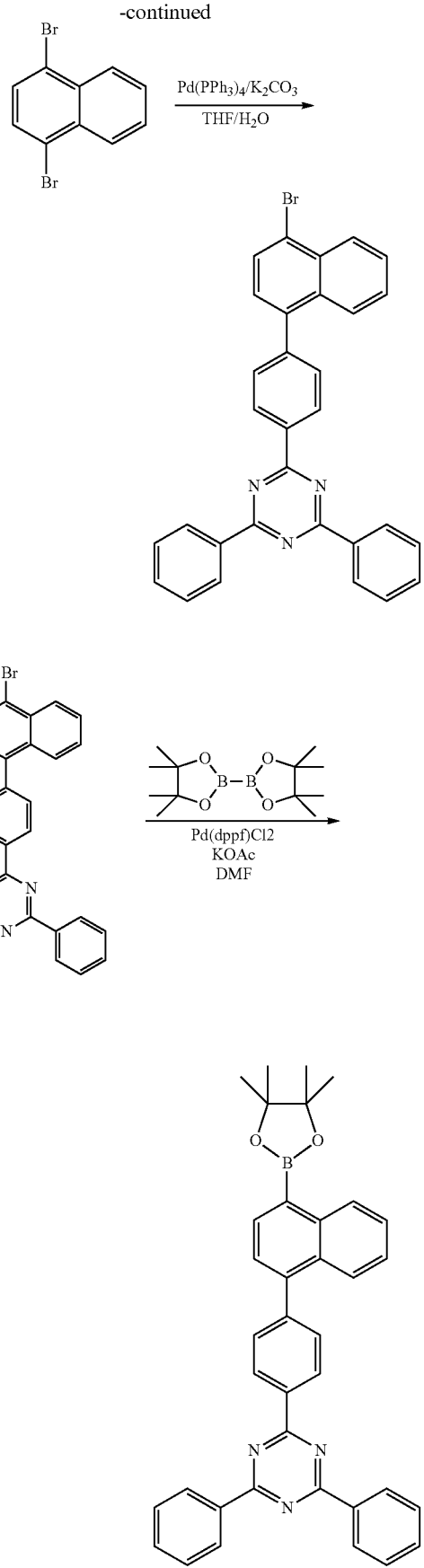

345
-continued
346
-continued
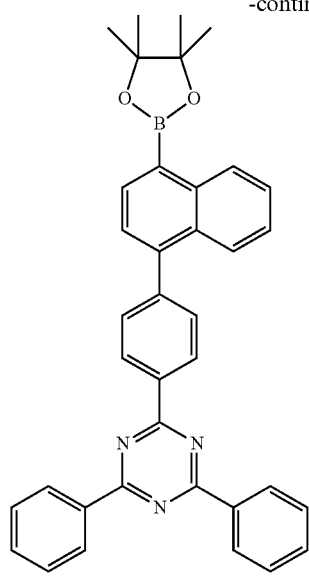
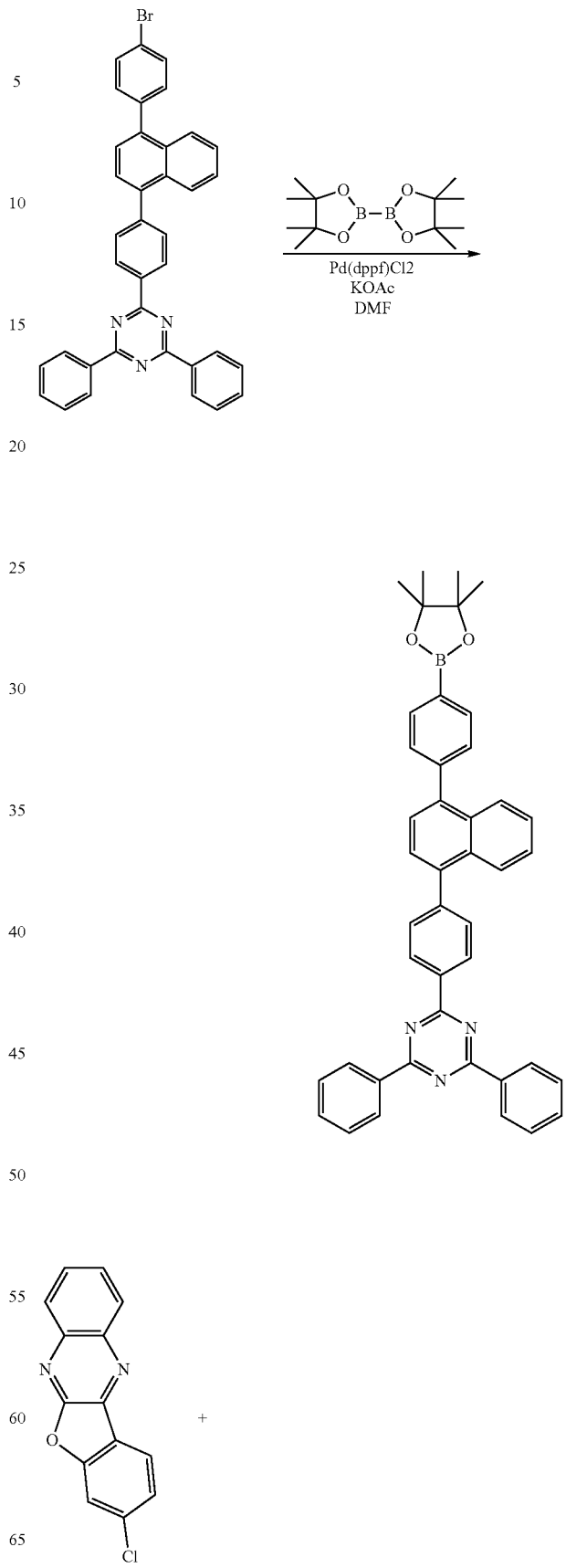

-continued

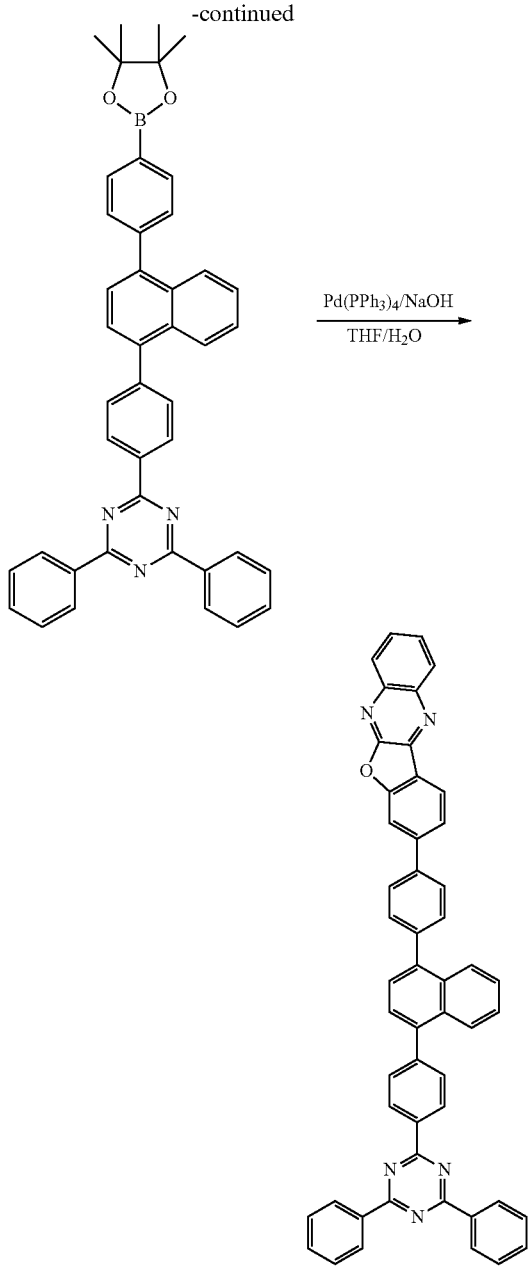

2-chloro-4,6-diphenyl-1,3,5-triazine (20 g, 74.7 mmol) was dissolved with DMF in a round bottom flask, and then 4,4,4',4',5,5,5',5'-octamethyl-2,2'-bi(1,3,2-dioxaborolane) (20.87 g, 82.18 mmol), Pd(dppf)Cl$_2$ (1.64 g, 2.24 mmol), KOAc (22 g, 224.11 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-diphenyl-6-(4,4,5,5-tetramethyl-1,3,2-dioxaborolan-2-yl)-1,3,5-triazine (18 g, 67.07%).

2,4-diphenyl-6-(4,4,5,5-tetramethyl-1,3,2-dioxaborolan-2-yl)-1,3,5-triazine (18 g, 50.11 mmol) was dissolved with THF, and then 1-bromo-4-iodobenzene (15.59 g, 55.12 mmol), Pd(PPh$_3$)$_4$ (1.74 g, 1.5 mmol), K$_2$CO$_3$ (20.77 g, 150.32 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 2-(4-bromophenyl)-4,6-diphenyl-1,3,5-triazine (13 g, 66.82%).

2-(4-bromophenyl)-4,6-diphenyl-1,3,5-triazine (13 g, 33.48 mmol) was dissolved with DMF in a round bottom flask, and then 4,4,4',4',5,5,5',5'-octamethyl-2,2'-bi(1,3,2-dioxaborolane) (9.35 g, 36.83 mmol), Pd(dppf)Cl$_2$ (0.73 g, 1 mmol), KOAc (9.86 g, 100.45 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-diphenyl-6-(4-(4,4,5,5-tetramethyl-1,3,2-dioxaborolan-2-yl)phenyl)-1,3,5-triazine (10 g, 68.6%).

2,4-diphenyl-6-(4-(4,4,5,5-tetramethyl-1,3,2-dioxaborolan-2-yl)phenyl)-1,3,5-triazine (10 g, 22.97 mmol) was dissolved with THF, and then 1,4-dibromonaphthalene (7.23 g, 25.27 mmol), Pd(PPh$_3$)$_4$ (0.8 g, 0.69 mmol), K$_2$CO$_3$ (9.52 g, 68.91 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 2-(4-(4-bromonaphthalen-1-yl)phenyl)-4,6-diphenyl-1,3,5-triazine (8 g, 67.69%).

2-(4-(4-bromonaphthalen-1-yl)phenyl)-4,6-diphenyl-1,3,5-triazine (8 g, 15.55 mmol) was dissolved with DMF in a round bottom flask, and then 4,4,4',4',5,5,5',5'-octamethyl-2,2'-bi(1,3,2-dioxaborolane) (4.34 g, 17.11 mmol), Pd(dppf)Cl$_2$ (0.34 g, 0.47 mmol), KOAc (4.58 g, 46.65 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-diphenyl-6-(4-(4-(4,4,5,5-tetramethyl-1,3,2-dioxaborolan-2-yl)naphthalen-1-yl)phenyl)-1,3,5-triazine (6 g, 68.6%).

2,4-diphenyl-6-(4-(4-(4,4,5,5-tetramethyl-1,3,2-dioxaborolan-2-yl)naphthalen-1-yl) phenyl)-1,3,5-triazine (6 g, 10.69 mmol) was dissolved with THF, and then 1-bromo-4-iodobenzene (3.33 g, 11.75 mmol), Pd(PPh$_3$)$_4$ (0.37 g, 0.32 mmol), K$_2$CO$_3$ (4.43 g, 32.06 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 2-(4-(4-(4-bromophenyl)naphthalen-1-yl)phenyl)-4,6-diphenyl-1,3,5-triazine (4.2 g, 66%).

2-(4-(4-(4-bromophenyl)naphthalen-1-yl)phenyl)-4,6-diphenyl-1,3,5-triazine (4 g, 6.77 mmol) was dissolved with DMF in a round bottom flask, and then 4,4,4',4',5,5,5',5'-octamethyl-2,2'-bi(1,3,2-dioxaborolane)(1.89 g, 7.45 mmol), Pd(dppf)Cl$_2$ (0.15 g, 0.2 mmol), KOAc (1.99 g, 20.32 mmol) were added and stirred under reflux at 130° C. for 4 hours. Upon completion of the reaction, DMF was removed from the reaction product via distillation and the reaction product was extracted with CH$_2$Cl$_2$ and water. The resulting organic layer was dried using MgSO$_4$ and concentrated, and the resulting compound was subjected to silicagel column and recrystallization to obtain 2,4-diphenyl-6-(4-(4-(4-(4,4,5,5-tetramethyl-1,3,2-dioxaborolan-2-yl)phenyl) naphthalen-1-yl)phenyl)-1,3,5-triazine (2.8 g, 65%).

3-chlorobenzofuro[2,3-b]quinoxaline (20 g, 78.53 mmol) was dissolved with THF, and then 2,4-diphenyl-6-(4-(4-(4-(4,4,5,5-tetramethyl-1,3,2-dioxaborolan-2-yl)phenyl) naphthalen-1-yl)phenyl)-1,3,5-triazine (55.08 g, 86.39 mmol), Pd(PPh$_3$)$_4$ (2.72 g, 2.36 mmol), NaOH (9.42 g, 235.6 mmol) and water were added and stirred under reflux at 100° C. for 3 hours. Upon completion of the reaction, the organic layer was extracted with E.A. and water, and was dried using MgSO$_4$ and concentrated. The resulting organic material was subjected to silicagel column and recrystallization to obtain 38.4 g (yield: 67%) of the final product.

The remaining compounds can be synthesized in similar ways.

TABLE 5

| Compound | FD-MS | Compound | FD-MS |
|---|---|---|---|
| 3-1-1 | Chemical Formula: C29H17N5S<br>Molecular Weight: 467.55<br>m/z: 467.12 (100.0%) | 3-1-2 | Chemical Formula: C34H20N4S<br>Molecular Weight: 516.62<br>m/z: 516.14 (100.0%) |
| 3-1-3 | Chemical Formula: C35H21N5S<br>Molecular Weight: 543.65<br>m/z: 543.15 (100.0%) | 3-1-4 | Chemical Formula: C39H24N4S<br>Molecular Weight: 580.71<br>m/z: 580.17 (100.0%) |
| 3-1-5 | Chemical Formula: C42H24N4S2<br>Molecular Weight: 648.80<br>m/z: 648.14 (100.0%) | 3-1-6 | Chemical Formula: C40H24N4S<br>Molecular Weight: 592.72<br>m/z: 592.17 (100.0%) |
| 3-1-7 | Chemical Formula: C47H27N5S2<br>Molecular Weight: 725.89<br>m/z: 725.17 (100.0%) | 3-1-8 | Chemical Formula: C51H31N5S<br>Molecular Weight: 745.90<br>m/z: 745.23 (100.0%) |
| 3-1-9~10 | Chemical Formula: C58H36N6S<br>Molecular Weight: 849.03<br>m/z: 843.27 (100.0%) | 3-1-11 | Chemical Formula: C58H36N6S<br>Molecular Weight: 849.03<br>m/z: 848.27 (100.0%) |
| 3-1-12 | Chemical Formula: C44H26N6S<br>Molecular Weight: 670.79<br>m/z: 670.19 (100.0%) | 3-1-13 | Chemical Formula: C44H26N3S<br>Molecular Weight: 698.81<br>m/z: 698.20 (100.0%) |
| 3-1-14 | Chemical Formula: C51H32N4S<br>Molecular Weight: 732.91<br>m/z: 732.23 (100.0%) | 3-1-15 | Chemical Formula: C48H28N4S2<br>Molecular Weight: 724.90<br>m/z: 724.18 (100.0%) |
| 3-2-1 | Chemical Formula: C29H17N5O<br>Molecular Weight: 451.49<br>m/z: 451.14 (100.0%) | 3-2-2 | Chemical Formula: C34H20N4O<br>Molecular Weight: 500.56<br>m/z: 500.16 (100.0%) |
| 3-2-3 | Chemical Formula: C35H21N5O<br>Molecular Weight: 527.59<br>m/z: 527.17 (100.0%) | 3-2-4 | Chemical Formula: C39H24N4O<br>Molecular Weight: 564.65<br>m/z: 564.20 (100.0%) |
| 3-2-5 | Chemical Formula: C42H24N4OS<br>Molecular Weight: 632.74<br>m/z: 632.17 (100.0%) | 3-2-6 | Chemical Formula: C40H24N4O<br>Molecular Weight: 576.66<br>m/z: 576.20 (100.0%) |
| 3-2-7 | Chemical Formula: C52H30N4OS<br>Molecular Weight: 758.90<br>m/z: 758.21 (100.0%) | 3-2-8 | Chemical Formula: C56H34N4O<br>Molecular Weight: 778.92<br>m/z: 778.27 (100.0%) |
| 3-2-9 | Chemical Formula: C63H39N5O<br>Molecular Weight: 882.04<br>m/z: 881.32 (100.0%) | 3-2-10 | Chemical Formula: C56H34N4O<br>Molecular Weight: 778.92<br>m/z: 778.27 (100.0%) |
| 3-2-11 | Chemical Formula: C49H29N5O<br>Molecular Weight: 703.81<br>m/z: 703.24 (100.0%) | 3-2-12 | Chemical Formula: C54H32N4OS<br>Molecular Weight: 784.94<br>m/z: 784.23 (100.0%) |
| 3-2-13 | Chemical Formula: C52H32N4O<br>Molecular Weight: 728.86<br>m/z: 728.26 (100.0%) | 3-2-14 | Chemical Formula: C59H37N5O<br>Molecular Weight: 831.98<br>m/z: 831.30 (100.0%), |
| 3-2-15 | Chemical Formula: C52H32N4O<br>Molecular Weight: 728.86<br>m/z: 728.26 (100.0%) | 3-2-16 | Chemical Formula: C44H26N4S<br>Molecular Weight: 642.78<br>m/z: 642.19 (100.0%) |
| 3-2-17 | Chemical Formula: C51H31N5O<br>Molecular Weight: 729.84<br>m/z: 729.25 (100.0%) | | |

Examples of Manufacturing Organic Electroluminescent Device

Examples 1-50 (Application Examples to Electron Transport Layer of Blue Organic Electroluminescent Device)

A glass substrate of Corning on which an ITO thin film of a specific resistance 15 Ω/cm² and a thickness of 1200□ was deposited, was immersed in the D.I. water in which detergent was dissolved, and then cleaned while applying ultrasonic wave. The detergent used was a product of Fischer Co. and the D.I. water filtered 2 times through a filter of Millipore Co. Ltd was used. After the ITO film was cleaned for 30 minutes, the ultrasonic cleanings were performed two times with the D.I. water each for 10 minutes. After the D.I. water cleanings, ultrasonic cleanings with isopropyl alcohol, acetone, and methanol solvent were performed in the order, and then the glass substrate was dried.

A film of 2-TNATA as a hole injection layer was deposited on the ITO anode film by vacuum-evaporation, and then a film of 4,4-bis[N-(1-naphthyl)-N-phenylamino]biphenyl (hereinafter referred to NPB) with a thickness of 30 nm was deposited on the hole injection layer as a hole transport layer by vacuum evaporation.

Subsequently, a light emitting layer having a thickness of 30 nm was deposited on the hole transport layer by vacuum-evaporating a mixture of 4,4'-bis[2-(4-(N,N-diphenylamino) phenyl) vinyl]biphenyl (hereinafter referred to as DPAVBi) as a dopant and ADN as a dopant at a weight ratio of 98:2.

Then, one of the compounds represented by Chemical Formula 1 of the present invention was deposited on the light emitting layer to a thickness of 30 nm by vacuum-evaporation to form an electron transport layer. Then, LiF was deposited to a thickness of 1 nm by vacuum-evaporation on the electron transport layer to form an electron injection layer, and then Al was deposited to a thickness of 300 nm on the electron injection layer by vacuum-evaporation to form a cathode, thereby manufacturing an organic electroluminescent device.

Comparative Example 1

An organic electroluminescent device was prepared in the same manner as in the above example except that ET1 was used instead of the compound represented by Chemical Formula 1 of the present invention as an electron transporting layer material.

<ET1> Alq3

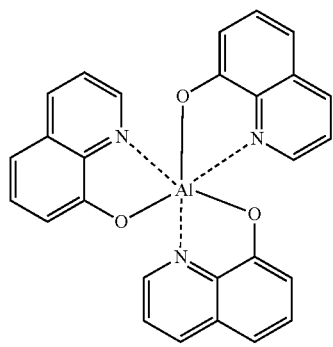

Comparative Example 2

An organic electroluminescent device was prepared in the same manner as in the above example except that ET2 was used instead of the compound represented by Chemical Formula 1 of the resent invention as an electron transport layer material.

<ET2>

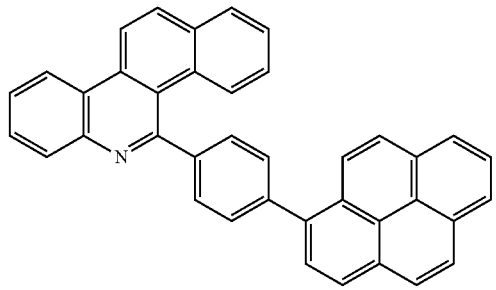

TABLE 6

| Example | ETL | Driving Voltage (V) | Current Efficiency (cd/A) | Emitting Color |
|---|---|---|---|---|
| Example 1 | Compound 1-1-1 | 5.75 | 6.31 | Blue |
| Example 2 | Compound 1-1-3 | 5.63 | 6.32 | Blue |
| Example 3 | Compound 1-1-6 | 5.71 | 6.35 | Blue |
| Example 4 | Compound 1-1-9 | 5.62 | 6.43 | Blue |
| Example 5 | Compound 1-2-2 | 5.59 | 6.55 | Blue |
| Example 6 | Compound 1-2-5 | 5.57 | 6.54 | Blue |
| Example 7 | Compound 1-2-17 | 5.49 | 6.52 | Blue |
| Example 8 | Compound 1-2-25 | 5.44 | 6.61 | Blue |
| Example 9 | Compound 1-3-4 | 5.48 | 6.65 | Blue |
| Example 10 | Compound 1-3-6 | 5.46 | 6.64 | Blue |
| Example 11 | Compound 1-3-14 | 5.47 | 6.66 | Blue |
| Example 12 | Compound 1-3-19 | 5.42 | 6.68 | Blue |
| Example 13 | Compound 1-3-28 | 5.45 | 6.61 | Blue |
| Example 14 | Compound 1-3-39 | 5.51 | 6.63 | Blue |
| Example 15 | Compound 1-3-53 | 5.50 | 6.60 | Blue |
| Example 16 | Compound 1-4-1 | 5.31 | 6.70 | Blue |
| Example 17 | Compound 1-4-2 | 5.30 | 6.71 | Blue |
| Example 18 | Compound 1-4-16 | 5.29 | 6.74 | Blue |
| Example 19 | Compound 1-4-17 | 5.31 | 6.70 | Blue |
| Example 20 | Compound 1-4-31 | 5.30 | 6.69 | Blue |
| Example 21 | Compound 1-4-32 | 5.28 | 6.76 | Blue |
| Example 22 | Compound 1-4-40 | 5.25 | 6.80 | Blue |
| Example 23 | Compound 1-4-43 | 5.27 | 6.77 | Blue |
| Example 24 | Compound 1-4-56 | 5.22 | 6.81 | Blue |
| Example 25 | Compound 1-4-58 | 5.30 | 6.72 | Blue |
| Example 26 | Compound 1-4-75 | 5.32 | 6.68 | Blue |
| Example 27 | Compound 1-4-99 | 5.31 | 6.55 | Blue |
| Example 28 | Compound 2-1-1 | 5.80 | 6.40 | Blue |
| Example 29 | Compound 2-2-2 | 5.74 | 6.42 | Blue |
| Example 30 | Compound 2-2-4 | 5.72 | 6.44 | Blue |
| Example 31 | Compound 2-2-7 | 5.67 | 6.48 | Blue |
| Example 32 | Compound 2-3-3 | 5.68 | 6.50 | Blue |
| Example 33 | Compound 2-3-5 | 5.64 | 6.46 | Blue |
| Example 34 | Compound 2-3-11 | 5.44 | 6.56 | Blue |
| Example 35 | Compound 2-3-17 | 5.45 | 6.52 | Blue |
| Example 36 | Compound 2-4-6 | 5.50 | 6.47 | Blue |
| Example 37 | Compound 2-4-8 | 5.43 | 6.43 | Blue |
| Example 38 | Compound 2-4-21 | 5.44 | 6.44 | Blue |
| Example 39 | Compound 2-4-31 | 5.42 | 6.46 | Blue |
| Example 40 | Compound 3-1-1 | 5.35 | 6.52 | Blue |
| Example 41 | Compound 3-1-5 | 5.32 | 6.54 | Blue |
| Example 42 | Compound 3-1-7 | 5.28 | 6.58 | Blue |
| Example 43 | Compound 3-1-9 | 5.30 | 6.55 | Blue |
| Example 44 | Compound 3-1-13 | 5.29 | 6.56 | Blue |
| Example 45 | Compound 3-1-15 | 5.27 | 6.60 | Blue |
| Example 46 | Compound 3-2-4 | 5.31 | 6.55 | Blue |
| Example 47 | Compound 3-2-8 | 5.32 | 6.57 | Blue |

TABLE 6-continued

| Example | ETL | Driving Voltage (V) | Current Efficiency (cd/A) | Emitting Color |
|---|---|---|---|---|
| Example 48 | Compound 3-2-11 | 5.29 | 6.61 | Blue |
| Example 49 | Compound 3-2-12 | 5.30 | 6.59 | Blue |
| Example 50 | Compound 3-2-17 | 5.32 | 6.57 | Blue |
| Comparative Example 1 | ET1 | 7.35 | 4.13 | Blue |
| Comparative Example 2 | ET2 | 6.65 | 5.65 | Blue |

As can be seen from the results of Table 6, a blue organic electroluminescent device (OLED) employing the compounds of the present invention has a lower driving voltage and a higher efficiency than the devices employing ET, Alq3 which is widely used as an electron transport layer material or ET2.

Examples 51-67 (Application Examples to Electron Transport Assisting Layer of Blue Organic Electroluminescent Device)

A glass substrate of Corning on which an ITO thin film of a specific resistance 15 Ω/cm² and a thickness of 1200□ was deposited, was immersed in the D.I. water in which detergent was dissolved, and then cleaned while applying ultrasonic wave. The detergent used was a product of Fischer Co. and the D.I. water filtered 2 times through a filter of Millipore Co. Ltd was used. After the ITO film was cleaned for 30 minutes, the ultrasonic cleanings were performed two times with the D.I. water each for 10 minutes. After the D.I. water cleanings, ultrasonic cleanings with isopropyl alcohol, acetone, and methanol solvent were performed in the order, and then the glass substrate was dried.

A hole injection layer having a thickness of 60 nm was deposited by vacuum-evaporating 2-TNATA on the ITO anode layer, and a hole transport layer having a thickness of 30 nm was deposited by vacuum evaporating 4,4'-bis [N-(1-naphthyl)-N-phenylamino]biphenyl (hereinafter, NPB) on the hole injection layer.

A light emitting layer having a thickness of 30 nm was deposited on the hole transport layer by co-evaporating ADN as a host and 4,4'-bis[2-(4-(N,N-diphenylamino)phenyl) vinyl]biphenyl (hereinafter, DPAVBi) as a dopant at a weight ratio of 98:2.

An electron transport assisting layer having a thickness of 5 nm was deposited on the light emitting layer by vacuum-evaporating one of the compounds represented by Chemical Formula 1 of the present invention, and an electron transport layer having a thickness of 25 nm was deposited on the electron transport assisting layer by vacuum-evaporating Alq₃. LiF having a thickness of 1 nm was deposited on the electron transport layer by vacuum evaporation to form an electron injection layer, and Al was vacuum-deposited on the electron injection layer by vacuum-evaporation to form a cathode having a thickness of 300 nm, thereby manufacturing an organic electroluminescent device.

Comparative Example 3

An organic electroluminescent device was prepared in the same manner as in the above manufacturing example except that an electron transport assisting layer was not deposited and Alq3 of a thickness of 30 nm was used as an electron transporting layer material.

Comparative Example 4

An organic electroluminescent device was prepared in the same manner as in the above manufacturing example except that BCP was used instead of the compound represented by Chemical Formula 1 of the present invention as an electron transporting assisting layer material.

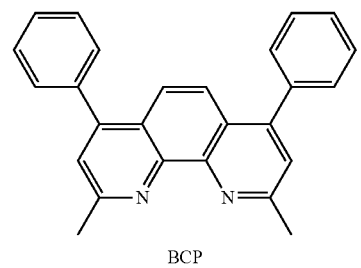

BCP

TABLE 7

| Example | Electron Transport Assisting Layer | Driving Voltage (V) | Current Efficiency (cd/A) | Emitting Color |
|---|---|---|---|---|
| Example 51 | Compound 1-1-5 | 6.43 | 6.32 | Blue |
| Example 52 | Compound 1-2-7 | 6.40 | 6.31 | Blue |
| Example 53 | Compound 1-2-22 | 6.42 | 6.36 | Blue |
| Example 54 | Compound 1-3-8 | 6.34 | 6.41 | Blue |
| Example 55 | Compound 1-3-31 | 6.36 | 6.41 | Blue |
| Example 56 | Compound 1-4-10 | 6.31 | 6.42 | Blue |
| Example 57 | Compound 1-4-50 | 6.40 | 6.33 | Blue |
| Example 58 | Compound 1-4-6 | 6.39 | 6.40 | Blue |
| Example 59 | Compound 2-2-13 | 6.34 | 6.45 | Blue |
| Example 60 | Compound 2-3-27 | 6.30 | 6.50 | Blue |
| Example 61 | Compound 2-3-49 | 6.32 | 6.49 | Blue |
| Example 62 | Compound 2-4-22 | 6.28 | 6.50 | Blue |
| Example 63 | Compound 2-4-87 | 6.32 | 6.52 | Blue |
| Example 64 | Compound 3-1-5 | 6.35 | 6.56 | Blue |
| Example 65 | Compound 3-1-13 | 6.32 | 6.58 | Blue |
| Example 66 | Compound 3-2-14 | 6.30 | 6.60 | Blue |
| Example 67 | Compound 3-2-16 | 6.29 | 6.61 | Blue |
| Comparative 3 | — | 7.35 | 4.13 | Blue |
| Comparative 4 | BCP | 7.25 | 5.85 | Blue |

As can be seen from the results of Table 7, a blue organic electroluminescent device (OLED) of Examples 51 to 67 employing the compounds of the present invention as an electron transport assisting layer has a slightly lower driving voltage and a substantially higher efficiency than the blue organic electroluminescence device of Comparative Example 3 which does not employ an electron transport assisting layer. In addition, a blue organic electroluminescent device employing the compounds of the present invention as an electron transport assisting layer exhibit greatly-improved performances in terms of current efficiency and driving voltage than the device of Comparative Example 4 employing BCP as an electron transport assisting layer.

While the present invention has been particularly shown and described with reference to exemplary embodiments thereof, it will be understood by those skilled in the art that various changes in form and details may be made therein without departing from the essential characteristics thereof. Thus, the embodiments disclosed herein are not intended to limit the invention but are to be considered in all respects as illustrative and not restrictive. The scope of protection of the present invention should be construed by the following claims, all of which are within the scope of the present invention.

The compound of the present invention can be used in an organic electroluminescent device and an organic EL display device including the same.

The invention claimed is:

1. A compound represented by chemical formula 1,

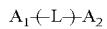  <Chemical Formula 1> wherein $A_1$ is represented by any one of the following structures,

Core 2-7

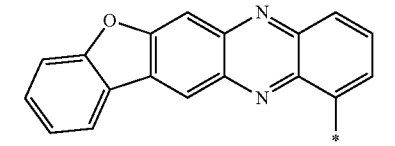

Core 2-8

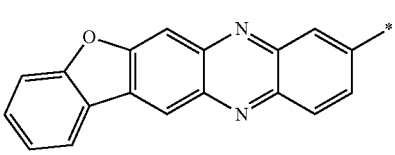

Core 2-9

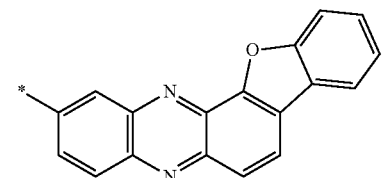

Core 2-11

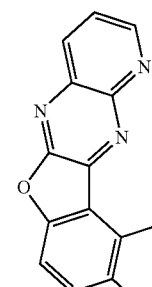

wherein L has the following structure, wherein $L_1$ to $L_3$ are each independently a direct bond; a substituted or unsubstituted arylene group; a substituted or unsubstituted heteroarylene group; or a substituted or unsubstituted $C_9$-$C_{60}$ fused polycyclic group,

wherein $A_2$ is any one selected from the following structures,

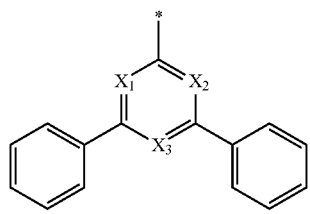

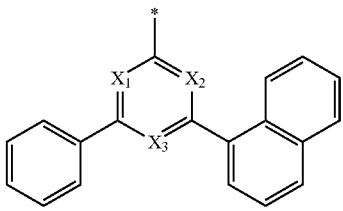

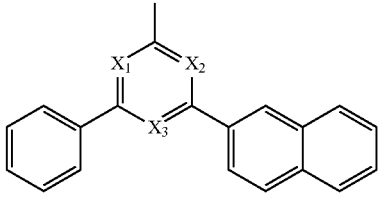

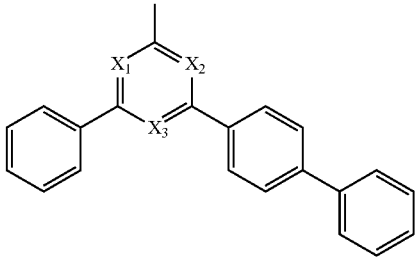

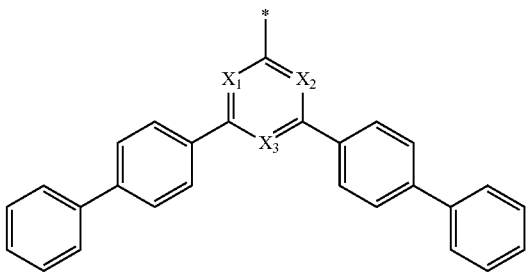

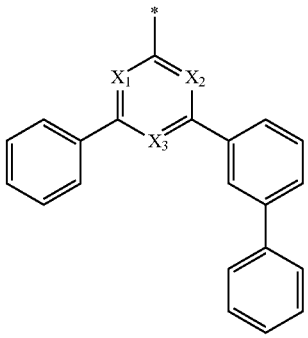

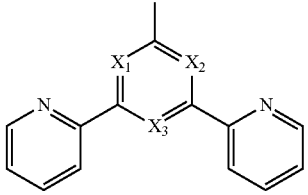

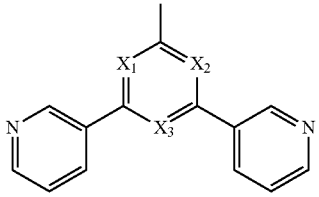

-continued

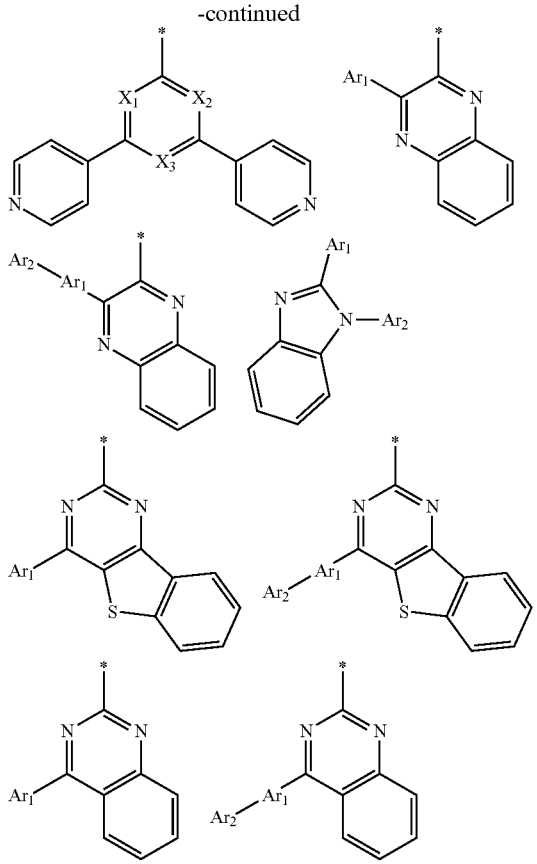

wherein X₁ to X₃ are each independently C or N, at least one of $X_1$ to $X_3$ is N, and $Ar_1$ and $Ar_2$ are each independently hydrogen, deuterium, a halogen group, a cyano group, a substituted or unsubstituted $C_1$ to $C_{60}$ alkyl group, a substituted or unsubstituted $C_3$ to $C_{10}$ cycloalkyl group, a substituted or unsubstituted $C_6$ to $C_{60}$ aryl group, or a substituted or unsubstituted $C_1$ to $C_{60}$ heteroaryl group, and wherein L or $A_2$ is bonded to a carbon position of $A_1$.

2. An organic electroluminescent device comprising:
a first electrode;
a second electrode facing the first electrode; and
an organic material layer interposed between the first electrode and the second electrode, wherein the organic material layer comprises the compound of claim 1.

3. The organic electroluminescent device of claim 2, wherein the first electrode is an anode, the second electrode is a cathode, and
wherein the organic material layer comprises i) a light emitting layer, ii) a hole transport region interposed between the first electrode and the light emitting layer and including at least one of a hole injection layer, a hole transport layer, and a hole transport assisting layer, and iii) an electron transport region interposed between the light emitting layer and the second electrode and including at least one of an electron transport assisting layer, an electron transport layer and an electron injection layer.

4. The organic electroluminescent device of claim 3, wherein, the electron transport region comprises the compound of chemical formula 1.

5. The organic electroluminescent device of claim 4, wherein the electron transport layer or the electron transport assisting layer of the organic electroluminescent device comprises the compound of chemical formula 1.

6. A display device including the organic electroluminescent device of claim 2, wherein the first electrode of the organic electroluminescent device is electrically connected to a source electrode or a drain electrode of a thin film transistor.

7. The compound of claim 1, wherein the compound of chemical formula 1 may be any one of the following compounds, 2-1-7

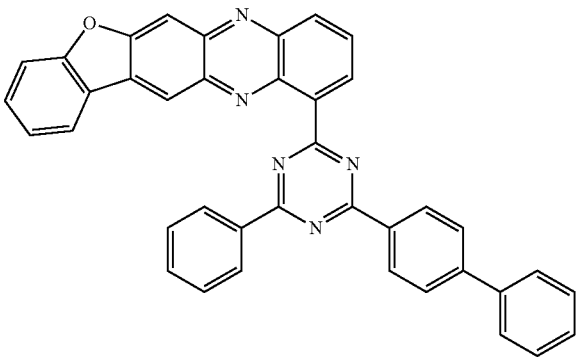

2-1-8

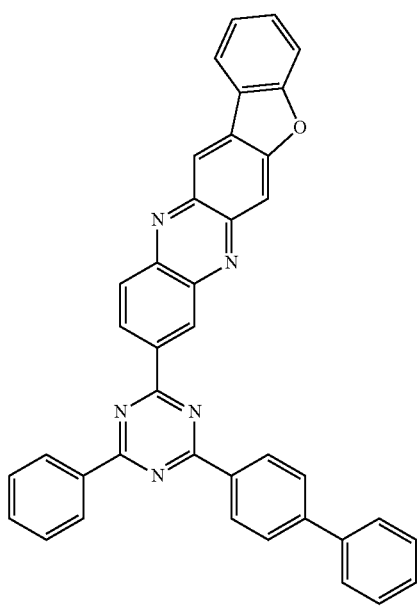

359
-continued
2-1-9
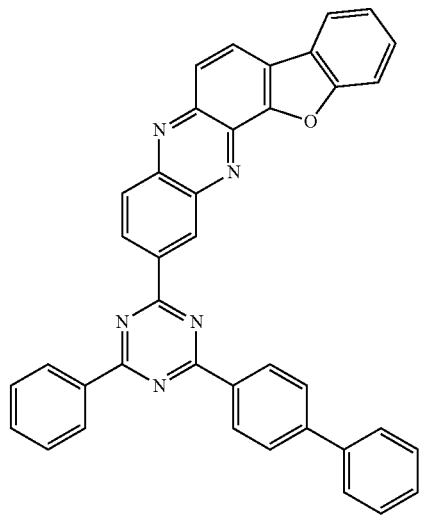
2-1-11
360
-continued
2-2-8
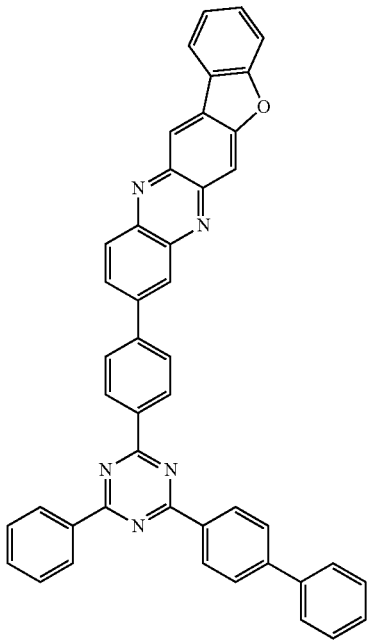
2-2-7
2-2-9
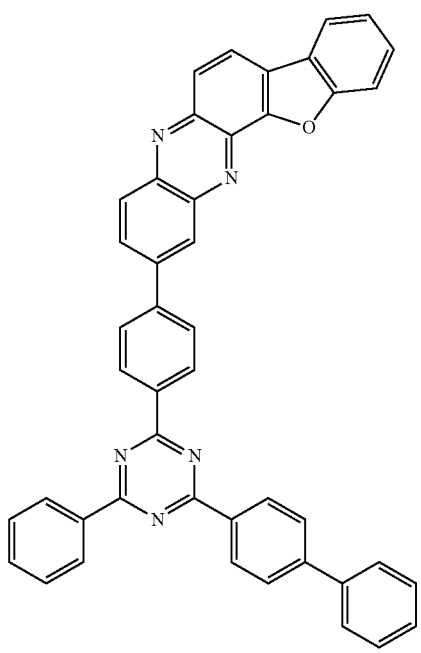

2-2-11
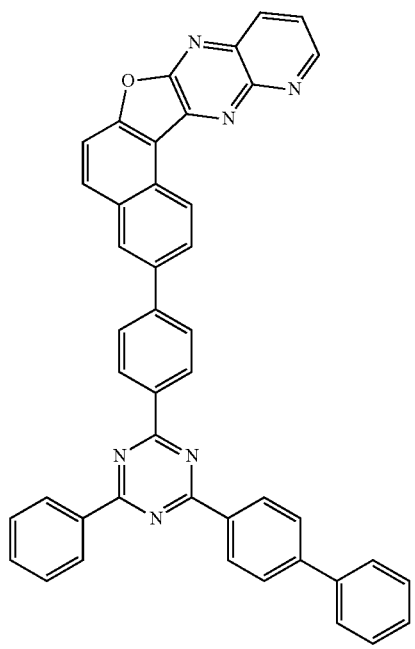
2-2-19
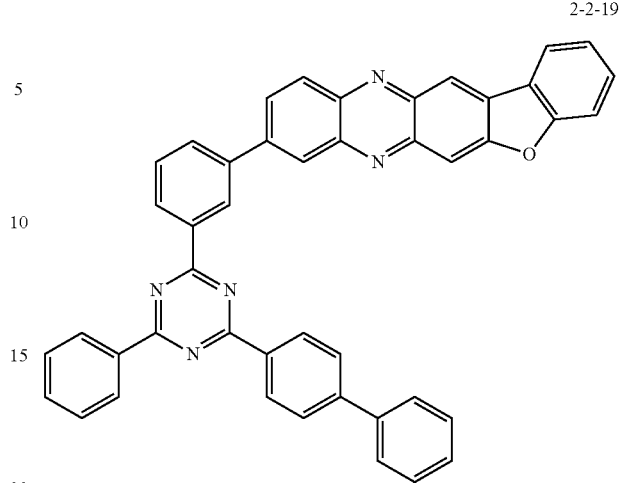
2-2-20
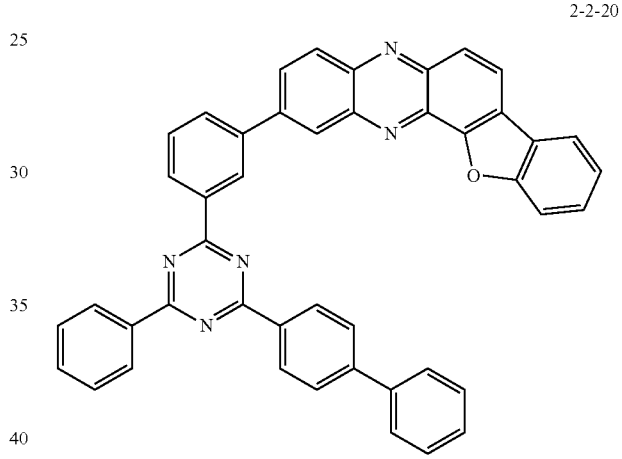
2-2-18
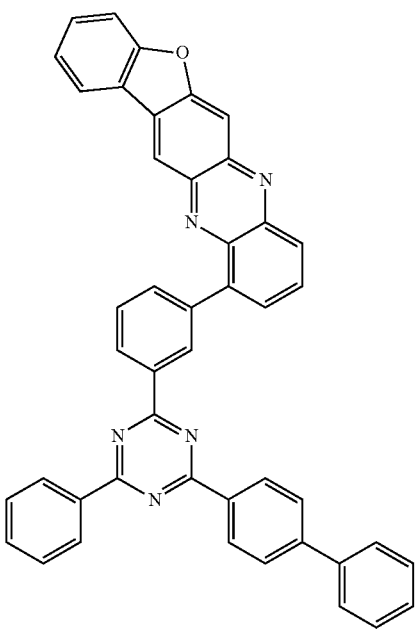
2-2-22
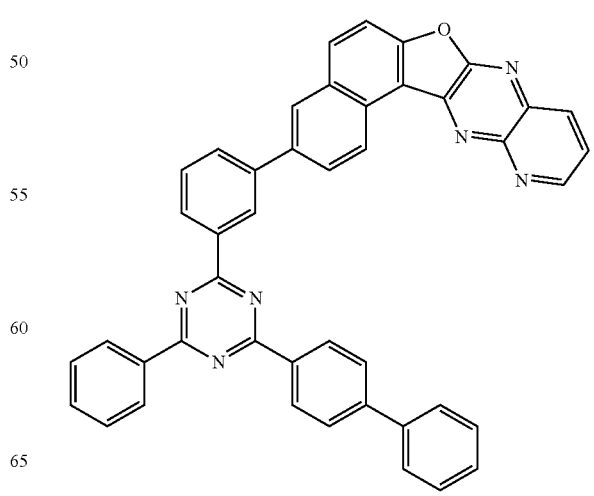

2-3-7
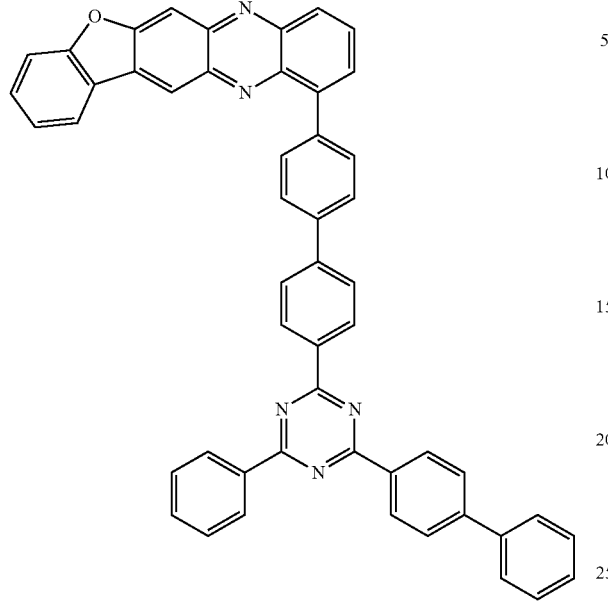
2-3-9
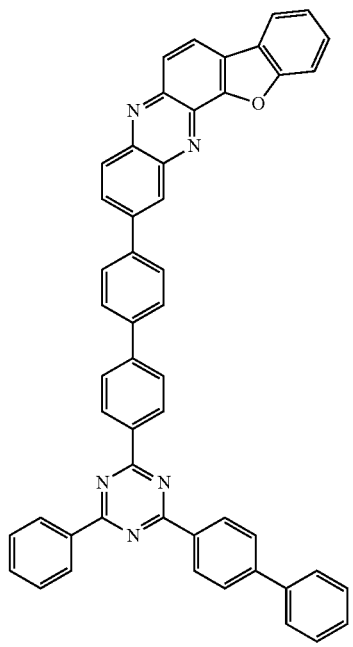
2-3-8
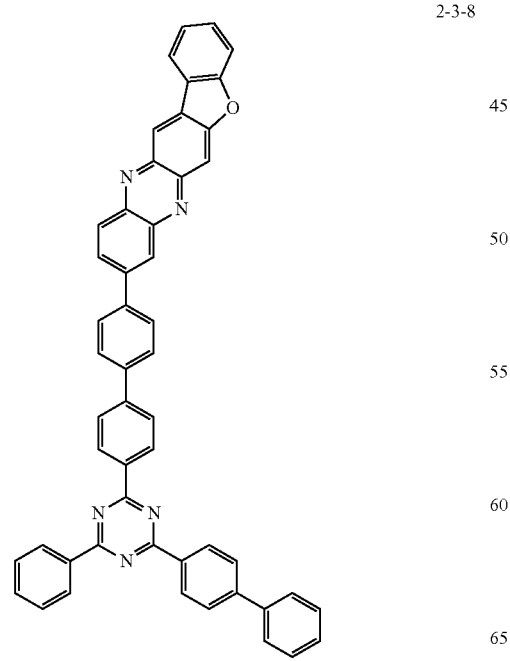
2-3-18
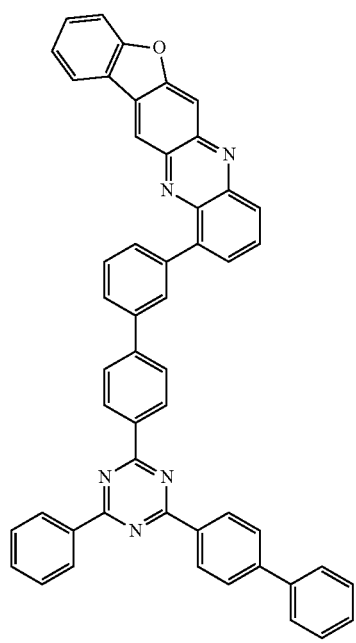

365
-continued
2-3-19
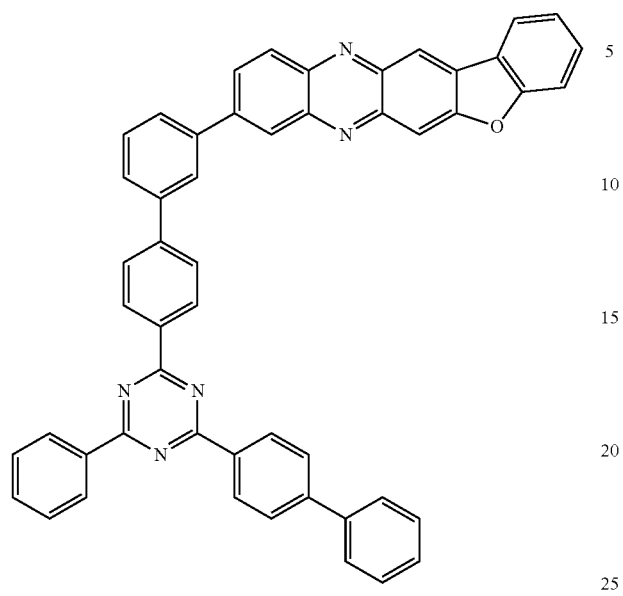
2-3-20
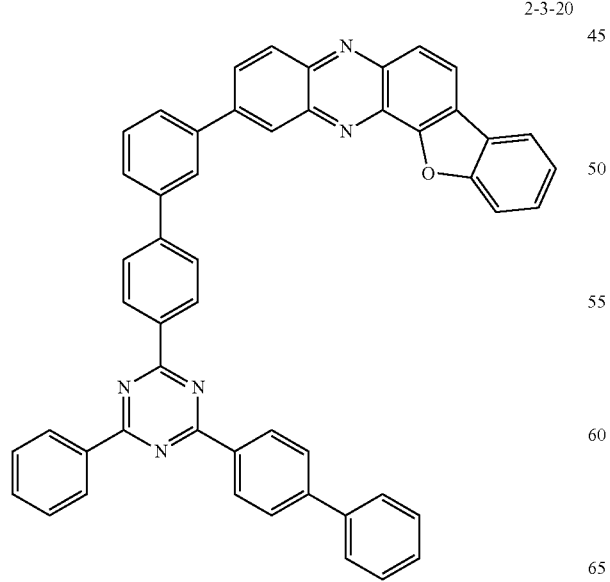
366
-continued
2-3-22
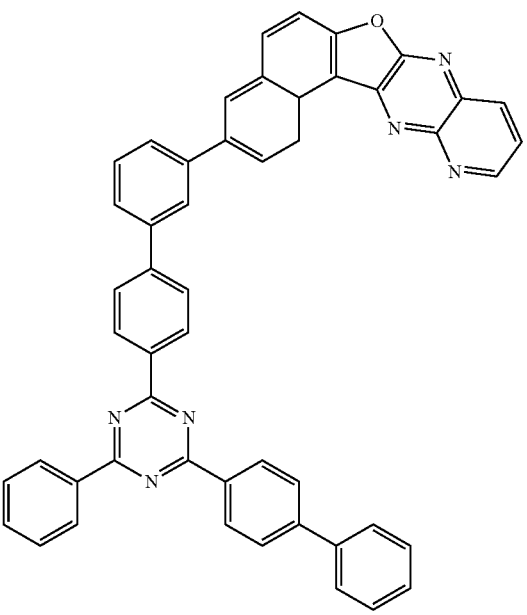
2-3-24
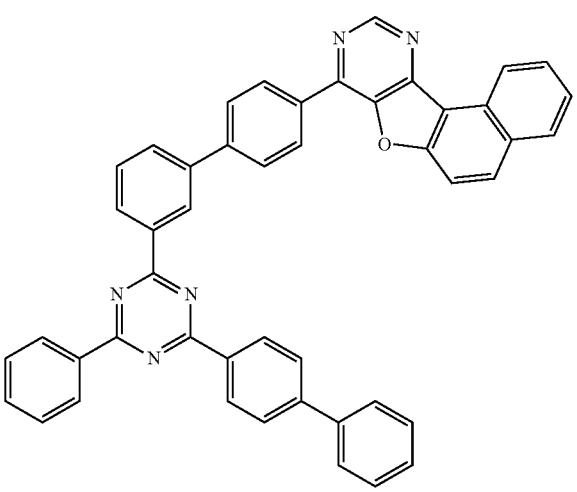

2-3-29
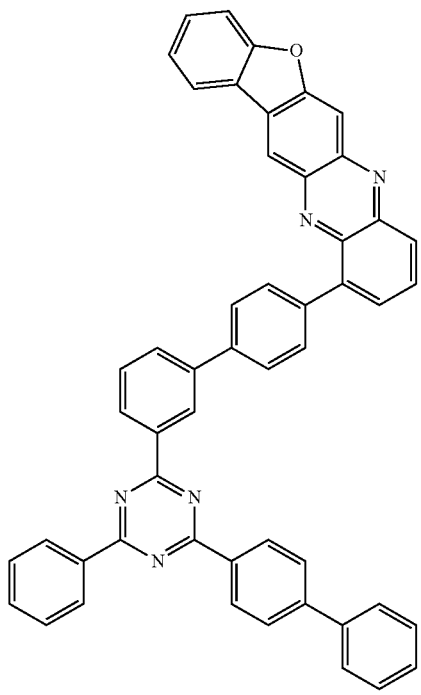
2-3-30
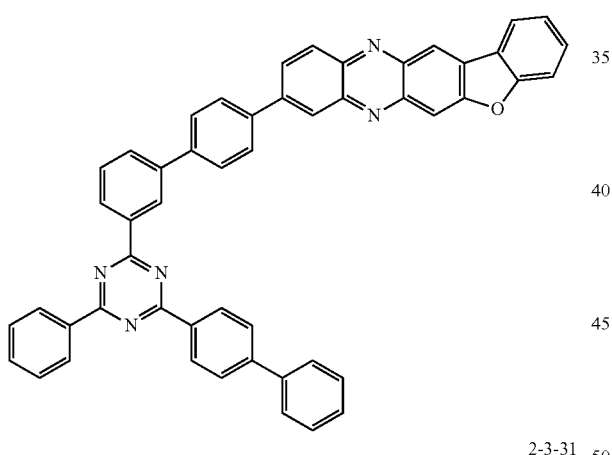
2-3-31
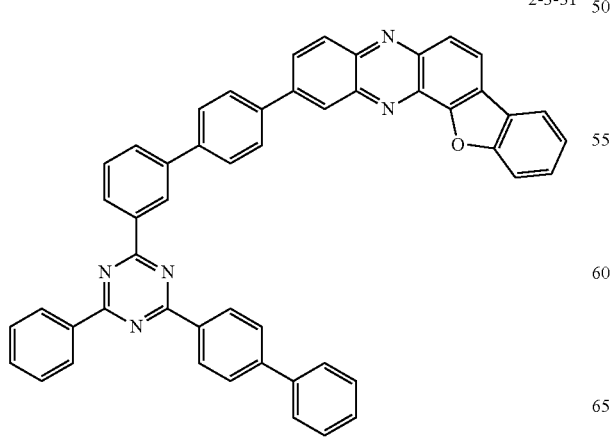
2-3-33
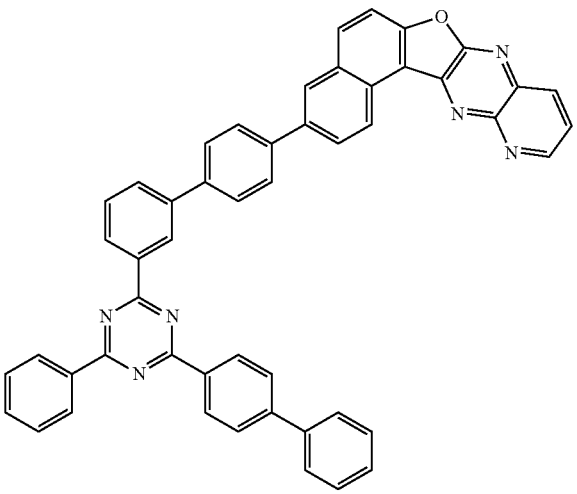
2-3-40
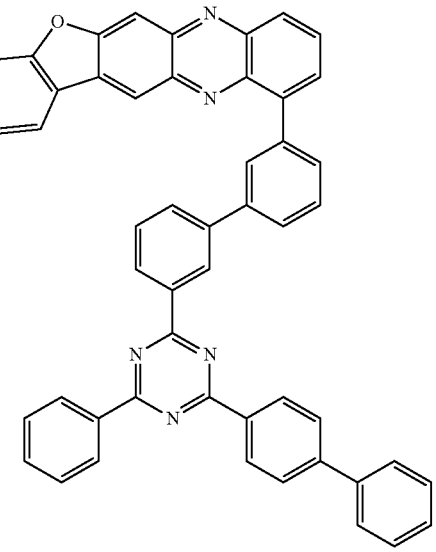

369
-continued
2-3-41
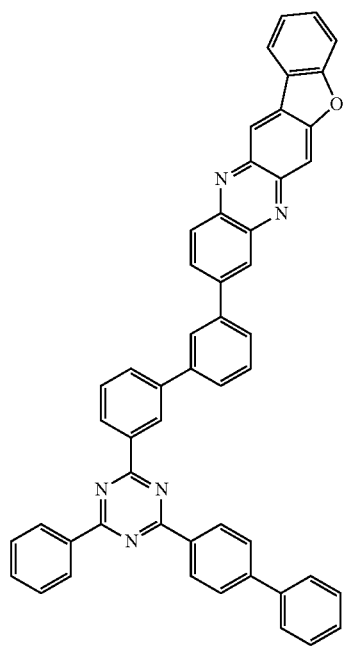
2-3-42
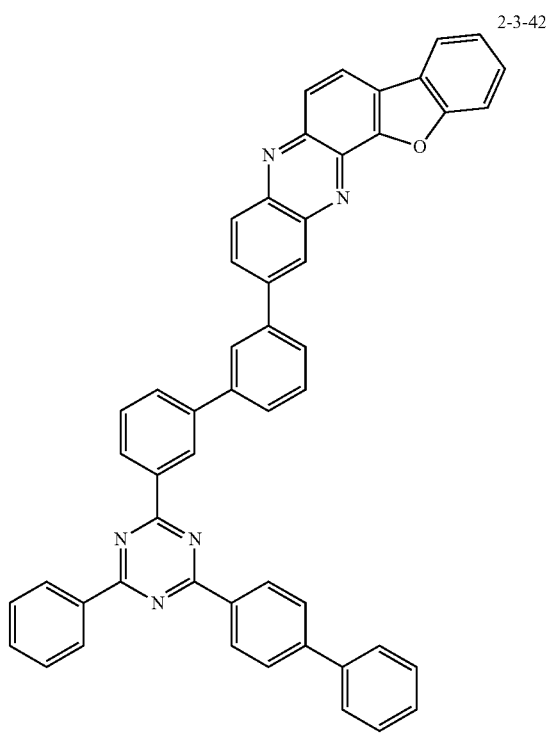
370
-continued
2-3-44
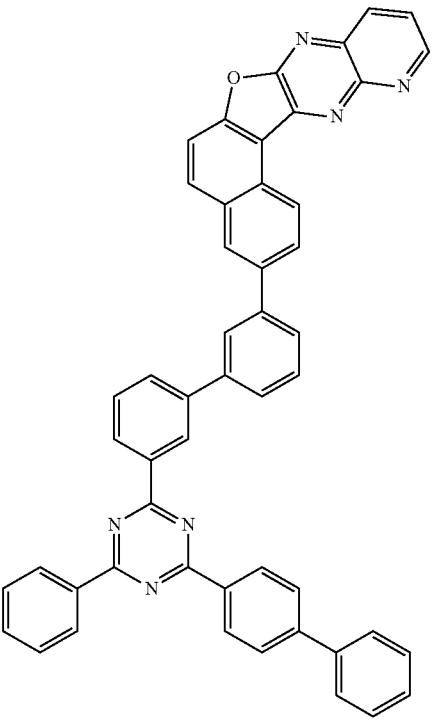
2-4-7
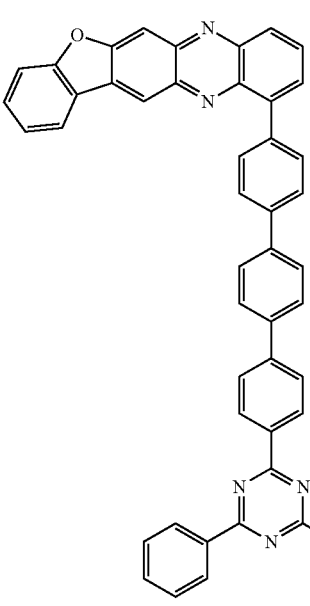

371
-continued
372
-continued
2-4-8
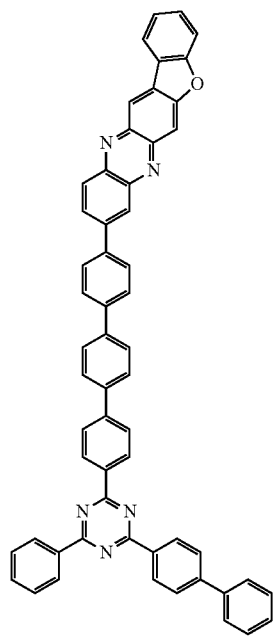
2-4-11
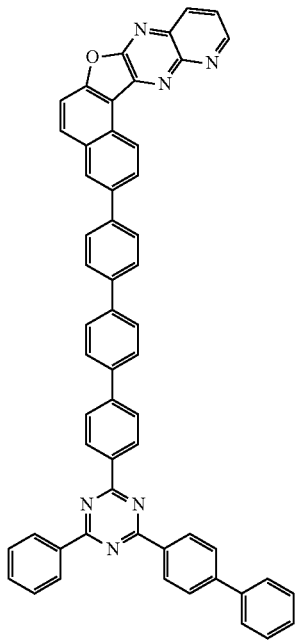
2-4-9
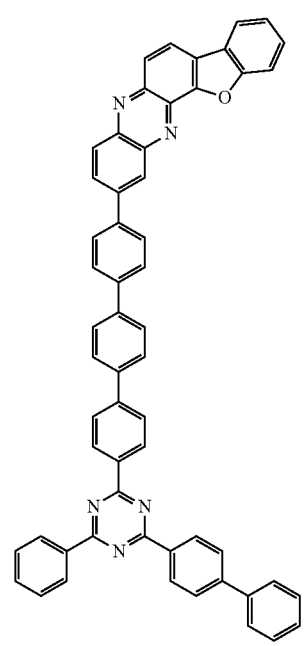
2-4-18
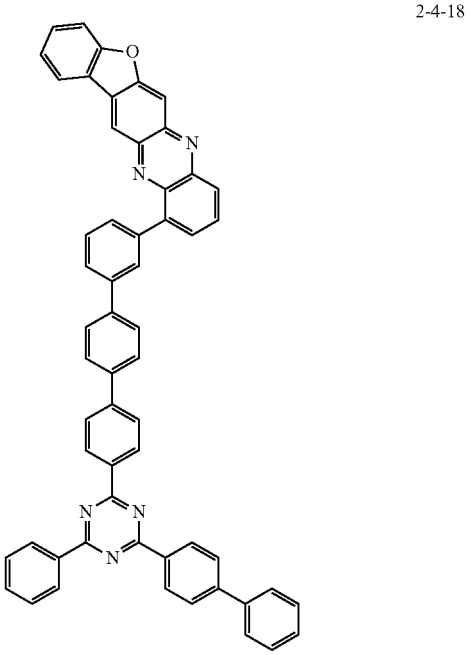

373
-continued
2-4-19
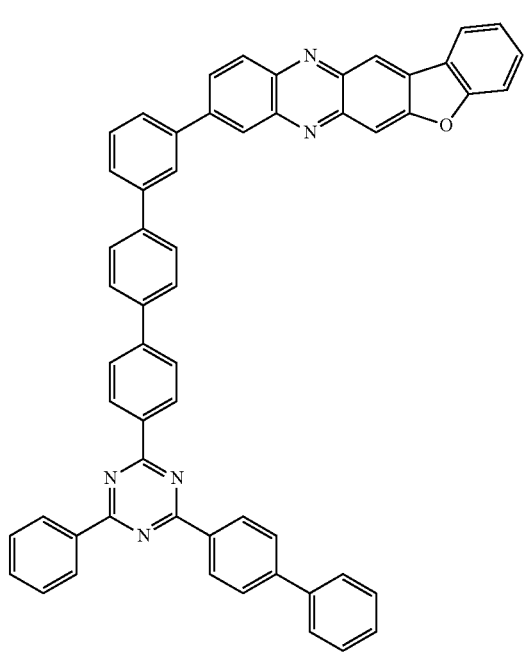
2-4-20
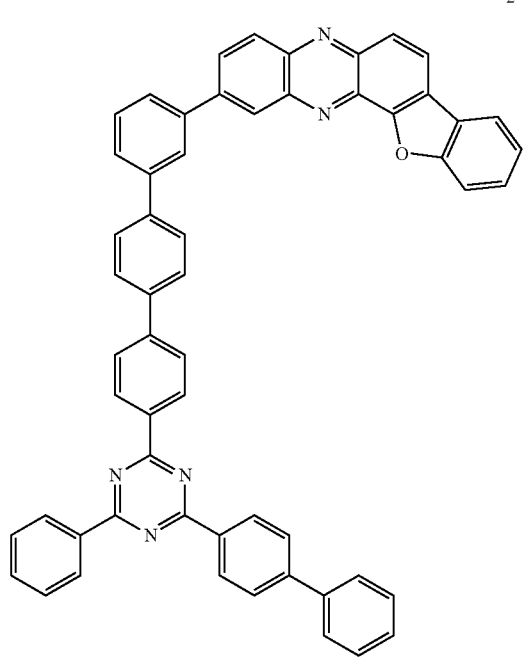
374
-continued
2-4-22
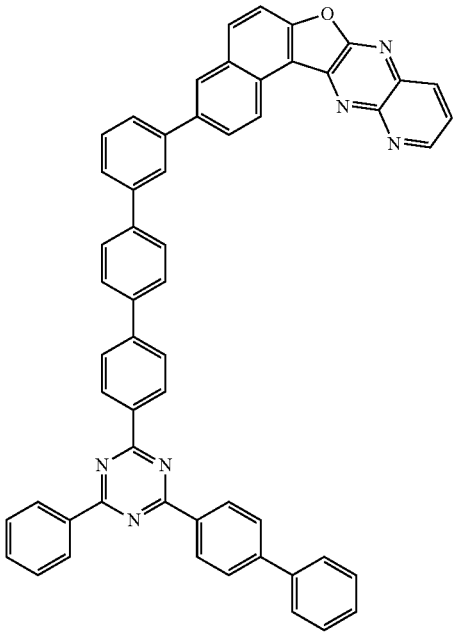
2-4-29
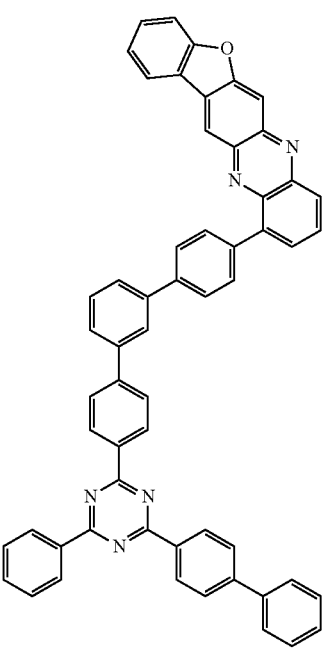

375
-continued
376
-continued
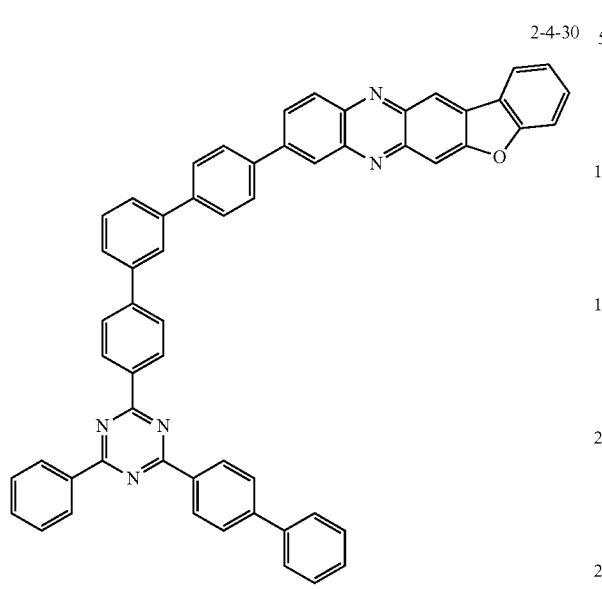
2-4-30
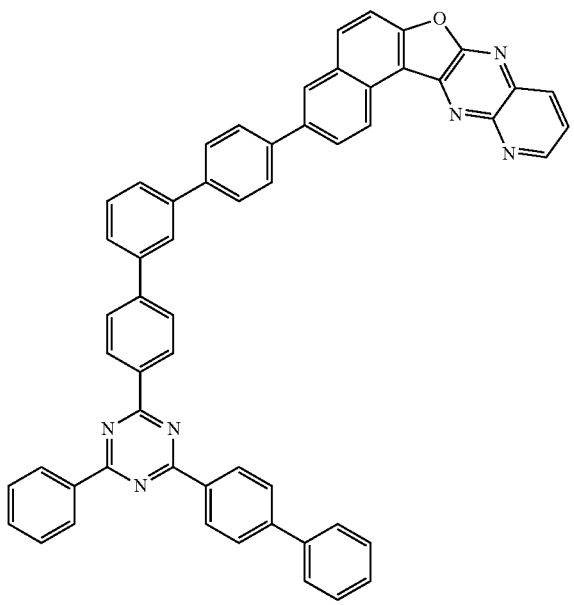
2-4-33
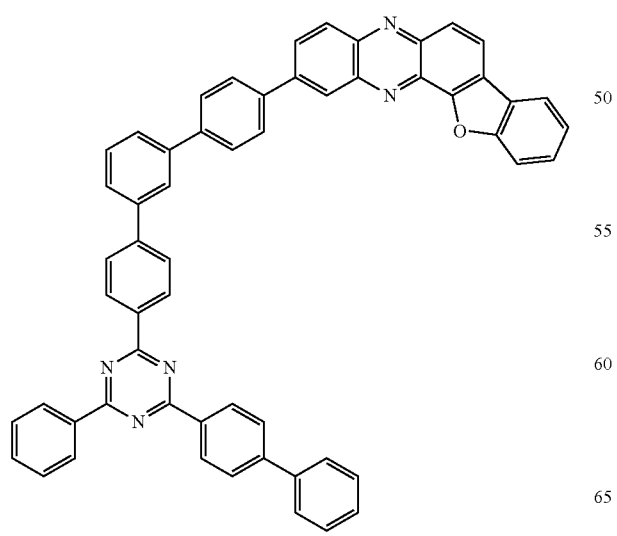
2-4-31
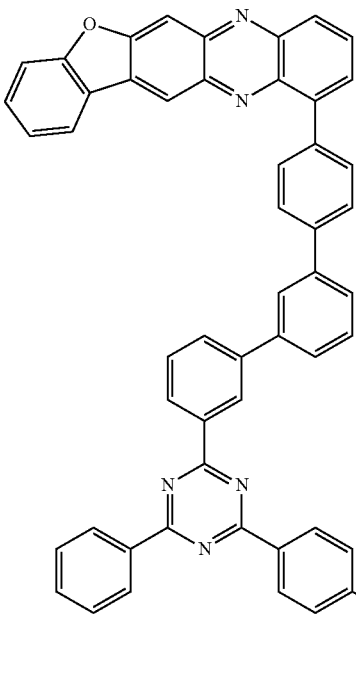
2-4-40

377
-continued
378
-continued
2-4-41
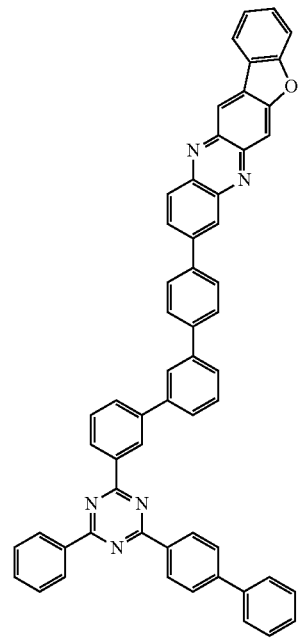
2-4-44
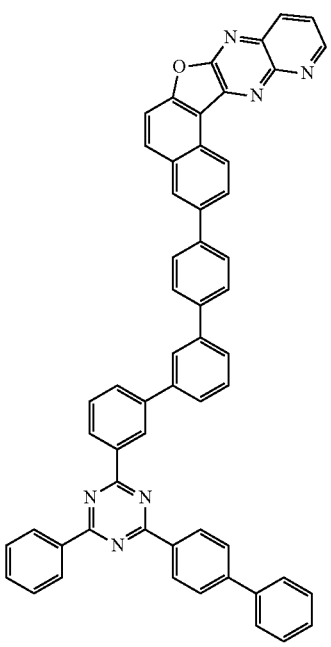
2-4-42
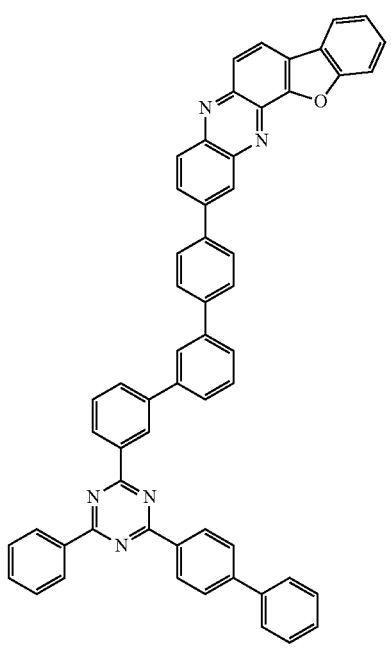
2-4-51

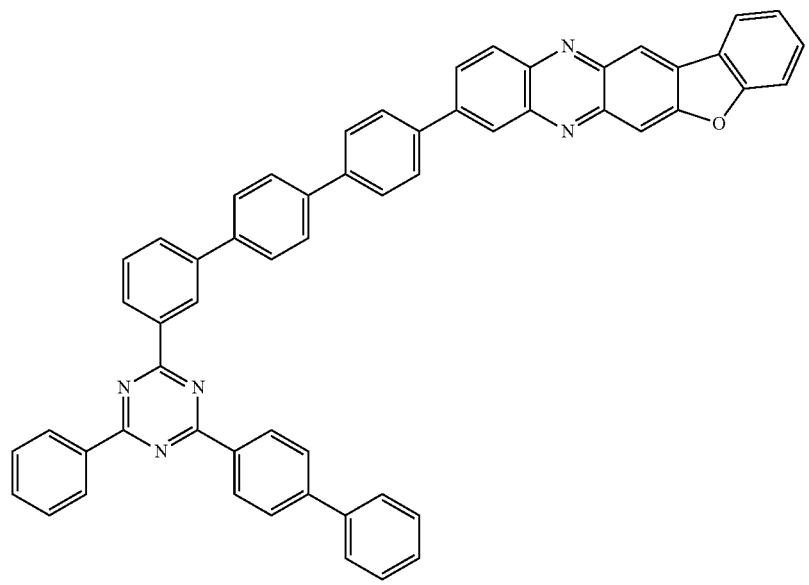
2-4-52
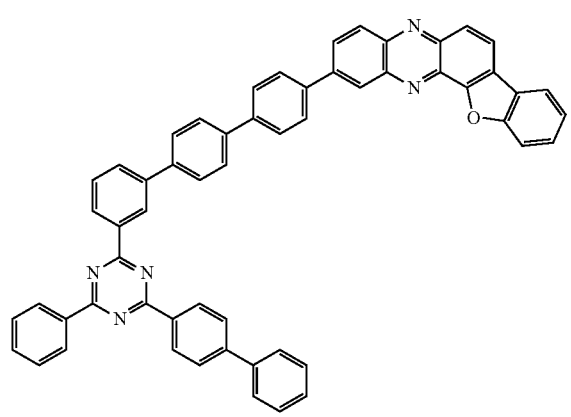
2-4-53
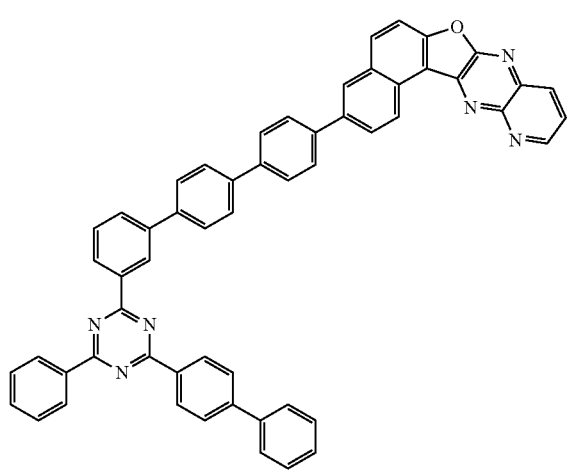
2-4-55

-continued
2-4-62
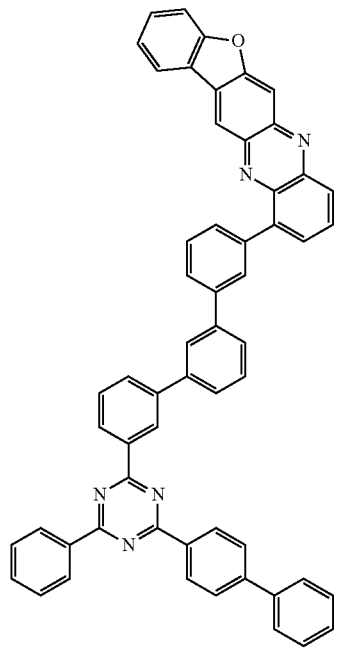
2-4-63
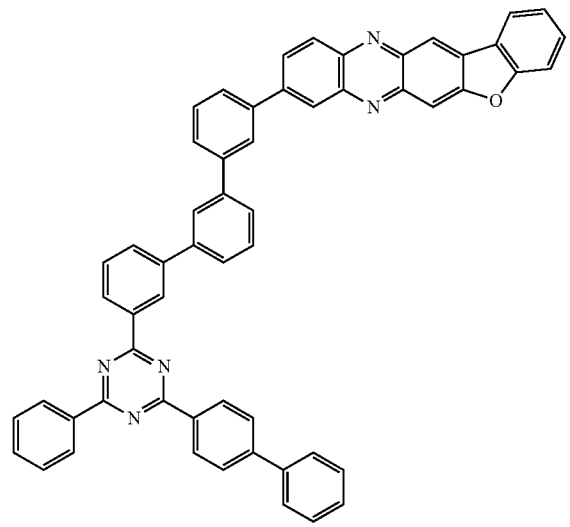
2-4-64
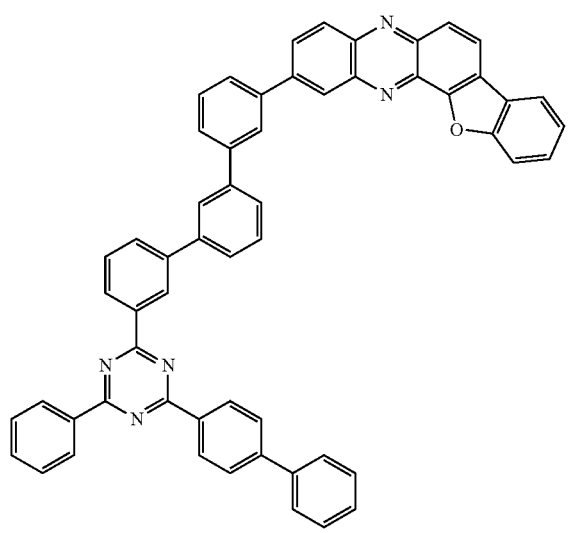
2-4-66
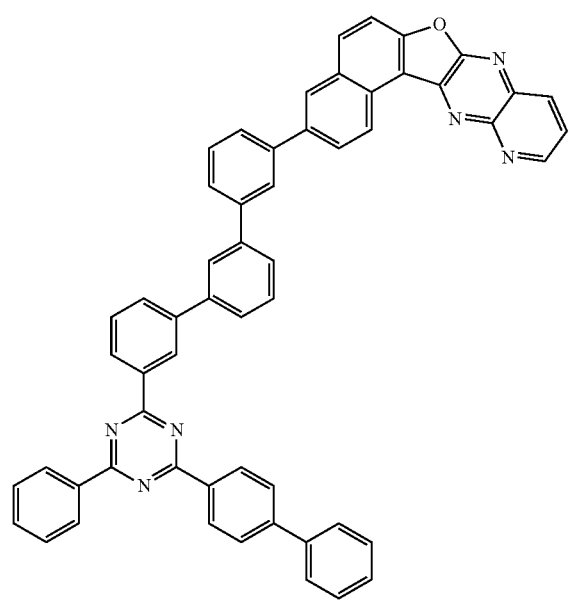

383
-continued
2-4-73
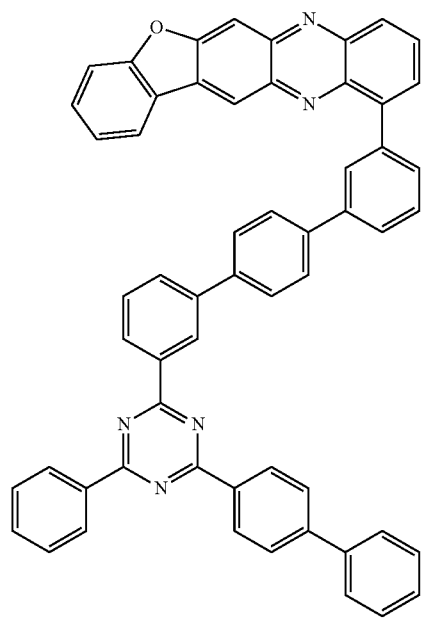
384
2-4-74
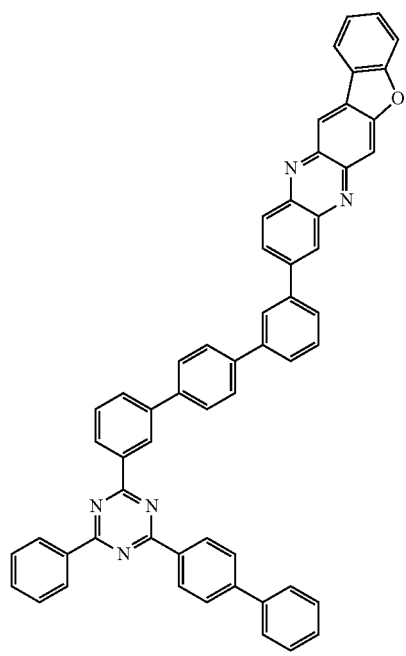
2-4-75
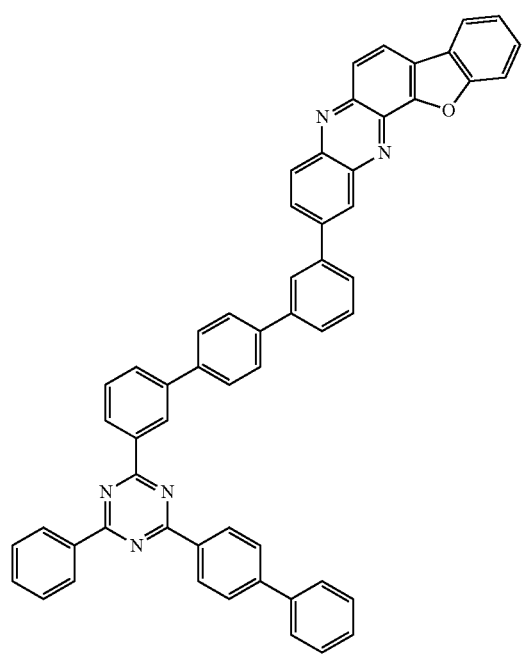
2-4-77
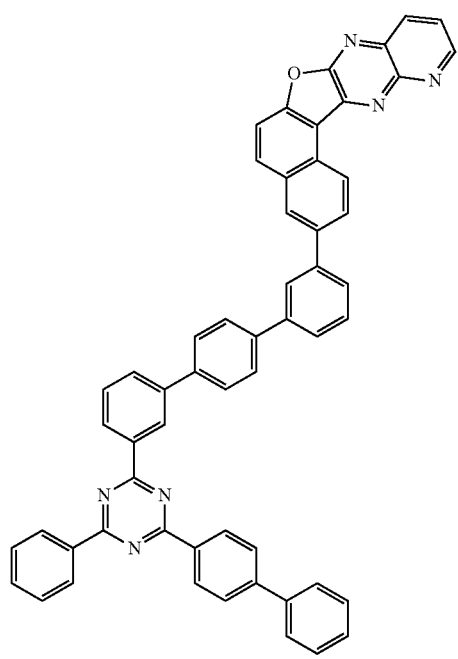

-continued
2-4-84
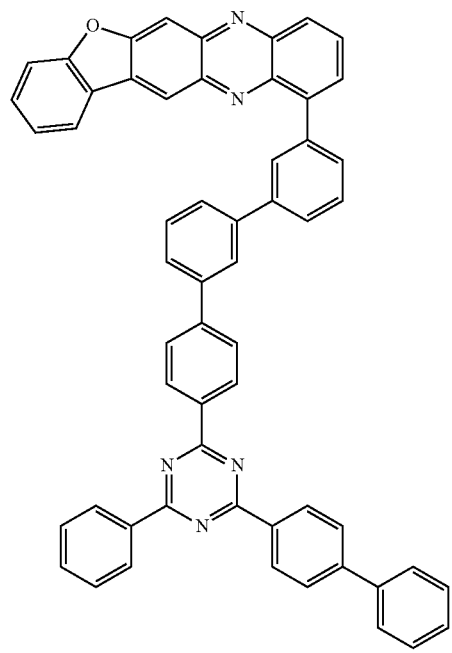
2-4-85
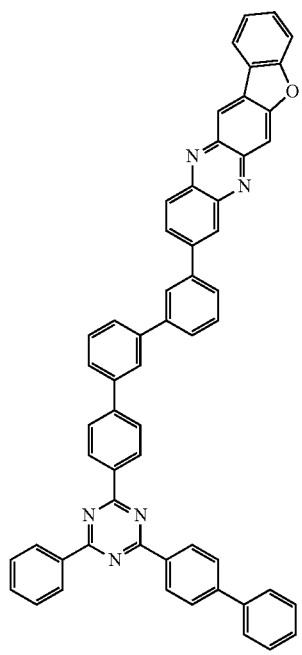
2-4-86
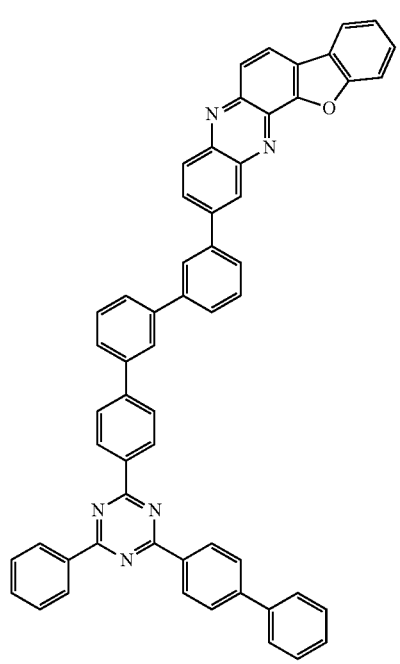
2-4-88
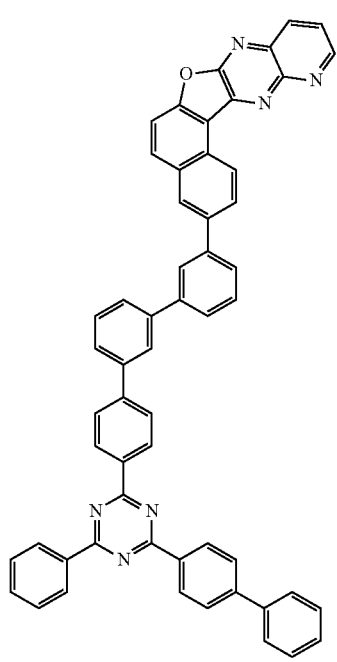

387
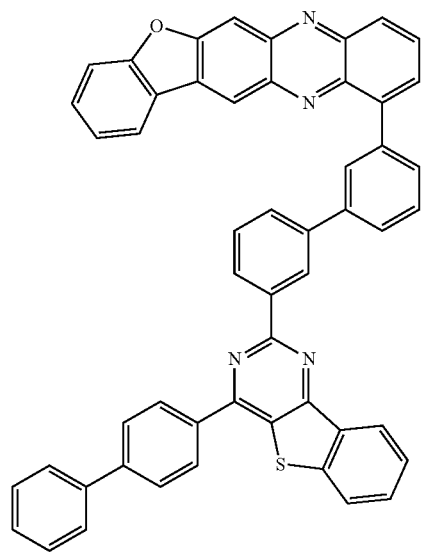
-continued
3-2-7
388
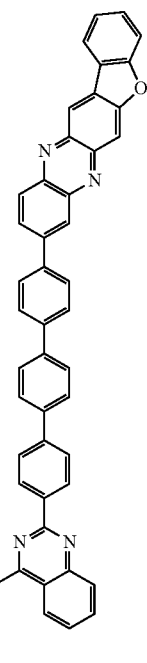
3-2-8
3-2-9
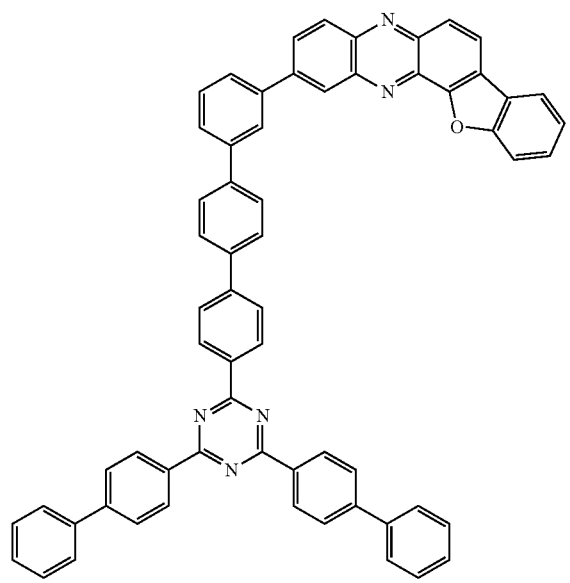
2-2-11
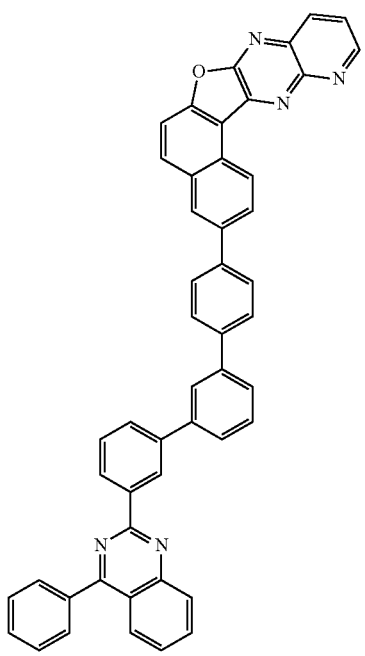
* * * * *